US010327866B2

(12) United States Patent
Lifshitz et al.

(10) Patent No.: US 10,327,866 B2
(45) Date of Patent: Jun. 25, 2019

(54) APPARATUS AND METHOD FOR ENDODONTIC TREATMENT

(71) Applicant: Fluidfile Ltd., Petach-Tikva (IL)

(72) Inventors: Amnon Lifshitz, Petach-Tikva (IL); Yehuda Darshan, Petach-Tikva (IL)

(73) Assignee: Fluidfile Ltd., Petach-Tikva (IL)

( * ) Notice: Subject to any disclaimer, the term of this patent is extended or adjusted under 35 U.S.C. 154(b) by 0 days.

(21) Appl. No.: 15/657,292

(22) Filed: Jul. 24, 2017

(65) Prior Publication Data
US 2017/0319292 A1    Nov. 9, 2017

Related U.S. Application Data

(63) Continuation of application No. 14/522,250, filed on Oct. 23, 2014, now Pat. No. 9,713,511, which is a (Continued)

(30) Foreign Application Priority Data

Apr. 15, 2012 (IL) .......................................... 219169

(51) Int. Cl.
*A61C 5/40* (2017.01)
*A61C 17/02* (2006.01)
(Continued)

(52) U.S. Cl.
CPC ............. *A61C 5/40* (2017.02); *A61C 1/0092* (2013.01); *A61C 3/025* (2013.01); *A61C 17/02* (2013.01);
(Continued)

(58) Field of Classification Search
CPC ....... A61C 5/40; A61C 1/0092; A61C 1/0061; A61C 1/087; A61C 1/12; A61C 3/025;
(Continued)

(56) References Cited

U.S. PATENT DOCUMENTS 3,739,983 A    6/1973  Jousson
4,021,921 A    5/1977  Detaille
(Continued)

FOREIGN PATENT DOCUMENTS

DE        19645644       5/1998
DE      102010051227     5/2012
(Continued)

OTHER PUBLICATIONS

Examination Report dated Aug. 29, 2017 From the Australian Government, IP Australia Re. Application No. 2013250709. (4 Pages).
(Continued)

*Primary Examiner* — Pedro Philogene
*Assistant Examiner* — David C Comstock

(57) ABSTRACT

An apparatus for endodontic treatment, comprising: a nozzle connected to a fluid source comprising: a tip small enough to be inserted into a pulp chamber of a tooth; an inner geometry which forms a flow parameters including non-axial flow direction of nozzle fluid flowing through the inner geometry such that discharge fluid discharged from the inner geometry increase rotation of root canal fluid within a root canal sufficiently to remove tissue from the root canal.

82 Claims, 61 Drawing Sheets

Related U.S. Application Data continuation-in-part of application No. 14/394,292, filed as application No. PCT/IL2013/050330 on Apr. 15, 2013.

(60) Provisional application No. 61/895,316, filed on Oct. 24, 2013, provisional application No. 61/894,762, filed on Oct. 23, 2013.

(51) Int. Cl.
| | | |
|---|---|---|
| *A61C 3/025* | (2006.01) | |
| *A61C 1/00* | (2006.01) | |
| *A61C 17/022* | (2006.01) | |
| *A61C 17/06* | (2006.01) | |
| *A61C 1/12* | (2006.01) | |
| *A61C 1/08* | (2006.01) | |

(52) U.S. Cl.
CPC ........ *A61C 17/0202* (2013.01); *A61C 17/022* (2013.01); *A61C 17/043* (2013.01); *A61C 1/0061* (2013.01); *A61C 1/087* (2013.01); *A61C 1/12* (2013.01); *A61C 17/0208* (2013.01)

(58) Field of Classification Search
CPC ... A61C 17/02; A61C 17/0202; A61C 17/022; A61C 17/043; A61C 17/0208
USPC ... 433/81, 88, 89, 91, 92, 95, 100, 216, 224
See application file for complete search history.

(56) References Cited

U.S. PATENT DOCUMENTS

| | | |
|---|---|---|
| 4,676,749 A | 6/1987 | Mabille |
| 5,295,828 A | 3/1994 | Grosrey |
| 5,484,283 A | 4/1996 | Franetzki |
| 6,224,378 B1 | 5/2001 | Valdes et al. |
| 6,497,572 B2 | 12/2002 | Hood et al. |
| 7,891,977 B2 | 2/2011 | Riva |
| 8,235,719 B2 | 8/2012 | Ruddle et al. |
| 8,297,540 B1 | 10/2012 | Vijay |
| 8,328,552 B2 | 12/2012 | Ruddle et al. |
| 8,388,345 B2 | 3/2013 | Ruddle |
| 9,084,651 B2 | 7/2015 | Laufer |
| 2001/0055742 A1 | 12/2001 | Hood et al. |
| 2003/0129560 A1 | 7/2003 | Atkin et al. |
| 2003/0215768 A1* | 11/2003 | Aumuller ................ A61C 1/05 433/130 |
| 2007/0042316 A1 | 2/2007 | Pichat et al. |
| 2007/0248932 A1 | 10/2007 | Gharib et al. |
| 2008/0319453 A1 | 12/2008 | Tavger |
| 2009/0004621 A1 | 1/2009 | Quan et al. |
| 2009/0130622 A1 | 5/2009 | Bollinger et al. |
| 2010/0092922 A1 | 4/2010 | Ruddle |
| 2010/0143861 A1 | 6/2010 | Gharib et al. |
| 2010/0152634 A1 | 6/2010 | Dove |
| 2010/0233649 A1 | 9/2010 | McPeek et al. |
| 2010/0272764 A1 | 10/2010 | Latta et al. |
| 2011/0111365 A1 | 5/2011 | Gharib et al. |
| 2011/0117517 A1 | 5/2011 | Bergheim et al. |
| 2011/0183284 A1 | 7/2011 | Yamanaka et al. |
| 2011/0189630 A1 | 8/2011 | Koubi |
| 2012/0141953 A1 | 6/2012 | Mueller |
| 2012/0237893 A1 | 9/2012 | Bergheim et al. |
| 2012/0276497 A1 | 11/2012 | Gharib et al. |
| 2013/0040267 A1 | 2/2013 | Bergheim et al. |
| 2013/0288195 A1* | 10/2013 | Mueller ................ B05B 1/3415 433/88 |
| 2014/0080090 A1 | 3/2014 | Laufer |
| 2015/0044631 A1 | 2/2015 | Lifshitz et al. |
| 2015/0125811 A1 | 5/2015 | Lifshitz et al. |
| 2016/0095679 A1* | 4/2016 | Khakpour .......... A61C 17/0202 433/81 |

FOREIGN PATENT DOCUMENTS

| | | |
|---|---|---|
| GB | 2011305 | 7/1979 |
| IL | 219169 | 7/2012 |
| JP | 01-313048 | 12/1989 |
| JP | 2004-313659 | 11/2004 |
| JP | 2005-052754 | 3/2005 |
| JP | 2006-247619 | 9/2006 |
| JP | 2010-247133 | 11/2010 |
| WO | WO 00/45731 | 8/2000 |
| WO | WO 2009/137815 | 11/2009 |
| WO | WO 2011/060327 | 5/2011 |
| WO | WO 2012/069894 | 5/2012 |
| WO | WO 2013/157000 | 10/2013 |
| WO | WO 2015/059707 | 4/2015 |

OTHER PUBLICATIONS

Examination Report dated Jun. 16, 2017 From the Instituto Mexicano de la Propiedad Industrial Re. Application No. 2014/012423 and Its Translation Into English.
Supplementary Partial European Search Report and the European Search Opinion dated Aug. 11, 2017 From the European Patent Office Re. Application No. 14855775.4. (10 Pages).
Communication Pursuant to Article 94(3) EPC dated Jun. 22, 2017 From the European Patent Office Re. Application No. 13778016.9. (6 Pages).
Examination Report dated Sep. 4, 2015 From the New Zealand Intellectual Property Office Re. Application No. 701422.
International Preliminary Report on Patentability dated May 6, 2016 From the International Bureau of WIPO Re. Application No. PCT/IL2014/050924.
International Preliminary Report on Patentability dated Oct. 30, 2014 From the International Bureau of WIPO Re. Application No. PCT/IL2013/050330.
International Search Report and the Written Opinion dated Mar. 19, 2015 From the International Searching Authority Re. Application No. PCT/IL2014/050924.
International Search Report and the Written Opinion dated Jul. 30, 2013 From the International Searching Authority Re. Application No. PCT/IL2013/050330.
Invitation Pursuant to Rule 63(1) EPC dated Apr. 20, 2017 From the European Patent Office Re. Application No. 14855775.4. (3 Pages).
Invitation to Pay Additional Fees dated Jan. 21, 2015 From the International Searching Authority Re. Application No. PCT/IL2014/050924.
Notice of Reasons for Rejection dated Feb. 21, 2017 From the Japan Patent Office Re. Application No. 2015-505069. (11 Pages).
Notification of the Request to Submit Additional Materials dated Jun. 22, 2016 From the Eurasian Patent Organization, Eurasian Patent Office Re. Application No. 201491890 and Its Translation Into English.
Office Action dated Apr. 4, 2017 From the Israel Patent Office Re. Application No. 219169 and Its Translation Into English. (4 Pages).
Office Action dated Apr. 5, 2017 From the State Intellectual Property Office of the People's Republic of China Re. Application No. 201380031375.8 and Its Summary Into English. (7 Pages).
Office Action dated Nov. 19, 2015 From the Israel Patent Office Re. Application No. 219169 and Its Translation Into English.
Office Action dated Jul. 28, 2016 From the State Intellectual Property Office of the People's Republic of China Re. Application No. 201380031375.8 and Its Translation Into English.
Official Action dated Jun. 6, 2017 From the US Patent and Trademark Office Re. U.S. Appl. No. 14/394,292. (24 pages).
Official Action dated Aug. 12, 2016 From the US Patent and Trademark Office Re. U.S. Appl. No. 14/394,292.
Official Action dated Jul. 15, 2016 From the US Patent and Trademark Office Re. U.S. Appl. No. 14/522,250.
Patent Examination Report dated Nov. 1, 2016 From the Australian Government, IP Australia Re. Application No. 2013250709.
Restriction Official Action dated Feb. 25, 2016 From the US Patent and Trademark Office Re. U.S. Appl. No. 14/394,292.

(56) References Cited

OTHER PUBLICATIONS

Search Report and Written Opinion dated Mar. 4, 2015 From the Intellectual Property Office of Singapore Issued by the Austrian Patent Office Re. Application No. 11201406430V.
Supplementary European Search Report and the European Search Opinion dated Dec. 9, 2015 From the European Patent Office Re. Application No. 13778016.9.
Translation dated May 24, 2017 of Office Action dated Apr. 5, 2017 From the State Intellectual Property Office of the People's Republic of China Re. Application No. 201380031375.8. (3 Pages).
Translation of Notice of Reasons for Rejection dated Feb. 21, 2017 From the Japan Patent Office Re. Application No. 2015-505069. (16 Pages).
Translation of Office Action and Search Report dated Oct. 10, 2015 From the State Intellectual Property Office of the People's Republic of China Re. Application No. 201380031375.8.
Jiang et al. "Evaluation of A Sonic Device Designed to Activate Irrigant in the Root Canal", Journal of Endodontics, 36(1): 143-146, Jan. 2010.
Notice of Reasons for Rejection dated Jul. 24, 2018 From the Japan Patent Office Re. Application No. 2016-525911 and Its Translation Into English.
Communication Pursuant to Article 94(3) EPC dated Jun. 26, 2018 From the European Patent Office Re. Application No. 14855775.4. (4 pages).
Examiniation Report dated Jun. 19, 2018 From the Australian Government, IP Australia Re. Application No. 2014338513. (6 Pages).
Notice of Reasons for Rejection dated Jun. 26, 2018 From the Japan Patent Office Re. Application No. 2015-505069 and Its Translation Into English. (5 Pages).
Examination Report dated Feb. 20, 2018 From the Instituto Mexicano de la Propiedad Industrial, IMPI, Direccion Divisional de Patentes Re. Application No. MX/a/2014/012423 and Its Translation Into English. (12 Pages).
Notification of the Request to Submit Additional Materials dated Feb. 18, 2018 From the Eurasian Patent Organiziation, Eurasian Patent Office Re. Application No. 201491890 and Its Translation Into English. (8 Pages).
Translation of Notification of Office Action dated Jan. 12, 2018 From the State Intellectual Property Office of the People's Republic of China Re. Application No. 201480070236.0. (11 Pages).
Translation of Notice of Reasons for Rejection dated Sep. 12, 2017 From the Japan Patent Office Re. Application No. 2015-505069. (11 Pages).
Notice of Reasons for Rejection dated Sep. 12, 2017 From the Japan Patent Office Re. Application No. 2015-505069. (5 Pages).
Notification of Office Action dated Jan. 12, 2018 From the State Intellectual Property Office of the People's Republic of China Re. Application No. 201480070236.0. (9 Pages).
Official Action dated Jan. 23, 2018 From the US Patent and Trademark Office Re. U.S. Appl. No. 14/394,292. (14 pages).
Translation dated Nov. 13, 2018 of Notification of Office Action dated Oct. 31, 2018 From the State Intellectual Property Office of the People's Republic of China Re. Application No. 201480070236.0. (7 Pages).
Notification of Office Action dated Oct. 31, 2018 From the State Intellectual Property Office of the People's Republic of China Re. Application No. 201480070236.0 and Its Summary in English. (9 Pages).
Requisition by the Examiner dated Jan. 7, 2019 From the Innovation, Science and Economic Development Canada, Canadian Intellectual Property Office Re. Application No. 2,869,836. (4 Pages).
Examination Report Notification dated Feb. 21, 2019(*) from the Instituto Mexicano de la Propiedad Industrial, Direccion Divisional de Patentes Re. Application No. MX/a/2014/012423 and its Translation into English (* Dated Oct. 25, 2018). (13 Pages).
Notice of Reason for Rejection Dated Mar. 5, 2019 From the Japan Patent Office Re. Application No. 2016-525911 and Its Translation Into English. (17 Pages).

\* cited by examiner

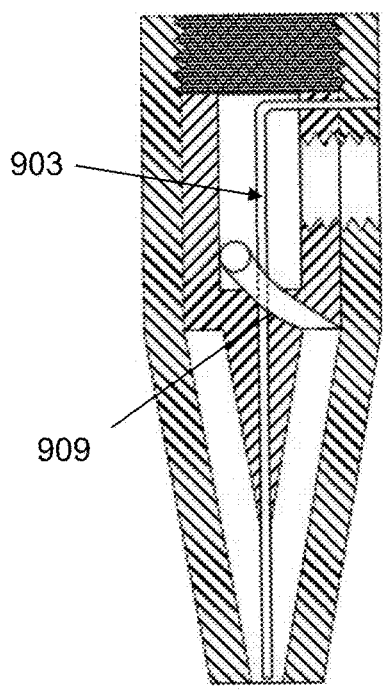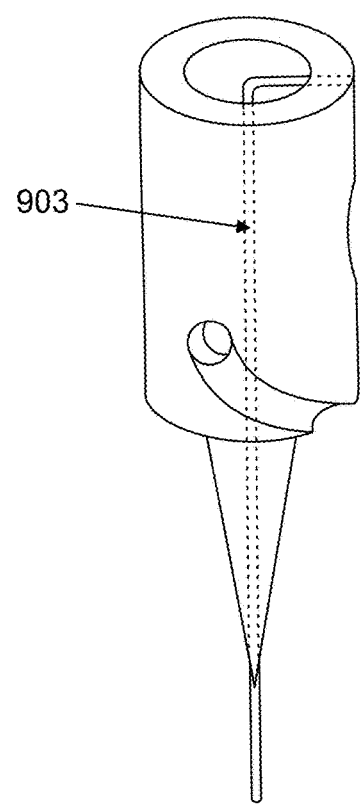
FIG. 9C                    FIG. 9D

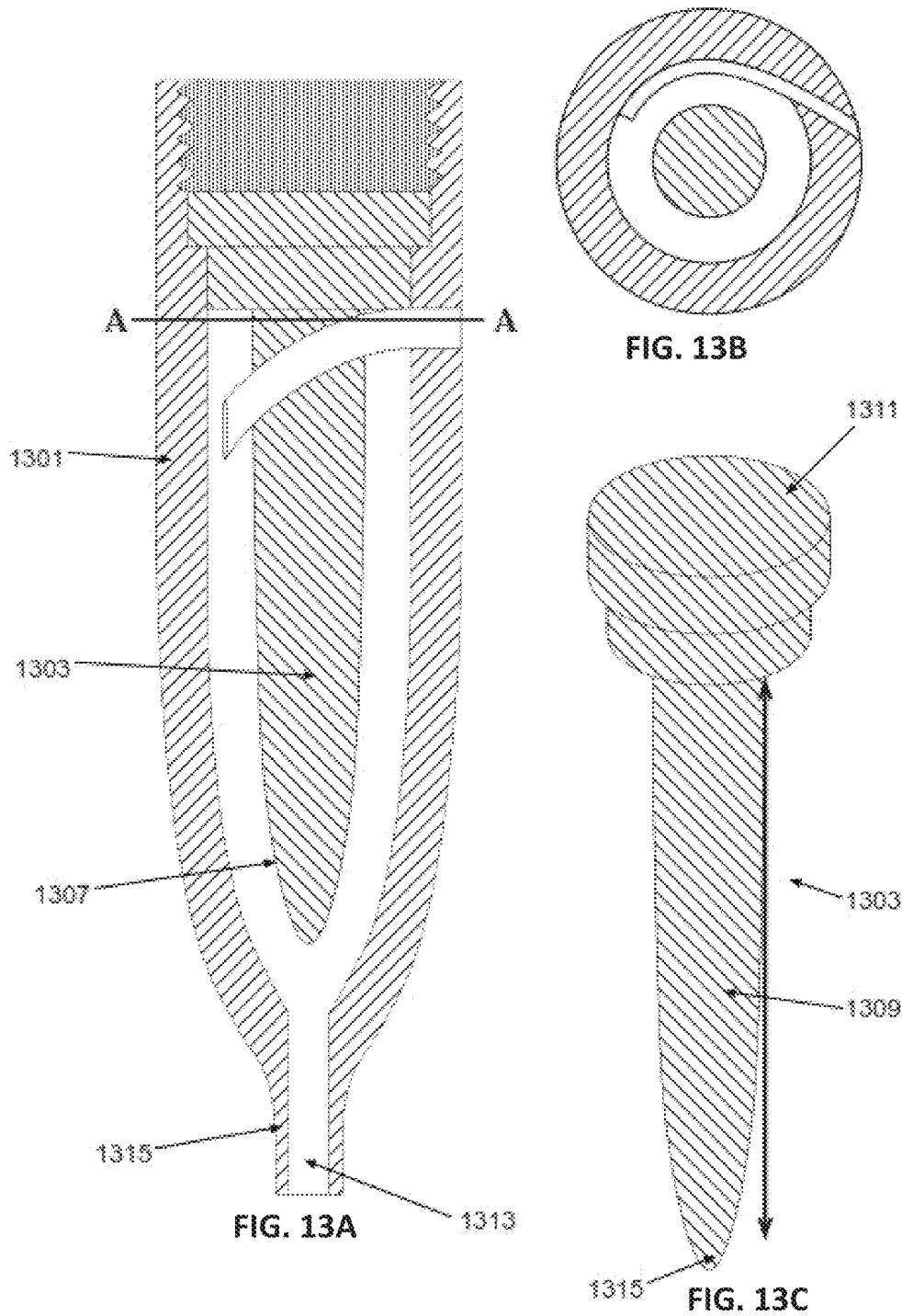

FEASIBILITY STUDY FOR: APPARATUS AND METHOD FOR ENDODONTIC TREATMENT

STUDY PURPOSE: feasibility test for novel apparatus and endodontic treatment

The process supported with "Before and After" evidence results which supported with CT imaging, Axial Mode for evaluate the thickness of the eroding layer in the root canal. Using Electro scan microscope (X 5000 magnification) testing the cleanliness of the root canal.

| Tooth Nr. | Total of canals per each specim. | Root Canal Type | | | | | Duration of Treatment in Seconds | | | Apex Pene-Tration | sidelong penetration by canal with a thin Wall | Average Eroding layer in microns | Comments |
|---|---|---|---|---|---|---|---|---|---|---|---|---|---|
| | | Stand. Canal (X) | Curve Canal (X) | Sharp Curved Canal (X) | Canal with Open Apex (X) | Extremely narrow canal (X) | 15 (X) | 30 (X) | 45 (X) | (Yes/No) | (Yes/No) | | |
| 1 | 2 | 1 | 1 | | 4 | | | x | | N | N | 100-200 | Apex was open initially; cleaning might have caused a slight widening of the opening |
| 2 | 4 | 1 | 2 | 1 | | | x | | | N | N | 100-200 | Hole accidently created on the side during the tooth opening |
| 3 | 3 | 1 | 1 | 1 | | 2 | | x | | N | N | 100-200 | |
| 4 | 4 | 2 | | 2 | 3 | 1 | | | x | N | N | 100-200 | Apex was open initially; cleaning might have caused a slight widening of the openings |
| 5 | 3 | 1 | 1 | 1 | | 2 | | | x | N | N | 100-200 | |
| 6 | 3 | | 2 | 1 | | | | x | | N | N | 100-200 | |
| 7 | 3 | 2 | 1 | | | | | | x | N | N | 100-200 | |
| 8 | 4 | 2 | 2 | 2 | | | | | x | N | N | 100-200 | |
| 9 | 3 | | 1 | 1 | 1 | 2 | x | | | N | N | 100-200 | Apex was open initially; cleaning might have caused a slight widening of the opening |
| 10 | 3 | 2 | | 1 | 3 | | | | | N | N | 100-200 | Apex was open initially; cleaning might have caused a slight widening of the opening |

FIG. 16A

| Tooth Nr. | Total of canal per each specim. | Root Canal type ||||| Duration of Treatment in Seconds ||| Apex Pene-tration | sidelong penetration by canal with a thin Wall | Average Eroding layer in microns | Comments |
| | | Stand. Canal | Curve Canal | Sharp Curved Canal | Canal with Open Apex | Extremely narrow canal | 15 | 30 | 45 | | | | |
| | | (X) | (X) | (X) | (X) | (X) | (X) | (X) | (X) | (Yes/No) | (Yes/No) | | |
| 11 | 3 | 1 | | 2 | 1 | 2 | | | | N | N | 100-200 | |
| 12 | 4 | 2 | 1 | 1 | 3 | 2 | | x | x | N | N | 100-200 | Apex was open initially; cleaning might have caused a slight widening of the opening |
| 13 | 3 | 3 | | | 1 | | | | | N | N | 100-200 | Apex was open initially; cleaning might have caused a slight widening of the opening |
| 14 | 4 | 1 | 2 | 1 | | | | | x | N | N | 100-200 | Hole accidentally created on the bottom between canal, during the tooth opening |
| 15 | 3 | 2 | 1 | 1 | 1 | 1 | | x | | N | N | 100-200 | Apex was open initially; cleaning might have caused a slight widening of the opening |
| 16 | 4 | 1 | 1 | 2 | | | x | | | N | N | 100-200 | 1 canal was broken before the cleaning procedure |
| 17 | 4 | 3 | | 1 | | | x | | | N | N | 100-200 | |
| 18 | 3 | 1 | | 2 | 3 | | x | | | N | N | 100-200 | Apex was open initially; cleaning might have caused a slight widening of the opening |
| 19 | 2 | 1 | 1 | | | | | | x | N | N | 100-200 | |
| 20 | 1 | 1 | | | | | | x | | N | N | 100-200 | |

FIG. 16A (continued)

| Tooth Nr. | Total of canal per each specim. | Root Canal type ||||| Duration of Treatment in Seconds ||| Apex Penetration | sidelong penetration by canal with a thin Wall | Average Eroding layer in microns | Comments |
|---|---|---|---|---|---|---|---|---|---|---|---|---|---|
| | | Stand. Canal (X) | Curve Canal (X) | Sharp Curved Canal (X) | Canal with Open Apex (X) | Extremely narrow canal (X) | 15 (X) | 30 (X) | 45 (X) | (Yes/No) | (Yes/No) | | |
| 21 | 1 | 1 | | | | | x | | | N | N | 100-200 | |
| 22 | 3 | 1 | 2 | | | | x | | | N | N | 100-200 | |
| 23 | 3 | 1 | | 2 | 2 | | x | | | N | N | 100-200 | Apex was open initially; cleaning might have caused a slight widening of the opening |
| 24 | 4 | 3 | 1 | 1 | 3 | | x | | | N | N | 100-200 | Apex was open initially; cleaning might have caused a slight widening of the opening |
| 25 | 3 | 1 | 2 | 2 | 1 | | x | | | N | N | 100-200 | Apex was open initially; cleaning might have caused a slight widening of the opening |
| 26 | 3 | 1 | 2 | | | | | x | | N | N | 100-200 | Apex was broken and open initially - (M) size for 3 canals |
| 27 | 3 | 1 | 1 | 1 | 2 | | | x | | N | N | 100-200 | |
| 28 | 4 | 2 | 1 | 1 | 2 | 2 | | x | | N | N | 100-200 | Apex was open initially; cleaning might have caused a slight widening of the opening |
| 29 | 2 | 1 | 1 | | 1 | | | | x | N | N | 100-200 | Apex was open initially; cleaning might have caused a slight widening of the opening |
| 30 | 3 | 2 | 1 | | 1 | 1 | | | x | N | N | 100-200 | Apex was open initially; cleaning might have caused a slight widening of the opening |

FIG. 16B

| Tooth Nr. | Root Canal type Tooth No | | | | | | Duration of Treatment in Seconds | | | Apex Penetration | sidelong penetration by canal with a thin Wall | Average Eroding layer in microns | Comments |
|---|---|---|---|---|---|---|---|---|---|---|---|---|---|
| | Total of canal per each specim. | Stand. Root Canal | Curve Canal | Sharp Curved Canal | Canal with Open Apex | Extremely narrow canal | 15 | 30 | 45 | | | | |
| | (X) | (X) | (X) | (X) | (X) | (X) | (X) | (X) | (X) | (Yes/No) | Yes/No | | |
| 31 | 4 | 1 | 2 | 1 | | 3 | | x | | N | N | 100-200 | |
| 32 | 4 | | 2 | 2 | | | | | x | N | N | 100-200 | |
| 33 | 4 | 2 | 1 | 1 | 2 | 1 | x | | | N | N | 100-200 | Apex was open initially, cleaning might have caused a slight widening of the opening |
| 34 | 3 | 1 | 2 | | | | | x | | N | N | 100-200 | |
| 35 | 3 | | 2 | 1 | | | x | | | N | N | 100-200 | |
| 36 | 3 | 1 | 1 | 1 | | 2 | | | x | N | N | 100-200 | |
| 37 | 3 | 2 | 1 | | | | | x | | N | N | 100-200 | Apex was open initially, cleaning might have caused a slight widening of the opening |
| 38 | 4 | 1 | 2 | 1 | 1 | 2 | | x | | N | N | 100-200 | Apex was open initially, cleaning might have caused a slight widening of the opening |
| 39 | 3 | 3 | | | | | | | x | N | N | 100-200 | |
| 40 | 1 | 1 | | | | 1 | | | x | N | N | 100-200 | |
| 41 | 1 | 1 | | | | | | x | | N | N | 100-200 | |

FIG. 16B (continued)

FIG. 18A
FIG. 18B
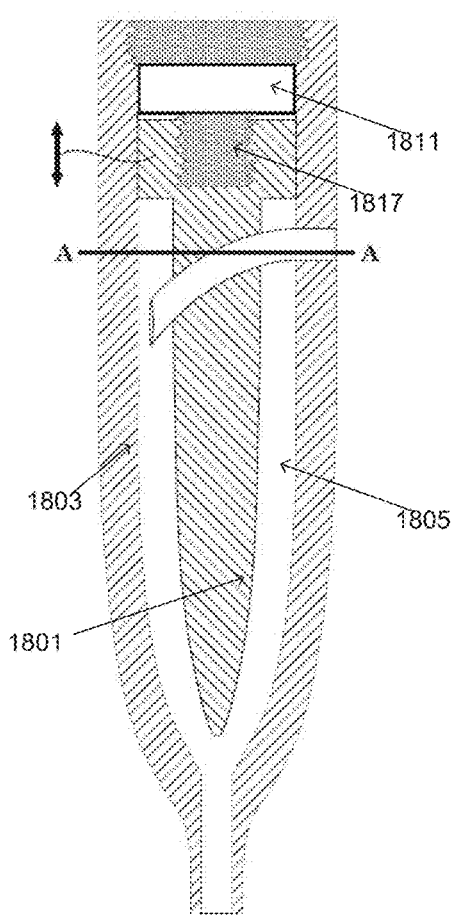
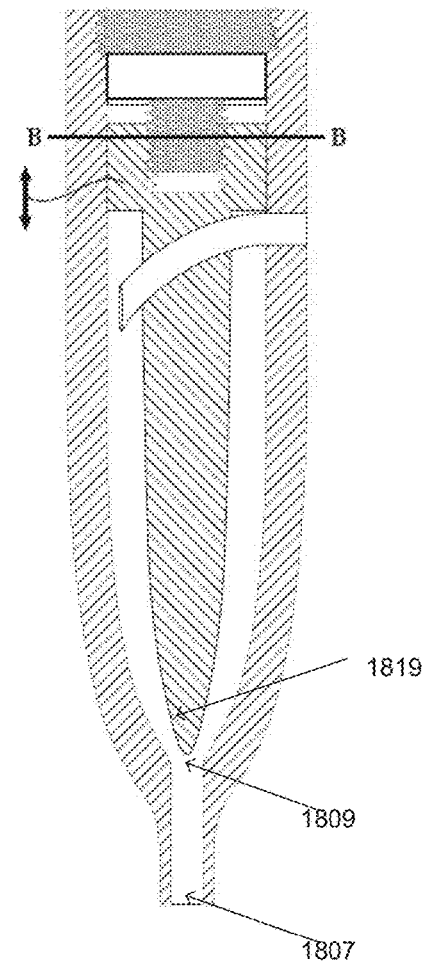
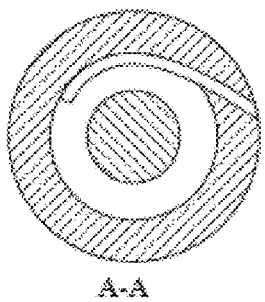
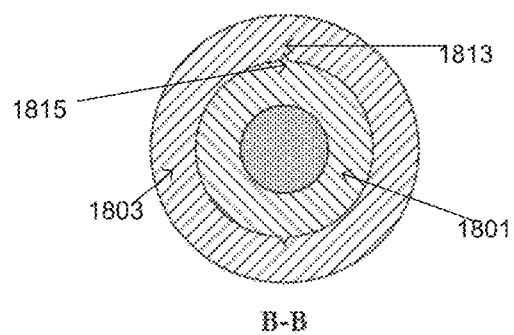
A-A
B-B

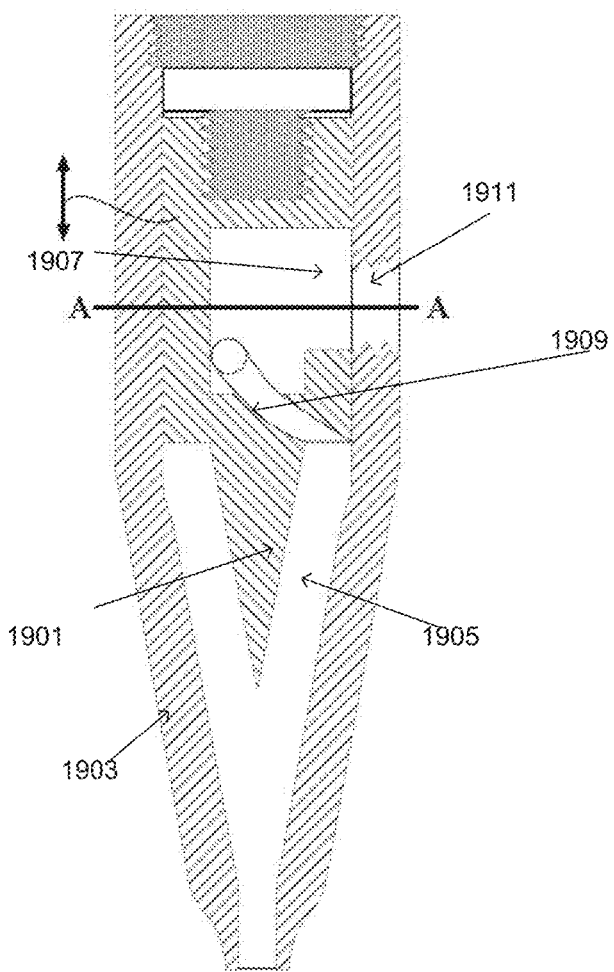
FIG. 19A
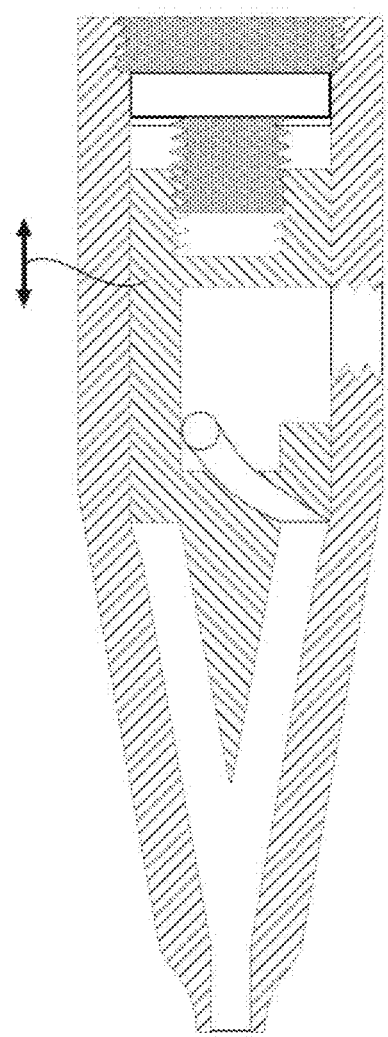
FIG. 19B
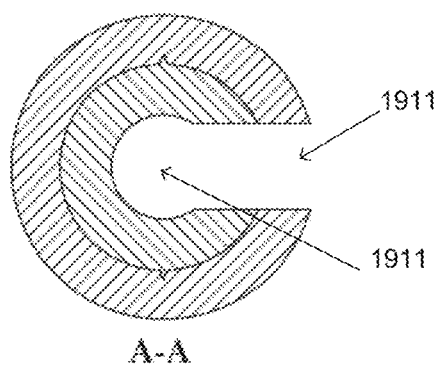
A-A

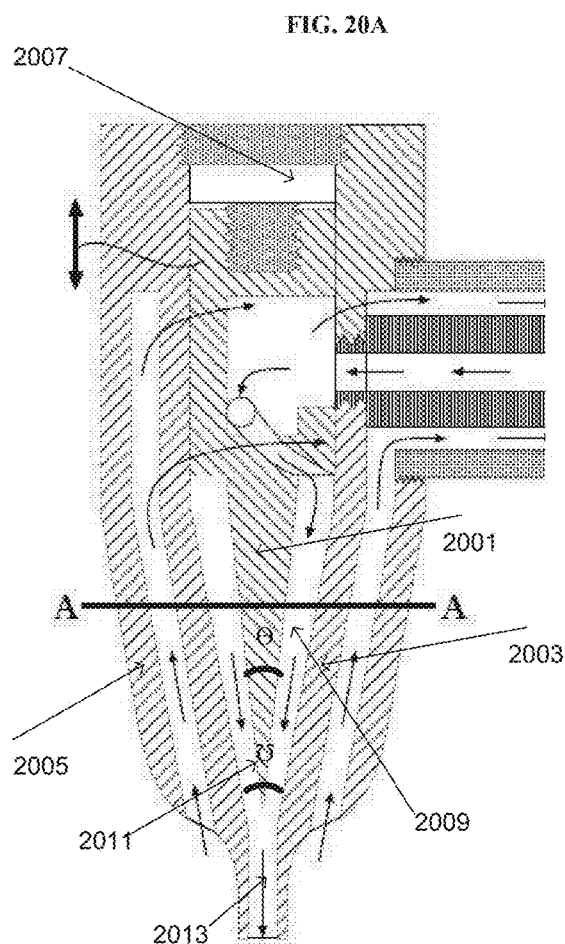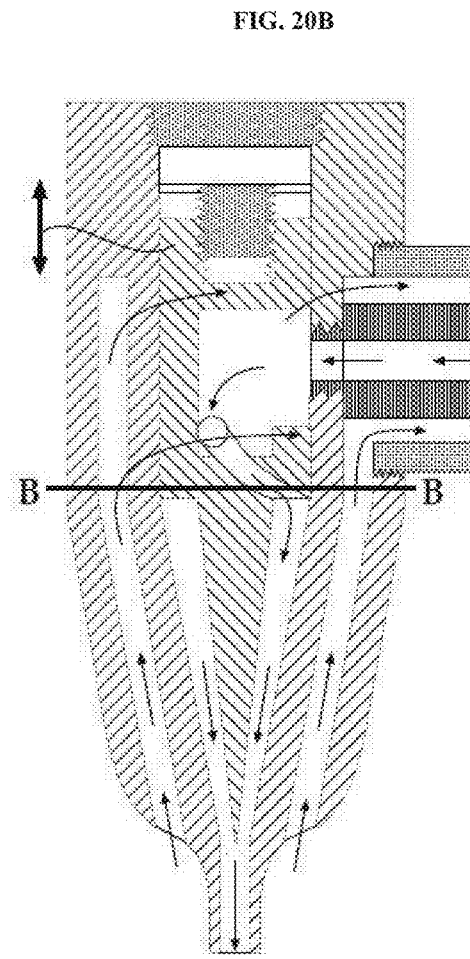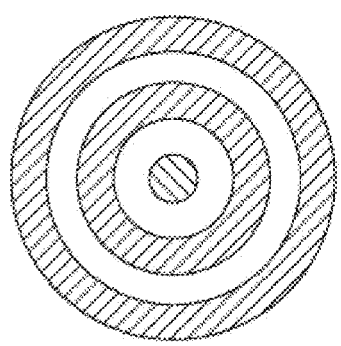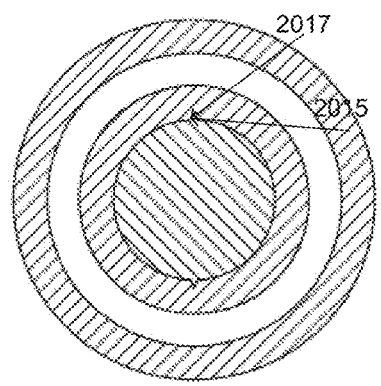
FIG. 20A  FIG. 20B
A-A  B-B

FIG. 21A
FIG. 21B
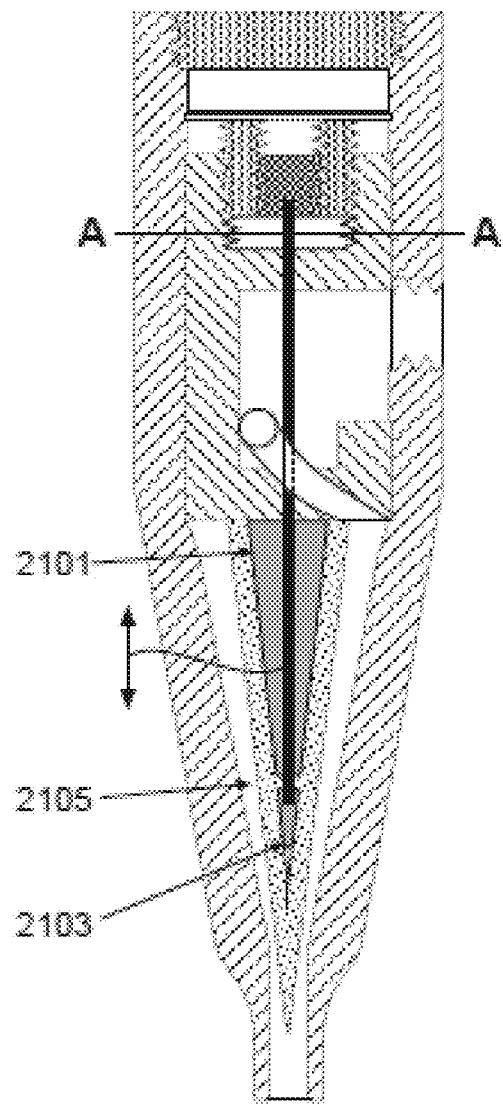
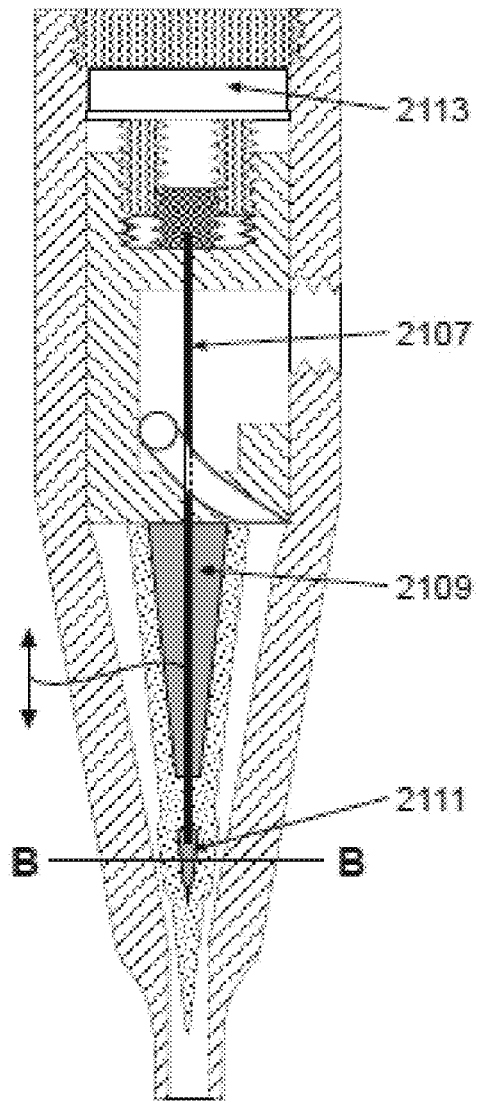
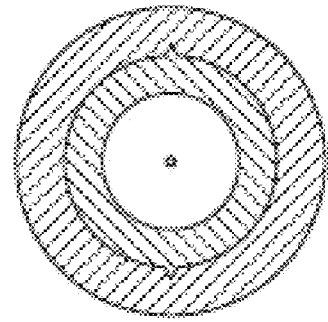
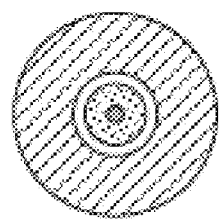
A-A
B-B

FIG. 22A
FIG. 22B
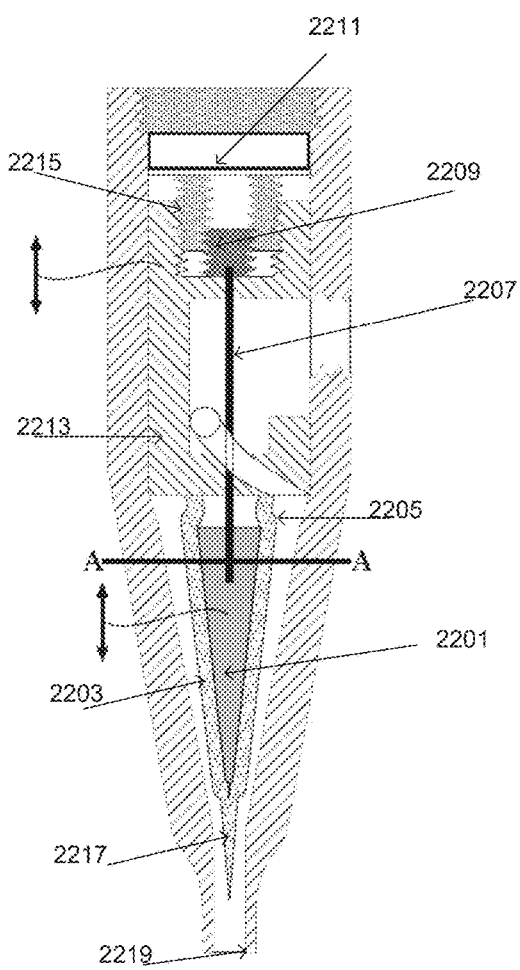
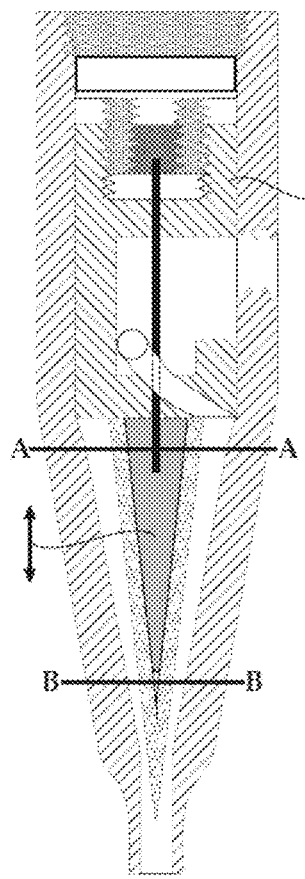
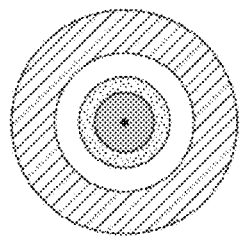
A-A
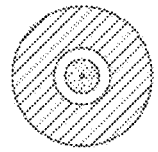
B-B

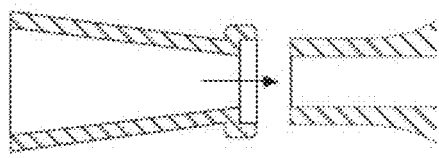
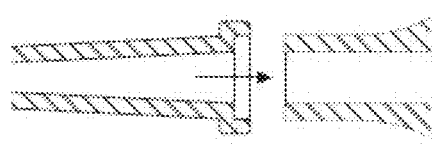
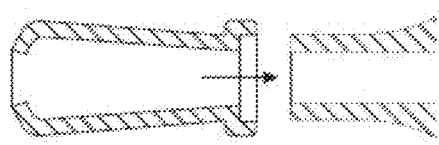
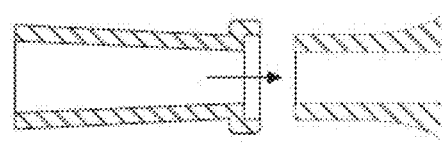
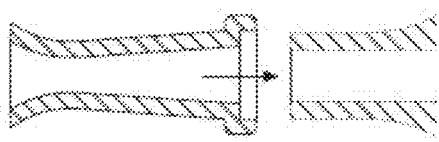
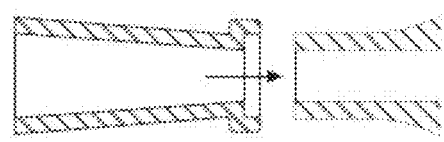
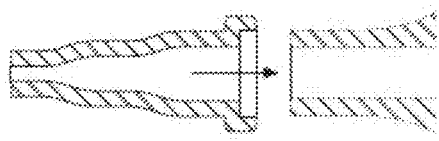
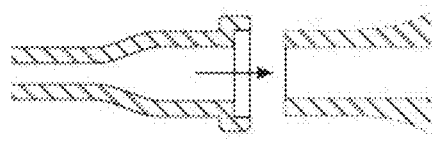
FIG. 38

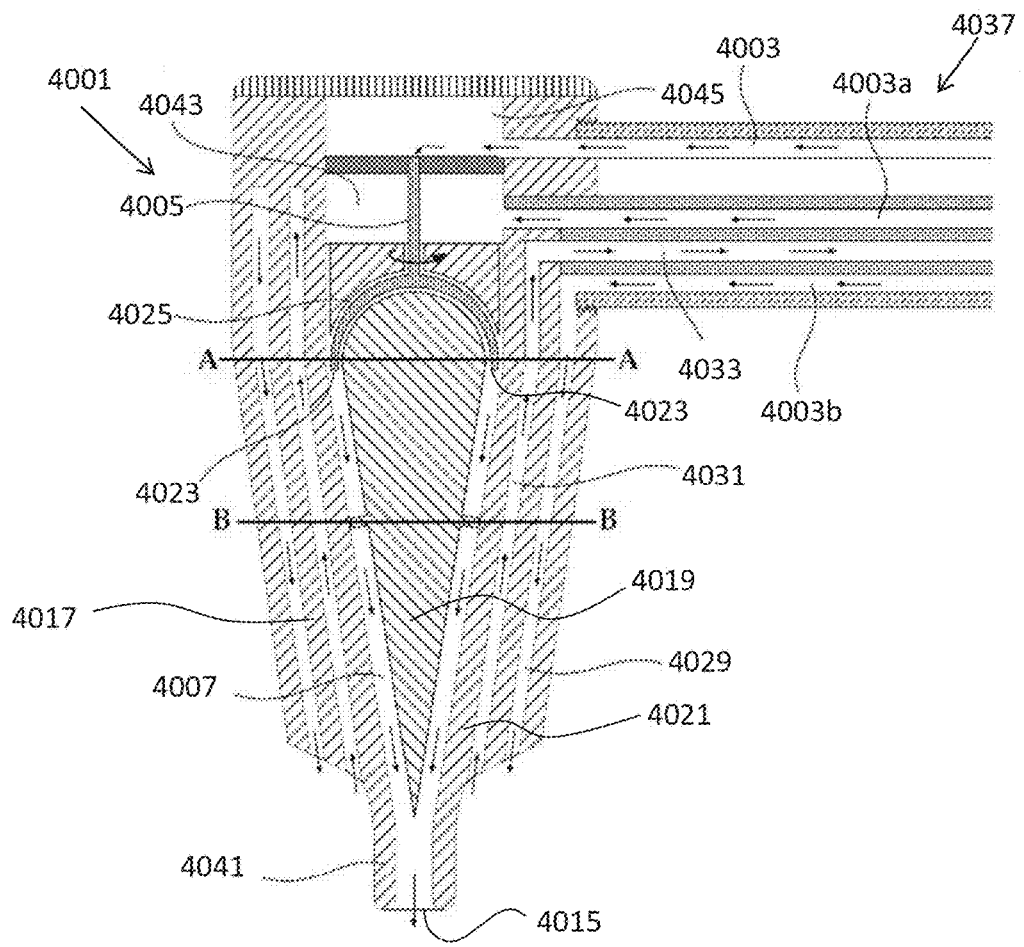
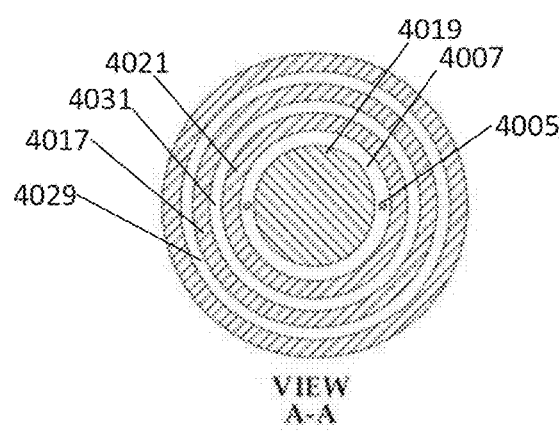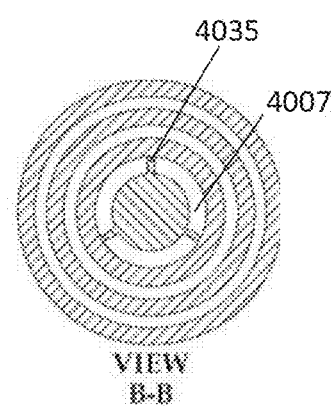
FIG. 40A
FIG. 40B
FIG. 40C

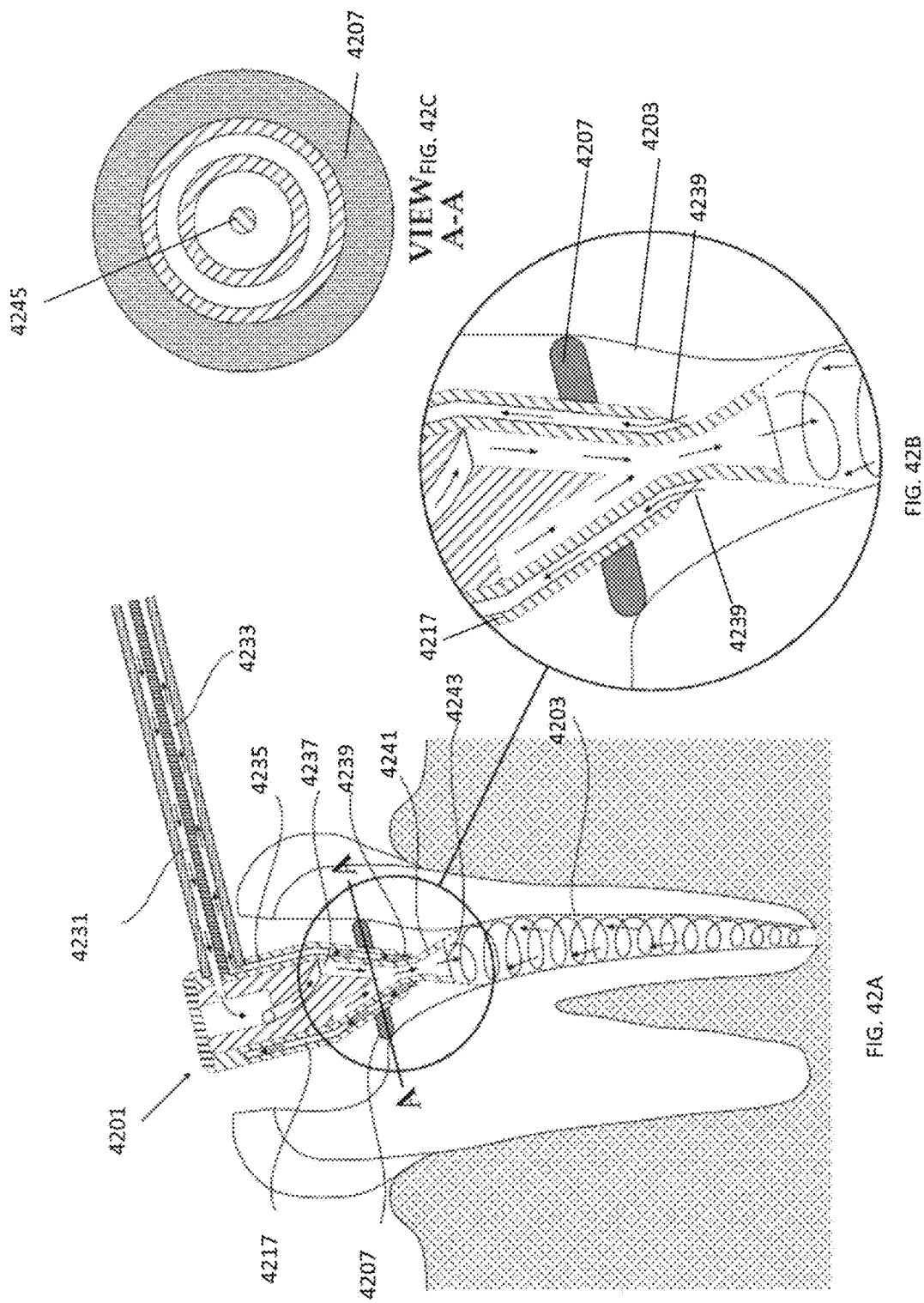

VIEW A-A

APPARATUS AND METHOD FOR ENDODONTIC TREATMENT

RELATED APPLICATIONS

This application is a continuation of U.S. patent application Ser. No. 14/522,250 filed on Oct. 23, 2014, which claims the benefit of priority of U.S. Provisional Patent Application Nos. 61/895,316 filed on Oct. 24, 2013 and 61/894,762 filed on Oct. 23, 2013.

U.S. patent application Ser. No. 14/522,250 is also Continuation-in-Part (CIP) of U.S. patent application Ser. No. 14/394,292 filed on Oct. 14, 2014, which is a National Phase of PCT Patent Application No. PCT/IL2013/050330 filed on Apr. 15, 2013, which claims the benefit of priority of Israel Patent Application No. 219169 filed on Apr. 15, 2012.

The contents of the above applications are all incorporated by reference as if fully set forth herein in their entirety.

FIELD AND BACKGROUND OF THE INVENTION

The present invention, in some embodiments thereof, relates to an apparatus and method for endodontic treatment and, more particularly, but not exclusively, to an apparatus and method for treating a root canal using one or more angled fluid jets.

In cases where a tooth is decayed, infected, or abscessed, a root canal procedure may be performed to eliminate infection and decontaminate the tooth. During the root canal procedure, substances such as nerve and pulp tissue are removed in order to prevent future infection.

Current methods for treating a root canal may involve the use of files, such as metal files, for removing tissue such as nerve tissue, magma, pulp tissue or blood vessels from the root canal. In some cases, a rotary file drill is used for shaping a root canal and optionally widening a portion of it to enable access. One of the risks of the use of files for endodontic treatment is the spreading of a smear layer, which may include organic and/or inorganic debris, on the root canal wall after instrumentation. Another potential risk of the use of files may include wounding of the root canal wall or apex.

Endodontic treatment devices have been disclosed by several publications.

U.S. Pat. No. 6,224,378 to Valdes et al. discloses "A method and apparatus for dental procedures using a dental hydrojet tool having a cannula extending therefrom. The cannula is connected to a source of high pressure liquid, and delivers a high velocity, high pressure jet. For root canal procedures, the cannula is directed through an opening formed in the crown of the tooth, and the hydrojet is directed at the pulp, nerve and vascular tissue within the interior chamber."

U.S. Pat. No. 4,021,921 to Detaille discloses "a device for treating the pulp canals and—chamber of a tooth, the crown of which presents a previously opened pulp-chamber in which said canals open, comprising an apparatus tightly adaptable to the crown of the tooth and providing in the pulp-chamber and the pulp-canals of said tooth for the circulation of a treating solution acting substantially upon the vasculo-nervous bundle or the necroticmagma of the tooth; the pressure of the treating solution being subjected within the pulp-chamber and the pulp-canals to periodical impulses combined to oscillations of substantially higher frequency."

SUMMARY OF THE INVENTION

The present invention, in some embodiments thereof, relates to an apparatus and method for endodontic treatment and, more particularly, but not exclusively, to an apparatus and method for treating a root canal using one or more angled fluid jets.

According to an aspect of some embodiments of the present invention there is provided an apparatus for endodontic treatment, comprising: a nozzle connected to a fluid source comprising: a tip small enough to be inserted into a pulp chamber of a tooth; an inner geometry which forms a flow parameters including non-axial flow direction of nozzle fluid flowing through said inner geometry such that discharge fluid discharged from said inner geometry increase rotation of root canal fluid within a root canal sufficiently to remove tissue from said root canal.

According to some embodiments of the invention, said flow parameters are sufficient to remove tissue from said root canal including an apex of said root canal. According to some embodiments of the invention, said flow parameters prevent tissue removal in an apical direction of a root canal apex. According to some embodiments of the invention, said at least one discharge fluid jet is at an angle to a vertical axis of said nozzle. According to some embodiments of the invention, said at least one discharge fluid jet enhances a helical flow pattern of said rotation of root canal fluid in said root canal. According to some embodiments of the invention, said inner geometry comprises a lumen and said nozzle fluid circulates along lumen walls, and an exit point of said nozzle fluid is located at a lumen wall at an exit aperture of said nozzle. According to some embodiments of the invention, said nozzle comprises an internal cone and an external cone defining a lumen between them for said nozzle fluid to flow through. According to some embodiments of the invention, said inner geometry comprises a lumen; wherein said nozzle comprises one or more part adapted to move to adjust a geometry of said lumen. According to some embodiments of the invention, an angle of said discharge fluid jet does not intersect a vertical axis of said nozzle. According to some embodiments of the invention, said nozzle fluid comprises liquid and at least one of gas and abrasive powder. According to some embodiments of the invention, a density of a particle of said abrasive powder is larger than a density of other particles comprising said nozzle fluid. According to some embodiments of the invention, said abrasive powder is salt that dissolves following abrasion of said root canal wall. According to some embodiments of the invention, said apparatus comprises one or more inlet connected to a suction source, through which inlet root canal fluid and debris is collected from said root canal. According to some embodiments of the invention, a diameter of said angled discharge fluid jet is approximately 10% of a diameter of an entrance of said root canal or smaller.

According to an aspect of some embodiments of the present invention there is provided an apparatus for endodontic treatment comprising: a nozzle connected to an input pipeline; wherein said nozzle comprises: a tip small enough to be inserted into a pulp chamber of a tooth; and a rotating element disposed inside a nozzle lumen; wherein said rotating element is operable to impart motion to nozzle fluid passing through said lumen such that, after said nozzle fluid is discharged from said lumen, the root canal fluid flows helically within a root canal.

According to some embodiments of the invention, said rotating element comprises an inlet connected to said input pipeline, through which inlet flows at least a portion of nozzle fluid supplied to said nozzle. According to some embodiments of the invention, said rotating element comprises a plurality of blades.

According to an aspect of some embodiments of the present invention there is provided an apparatus for endodontic treatment comprising: a nozzle connected to an input pipeline; wherein said nozzle comprises: a tip small enough to be inserted into a pulp chamber of a tooth; and a inner cone disposed inside a nozzle lumen; wherein said inner cone is adapted to move with respect to said nozzle lumen thereby changing parameters of a nozzle flow through said nozzle lumen.

According to some embodiments of the invention, said nozzle comprises an outer cone and nozzle fluid flow is through a lumen defined between said outer cone and said inner cone.

According to an aspect of some embodiments of the present invention there is provided an apparatus for endodontic treatment comprising: a nozzle connected to an input pipeline comprising: a tip small enough to be inserted into a pulp chamber of a tooth; a lumen; wherein said input pipeline extends into said lumen such that flow of pipeline fluid from said pipeline impinges on walls of said lumen such that said nozzle fluid within said lumen has a helical pattern along walls of said lumen.

According to an aspect of some embodiments of the present invention there is provided an apparatus for endodontic treatment comprising: one or more chamber containing material comprising: one of more of: pressurized gas, fluid and abrasive material; a nozzle comprising a tip small enough to be inserted into a pulp chamber of a tooth; said nozzle shaped to create a beam comprising at least one discharge fluid jet in an angle to a vertical axis of said nozzle, so that said jet flows along a wall of a root canal to remove tissue; and a pipeline connecting said chamber lumen and a nozzle lumen.

According to some embodiments of the invention, the apparatus comprises more than one chamber, wherein each said chamber is connected to said nozzle lumen by a pipe, wherein said beam is at least partially created by said material; wherein material flowing from each chamber mixes within said nozzle lumen. According to some embodiments of the invention, the apparatus comprises a powder cartridge connected between said chamber and said nozzle lumen; wherein said powder cartridge comprises internal cylinders formed with holes of various sizes for filtration of components within said cartridge.

According to an aspect of some embodiments of the present invention there is provided a system comprising: a nozzle comprising a tip small enough to be inserted into a pulp chamber of a tooth; said nozzle shaped to create a beam comprising at least one discharge fluid jet in an angle to a vertical axis of said nozzle, so that said jet flows along a wall of a root canal to remove tissue; and a powder cartridge connected to a nozzle lumen; a pipeline connecting one of a fluid tank and a compressor to said powder cartridge.

According to some embodiments of the invention, said powder cartridge comprises internal cylinders formed with holes of various sizes for filtration of components within said cartridge.

According to an aspect of some embodiments of the present invention there is provided a method for endodontic treatment comprising: discharging at least one fluid jet in a manner which increases speed of rotation of root canal fluid in a root canal, said rotating root canal fluid within said canal removing material from said root canal.

According to some embodiments of the invention, said discharging comprises discharging at least one angled discharge fluid jet, from a nozzle, at an angle where said angle of said discharge fluid jet does not intersect a vertical axis of said nozzle. According to some embodiments of the invention, said angled discharge fluid jet is created by circulating said fluid helically within a nozzle of an apparatus. According to some embodiments of the invention, said removing comprises separating soft tissue from said wall of a root canal. According to some embodiments of the invention, said soft tissue comprises at least one of nerve tissue, pulp tissue, and or blood vessels. According to some embodiments of the invention, said rotating root canal fluid within said canal flows helically along a wall of said root canal. According to some embodiments of the invention, said root canal comprises at least one narrowing portion, and said rotating root canal fluid within said canal flows through said narrowing portion along a wall of said root canal. According to some embodiments of the invention, said root canal comprises at least one wide portion, and said rotating root canal fluid within said canal flows through said wide portion along a wall of said root canal. According to some embodiments of the invention, said root canal comprises at least one of a curvature and branching, and said rotating root canal fluid within said canal flows through said at least one curvature and branching. According to some embodiments of the invention, the method comprises aligning said nozzle with respect to an entrance of said root canal so that a vertical axis of said nozzle unites with a vertical axis of said root canal; wherein said rotating root canal fluid within said canal does not directly hit a root canal apex. According to some embodiments of the invention, said root canal fluid in said canal has a level reaching to a tip of said nozzle. According to some embodiments of the invention, the method comprises eroding a layer of dentin tissue from at least a portion of a root canal wall. According to some embodiments of the invention, eroding is obtained by abrasive particles of said root canal fluid applying radially outward force onto said root canal wall. According to some embodiments of the invention, said abrasive particles rotate about an axis of said angled jet. According to some embodiments of the invention, the method does not leave a smear layer on said root canal wall. According to some embodiments of the invention, the method comprises suctioning root canal fluid and debris from said root canal. According to some embodiments of the invention, suctioning comprises suctioning said root canal fluid and debris in pulses. According to some embodiments of the invention, discharging comprises discharging said at least one discharge fluid jet in pulses. According to some embodiments of the invention, the method comprises suctioning root canal fluid and debris from said root canal in pulses. According to some embodiments of the invention, pulses are controlled through a control panel electrically connected to said apparatus. According to some embodiments of the invention, discharging includes clearing a root canal to prepare for sealing. According to some embodiments of the invention, said rotating root canal fluid within said canal removes material from tubules extending from said root canal. According to some embodiments of the invention, said root canal fluid in said root canal fills at least 20% of a volume of said root canal. According to some embodiments of the invention, said root canal fluid in said root canal comprises at least 10% liquid.

According to an aspect of some embodiments of the present invention there is provided a method for endodontic treatment comprising: placing a nozzle at an entrance to a root canal; discharging at least one fluid jet, from said nozzle, at an angle which causes said fluid jet to flow along a wall of a root canal; and suctioning root canal fluid and debris from said root canal; wherein said discharging and said suctioning are controlled to maintain one or more of root canal fluid flow along said wall, root canal fluid flow at a root canal apex.

According to some embodiments of the invention, discharging and said suctioning are alternating.

According to an aspect of some embodiments of the present invention there is provided a method for endodontic treatment comprising: placing a nozzle at an entrance to a root canal; inserting fluid into a lumen defined between nozzle inner walls and an element adapted to move within said nozzle walls; discharging at least one discharge fluid jet from said lumen at an angle which causes said discharge fluid jet to flow along a wall of said root canal; and changing a geometry of said lumen, by moving said element, to change a velocity of said fluid jet.

According to some embodiments of the invention, said element is an internal cone and said lumen is defined between said internal cone and said nozzle inner walls and changing comprises moving said internal cone with respect to said nozzle inner walls.

According to some embodiments of the invention, moving comprises retracing and advancing said internal cone in the proximal and distal directions within said nozzle inner walls. According to some embodiments of the invention, comprises moving said internal cone in a lateral direction within said nozzle inner walls. According to some embodiments of the invention, moving comprises changing an angle of a vertical axis of said inner cone with respect to a vertical axis of said nozzle inner walls.

According to an aspect of some embodiments of the present invention there is provided an apparatus for endodontic treatment comprising: a nozzle connected to an input pipeline; wherein said nozzle comprises: a tip small enough to be inserted into a pulp chamber of a tooth; a lumen through which fluid flows through the nozzle; and a element located inside said lumen which, when moved, changes a geometry of said lumen thereby changing flow parameters through said nozzle.

According to some embodiments of the invention, said element is a rotating element; wherein said rotating element is operable to impart motion to fluid passing through said lumen. According to some embodiments of the invention, said rotating element comprises an inlet connected to said input pipeline, through which inlet flows at least a portion of fluid supplied to said nozzle. According to some embodiments of the invention, said element is an inner cone; wherein a position of said internal cone is adjustable within said lumen in proximal and distal directions.

According to an aspect of some embodiments of the present invention there is provided an apparatus for mixing particles with fluid comprising: an outer element connected to an fluid source, said outer element comprising a plurality of inlets through which fluid from said fluid source pass; an inner element disposed inside a lumen of said outer cylinder comprising a plurality of inlets through which fluid from said outer element pass into a lumen of said inner element; an outlet connected to said lumen of said inner element; wherein flow of fluid through the apparatus from said fluid source to said outlet collects particles within one or more of said inner element and said outer element.

According to some embodiments of the invention, said outer element inlets and said inner element inlets are different sizes for filtration of one or more of fluid and particles.

According to some embodiments of the invention, said powder cartridge comprises internal cylinders formed with holes of various sizes for filtration of components within said cartridge. According to some embodiments of the invention, the method comprises circulating fluid along nozzle lumen walls; wherein discharging comprises discharging said jet from said nozzle from an edge of an exit aperture of said nozzle. According to some embodiments of the invention, discharging and suctioning are balanced to maintain fluid within said root canal. According to some embodiments of the invention, discharging and suctioning are balanced to maintain flow of fluid along root canal walls. According to some embodiments of the invention, pulses are controlled through a control panel electrically connected to said nozzle. According to some embodiments of the invention, discharging and said suctioning includes clearing a root canal to prepare for sealing. According to some embodiments of the invention, removing comprises removing material from tubules extending into said tooth from said root canal.

According to an aspect of some embodiments of the present invention there is provided a method for endodontic treatment comprising: placing a nozzle at an entrance to a root canal; inserting fluid into a lumen of said nozzle; discharging at least one fluid jet from said lumen at an angle which causes said fluid jet to flow along a wall of said root canal; and changing one or more of a shape or size of said lumen to change a velocity of said fluid jet.

According to some embodiments of the invention, changing comprises moving an internal cone inside said lumen. According to some embodiments of the invention, said moving comprises retracing and advancing said internal cone in the proximal and distal directions within said lumen. According to some embodiments of the invention, changing comprises rotating a rotating element inside said lumen. According to some embodiments of the invention, inserting comprises inserting fluid into said lumen through said rotating element.

According to an aspect of some embodiments of the present invention there is provided an apparatus and method for endodontic treatment.

According to an aspect of some embodiments of the present invention there is provided an apparatus for endodontic treatment comprising a nozzle, the nozzle comprising a tip small enough to be inserted through a pulp chamber of a tooth, the nozzle is shaped to create a beam comprising at least one fluid jet in an angle to a vertical axis of the nozzle, so that it flows along a wall of a root canal to remove soft tissue in a helical flow pattern, and the nozzle is connected to an input pipeline. In some embodiments, the nozzle is positionable above an entrance of the root canal such that the vertical axis of the nozzle unites with a vertical axis the root canal. According to some embodiments, the nozzle comprises an internal cone and an external cone defining a lumen between them for the fluid to flow through. According to some embodiments, the nozzle comprises a tube extending between a lumen of the internal cone and the lumen between the internal cone and the external cone. According to some embodiments, the fluid circulates in a helical flow through the lumen for exiting the nozzle in an angle, wherein an exit point of the fluid is located along walls of the nozzle at a location of an exit aperture. In some embodiments, the lumen between the cones is modified by movement of the internal cone with respect to the external cone. In some embodiments, movement comprises retraction and advancement of the internal cone in the proximal and distal directions within the external cone. In some embodiments, movement comprises positioning the internal cone at a different angle with respect the external cone. In some embodiments, a velocity of the flow ranges between 200-300 m/sec. In some embodiments, the nozzle is adapted for discharging at least 1000 angled fluid jets simultaneously. According to some embodiments, the angled fluid jet does not intersect a vertical axis of the nozzle. According to some embodiments, the nozzle comprises channels for creating at least one angled jet. According to some embodiments, there is provided a system comprising: the apparatus, a liquid tank, and an air compressor, wherein the input pipeline of the apparatus passes through a handle to connect the liquid tank and/or air compressor to the nozzle. According to some embodiments, the system is electrically controlled using a control panel configured for operating an electric circuit. In some embodiments, the handle comprises a fusion tank for mixing between liquid, gas, and/or abrasive powder. In some embodiments, the handle comprises a disposable powder cartridge. In some embodiments, the powder cartridge comprises internal cylinders formed with holes of various sizes for filtration of components. According to some embodiments, the fluid comprises gas and/or liquid and/or abrasive powder. According to some embodiments, the gas is air, and the fluid comprises between 50-95% air, and between 5-50% liquid. In some embodiments, a density of a particle of the abrasive powder is larger than a density of other particles comprising the fluid. In some embodiments, the abrasive powder is salt that dissolves following abrasion of the root canal. According to some embodiments, the nozzle is shaped so that the fluid exits the nozzle as an aerosol. According to some embodiments, the apparatus is connected to an air compressor with a pressure ranging between 5-200 PSI. According to some embodiments, the apparatus is connected to a fluid tank which provides fluid at a volumetric flow rate ranging between 0.1-50 ml/sec. According to some embodiments, the angled jet has tangential and vertical velocity components in respect to the root canal wall. According to some embodiments, the apparatus comprises a suction cone for collecting returning fluid and debris, and the suction cone has a tip sized to fit within a pulp chamber of a tooth. In some embodiments, the apparatus is connected to a device suitable for removing the fluid and debris externally to the tooth. In some embodiments, the apparatus is suitable for treating a root canal of a tooth in a human mouth. In some embodiments, a diameter of the angled jet is 10% of a diameter of an entrance of the root canal, or smaller.

According to some embodiments there is provided a method for endodontic treatment comprising discharging at least one fluid jet in a manner which enhances rotation of fluid in a root canal, the rotation sufficient to remove material from a wall of the canal. According to an aspect of some embodiments of the present invention there is provided a method for endodontic treatment comprising discharging at least one fluid jet at an angle which causes it to flow along a wall of a root canal so that the flow removes material from the root canal wall. According to some embodiments, removing comprises separating soft tissue from the root canal wall. According to some embodiments, the flow comprises a helical flow along the root canal wall. According to some embodiments, the root canal comprises at least one narrowing portion, and the flow comprises flowing through the narrowing portion along the wall of the root canal.

In some embodiments, the root canal comprises at least one wide portion, and the flow passes through the wide portion along the wall of the root canal. According to some embodiments, the root canal comprises a curvature and/or a branching, and the flow comprises flowing through the curvature and/or the branching. According to some embodiments, the method comprises positioning a nozzle above an entrance to the root canal so that at least one angle fluid jet hits a wall of the root canal. In some embodiments, positioning comprises aligning the nozzle with respect to an entrance of the root canal so that a vertical axis of the nozzle unites with a vertical axis of the root canal.

In some embodiments, the method comprises discharging at least 20000 jets. In some embodiments, the fluid jet merges with fluid contained within the root canal for intensifying a circulating motion of the fluid. In some embodiments, the fluid in the canal has a level reaching to a tip of the nozzle. According to some embodiments, fluid flows along the wall of at least a portion of the root canal so that the fluid returns upwards along at least a portion of a central lumen of the root canal. According to some embodiments, the method comprises eroding a layer of dentin tissue from at least a portion of the root canal wall. In some embodiments, eroding is obtained by abrasive particles of the fluid applying radially outward force onto the root canal. According to some embodiments, the layer has thickness ranging between 100-200 µm. According to some embodiments, the angled jet is created by circulating the fluid in a helical flow within a nozzle of an apparatus. According to some embodiments, the soft tissue comprises nerve tissue, and/or pulp tissue and/or blood vessels. According to some embodiments, the method does not leave a smear layer on the root canal wall. According to some embodiments, directing comprises directing the fluid jets in pulses. In some embodiments, a duration of a pulse ranges between 1-25 seconds, and debris and excess fluid are removed in intervals between pulses. In some embodiments, the pulses are controlled through a control panel electrically connected to the apparatus. According to some embodiments, directing includes clearing a root canal to prepare for sealing. In some embodiments, the components of the fluid rotate about an axis of the angled jet. In some embodiments, the flow removes material from tubules extending from the root canal. In some embodiments, within a root canal dentine wall, a layer of tubules is removed, exposing further tubules which are clean and non-contaminated.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A-9D are illustrations of a conical nozzle comprising a pipe extending between a handle and an exit aperture of the nozzle, according some embodiments of the invention;

FIGS. 13A-13D are illustrations of a nozzle comprising a cone and a pin shaped element occupying at least a portion of the internal lumen of the cone, according to some embodiments of the invention;

FIGS. 16A-16B is a table of experimental results of an experiment for testing the feasibility of an apparatus for endodontic treatment, according to some embodiments of the invention;

FIGS. 18A-18B show a conical nozzle in which a lumen between the internal cone and external cone can be modified, according to some embodiments of the invention;

FIGS. 19A-19B illustrate an additional configuration of a nozzle comprising an internal cone movable with respect to an external cone, according to some embodiments of the invention;

FIGS. 20A-20B illustrate a nozzle comprising a suction cone and an internal cone that are movable with respect to an external cone, according to some embodiments of the invention;

FIGS. 21A-21C illustrate an internal cone comprising an expandable portion, according to some embodiments of the invention;

FIGS. 22A-22B illustrate an internal cone comprising an expandable portion configured to occupy a relatively large volume of the lumen between the cones, according to some embodiments of the invention;

FIG. 38 shows various configurations of needle-like tubes which can be assembled onto a nozzle, according to some embodiments of the invention;

FIG. 40A is a simplified schematic cross sectional view of a nozzle including a rotating inlet element, according to some embodiments of the invention;

FIGS. 40B-40C are simplified schematic cross sectional views of a nozzle including a rotating inlet element, according to some embodiments of the invention;

FIG. 42A is a simplified schematic cross sectional view of a nozzle treating a root canal, controlling apical parameters, according to some embodiments of the invention;

FIG. 42B is a simplified schematic cross sectional view of a nozzle treating a root canal, controlling apical parameters, according to some embodiments of the invention;

FIG. 42C is a simplified schematic cross sectional view of a nozzle surrounded by a sealing element, according to some embodiments of the invention;

DESCRIPTION OF SPECIFIC EMBODIMENTS OF THE INVENTION

Figure 1:
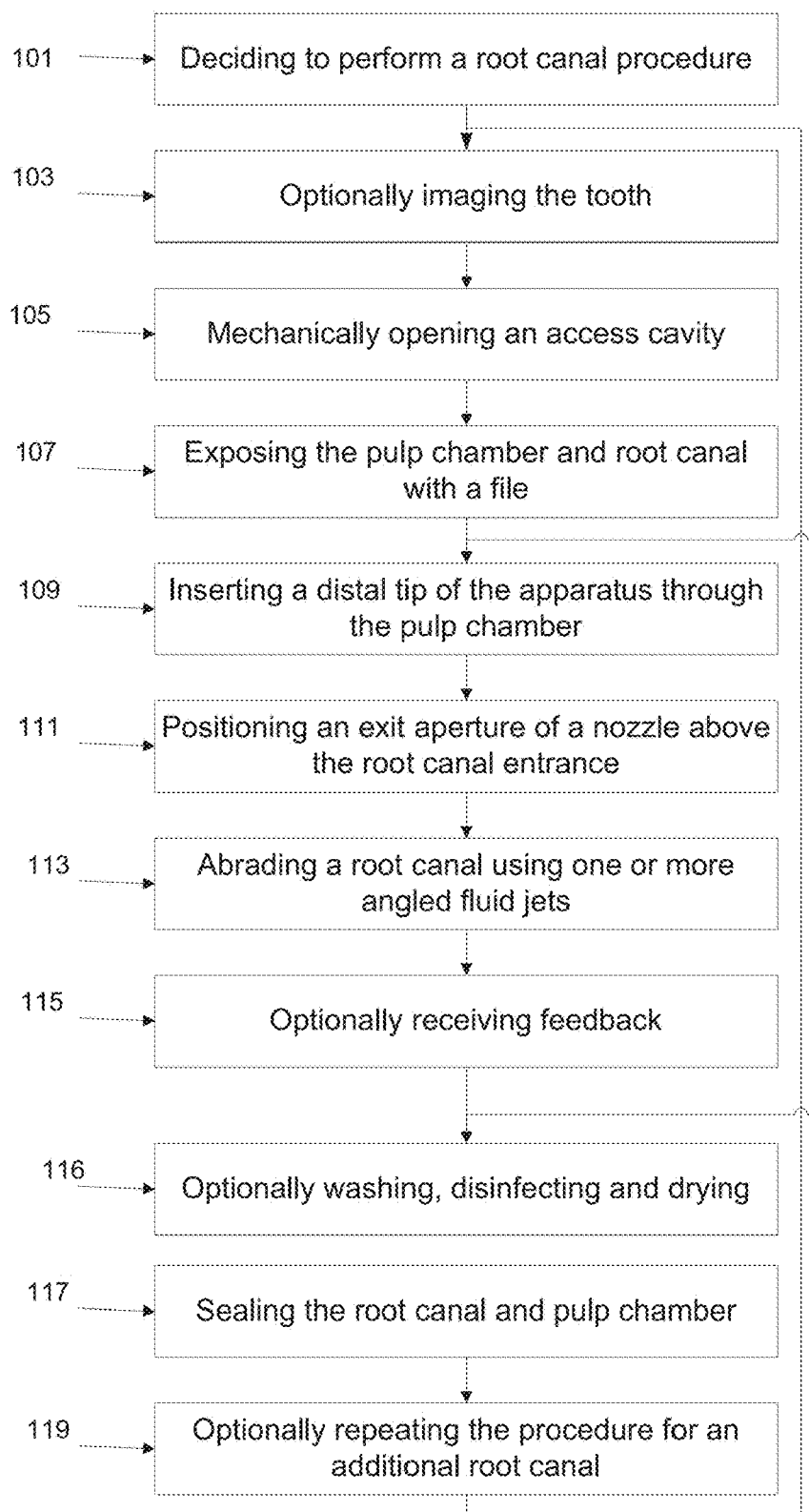
FIG. 1 is a flowchart of an exemplary endodontic treatment procedure, according to some embodiments of the invention.

The present invention, in some embodiments thereof, relates to an apparatus and method for endodontic treatment and, more particularly, but not exclusively, to an apparatus and method for treating a root canal using one or more angled fluid jets.

In some embodiments, the apparatus is used for cleaning, abrading, and/or decontaminating a root canal of a tooth before sealing the tooth.

Overview

A general aspect of some embodiments of the invention relates to cleaning and/or abrading a root canal (e.g. in a human tooth within a human mouth) where a flow of fluid, for example a fluid jet (e.g. an angled fluid jet) or a plurality of jets (e.g. a plurality of angled fluid jets) and/or a flow beam and/or a flow cone is discharged hitting fluid within a root canal. In some embodiments, the flow is discharged from a nozzle inserted into the tooth (e.g. into a pulp chamber and/or into a root canal). In some embodiments, the flow from the nozzle (e.g. one or more jet, beam) comprises significant non-axial (e.g. at an angle to a vertical axis of the nozzle) velocity components, for example, more than 10%, more than 30%, more than 50%, more than 90% non-axial components, or lower or higher or intermediate percentages. In some embodiments, the flow from the nozzle includes a small proportion of axial velocity components. In some embodiments, the flow includes less than 60%, or less than 40%, or less than 20%, or less than 10%, or lower or higher or intermediate percentages axial velocity components.

In some embodiments, for example, when the root canal is at least partially filled with fluid, the flow, (e.g. jet/s and/or a beam) hits fluid within the root canal causing and/or intensifying spinning motion of the fluid within the canal. In some embodiments, the jet/s and/or beam increase a speed of rotation of the fluid within the canal and/or a proportion of fluid which is rotating within the canal.

In some embodiments, the flow from the nozzle intensifies spinning of fluid adjacent to the root canal walls (e.g. fluid within 1 mm or 0.5 mm or 0.25 mm or 0.1 mm or 0.01 mm from the root canal walls), for at least a coronal portion of the root canal (e.g. the upper 10%, or 30%, or 50%, or 70%, or 90%, or the entire root canal, or intermediate, higher or lower percentages of the root canal).

In some embodiments, the flow from the nozzle (e.g. one or more jet, beam) does not travel through air after discharge from the nozzle, but may directly hit fluid within the root canal or is contiguous with such fluid (e.g. a nozzle exit aperture is level with or under the surface of fluid within the root canal). In some embodiments, when discharge from the nozzle is contiguous with fluid within a root canal, movement (e.g. rotation) of fluid within the nozzle (e.g. due to viscosity and/or surface tension) causes fluid within the root canal to move, for example, in the same direction and/or with approximately (e.g. within 20% of) the same velocity.

Alternatively, in some embodiments, the flow discharged from the nozzle hits fluid within the root canal indirectly, for example, hitting a portion of the tooth (e.g. root canal wall) before hitting and/or merging with the fluid in the root canal. For example, in some embodiments, the flow discharged from the nozzle passes through an air gap before hitting the fluid in the root canal. In some embodiments, an air gap between a nozzle aperture and fluid in the root canal is measured by a straight line between an exit point of fluid from the exit aperture (or a central point of the aperture) and a point on the fluid level in the canal where discharge hits the fluid in the canal (or a central point on the fluid level in the canal. In some embodiments, the air gap is 0.1 mm, or 0.5 mm, or 1 mm, or 3 mm, or 5 mm or lower, or higher, or intermediate distances.

A general aspect of some embodiments of the invention relates to a nozzle for insertion into a tooth (e.g. a tooth pulp chamber and/or a tooth root canal) where the behavior of material discharged from the nozzle is controlled and/or adjusted by movement of one or more part of the nozzle.

In some embodiments, movement is movement which changes the size and/or shape of a nozzle lumen. In some embodiments, an inner cone moves within a nozzle lumen e.g. with respect to an external cone. In some embodiments, an inner cone moves distally-proximally within the lumen. In some embodiments, an inner cone moves changing an angle of vertical axis of the inner cone with respect to a vertical axis of the nozzle lumen and/or external cone. In some embodiments, reduction of a lumen size increases flow rate and/or pressure of fluid passing through the nozzle.

In some embodiments, one or more part of the nozzle rotates. In some embodiments, the nozzle includes an internal rotating element located within a lumen of the nozzle which stirs and/or moves and/or agitates fluid (e.g. liquid and/or gas and/or abrasive powder and/or nonabrasive powder) passing through the lumen.

In some embodiments of the invention, momentum, potentially including angular momentum, is transferred from the motion of the rotating element to the fluid passing through the nozzle lumen and/or fluid passing through the rotating element before the fluid is ejected from the nozzle: In some embodiments, movement of the rotating element causes fluid with the nozzle lumen to rotate and/or have helical movement. In some embodiments, movement of the rotating element causes fluid in the lumen to flow along the lumen walls, for example, due to centrifugal force applied to the fluid by the rotating element. Potentially, fluid exiting the nozzle does so at an angle which is broadened by the tangential component of its momentum at the exit aperture of the nozzle.

In some embodiments, for example, due to fluid surface tension and/or cohesion between fluid parts, fluid with helical and/or rotational movement within the lumen continues to move with helical and/or rotational movement once discharged from the nozzle (e.g., in an airspace and/or inside the root canal).

In some embodiments, movement of the material is such that, after the fluid is discharged from the lumen, the fluid flows helically within the root canal e.g. due to the angle the discharged jet/beam to the root canal wall, e.g. due to maintaining of helical flow initiated in the nozzle lumen.

In some embodiments, a rotating element stirs fluid in a wide diameter/cross sectional area portion of a nozzle lumen (e.g. the widest 10%, or 30%, or 50%, or 70%, of the nozzle lumen length, or lower, higher or intermediate percentages) and, as the fluid flows distally through the lumen to a nozzle exit aperture, the lumen diameter/cross sectional area reduces (e.g. the lumen is a cone shaped lumen), the fluid continues to rotate.

In some embodiments, the rotating element includes one or more inlet through which fluid (a portion of or all of the fluid passing through the nozzle) flows into the nozzle lumen.

In some embodiments, the rotating element includes blades which are shaped and/or angled such that rotation of the blades pushes fluid towards the nozzle exit aperture.

In some embodiments, a shape of discharged rotating fluid changes upon entry into a root canal, in some embodiments following the shape of the root canal. For example, in some embodiments, discharged rotating fluid flows along the root canal walls (e.g. due to centripetal force of the rotating fluid and/or due to surface tension and/or boundary effects). In some embodiments, rotating of fluid along the root canal walls widens the walls of the root canal optionally increasing a size of the root canal in all three dimensions.

An aspect of some embodiments relates to cleaning and/or abrading a root canal using concurrent control of discharge of fluid into a root canal and removal (e.g. suction by suction) of material from the root canal. In some embodiments flow of fluid and/or pressure is controlled within the root canal. In some embodiments, the root canal is sealed such that material can only enter or exit the root canal through a nozzle (e.g. the root canal is sealed at a coronal opening of the root canal). A potential benefit of sealing is prevention of introduction into the root canal of atmospheric contaminants such as dirt, bacteria. In some embodiments, control of discharge and suction controls a depth (apically) of penetration of fluid and/or a depth (apically) of abrasion and/or pressure within the canal and/or at the canal apex and/or a canal region proximal to the apex and/or a quantity of fluid within the root canal. A potential benefit being reduction of risk of rupture and/or break-through of the root canal at the apex.

In some embodiments, discharge of fluid into the root canal and/or suction of material from the root canal are in pulses. A discharge pulse is a discrete action where discharge is for a time period where before and after the pulse there is no discharge. Similarly, a suction pulse is a discrete action where suction is for a time period where before and after the pulse there is no suction.

In some embodiments, discharge and suction are controlled such that the root canal remains at least partially filled with fluid.

In some embodiments, discharge and suction are in alternating pulses, where a discharge pulse is followed by a suction pulse. In some embodiments, suction and discharge pulses overlap, were there is a time period where both suction and discharge occur. In some embodiments, between discharge and suction pulses there is a pause where there is neither suction nor discharge. In some embodiments, discharge and suction are in simultaneous pulses.

In some embodiments, parameters of discharged fluid from the nozzle (e.g. speed, volume, angular velocity, location of discharge) and/or parameters of suction (e.g. pressure or suction, quantity of material removed, position within the root canal where suction is supplied) are controlled to achieve desired flow characteristics and/or parameters within the root canal, for example, quantity of material within the canal, speed of rotation of fluid within the root canal.

An aspect of some embodiments relates to mixing fluid (e.g. air and/or liquid) with abrasive powder before discharging the fluid including powder from a nozzle. In some embodiments, fluid is passed through (e.g. under pressure) a powder cartridge including powder (e.g. abrasive powder). In an exemplary embodiment, the powder cartridge includes internal cylinders each cylinder including holes for passage of the fluid (e.g. air) through the power cartridge, for example, to mix powder within cylinder/s with the fluid and/or for ejection of components (e.g. abrasive powder) from one cylinder to another cylinder and/or out the powder cartridge. Optionally, in some embodiments, powder cartridge components are non-cylindrical. In some embodiments, the powder cartridge includes internal cylinders each cylinder including holes for filtration of components (e.g. abrasive powder).

An aspect of some embodiments relates to cleaning and/or abrading a root canal using a system including a nozzle where fluid is supplied to the nozzle (e.g. through a pipe) by one or more chamber, for example, within an (optionally disposable) pressurized gas container (e.g. a canister) containing pressurized gas and one or more of fluid and abrasive material. In some embodiments, the nozzle is connected to more than one chamber containing material (e.g. gas and/or liquid and/or abrasive powder). In an exemplary embodiment, the system includes a first chamber containing pressurized gas and fluid and a second chamber containing abrasive powder.

In an additional exemplary embodiment, a system supplies, e.g. using chamber/s containing pressurized gas, more than one flow of material to the nozzle, where the flows meet and/or mix within the nozzle. For example, in some embodiments a first flow includes abrasive powder and gas and a second flow includes liquid. In some embodiments, abrasive powder is mixed with gas and liquid in the container and/or at a container exit.

In some embodiments, a supply apparatus is integrally packaged

In some embodiments, a geometry of the nozzle and/or other parameters such as the fluid composition, the fluid pressure, or others may be selected to achieve the desired conditions (e.g. pressure of fluid flow, speed of fluid rotation and speed/pressure of flow of fluid from the nozzle tip).

In some embodiments fluid flow within the nozzle (and optionally a rotating element) is not exposed to the atmosphere, for example, preventing introduction of contaminants into the tooth and/or preventing degradation of the fluid and/or component/s of the fluid. Degradation being e.g. by atmospheric contaminants such as dirt, bacteria, e.g. by exposure of reactive fluid component/s to atmospheric oxygen.

Optionally, in some embodiments, flow input parameters (e.g. flow rate, flow composition) are varied with rotation to provide desired jet/beam characteristic and/or parameter.

Optionally, a nozzle includes a narrow, needle like tip, for example, providing a narrow beam of jets for cleaning of a narrow root canal and/or providing a focused, high pressure beam and/or facilitating insertion of the tip into a narrow root canal.

Optionally, a nozzle tip (e.g. a needle like tip) includes an angled outlet aperture, or a rounded edged outlet aperture, or any other shape outlet aperture. In some embodiments, a shape of a nozzle outlet aperture changes beam flow characteristics and/or parameters, for example, flow direction, and/or improving acceleration of fluid circulation and/or spinning rate in the root canal. In some embodiments, a shape of nozzle tip is selected to affect flow direction of fluid discharged through the tip, for example, by flow sticking to a surface of the nozzle tip edge, for example a notch, a projection, an angled section.

Optionally, at least a portion of an inner surface of lumen walls is textured (e.g. grooved), potentially assisting and/or enabling helical flow of the fluid e.g. as flow is preferentially in the direction of helical grooves which spiral downward towards a nozzle outlet.

In some embodiments, nozzle structures (e.g. lumens, suction cones, nozzle tip) are cone-shaped. Alternatively, in some embodiments, one or more nozzle structure has a portion with parallel walls, and/or rounded walls (e.g. a straight walled portion terminating in a semi-hemispherical portion). In some embodiments, one or more nozzle structure has a different shape, for example, a nozzle with an outer cone shape and a cylindrical lumen. In some embodiments, an angle of the cone-shaped walls of a nozzle structure to a nozzle structure long axis is 5-75 degrees, or 20-60 degrees, or lower or higher or intermediate angles. In some embodiments, a nozzle has a flattened shape at a nozzle tip. In some embodiments, a cross sectional area of a nozzle tip enlarges distally (e.g. as illustrated in FIGS. 42A-B).

An aspect of some embodiments of the invention relates to cleaning and/or abrading a root canal using one or more angled fluid jets. In some embodiments, once the angled jet hits the root canal wall, the force exerted by the wall channels the jet to travel down the root along the wall. In some embodiments, the angle includes a component outside the plane of the axis of root canal, so that the flow spins in a helical flow along some or all the root canal. In some embodiments, the fluid advances along the root canal wall to remove organic substance and/or abrade the canal wall. In some embodiments, the angled fluid jet does not cross a vertical axis of the root canal and/or a vertical axis of the nozzle. In some embodiments, as described below, an angled jet or a plurality of angled jets are not used, but instead a flow beam than comprises significant non-axial velocity components is used. In some embodiments, the beam does not travel through air when exiting the nozzle, but may directly hit fluid within a root canal or be contiguous with such fluid.

In some embodiments, the jet does not flow straight downwards towards the apex of the root canal. In some embodiments, one or more jet meets the root canal wall at an angle to a plane of the root canal wall where the jet meets the root canal, of 20-45 degrees, or 30-45 degrees, or lower, or higher, or intermediate ranges and/or angles to the root canal wall.

In some embodiments, the passing of the flow through the canal is facilitated by the fluid advancing along the wall. In some embodiments, the flow of fluid passes through a narrowing portion of the root canal to clean and/or abrade the narrowing and/or distal section of the root canal. In some embodiments, the flow of fluid continues to the apex of the root canal. In some embodiments, at least some of the fluid flows back up through the root canal (herein termed returning fluid), washing away soft tissue such as nerve tissue, blood vessels, magma and/or debris. In some embodiments, since the flow of fluid advances along the canal wall, the returning fluid passes upwards through the center of the canal.

Optionally, the resulting flow path allows continual irrigation for cleaning and/or abrading the root canal. In some embodiments, maximum abrasion of the fluid flow is where the fluid flow changes direction, for example, where the flow returns upwards (e.g. in a coronal direction) through the root canal, e.g. at the apex. Alternatively, in some embodiments, for example, due to friction and/or turbulence, as the fluid flows apically abrasion reduces.

Optionally, fluid including liquid and/or gas (including different ratios of liquid to gas) is self-abrasive, for example, where bubbles within fluid abrade the root canal. Optionally, fluid where bubbles abrade the root canal includes nonabrasive powder. In some embodiments, bubbles include powder and/or act as powder and/or are abrasive.

Optionally, irrigation is performed periodically to allow fluid to exit the canal. In some embodiments, a volumetric flow rate of fluid that passes through the root canal ranges between 0.5-50 ml/second, for example between 1-9 ml/second, 30-40 ml/second.

In an exemplary embodiment of the invention, the flow travels along the wall of the root canal for at least 20%, 50%, 70%, 90% or intermediate or greater percentages of the length of the root canal. In some embodiments, flow travels along at least 20%, or at least 50%, or at least 70%, or at least 90%, or substantially all of the surface area of the root canal. In some cases, part of the flow, for example, at the distal end of the canal, includes a significant turbulent flow (e.g., away and towards the wall). In some embodiments, the flow travels a length of 0.1 mm, 0.5 mm, 1 mm, 2 mm, 3 mm along the wall of the canal. Optionally, the flow travels beyond the fluid level within the canal, for example 0.2 mm, 0.6 mm, 1 mm, beyond. In some embodiments, the fluid level is defined as a level which contains 30%, 50%, 70% of fluid vs. an air/void component.

In some embodiments, the direction and/or magnitude of the momentum of the fluid exiting a nozzle of the apparatus is determined by the structure of the nozzle. In an exemplary embodiment, the fluid is circulated in a lumen formed between two cones within the nozzle so that it exits the nozzle in an angle to a vertical axis of the nozzle. In another embodiment, passing the fluid within a structural element of the nozzle, such as an inclined tube configured on a plane that crosses the vertical plane of the tooth may create the angled direction of the jets.

In some embodiments, a flow (e.g. a fast flow) of fluid passes through the root canal and optionally enters at least a portion (e.g. 1%, 4%, 5%, 10%, 20%, 50%, 100%) of the dentinal tubules. In some embodiments, a ratio between gas (such as air) and liquid (such as water, disinfectant, antiseptic medication, and/or any other solution) is used. In one example, a fluid may comprise 90% air and 10% liquid. Other examples include 80% air and 20% liquid, 98% air and 2% liquid, 30% air and 70% liquid. In some embodiments, the selected ratio may affect parameters such as the elasticity of the fluid, the velocity of the fluid, and/or the flow rate. Optionally, components of the fluid such as air bubbles (e.g. pressurized gas bubbles) may facilitate the removal of organic substance from the canal wall and/or erode root canal hard tissue (e.g. dentine). In some embodiments, fluid including bubbles includes nonabrasive powder.

In some embodiments, a relatively low source pressure of the jet or a beam of jets exiting a nozzle is used, for example ranging between 10-200 PSI, 50-100 PSI, 20-30 PSI, 200-300 PSI. In some embodiments, the pressure of the angled jet when hitting a wall of the root canal is lower, for example ranging between 5-150 PSI, 10-30 PSI, 70-120 PSI.

In some embodiments, the fast flow of fluid erodes a layer of tissue, for example dentin tissue. Optionally, eroding is accomplished by adding abrasive particles to the fluid, which are then pushed against the walls of the canal, sweeping away a layer of dentinal tissue, magma, debris and/or bacteria. In some embodiments, eroding of at least or 50-80%, or 20-30%, or 80-90%, or 40-70%, or substantially all of a surface of the root canal wall is performed.

In some embodiments, the flow of fluid smoothes the root canal wall, for example removing grooves. A potential advantage of smooth or groove-free canal walls and/or a lack of a smear layer is that there is no need or there is a reduced need for chemical and/or disinfecting flushes of the root canal.

In some embodiments, a layer of eroded dentine tissue is thin in comparison to traditional root cleaning treatments, a potential benefit being a less invasive treatment and/or a stronger tooth after treatment, and/or less risk of rupturing the root canal. In some embodiments, the layer has thickness ranging between 100-200 μm, or between 40-400 μm, or less than 400 μm.

In some embodiments, the root canal wall is subjected to shear forces exerted by the flow of fluid. Optionally, a thin layer of tissue is removed due to the applied force.

In some embodiments, turbulent flow may be observed in at least a portion of the root canal, for example in proximity to the apex. Optionally, a turbulent flow may increase the shear forces exerted by the flow of fluid. In some embodiments (for example, when fluid is discharged into a root canal containing fluid) a root canal is cleaned and/or abraded by turbulent fluid flow in the canal. In some embodiments, debris and/or eroded material is not pushed into root canal walls, but is pulled away (e.g. into a central portion of the root canal) and/or pushed along root canal walls. A potential benefit being that debris and/or contamination is not pushed into tubules.

In some embodiments, various parameters of the apparatus and/or system such as the angle of the fluid jet, the ratio between gas and liquid, the type of abrasive powder and/or any other parameters or combinations of them may be selected to optimize the effectiveness of the apparatus and/or system. In some embodiments, structural components of the nozzle such as an internal cone within the nozzle are movable with respect to each other. Optionally, the movement modifies a volume of the lumen. In some embodiments, a structure of an internal cone can be modified to change a shape of the lumen, for example by comprising a radially expanding portion which occupies a volume of the lumen. Optionally, the modification of the lumen affects the flow parameters of fluid passing within the nozzle and/or exiting the nozzle.

In an exemplary embodiment of the invention, a plurality of jets are used. Optionally, the use of a plurality of jets allows more freedom (e.g. less manual precision and/or allowing matching to various geometries) in the orientation of the nozzle, as it is more likely that at least one jet will have an angle needed for proper treating of the root canal. Optionally or alternatively, the use of multiple jets may assist in ensuring that all portions of the root canal wall are hit by fluid flow at sufficient velocity and/or other parameters.

In some embodiments, the jets will be contiguous with each other, for example, in the form of a cone and/or a segment thereof. Alternatively, a cone shaped flow is formed without distinct angled jets. Additionally or alternatively, the cone shaped flow or other form of flow comprises a vertical velocity component as well as a circumferential velocity component. Additionally or alternatively, the velocity comprises a radial component. Exemplary ratios of a relative weight of each of the components out of the total velocity may include 70% vertical component, 20% circumferential component, 10% radial component, or 40% vertical, 30% radial, and 30% circumferential, or other ratios thereof. In some embodiments, for example when the root canal is at least partially filled with fluid, the angled jet hits the fluid within the canal. Optionally, the jet merges with the fluid, and may intensify the spinning motion of the flow within the canal. An aspect of some embodiments relates to cleaning and/or abrading a root canal using turbulent flow in the canal. In some embodiments, the turbulent flow is created by providing one or more fluid jets at an angle. In some embodiments, the turbulent flow is created by providing a spinning beam of fluid which merges with fluid within the canal.

In an exemplary embodiment of the invention a turbine such as an air turbine is coupled to an internal pipe within the nozzle, the turbine configured for rotating the pipe so that fluid circulates within the pipe. In some embodiments, the turbine spins a cone of the nozzle which contains the fluid. In some embodiments, the circulating flow of fluid exits the nozzle and enters the root canal, where the spinning momentum may cause the flow the flow along the canal walls, thereby removing tissue.

Various embodiments are described in this application, some of which describe a relation between the nozzle structure and the flow regime within the nozzle, the nozzle structure and the flow within the canal, the shape of the beam and the flow within the canal, desired flow parameters of flow effects in the canal, or others. In an exemplary embodiment of the invention, a geometry of the nozzle and/or other parameters such as the fluid composition, the fluid pressure, or others may be selected to achieve the desired conditions. In some embodiments, a calibration is performed to match up such parameters and achieve a desired effect, optionally using different parameter value sets for different dental conditions. An exemplary device may include a knob which selects different parameter sets determined by such a calibration, and/or according to the selected nozzle geometry.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments, a nozzle tip is sufficiently small such that at least a portion of the tip can be inserted into a pulp chamber of a tooth. In some embodiments, a maximum extent of a nozzle tip perpendicular to a vertical axis of the nozzle is less than 0.05 mm, or 0.1 mm, or 0.2 mm or 0.5 mm, or 1 mm, or 2 mm, or 5 mm, or 10 mm, or smaller, or larger, or intermediate measurements.

In some embodiments, tissue is removed from a root canal, for example by rotating fluid within the root canal, at a rate of at least 1 μg/s, or 0.1 mg/s, or 1 mg/s, or 20 mg/s, or lower, or higher or intermediate rates.

In some embodiments, discharge of fluid from a nozzle into fluid within a root canal causes the flow within the root canal to start rotating helically and/or for a speed (e.g. revolutions per second) of already rotating fluid within the canal to increase and/or for a number of revolutions of the fluid along the wall of the root canal to increase.

In some embodiments, fluid in said root canal fills at least 5%, or at least 10%, or at least 20%, or at least 30%, or at least 50%, or at least 90% or lower, or higher or intermediate percentages of a volume of said root canal.

In some embodiments, fluid in said root canal comprises at least 10% liquid, or at least 20%, or at least 30%, or at least 50%, or at least 90% or lower, or higher or intermediate percentages.

A Description of an Endodontic Procedure, According to Some Embodiments of the Invention Referring now to the drawings, FIG. 1 is a flowchart of an endodontic treatment procedure, in accordance with an exemplary embodiment of the invention.

In some cases, for example if a tooth is decayed, infected, and/or cracked, a dentist may decide to perform procedure for treating the root canal of a human tooth, e.g. as described at 101.

Commonly, the number of root canals in a tooth depends on the number of the tooth roots, for example ranging between 1-5. In some cases, such as in root canal anastomosis, a single canal may split into branching canals.

In some embodiments, a root canal procedure includes removing pulp tissue (pulpectomy), magma, nerve tissue, and/or blood vessels from the pulp chamber and root canal to prevent future infection and/or an abscessed tooth. In some embodiments, the root canal procedure includes shaping the root canal. In some embodiments, the root canal procedure includes decontaminating the tooth. A feature of some embodiments includes not performing one or more of the above, for example not performing shaping of the root canal.

In an exemplary embodiment of the invention, for example, as will be described below, the root canal is cleaned without leaving a smear layer which, for example, would otherwise block tubules and/or serve as a substrate for infection.

Prior to and/or during the procedure, imaging of the tooth may be performed, as described at 103. For example, X-ray imaging may be performed to determine the shape (or number) of the root canals and/or detect signs of infection.

At 105, an access cavity to the pulp chamber and root canal is created through the crown of the tooth, for example using a dental drill. Once the access cavity is created, the entrance to the root canal is exposed, as described at 107, optionally using a root canal file inserted through the access cavity into the pulp chamber. In some embodiments, access is provided via a side of the tooth. This may be possible if no files are used on the root canal, for example, as described below.

At this stage, in order to clean, shape and/or decontaminate the root canal through the exposed entrance, a distal tip of the apparatus, optionally including a nozzle as will be further described, is inserted through the pulp chamber, as described at 109, and an exit aperture of the nozzle is positioned above the exposed entrance to the root canal, as described at 111. Optionally, the exit aperture of the nozzle is positioned within the root canal, as will be further described. Optionally, the exit aperture of the nozzle is positioned in an angle to the root canal entrance. At 113, one or more angled fluid jets discharged from the exit aperture of the nozzle passes through the root canal, as will be explained by the following figure. In some embodiments, as the flow of fluid advances along the root canal wall, it removes tissue. In some embodiments, the flow of fluid removes organic substance such as pulp tissue, nerve tissue, blood vessels, magma and/or debris from the root canal. In some embodiments, the flow of fluid erodes a thin layer of dentin tissue from the wall of a root canal. In some embodiments, the flow of fluid smoothes the root canal wall. In some embodiments, the flow of fluid disinfects the root canal.

In some cases, manual cleaning (e.g. using a file or other methods known in the art) is used to remove some or all bulk debris from a canal before using fluid jets as described herein. Optionally, fluid jets are used to remove a smear layer created by manual cleaning.

At 115, the dentist may optionally evaluate the effectiveness of the cleaning and/or abrading procedure, for example by inserting a file to reach the apex of the root canal and test for remains of infected tissue. Optionally, a dentist may re-wash and/or dry and/or disinfect the root canal (116).

At this stage, sealing of the root canal (and/or the pulp chamber) is optionally performed (117). Optionally, sealing includes filling a hollow interior of the root canal.

In some embodiments, a rubber compound such as Gutta Percha material may be used for sealing the root canal. Optionally, the Gutta Percha material is softened and injected into the root canal, in which it then hardens. Alternatively, a more solid form of Gutta Percha, for example shaped as a cone, is inserted into the root canal to fill it. In some embodiments, the sealing process begins by inserting the filling material to the apex of the root canal, and then advancing upwards. In some embodiments, a temporary filling is used, which is later replaced by a permanent filling.

In various acts described above, techniques that are known in the art may be used. The acts described at 109-113 desirably use an embodiment of an inventive apparatus and method for cleaning and/or abrading a root canal, for example, as described below.

Optionally, the procedure described at 101-117 is repeated for one or more additional root canals, for example an additional root canal of the same tooth and/or a root canal of a different tooth. Optionally, sealing is performed for the one or more root canals that were treated.

Various types of root canals may be treated using the described methods and/or apparatuses, such as a curved shaped canal, L shaped canal, C shaped canal, S-shaped canal, V-shaped canal, U-shaped canal, isthmus canal, root canal anastomosis, webs canal, fins canal, lateral canal, accessories canal, MB2 canal, root canal type 1-8.

Figure 2:
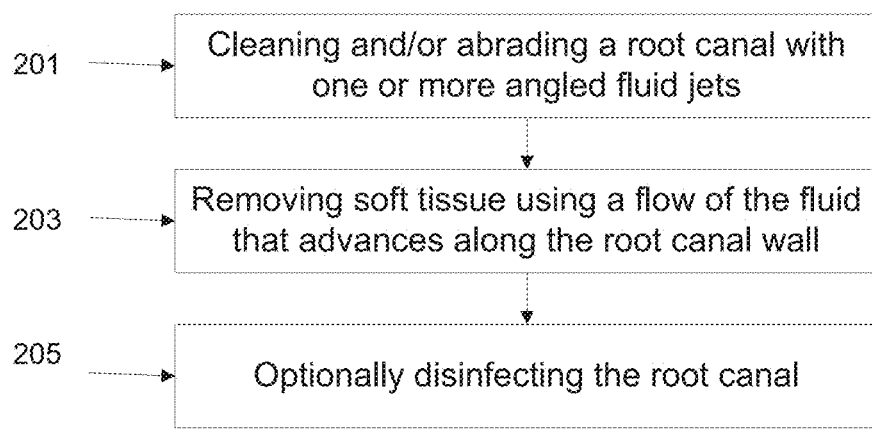
FIG. 2 is a flowchart of an exemplary method for cleaning and/or abrading a root canal using one or more angled fluid jets, according to some embodiments of the invention.

FIG. 2 is a flowchart of an exemplary method for cleaning and/or abrading a root canal using one or more angled fluid jets, according to some embodiments of the invention.

At 201, one or more angled fluid jets are directed into a root canal to clean and/or abrade it.

In some embodiments, a jet is a directed flow of fluid, optionally exiting from an exit aperture of a nozzle. Different embodiments may have jets with different shapes and/or forms. For example, the jet may have a narrow ray form. In some embodiments, a beam of a plurality of jets is used. In some cases, the jet is thin and flat and may spread out angularly. In other embodiments, a jet is substantially pencil like, but spreads when contacting the root canal wall. In an exemplary embodiment of the invention, the jet shape is determined by the shape of the nozzle used. For example, in some embodiments, the jet/beam shape is determined by the shape of the tip of the nozzle used. For example, in some embodiments, a shape of a jet/beam discharged is the same shape as a shape of the nozzle outlet. For example, in some embodiments, a nozzle with a narrow tip portion (e.g. see FIG. 9B) discharges a narrow jet/beam. In some embodiments, the shape of the jet may depend on the fluid parameters, such as air/liquid ration and/or pressure and/or pulsatility. In other embodiments, the nozzle may be able to selectively provide one of several jet forms. Optionally, at least a portion of the nozzle is shaped as a needle-like tube, forming a relatively narrow passage for the fluid to flow through.

In some embodiments, each of a plurality of angled jet has hits the root canal wall at a different angle so that the plurality of jets are channeled to flow together along the root canal wall in a helical pattern, as will be further described. In some embodiments, a helical pattern within a nozzle and/or within a root canal is where the path of fluid flow changes angle while flowing apically. In some embodiments, the fluid flow follows a number of revolutions where a direction of the fluid flow repeats, at least in an axis perpendicular to a vertical axis of the root canal.

In some embodiments, the one or more jets are directed into the root canal. In some embodiments, at least a portion of a single jet or a plurality of jets hits the wall of the root canal. In some embodiments, force exerted by the wall channels the jets to advance along the root canal wall. In some embodiments, the fluid flows in a helical flow pattern along the walls of the root canal, for example, as will be further described in the following figure.

In some embodiments, as will be further explained, the one or more jets are discharged from a nozzle such that they are angled to a vertical axis of the nozzle. In some embodiments, the one or more jets enter the root canal such that they are angled to a vertical axis of the root canal. Optionally, the vertical axis of the nozzle unites with the vertical axis of the root canal.

In some embodiments, the shunting of the one or more jets in a specific angle and/or direction is created by a designated inner structure of the nozzle, for example, as will be further explained below.

In some embodiments, a plurality of angled jets such as 2, 4, 8, 12, 50, 1000, 2000, 3000, or any intermediate or higher numbers are used. In some embodiments, the nozzle is adapted for discharging at least 2, or at least 4, or at least 8, or at least 12, or at least 50, or at least 1000, or at least 2000, or at least 3000 angled fluid jets simultaneously. A potential advantage of using a plurality of jets may include a more effective cleaning and/or eroding of the canal wall. For example, in some embodiments, a large number of jets (e.g. more than 5, 10, 50, 100, 300, 1000) means that the entire root canal wall is contacted by the jet. In some embodiments, a larger number of jets and constant liquid flow rate (e.g. jets have a higher proportion of air) results in faster circulation of fluid within the root canal.

In some embodiments, a plurality of jets includes disinfecting material and/or abrasive material.

Optionally, a thickness of the layer of tissue eroded by the flow is substantially equal at various portions of the root canal.

In some embodiments, rotational flow of fluid along the canal walls means that the root canal wall continues to be abraded when the shape of the wall changes due to the abrasion process (e.g. the fluid continues to flow along the canal walls despite changes in shape and/or angle of the walls). In some embodiments, rotation flow of the fluid along the canal walls causes enlargement of the canal in all three dimensions. In some embodiments, abrasion is complex shaped, for example, in a shape other than cylindrical.

In some embodiments, characteristics and/or parameters of the flow and/or fluid (e.g. speed, number of jets, angle of jets, composition of fluid) are changed to be suitable for abrading the root canal during treatment, for example, to maintain erosion as the canal widens. In some embodiments, a proportion of abrasive powder in the fluid and/or a speed of fluid flow is increased during a treatment, for example, so that the root canal wall continues to be abraded as the root canal increases in size (due to abrasion). In some embodiments, abrasion is reduced (e.g. by reducing a proportion of abrasive powder in the fluid and/or a speed of fluid flow) during treatment, for example, to smooth the root canal wall after the majority of the abrasion/erosion has occurred.

In some embodiments, one or more portion of a root canal is smoothed, for example due to fluid flow and/or abrasion.

Another potential advantage of using a plurality of jets includes the ability to select a hitting angle, for example an angle of 30°, 45°, 70° between the angled jet and the root canal wall, and additionally and/or alternatively to assure that at least some of the jets of the beam will hit the root canal wall.

In some embodiments, a single angled jet may be used, for example being narrow enough to effectively advance along the canal wall, creating a thin coating-like layer of fluid. Optionally, in the above described phenomena, the angled jets advance along the canal wall, optionally allowing some or all of the returning fluid to flow back up through a central lumen along the vertical axis of the canal, as will be shown by the following figure. For example, 60-80%, 40-50%, 80-95% of the fluid may flow back through the central lumen, and 10-30%, 5-8%, 30-40%, may flow back up along the canal wall.

In some embodiments, as described at 203, the flow of fluid passing through the root canal removes soft tissue such as pulp tissue, magma, nerve tissue, and/or blood vessels. In some cases, the tissue removed is infected tissue. In some embodiments, the flow of fluid flushes away organic substance and/or debris. In some embodiments, flow of fluid cuts soft tissue (e.g. nerves and blood vessels) without pulling the soft tissue from the tooth e.g. a blood vessel is cut in half, with half of the vessel remaining in the tooth. In some embodiments, abrasion removes a layer of dentine, cutting tubules and/or blood vessels within the dentine, optionally including an apical area and/or apex (e.g. cutting blood vessels) of the root canal.

Optionally, a thickness of the layer of tissue eroded (e.g. soft tissue and/or dentine) by the flow (e.g. rotation of fluid within the root canal) is substantially equal at various portions of the root canal. In some embodiments, a thickness of the layer of tissue eroded is between 50-90 µm thick, or between 10-150 µm thick, or between 100-200 µm thick, or lower, or higher, or intermediate thicknesses.

In some embodiments, the flow of fluid erodes a layer of tissue, for example a thin layer, such as a thin layer of dentin tissue. Optionally, the flow of fluid causes widening of the canal. In some embodiment, the flow of fluid smoothes the surface of the root canal wall. For example, the thickness of the eroded layer may range between 100-200 µm, 10-70 µm, 200-300 µm. Optionally, the thickness of the eroded layer and/or the amount of debris removed by the flow depends on various parameters, such as the application time.

In some embodiments, the fluid comprises liquid, such as water and/or antibacterial liquid. Additionally and/or alternatively, the fluid comprises gas, such as air. Optionally, the mixture of air and liquid dispersed from the nozzle is an aerosol. Optionally, the pressure of the aerosol exiting a nozzle ranges between 10-200 PSI.

In some embodiments, a ratio between air and liquid is selected according to the need, for example a ratio between air and liquid may affect the viscosity of the fluid which in turn may affect the velocity of the fluid flowing through the canal.

In some embodiments, the gas is air, and the fluid comprises between 50-95% air, and between 5-50% liquid, or the fluid comprises between 20-95% air and between 5-80% liquid or lower, or higher, or intermediate ratios of liquid to air.

In an exemplary embodiment, the fluid comprises between 60-90% air, and between 10-40% liquid, such as 70% air and 30% liquid, 85% air and 15% liquid, 98% air and 2% liquid, or another higher or lower ratio, or an intermediate ratio.

In some embodiments, composition (e.g. percentage of components within the fluid) of the fluid comprising liquid and one or more of air, abrasive material and disinfecting material is chosen to be suitable for the type of treatment and/or the type of root canal. For example, in some embodiments, a proportion of abrasive powder is increased to increase a rate of erosion of the root canal walls. For example, in some embodiments, disinfecting material is increased and/or added to the fluid at the end of the treatment, e.g. to leave a sterile and/or clean root canal. In some embodiments, for example, if there is a buildup of debris in the root canal, a proportion of gas (e.g. air) in the flow is increased to increase a speed of the flow, for example to flush the root canal from debris. In some embodiments, a proportion of gas in the fluid is reduced for flushing the canal, e.g. as a final stage of treatment.

In another example, the ration between air and liquid is 90% liquid, and 10% air. In another example, the fluid comprises 100% liquid. Optionally, by having fluid with relatively high air content, faster spinning motion may be obtained. Optionally, by obtaining a relatively high angular velocity of the spinning fluid, the radially outward force (i.e. centrifugal force) applied by the flow and/or by particles of the flow such as abrasive powder particles onto the root canal wall is increased. A potential advantage includes eroding a thicker layer of tissue, thereby optionally increasing the treatment effectiveness. Optionally, a friction produced between the gas (e.g. air) components of the fluid when contacting the root canal wall is relatively low with respect to the friction produced by the abrasive particles of the fluid during contact with the root canal wall. In some embodiments, a density of an abrasive particle is higher than a density of a liquid and/or gas particle comprising the fluid. In some embodiments, the percentage of abrasive powder in the fluid ranges between 0.05-15%, such as 0.1%, 2%, 10%, or higher, for example, 20%, 50%.

In some embodiments, eroding of the tissue is achieved by adding abrasive particles such as an abrasive powder to the fluid. Optionally, the abrasive powder comprises between 0.01-3%, 2-2.5%, 0.8-1.2%, 3-8%, 5-7% of the fluid.

In some embodiments, the abrasive powder includes natural/organic material and/or mixed material (e.g. containing more than one component), and/or synthetic material.

In some embodiments, the fluid does not include abrasive powder and abrades the canal itself e.g. in some embodiments, bubbles within the fluid abrade the canal. In some embodiments, abrasive properties of fluid are affected by fluid density and/or viscosity, and/or particle size.

In some embodiments, abrasive particles can change form and/or volume (e.g. dissolve, e.g. absorb fluid to enlarge).

In some embodiments, size and/or proportion and/or composition of abrasive particles affect flow within the nozzle and/or nozzle tip and/or angle jets and/or from the nozzle outlet and/or within the root canal. In some embodiments, abrasive particles size and/or type are selected to be suitable for the type of treatment and/or type of root canal. For example, in some embodiments, large abrasive particles are selected for a canal which requires heavy abrasion. In some embodiments, a temperature of fluid and/or other components (e.g. abrasive powder and/or gas) is selected for the type of treatment and type of canal. For example, in some embodiments, a higher fluid temperature is used for cauterization. For example, in some embodiments, a higher temperature fluid has lower viscosity optionally associated with higher velocity flow, for example facilitating a heavy abrasive particle load with high velocity rotation of fluid. Some examples of abrasive powder that may be added to the mixture of air and liquid include crystallite, silicon powder, garnet powder, aluminum powder, magnesium powder, ceramic powder, plastic powder, synthetic, emery powders, sea shell powder, cement powder, salt, ground seeds, diamond powder, carbide powder, glass powder, iron/iron oxide powder, steel powder, aluminum oxide powder, baking soda, acrylic powder, granite powder, fruit powder, tree shell powder, plant seed powder, sea sand powder, synthetic diamond powder, stone powder, marble powder, copper powder, silica and/or combinations of the above. In some embodiments, the powder grains may have a diameter ranging between 2-500 μm, 10-50 μm, 3-6 μm, 0.1-1 μm, 0.5-2 μm. In some embodiments, the powder grains may be selected according to the type of tissue that is to be removed. In some embodiments, air bubbles can act as an abrasive substance, for example to erode tissue, for example hard tissue (e.g. dentine). In some embodiments, reducing a size of the nozzle lumen increases a number of bubbles within the fluid, generating more abrasion. In some embodiments, pressure of air within the flow is increased, increasing a pressure of the bubbles, increasing abrasion. In some embodiments, the powder may comprise a disinfection component. In some embodiments, the powder particle may generate a disinfection process during the cleaning and/or eroding process in the canal.

In some embodiments, the flow of fluid disinfects the root canal, as described at 205, for example by adding disinfectant to the fluid. Optionally, an antibacterial substance and/or medicine is added. In one example, Sodium Hypochlorite is added to the fluid to be passed through the root canal, optionally followed by saline and hydrogen peroxide, to disinfect the root canal. In some embodiments, there are three fluid sources that can be used such as water, disinfectant, and medicine. Optionally, the fluid comprises one or more of these liquids.

In some embodiments, the duration of the process of removing organic substance, eroding the tissue and/or disinfecting the interior of the root canal ranges between 15-45 seconds, for example 20 seconds, 27 seconds, 43 seconds. In some embodiments, for example if the root canal has an extremely narrow portion, the duration of the above process may range between 45-60 seconds, for example 50 seconds, 55 seconds. Optionally, shorter, intermediate and/or longer time periods are required to complete the process. In some embodiments, the treatment is provided in periodic pulses, for example a 10 second duration followed by a 10 second interval, or a 2 second duration followed by a 5 second interval, or another combination of larger, smaller and/or intermediate intervals. In some embodiments, during the interval access fluid is collected from the root canal, for example by suctioning.

In some embodiments, a duration of a pulse ranges between 0.2-0.3, or 0.5-1, or 1-25 seconds, or intermediate values, and, optionally, debris and excess fluid are removed in intervals between pulses. In some embodiments, the pulses are controlled through a control panel electrically connected to the apparatus. In some embodiments, pulses have different durations, and/or flow rates and/or volumes of discharged fluid. In some embodiments 0.1-300 cc/s, or 0.5-155 cc/s, or 0.5-70 cc/s, or any intermediate, larger or smaller ranges and/or values of fluid flow in a pulse.

In some embodiments, suction and/or removal of material from the root canal enables flow of fluid along the root canal wall. For example, because suction empties and/or partially empties the root canal revealing portions and/or the entire root canal wall. For example, because suction creates negative pressure within the root canal, encouraging flow of fluid along the root canal wall.

In some embodiments, suction increases the speed of circulation of the fluid inside the root canal (e.g. due to lack of or reduction in resistance from fluid in the root canal and/or due to reduction of pressure in the root canal). In some embodiments, suction increases the speed of circulation of fluid at the root canal apex and a lower portion of the root canal proximal to the apex.

In some embodiments, suction reduces pressure at the root canal apex and/or an apical portion of the root canal proximal to the apex, potentially reducing the risk of rupture of the apex and/or break-through at the apex.

In some embodiments, the treatment time period and/or the length of the periodic pulses of the treatment are determined according to a ratio between air and liquid in the fluid and/or a ratio between air and powder and/or a ration between liquid and powder. Optionally, operation parameters of the apparatus are determined according to calibrated values.

Figure 3:
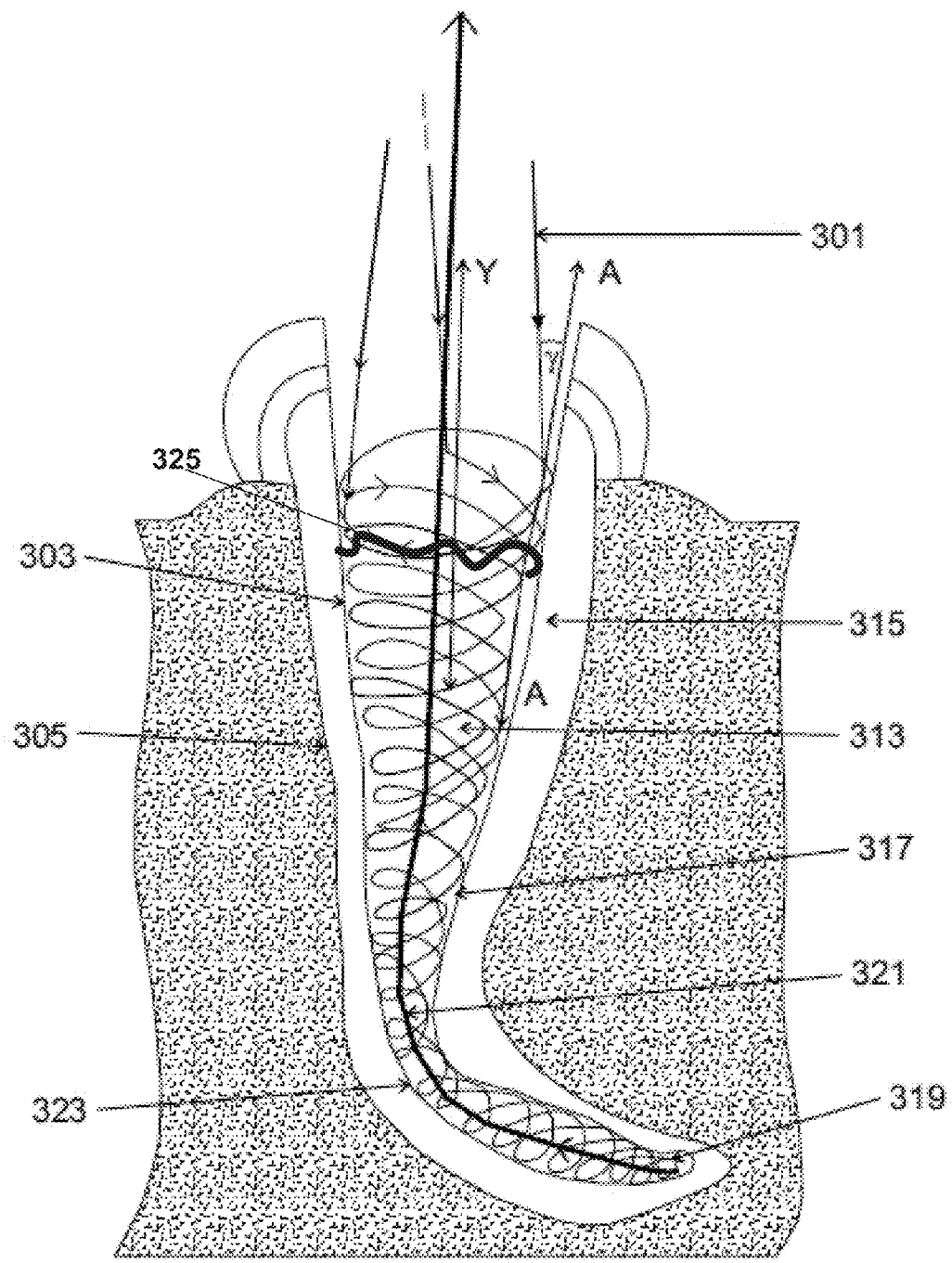
FIG. 3 is an illustration of angled fluid jets entering a root canal and advancing along the root canal wall in a helical flow, according to some embodiments of the invention.

Application of Fluid by the Apparatus into the Root Canal, According to Some Embodiments of the Inventions FIG. 3 shows angled fluid jets entering a root canal and advancing along the root canal wall in a helical flow, according to some embodiments of the invention.

In some embodiments, angled fluid jet 301 hits wall 303 of the root canal 305. In some embodiments, the plane in which the angled fluid jet passes before and/or during entrance to the root crosses a vertical plane of the tooth, for example a plane in which vertical axis y passes, as will be explained.

In some embodiments, an angle γ is formed between jet 301 and an axis extending longitudinally along the canal wall 303, such as axis AA. In some embodiments, for example if a portion of the root canal is shaped as a cylinder, axis AA may be parallel to vertical axis y. In some embodiments, angle γ is an acute angle, for example ranging between 10-85 degrees, for example 20 degrees, 45 degrees, 73 degrees. In some embodiments, angle γ is zero.

In some embodiments, one angled jet 301 or a plurality of angled jets hit the root canal wall. In some embodiments, the jets advance along the root canal wall. In some embodiments, once the jets hit the root canal wall, the force exerted by the wall channels the jets to spin in a helical flow 313 through the root canal. Optionally, other forms of flow such as longitudinal stream lines along the root canal wall are formed.

Additionally or alternatively, when root canal 305 is at least partially filled with fluid, for example during steady state operation of the apparatus, angled jet 301 hits the fluid 325 within the canal. Optionally, jet 301 merges with the fluid, and may intensify the spinning motion of flow 313 within the canal.

In some embodiments, a centrifugal force may be applied to canal wall 303 by spinning flow 313. Optionally, a spiral path of the flow is maintained due to rotational momentum acquired when the fluid is advanced within and/or discharged by the nozzle of the apparatus. Optionally, the spinning pattern of flow 313 is achieved when a sufficient amount of angled jets enters the canal, such as, 3, 10, 100, 1000, 20000 jets or intermediate, larger or smaller amount, such that the jets merge together to form the helically spinning flow. Optionally, the plurality of applied jets comprise different angles, for example so that they cover the root canal opening circumferentially. Optionally, by hitting the opening circumferentially, a homogenous distribution of the flow is achieved with respect to a periphery of the root canal.

In some embodiments, flow 313 advances along a portion 315 of the root canal. In some embodiments, portion 315 is cylindrical. In some embodiments, flow 313 passes through a narrowing portion 317 of the root canal. In some embodiments, flow 313 passes through a narrowing portion and then through a widening portion. In some embodiments, flow 313 passes through a curve 323.

In some embodiments, narrowing portion 317 includes a portion having a diameter less than 0.1 mm, less than 0.05 mm, and/or intermediate or smaller values. In some embodiments, curve 323 has a radius of curvature less than 0.05 mm, less than 0.08 mm, and/or intermediate or smaller numbers. In some embodiments, a length of a root canal past curvature and/or past a narrowing which the fluid flows through ranges, for example, between 0.1-4 mm, for example 1 mm, 0.5 mm, 2 mm.

In some embodiments, flow 313 reaches apex 319 of the root canal. In some embodiments, flow 313 passes through branches of the root canal, for example reaching at least a portion of branching dentinal tubules, (not shown in this figure). In some embodiments, for example if the anatomy of root canal 305 is unusual, such as an L-shaped or C-shaped root canal, and/or if root canal 305 has an extremely narrowing portion, flow 313 may pass through and clean at least most of the canal. A potential advantage of cleaning and/or eroding the root canal using the flow of fluid includes the ability to reach locations such as curves, narrowings and/or branches of the root canal which otherwise would have been impossible or hard to reach, for example when using a file. Optionally, a centrifugal force that is applied to canal wall 303 by flow 313 (for example by abrasive powder particles within the fluid) increases a thickness of the eroded layer, thereby optionally increasing treatment effectiveness.

In some embodiments, root canal wall 303 is subjected to shear forces, which may be applied by flow 313. Optionally, due to the shear forces, a thin layer of tissue such as dentin tissue is removed by the flow. In some embodiments, the removal of tissue is homogenous. In some cases, for example in a narrowing and/or curvy portion of the root canal, the removal is non-homogenous. In some embodiments, homogenous removal depends on the diameter of root canal 305. For example, in a narrowing having a smaller diameter than 0.1 mm, removal may be non-homogenous. Optionally, in that case, a file may be used for widening the narrowing. In some embodiments, the thickness of the dentin layer removed by the flow of fluid ranges between 10-300 µm, or between 100-200 µm, for example 50 µm, 80 µm, 12 µm. Optionally, intermediate and/or lower thickness layers are removed. In some embodiments, the shear viscosity of the fluid affects the thickness of the removed layer.

In some embodiments, for example, as the root canal is abraded gradually and as, in some embodiments, debris is removed from the canal by the abrading flow, treatment does not result in a smear layer on the root canal walls.

In some embodiments, for example, if a drill has been used to remove material (e.g. generating a smear layer on the root canal walls) removal of material (e.g. a layer of dentine) removes a contaminated layer of material from the root canal In some embodiments, removal of a layer of dentine, for example a layer 100-200 μm thick of dentine from the root canal reveals tubules.

In some embodiments, a rate of removal is controlled, for example, by applying shorter pulses, for example to prevent perforation. In some embodiments, imaging may be performed, for example during treatment, to decide if additional cleaning and/or abrading is needed.

In some embodiments, flow 313 reaches apex 319 of the root canal. In some embodiments, flow 313 may become turbulent along some portions of the root canal, for example in proximity to apex 319.

In some embodiments, flow 313 erodes apex 319, optionally resulting in a duller root canal. In some embodiments, the flow 313 is applied so that it does not widen a natural opening of the apex, for example ranging between 0.3-0.5 mm, 0.1-0.2 mm, 0.4-0.5 mm. Optionally, treatment duration is selected so that penetration of at least some of the flow through the apex is avoided.

In some embodiments, at least some portion of flow 313, optionally including the removed organic substance and/or debris, returns back up through the canal. Optionally, when a lumen of the canal is filled with fluid up to its maximal capacity, at least some of the fluid is caused to exit the canal. Optionally, the amount of fluid that accumulates within the canal before at least some of the fluid is caused to exit the canal is determined by the components of the fluid and their respective amounts, for example determined by the gas-liquid ratio of the fluid. Optionally, fluid accumulating within the canal applies pressure on the apex and/or on the canal wall, and/or on tubulates, and/or branches, and/or on isthmus canals and/or on accessory canals.

Optionally, the flow passes along path 321, for example in a central lumen along vertical axis y. A potential advantage of the advancing and returning flow path may include the ability to use a large volume of fluid to clean the root canal. For example, a volumetric flow rate may range between 0.5-50 ml/sec, 10-30 ml/sec, 1-5 ml/sec.

In some embodiments, the velocity of flow 313 passing through root canal 305 may be affected by various parameters, such as the ratio between air and liquid of the fluid, the diameter of the root canal (which may vary along portions of the root canal), the viscosity of the fluid, the initial velocity of the fluid in the jet, the angular velocity of the fluid, the vertical velocity of the fluid, the ratio between components such as gas, liquid and powder in fluid, the centrifugal acceleration of the fluid, and/or other parameters or combinations of them. Optionally, the velocity of flow 313 increases along some portions of the root canal, for example in a narrowing portion. Optionally, the typically conical shape of the root canal, in which a diameter of the root canal decreases, causes the velocity of the fluid to increase as it advances towards the apex. In one example, the velocity of flow 313 advancing along the root canal wall ranges between 0.5-50 m/sec, 30-80 m/sec, 50-300 m/sec, 10-100 m/sec, 0.6-2 mm/sec, 180-350 m/sec, or any intermediate, larger or smaller ranges. In some embodiments, the flow velocity upon exiting to the atmosphere is, for example, 120 m/sec. Optionally, the velocity of flow 313 changes according to a current location within the root canal. For example, rotational flow velocity potentially increases with increasing root canal depth, while axial velocity decreases. In some embodiments, an estimated level of dynamic stress applied during operation of the nozzle within the root canal is about 6 PSI, corresponding to a root canal wall velocity range of about 30-80 m/sec. In some embodiments, the velocity of the flow enables a relatively high volumetric flow rate, for example 50 ml/sec.

Figure 4A:
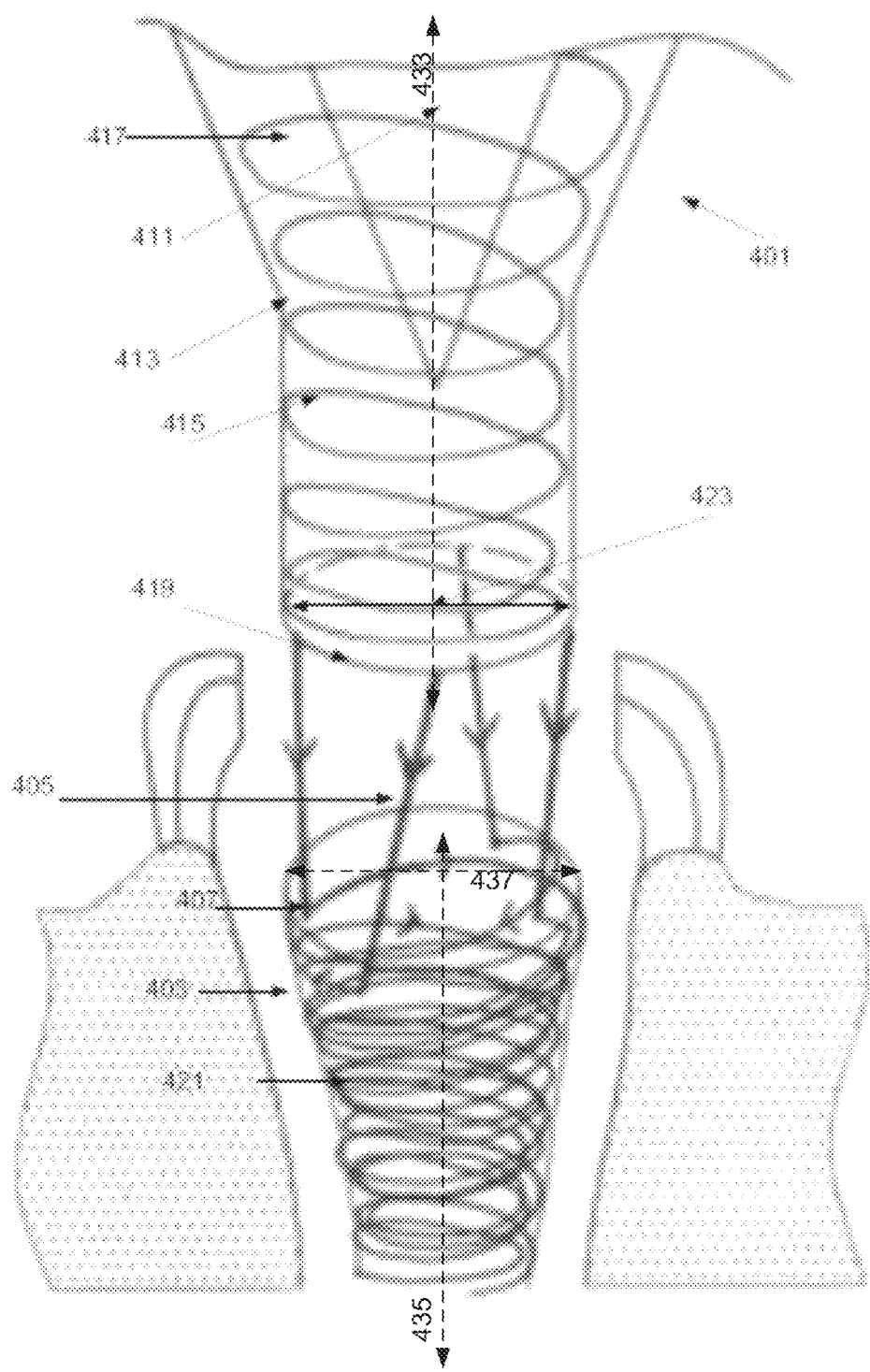
FIGS. 4A-4C are illustrations of a conical nozzle positioned at an entrance to a root canal, according to some embodiments of the invention.
Figure 4B:
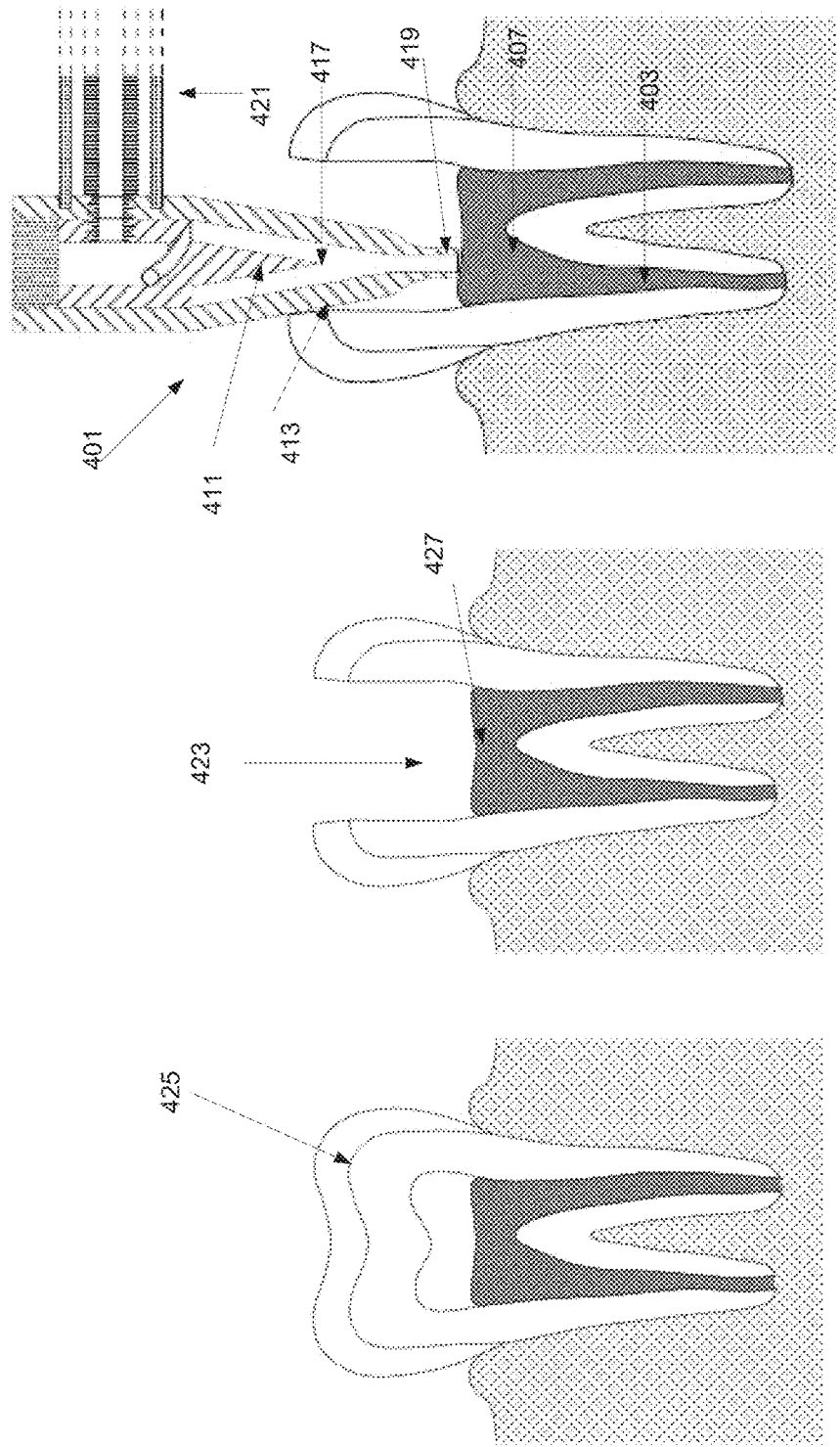
Figure 4C:
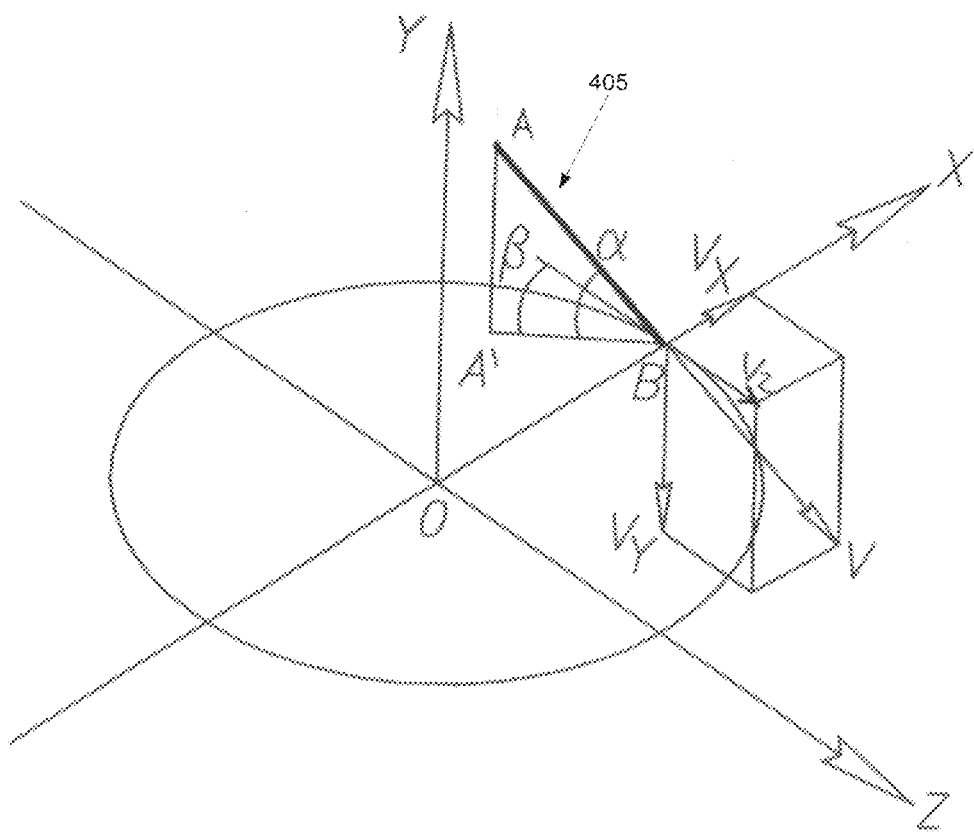

FIG. 4A illustrates a conical nozzle 401 positioned above the entrance to root canal 403, according to some embodiments of the invention. FIG. 4B illustrates an apparatus comprising conical nozzle 401 and a handle 421, positioned within access cavity 423 of a tooth above the entrance to root canal 403. FIG. 4C is a geometric representation of an angled fluid jet 405.

As seen in FIG. 4A, at least one angled fluid jet 405 is discharged from nozzle 401 and directed into entrance 407 of root canal 403.

In some embodiments, for example, as will be further described in FIG. 7, nozzle 401 includes one or more conical structures. Optionally, nozzle 401 includes an internal cone 411 positioned within an external cone 413. In some embodiments, circulating the fluid in a lumen between cones 411 and 413 creates the angled direction of fluid jet 405 or a plurality of fluid jets.

In some embodiments, the angled direction of fluid jet 405 or a plurality of fluid jets is obtained by the conical structure of nozzle 401. In an exemplary embodiment, fluid 415 flows into internal cone 411, passes (for example through a slanted tube as will be shown further on) into external cone 413, and circulates within a narrowing lumen 417 between external cone 413 and internal cone 411, until reaching exit aperture 419 of nozzle 401. In some embodiments, the velocity of the fluid is increased and/or decreased when circulating through the lumen, for example by changing the radius of the circulating path.

In some embodiments, the diameter of a portion of nozzle 401, for example a diameter of exit aperture 419 is smaller than a diameter of the root canal opening. In some embodiments, a diameter of the angled jet measured at the exit aperture of the nozzle is 2%, or 5%, or 10%, or 30%, or 50%, or lower, or higher, or intermediate percentages of a diameter of an entrance of the root canal, or smaller. Additionally or alternatively, a diameter of aperture 419 is smaller than a diameter of the pulp chamber of a tooth. Alternatively, the diameter of aperture 419 is similar to the diameter of the root canal opening and/or the diameter of the pulp chamber.

In some embodiments, nozzle 401 and/or exit aperture 419 of nozzle 401 are positioned above entrance 407 to root canal 403, for example 1 mm, 7 mm, 1 cm and/or intermediate or higher distances above. In some embodiments, as shown for example in FIG. 4A, exit aperture 419 is positioned vertically above entrance 407 such that a longitudinal axis 433 of nozzle 401 and a longitudinal axis 435 of root canal 403 unite. Optionally, when both axes unite, the exit aperture of the nozzle and the root canal opening act as a unified structure, imposing a similar flow regime of the fluid that advances from the nozzle and into the root canal. Optionally, the velocity of the fluid is maintained when passing between the nozzle and the root canal. In some embodiments, the velocity of the fluid increases, for example if pressure in the root canal is lower than the pressure within the nozzle.

A potential advantage may include irrigating root canal 403 with one or more angled fluid jets 405 while nozzle 401 is positioned directly above entrance 407 of root canal 403. Another potential advantage of discharging angled jets may include preventing the need for a diverting element for causing fluid discharged by the nozzle to contact the root canal wall.

Alternatively, in some embodiments, nozzle 401 is positioned such that axis 433 of the nozzle and axis 433 of the root canal do not unite. Optionally, axis 433 is parallel to axis 435. Alternatively, nozzle 401 is positioned such that axis 433 is at an angle to axis 435 of the root canal.

In some embodiments, a diameter of angled jet 405 is smaller than a diameter 423 of exit aperture 419. For example, if a diameter of exit aperture 419 is 0.8 mm, a diameter of fluid jet 405 for example when passing through exit aperture 419 may be 10 μm, 90 μm 0.5 mm, 0.1 mm, 0.3 mm, and/or intermediate or lower diameters. In some embodiments, the diameter of angled jet 405 changes as it flows between exit aperture 419 and entrance 407 to the root canal. In some embodiments, a maximal diameter of angled jet 405 is 30%, 20%, 10%, 4%, 2%, 0.15%, 1%, 0.2%, or intermediate or smaller percentages of a maximal diameter 437 of root canal entrance 407.

In some embodiments, when a plurality of angled jets 405 are used, a distance between any pair of angled jets exiting through exit aperture 419 ranges between 0.01-3 mm, such as 0.05 mm, 0.8 mm, 2 mm. Optionally, this distance affects the formation of a coating-like layer of the flow of fluid advancing along root canal wall 421, for example, as described above.

In an exemplary embodiment, a relatively high number of angled jets is discharged by the nozzle, for example ranging between 2000-60,000 jets, such as 3000, 15,000, 45,000, jets. Optionally, a diameter of a single jet out of the plurality of jets in such a case ranges between, 1 μm-2 mm, such as 50 μm, 1 mm, 1.5 mm. In some embodiments, as fluid 415 circulates within lumen 417, a direction and/or magnitude of its momentum are determined by the structure of nozzle 401. In some embodiments, one or more parameters are selected (by a dentist and/or manufacturer) to create the designated flow of fluid along the root canal wall for the removal of soft tissue. In some embodiments, these parameters include: the number of angled fluid jets, the pressure of the angled fluid jets, the velocity of the jets, the diameter of the jets, the viscosity of the fluid, the ratio between gas and liquid, the amount of abrasive powder added to the fluid, the duration of the treatment, the positioning of the nozzle, and/or any other parameters or combinations of them. In one example, the velocity and pressure of the fluid jet may be selected so that once the jet hits a wall at the root canal entrance, fluid does not spray beyond the entrance to the root canal, for example in the direction of the crown of the tooth. In some embodiments, parameters may depend on each other, for example the ratio between gas, liquid and/or may affect the viscosity of the fluid.

Table 1, now made reference to, presents a table of parameters describing relative amounts and amounts of flow useable with some exemplary embodiments of the invention, for example, embodiments where fluid discharged from a nozzle intensifies rotation of fluid within a root canal. The mass and volumetric flow rates and air/fluid mix percentages are exemplary. It should be understood that values in ranges between the given values, or higher or lower are also used and/or producible in some embodiments of the invention.

TABLE 1

| Flow | Air | | Fluid | |
|---|---|---|---|---|
| Rate (cc/min) | % Air | Mass Rate (kg/min) | % Fluid | Mass Rate (kg/min) |
| 1 815 | 84% | 0.00425 | 16% | 0.1293 |
| 2 682 | 80% | 0.00338 | 20% | 0.1364 |
| 3 570 | 75% | 0.00266 | 25% | 0.1421 |
| 4 456 | 65% | 0.00184 | 35% | 0.1594 |

In some embodiments, (e.g. embodiments where fluid discharged from a nozzle intensifies rotation of fluid within a root canal) a pressure of air at an exit from a nozzle aperture is, for example, about 75 PSI. In some embodiments of the invention, a pressure of fluid at an exit from a nozzle aperture is, for example, about 75 PSI. In some embodiments of the invention, the pressures are, for example, about 50-60 PSI, about 60-65 PSI, about 65-70 PSI, about 70-75 PSI, about 60-80 PSI, about 75-100 PSI, about 90-130 PSI, or another higher or lower range of pressures suitable for producing cleansing of the pulp chamber.

Associated, for example, with line 1 of Table 1 are other parameters describing flow through the nozzle in some embodiments of the invention (e.g. embodiments where fluid discharged from a nozzle intensifies rotation of fluid within a root canal). These include a velocity at the slanted tube of about 27 m/sec (for a 0.8 mm tube exit aperture), corresponding to a tangential velocity of about 24.5 m/sec, and an axial velocity of about 11.5 m/sec (for a 25° slanted tube angle). In some embodiments, the flow velocity is 5-10 m/sec, 10-20 m/sec, 20-22 m/sec, 22-25 m/sec, 24-30 m/sec, 20-30 m/sec, 25-40 m/sec, 35-50 m/sec, or another larger or smaller velocity. In some embodiments, velocity components (e.g. of flow discharged from the nozzle) are divided between axial and tangential velocities according, for example, to the angle set by the slanted tube and/or an angle set by a lumen of the nozzle (e.g. conical lumen of the nozzle). In some embodiments of the invention, the tangential velocity is, for example, 5-10 m/sec, 8-15 m/sec, 10-20 m/sec, 15-30 m/sec, 25-35 m/sec, 20-40 m/sec, 40-60 m/sec, or another larger or smaller velocity. In some embodiments of the invention, the axial velocity is, for example, 5-10 m/sec, 7-15 m/sec, 8-20 m/sec, 15-22 m/sec, 20-25 m/sec, 22-30 m/sec, or another larger or smaller velocity.

Rotational velocity parameters describing flow through the nozzle comprise (e.g. in embodiments where fluid discharged from a nozzle intensifies rotation of fluid within a root canal), for example, a rotational velocity at the top of the cone of about (2 k-15 k) 8,000-12,000 RPM (optionally in the range of 2,000-4,000 RPM, 3,000-5,000 RPM, 4,000-8,000 RPM, 7,000-13,000 RPM, or 10,000-15,000 RPM, or a larger or smaller RPM) and a rotational velocity at the bottom of the cone of about 95,000 to 135,000 RPM (optionally in the range of 30,000-40,000 RPM, 30,000-50,000 RPM, 40,000-80,000 RPM, 70,000-130,000 RPM, or 100,000-160,000 RPM, or a larger or smaller RPM). These correspond also, for example, to a centrifugal acceleration near the top of the cone of about 150-220 m/s$^2$. In some embodiments, the centrifugal acceleration near the top of the cone is about 100-120 m/s$^2$, about 115-140 m/s$^2$, about 130-150 m/s$^2$, about 140-180 m/s$^2$, about 170-200 m/s$^2$, about 190-220 m/s$^2$, about 210-250 m/s$^2$, or another larger or smaller range of angular velocities. In some embodiments, the rotational speeds are higher or lower by, for example, 10-15%, 12-20%, 17-25%, 20-50%, or another higher or lower range of relative rotational speeds.

In some embodiments of the invention, (e.g. embodiments where fluid discharged from a nozzle intensifies rotation of fluid within a root canal) the mixing of gas and fluid (for example, air and water), contributes to the determination of a Reynolds number at the exit aperture of the slanted tube and/or at other places in the nozzle apparatus and/or external to the nozzle apparatus. In some embodiments for example, the Reynolds number at the exit aperture of the slanted tube is in the range of 22,500 to 49,000 (for a 0.8 mm exit aperture). In some embodiments, the range of Reynolds numbers at the exit aperture of the slanted tube is, for example, about 5,000-12,000, about 10,000-15,000, about 12,000-22,000, about 20,000-30,000, about 28,000-40,000, about 35,000-60,000, about 50,000-85,000, about 80,000-120,000, about 100,000-180,000 or another higher or lower range of Reynolds numbers.

In some embodiments, a desired effect is achieved by selecting various parameters. In some embodiments, a table is used for selection of parameters, where device parameters and/or treatment parameters (e.g. fluid parameters such as fluid speed, fluid pressure, fluid composition, treatment length) are listed based on inputs such as characteristics and/or parameters of a root canal (e.g. diameter, shape, type of tissue to be removed, extent of tissue to be removed).

In some embodiments, a desired effect is achieved by inserting inputs into a function or neural network.

In some embodiments, a desired effect is achieved by changing a portion of the apparatus. For example, in some embodiments, an apparatus includes interchangeable nozzles, where different nozzles are adapted for different treatments and/or desired effect. For example, a different nozzle for a curved root canal, a different nozzle for a straight canal, a different nozzle for abrading a root canal and a different nozzle for flushing a root canal. For example, different a supply apparatus for each of abrading a root canal and smoothing a root canal and flushing a root canal.

In some embodiments, a desired effect is achieved by changing device parameters and/or treatment parameters according to feedback. In some embodiments, feedback is manual, where a user witnesses the treatment and changes parameters based on the visual and/or manually measured parameters. In some embodiments, feedback is automatic, for example, the apparatus includes one or more sensor e.g. thermometer e.g. scale for weighing extracted material from the tooth and, for example, a processing application changes device and/or treatment parameters based on measured parameters.

In some embodiments, (e.g. embodiments where fluid discharged from a nozzle intensifies rotation of fluid within a root canal) one or more jet flows along a wall of the nozzle. In some embodiments, a jet follows a path where the jet exits the nozzle (e.g. through exit aperture 419) while in contact with a nozzle wall, for example exiting a nozzle exit aperture at a periphery of the exit aperture. In some embodiments, jet 405 passes through exit aperture 419 adjacent to the wall of nozzle 401, for example an exit point of jet 405 from nozzle 401 is positioned along a periphery of aperture 419, defined by the walls of the nozzle. Optionally, jet 405 does not exit aperture 419 from a central point of the aperture.

In some embodiments, as seen on FIG. 4B, an access cavity 423 is created, as previously mentioned, through crown 425 of the tooth. Optionally, access cavity 423 passes through layers of dentin and enamel tissue. In some embodiments, access cavity 423 exposes pulp chamber 427. In some embodiments, pulp chamber 427 is cleaned using the described system and/or method. Optionally, the pulp chamber is cleaned using other means. In some embodiments, the system and/or method as described are used for cleaning and/or abrading any other part of the tooth, but may have special advantages when used for treating a root canal.

In some embodiments, at least a portion of nozzle 401 passes through access cavity 423. In some embodiments, at least a portion of nozzle 401 is inserted through pulp chamber 427. In some embodiments, at least a portion of nozzle 401, for example the tip including exit aperture 419, is narrow enough to enter into at least a portion of the internal lumen of root canal 403.

In some embodiments, nozzle 401 is connected to a handle 421. In some embodiments, an input pipeline passes through handle 421 and connects to nozzle 401, as will be further explained. In some embodiments, handle 421 is used for maneuvering nozzle 401 (e.g. a user grasps handle 421).

FIG. 4C is a geometrical representation of angled jet 405. In the described figure, angled jet 405 exits a nozzle at point A, and hits root canal wall at point B. In some embodiments, point B is located on a circumference of the root canal entrance. Alternatively, point B is located below the circumference of the root canal entrance, for example 0.1 mm, 1 mm, 3 mm and/or intermediate distances below.

As shown in this figure, axis x extends along a diameter of the root canal, perpendicular to the root canal wall. As mentioned herein, axis y is vertical axis running longitudinally, for example in parallel to the root canal wall. Axis z is perpendicular to both axis x and y. Line A'B is a projection of angled jet 405 on the xz plane. In some embodiments, an angle α between angled jet 405 (line AB) and the xz plane, is a sharp angle, for example an angle between 10-85°, such as 20, 35, 75°. In some embodiments, an angle β between the projection A'B of angled jet AB and tangential axis z is a sharp angle, for example an angle smaller than 90°, such as 20°, 50°, 70°. In some embodiments, the size of angle β affects the path of the flow. A potential advantage of a sharp angle β, for example ranging between 5-10°, 15-20°, includes creating a more effective flow path, in which the flow passes closely along the canal wall. Optionally, the size of angle β may affect the radii of the helical flow through the root canal. In some embodiments, angle β may be selected to encourage adhesion of flow to wall and/or reduce bouncing. Optionally, for example if the longitudinal axis of the nozzle unite with the longitudinal axis of the root canal, as previously mentioned, a similar angle β is formed with respect to exit aperture 419 of the nozzle (i.e. tangential to the walls of the nozzle at exit aperture 419).

In some embodiments, a velocity vector V of angled jet 405 (line AB) can be described by its three velocity components along the axis, showed in this figure as Vx (along axis x), Vy (along axis y) and Vz (along axis z). In one example, velocity component Vy may be 2-50 m/sec, and the velocity component Vz may be 0.5-25 m/sec.

In some embodiments, additionally and/or alternatively to the angled jets, an axial jet (for example extending in parallel to vertical axis y) may be used.

In some embodiments, the fluid forming jet 405 and/or components of the fluid rotate around the jet's axis.

In some embodiments, any of the described above ideas and/or methods or combinations them may be implemented in the embodiments described below and/or any other embodiment of the invention.

Figure 5:
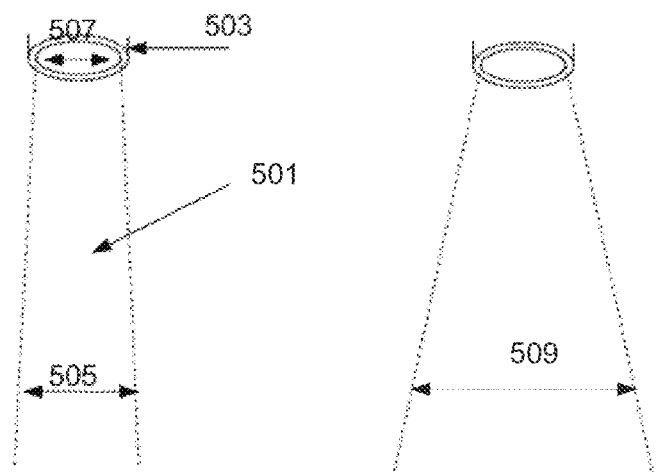
FIG. 5 is a side view of various outlines of a beam of angled fluid jets exiting a nozzle, according to some embodiments of the invention.

FIG. 5 shows a side view of various outlines of a beam 501 of angled fluid jets (not shown in this figure), according to some embodiments of the invention. The outlines of the beams shown in this figure describe beams that exit a nozzle 503, which have not yet entered a root canal.

In some embodiments, as previously described, a beam of a plurality of angled fluid jets is discharged from nozzle 503. In some embodiments, the structure of the nozzle affects the shape of the beam. In some embodiments, the size and/or shape of the tip of the nozzle affects the shape of beam. For example, an elongated tip, as will be further shown, may be used to create a narrower, focused beam of angled jets. Alternatively, a shorter tip may be used to create a more scattered beam of angled jets.

In some embodiments, a diameter 505 of a beam extends beyond a diameter 507 of the exit aperture of the nozzle. In some embodiments, as shown in this figure, a diameter of the beam changes, for example increases as the flow advances towards the root canal entrance. Optionally, this outline is created due to opposite angled jets (for example jets exiting from opposite ends of a diameter of the nozzle). In some embodiments, for example as shown in this figure, various beams may have different diameters at a certain axial distance from the exit aperture of the nozzle. For example, diameter 505 is shorter than diameter 509.

In some embodiments, the outline of the beam is the circumscribing shape of the beam. Optionally, the outline of the beam is fully filled with flowing fluid. Alternatively, the outline of the beam is formed with constant spaces, for example between angled jets comprising the beam. Alternatively, the beam is formed with transient spaces.

In some embodiments, a large number of angle jets make up the circumscribed beam. In some embodiments, the circumscribed beam is a symmetric shape, for example, with circular cross-section. In some embodiments, the circumscribed beam, once discharged into a root canal, matches the shape of the root canal.

In some embodiments, for example when an exit aperture of the nozzle is positioned within a lumen of the root canal, the jets of the beam may immediately hit the root canal wall, which may channel the fluid to a helical flow along the wall.

In some embodiments, the designated flow along the root canal wall is a result of the original direction in which the angled jets exit the nozzle, and/or a result of the angle created when the jets hit the root canal.

In some embodiments, at least some of the angled jets flow in the same direction.

In some embodiments, a ratio between air and liquid affects the shape of the beam. Optionally, the fluid density affects the shape of the beam.

In some embodiments, the beam shape is affected by one or more of the following: a vertical velocity component of fluid within the nozzle, an angular velocity component of the fluid within the nozzle, a centrifugal effect formed within the nozzle, a pattern of flow (e.g. circular) within the nozzle, a pressure difference between the nozzle and the atmospheric pressure and/or pressure formed within the canal.

In some embodiments, structural elements such as internal guide tubes within the nozzle may affect the shape of the beam. In some embodiments, the outline of the beam may have other shapes such as, for example, a bottle-neck shape, a cylindrical shape, a bell shape, and/or any other shapes.

In some embodiments, the exit aperture comprises a circular rim. Alternatively, the exit aperture comprises a rim having a different shape, for example elliptical. In some embodiments, at least a portion of the fluid flows adjacent and/or on the walls of the nozzle, for example forming a central portion of the exit aperture in which air exists.

In some embodiments, structural components of the nozzle are movable for example to manipulate a geometry of the beam, for example change a beam diameter.

In some embodiments, the angle jet and/or beam of angled jets exit through a center of the exit aperture. Additionally or alternatively, the jet or beam exit the nozzle while flowing along the walls of the nozzle at the exit aperture.

In some embodiments, the beam is shaped a cylinder, for example having a diameter ranging between 0.2-4 mm, such as 0.3 mm, 1 mm, 2.3 mm. The beam may rotate around its axis. The rotating beam may widen to a conical configuration, comprising one more angled jets which are formed at the external periphery of the beam.

In some embodiments, fluid exiting the nozzle may partially stick to the nozzle walls at the exit aperture. In some embodiments, the beam will be diverted as a result of adhering to the wall.

In some embodiments, the flow forming the beam comprises a turbulent flow regime, which may affect the shape of the beam and/or may divert the beam.

In some embodiments, the beam is shaped as a cone and the flow within the cone flows at an angle. Optionally, the cone is a continuous cone. In some embodiments, the flow does not flow only along a longitudinal axis of the cone, but further comprises a circumferential component, so that it effectively comprises a plurality of angled jets. In some embodiments, the velocity of the fluid determines the angular spread of the cone. For example, the vertical and/or angular velocity component of the fluid may affect the angular spread of the cone. In some embodiments, a pressure difference between the nozzle and externally to the nozzle, for example in the root canal, affects the angular spread of the cone. In some embodiments, the centrifugal acceleration of the fluid within the nozzle affects the angular spread of the cone.

In some embodiments, the cone shaped beam is formed of a single angled jet. Alternatively, the cone shaped beam is formed of a plurality of jets flowing on a plane defined by the cone and/or at an angle to a plane defined by the cone.

In some embodiments, an angular velocity of the flow ranges between 1-300°/sec, such as 1°/sec, 10°/sec, 100°/sec.

In some embodiments, a thickness of the walls of the cone (i.e. flow walls) ranges between 0.01-5 mm, such as 0.03 mm, 0.1 mm, 2 mm, 4.5 mm.

Exemplary Apparatus Structure, According to Some Embodiments of the Invention

Figure 6A:
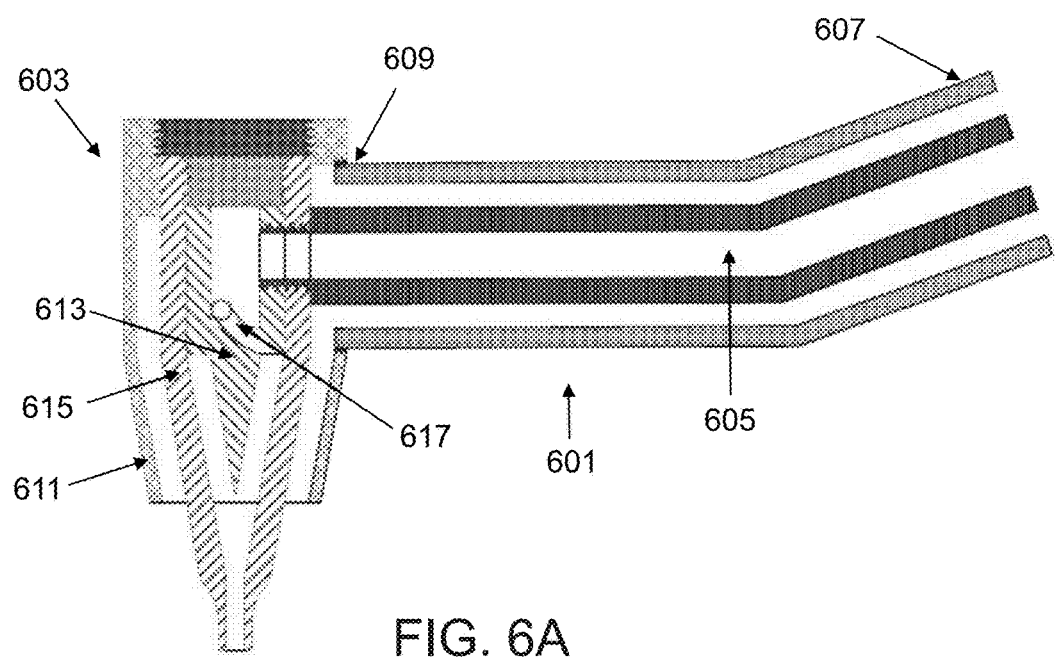
FIGS. 6A-6B are a cross section and an outline view of an apparatus comprising a handle and a conical nozzle, according to some embodiments of the invention.
Figure 6B:
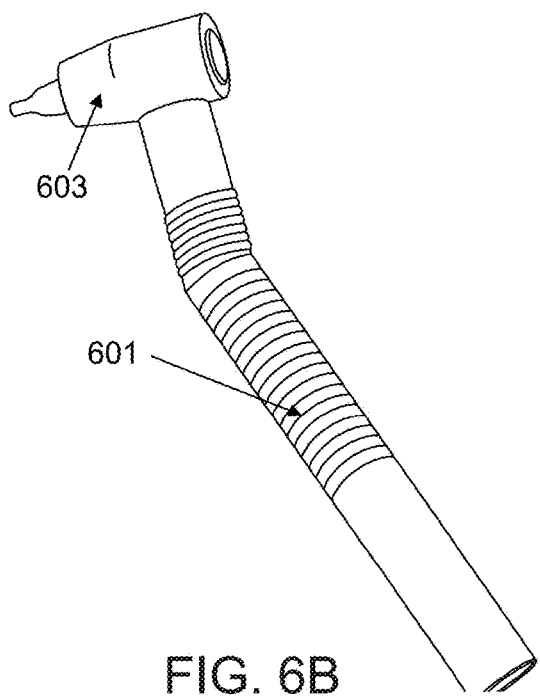

FIG. 6A is a cross section view of an embodiment of an apparatus comprising a handle 601 and a nozzle 603, for cleaning and/or abrading a root canal with one or more angled fluid jets. FIG. 6B is an outline of the apparatus comprising the handle and nozzle.

In some embodiments, handle 601 comprises one or more pipes 605, optionally passing longitudinally along an internal lumen of the handle.

In some embodiments, pipe 605 ends at its distal end in an entrance aperture to nozzle 603, for example an entrance aperture leading to an internal cone of the nozzle, as will be further described.

In some embodiments, a proximal end 607 of handle 601 is configured for manual gripping by a user.

In some embodiments, a distal end 609 of handle 601 connected to nozzle 603 is configured for insertion into a tooth, for example through a pulp chamber, to allow the positioning of an exit aperture of nozzle 603 above a root canal entrance as previously described. Optionally, handle 601 comprises a narrowing portion in proximity to nozzle 603 (not shown in this figure), which may facilitate inserting distal end 609 through, for example, an access cavity created in a tooth. In some embodiments, a height of the nozzle is small enough to enable its insertion into the mouth, for example ranging between 5-15 mm.

In some embodiments, inner pipe 605 extends beyond the proximal end 607 of handle 601. Optionally, liquid passes through inner pipe 605, for example by being connected at the proximal end to a liquid tank. Optionally, air passes through inner pipe 605, for example by being connected at the proximal end to an air compressor. In some embodiments, the fluid comprising both air and liquid passes through pipe 605. In some embodiments, two pipes are used, one for passing liquid and the other for passing air. In some embodiments, air and abrasive powder (for example transferred from an abrasive powder tank) pass together through at least one of the pipes. In some embodiments, a pipe may be surrounded by another pipe (co-centered pipes), such that the inner pipe is used, for example, for transferring liquid, and the outer pipe is used, for example, for transferring air. In some embodiments, air, liquid, abrasive powder and/or combinations of them pass through at least one of the pipes through the handle.

In some embodiments, the pipes may connect, for example at the proximal end 607 of handle 601, to create the fluid of air and liquid which then circulates within nozzle 603 until discharged in the form of angled jets.

In some embodiments, nozzle 603 has conical structure, for example, as will be explained in the following figure. In some embodiments, nozzle 603 comprises an internal cone 613 positioned within an external cone 615. In some embodiments, a slanted tube 617 is used for passing fluid from internal cone 613 to a lumen between the two cones, for example, as will be explained by the next figure. In some embodiments, the slanted tube 617 may deflect in any direction within the internal cone. Optionally, one or more additional tube (e.g. additional slanted tubes next to slanted tube 617) is used for passing fluid from internal cone 613 to a lumen between the two cones and/or is located in the region of space above internal cone 613.

In some embodiments, nozzle 603 comprises an additional cone 611, for example used for suctioning the fluid returning upwards through the root canal, for example, as will be further explained in FIG. 10. In some embodiments, the sucked fluid may pass through the handle, for example passing in an opposite direction to the air and/or liquid passed into nozzle 603. Optionally, the sucked fluid passes through one or more pipes in the handle. Optionally, proximal end 607 of handle 601 is connected to a pipe and/or tank and/or any other element used for disposing the sucked fluid.

In some embodiments, the nozzle and/or any components of it and/or the handle may be made of various materials, such as, for example, one or more of stainless steel, titanium, aluminum, anodized coated aluminum, PPM, plastic, or other biocompatible and/or sterilizable materials and/or combination of materials. In some embodiments, at least a part of the nozzle and/or handle is disposable. In an exemplary embodiment of the invention, the nozzle is formed of rigid materials and/or geometries, however, a tip thereof may be made flexible.

In some embodiments, the nozzle may be manufactured and/or used separately from the handle and/or the rest of the system, described below.

In some embodiments, the handle may comprise controls such as on/off button to control the duration of the treatment, a dial to control the ration between air and liquid, etc. In some embodiments, the device comprises a calibration table and settings are selected according to the table.

Figures 7A, 7B:
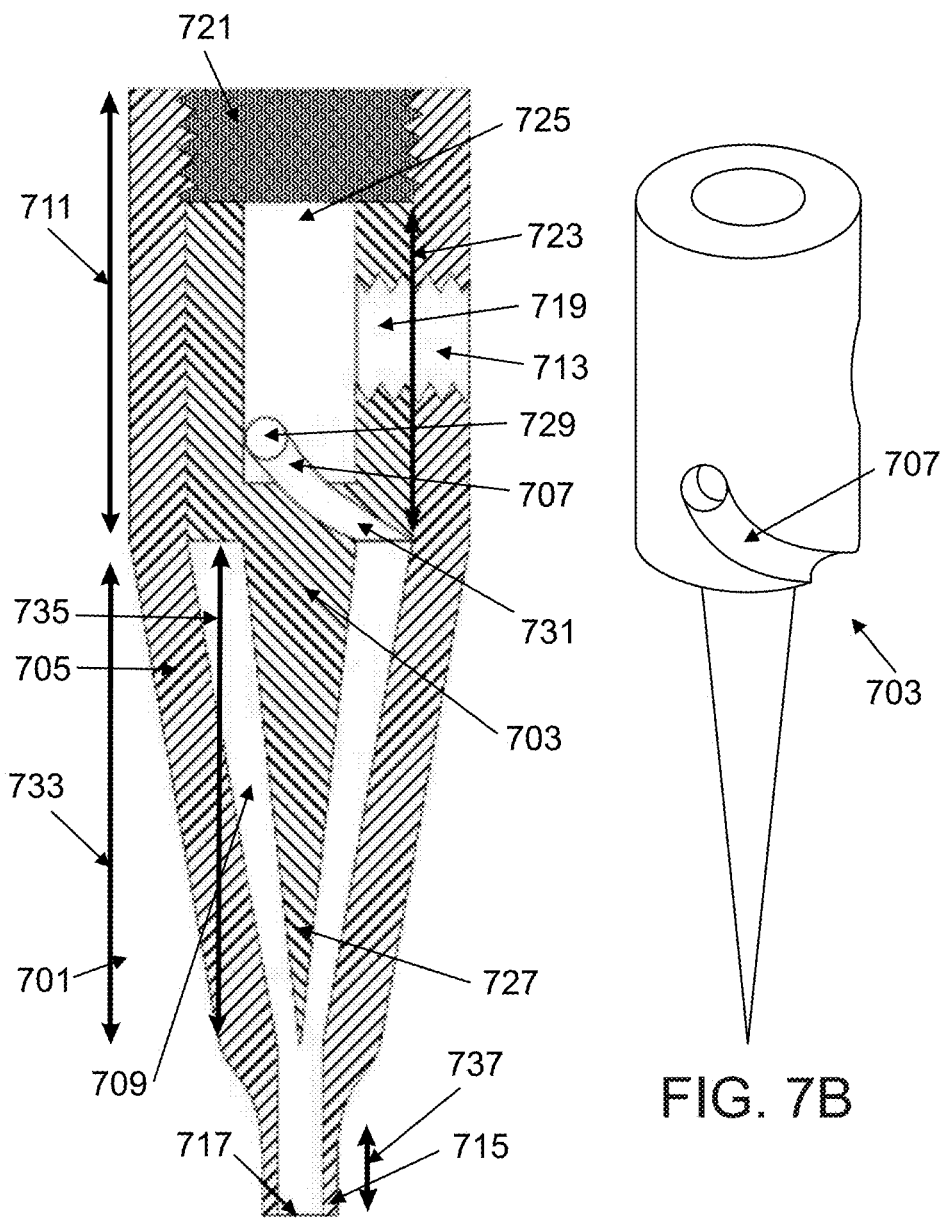
FIGS. 7A-7B are a cross section of a conical nozzle and a side view of an internal cone configured within the conical nozzle, according to some embodiments of the invention.

FIG. 7A is cross section view of a conical nozzle 701, and FIG. 7B a side view of an internal cone 703 configured within conical nozzle 701, according to some embodiments of the invention.

In some embodiments, nozzle 701 comprises an internal cone 703 positioned within an external cone 705. In some embodiments, internal cone 703 and external cone 705 are connected by a tube, for example a slanted tube or channel 707 extending between an inner lumen of internal cone 703 and a lumen 709 between an external face of internal cone 703 and an internal face of external cone 705.

In some embodiments, external cone 705 has a cylindrical upper portion 711. In some embodiments, external cone 705 has a recess 713 for example configured along a face the cylindrical upper portion 711, optionally in continuance to a pipe of a handle as described above, for allowing fluid to enter into internal cone 703. In some embodiments, the recess may be circular, triangular, rectangular or any shape allowing the flow of fluid through into internal cone 703. Optionally, the size and/or shape of the recess is determined according to the size and/or shape of an entrance aperture 719 to internal cone 703.

In some embodiments, external cone 705 has an exit aperture 715, which may be positioned above the entrance to a root canal. In some embodiments, the exit aperture may is circular, for example having a diameter 717 ranging between 0.3-2 mm. Optionally, the diameter of the exit aperture is determined according to a need, for example according to a diameter of the root canal entrance.

In some embodiments, external cone 705 comprises a narrow needle-like tip portion 737. In some embodiments, the length of narrow needle-like tip portion 737 ranges between 0.2-7 mm. In some embodiments, narrow tip 737 (comprising exit aperture 715) is inserted into a lumen of the root canal. Optionally, narrow tip portion is inserted to a distance of 0.2 mm, 0.5 mm, 1 mm, 2.5 mm and/or any intermediate or higher distances measured longitudinally from the root canal entrance. In some embodiments, an external diameter of tip portion 737 ranges between 0.5-2.5 mm, and an internal diameter (optionally being the diameter of the exit aperture, as previously mentioned) ranges between 0.3-2 mm. in some embodiments, the diameter of tip portion 737 is small enough to allow insertion of tip portion 737 into at least a portion of the root canal. Optionally, tip portion 737 is flexible, for example made of flexible material. In some embodiments, needle like tip portion 737, for example shaped as a narrow tube, is made of a disposable material. Optionally, needle like tip portion 737 can be assembled on the nozzle, for example by a user.

In some embodiments, cylindrical upper portion 711 is covered by a covering lid 721, for example for preventing fluid from exiting through the top of nozzle 701.

In some embodiments, covering lid 721 may be screwed on top of the cylindrical upper portion 711.

In some embodiments, internal cone 703 comprises a cylindrical upper portion 723, which may be sized and/or shaped according to cylindrical upper portion 711 of external cone 705.

In some embodiments, internal cone 703 comprises an entrance aperture 719, for example configured along a face of the cylindrical upper portion 723. In some embodiments, entrance aperture 719 is configured in continuance to recess 713 of external cone 705. In some embodiments, the entrance aperture may be circular, triangular, rectangular or any shape allowing the flow of fluid through.

In some embodiments, cylindrical upper portion 723 fits within cylindrical upper portion 711 such that no space is formed between them, for example preventing fluid from flowing between the two upper portions of the cones. In some embodiments, a diameter of cylindrical upper portion 723 is only slightly smaller than a diameter of cylindrical upper portion 711. For example, a diameter of cylindrical upper portion 723 ranges between 2-18 mm and a diameter of cylindrical upper portion 711 ranges between 3-20 mm.

In some embodiments, a top 725 of cylindrical upper portion 723 is open. In some embodiments, if cylindrical portion 723 of internal cone 703 extends to the same height as cylindrical portion 711, covering lid 721 may cover both internal and external cones.

In some embodiments, a tip 727 of internal cone 703 is closed, to avoid fluid from passing through. In some embodiments, tip 727 extends to exit aperture 715, and/or extends beyond exit aperture 715, for example 1 mm beyond.

In some embodiments, a slanted tube 707 extends between an inner lumen of internal cone 703 and a lumen 709 between an external face of internal cone 703 and an internal face of external cone 705. Optionally, the entrance 729 to slanted tube 707 serves as the exit aperture for the fluid exiting internal cone 703. Optionally, exit 731 of slanted tube 707 is configured at the lowest point along a face of the cylindrical upper portion 723, such that it leads to lumen 709.

In some embodiments, the size of lumen 709 is determined according to a difference in diameters of narrowing portions 733 and 735 of external cone 705 and internal cone 703 respectively. For example, an initial diameter of narrowing portion 733 is 3 mm and an initial diameter of narrowing portion 735 is 0.3 mm. In some embodiments, a distance between the internal and external cones forming lumen 709 is constant, for example a distance of 1 mm. In some embodiments, a distance between the internal and external cone changes, for example increases along a vertical axis.

In some embodiments, the flow in lumen 709 increases in velocity as it advances from the upper part of the lumen (e.g. close to exit 731), distally towards the lower part of lumen 709.

In some embodiments, fluid, optionally including liquid, air, and/or abrasive powder or combinations of the above, flows through recess 713 of external cone 705, into entrance aperture 719 of internal cone 703, and into a lumen of internal cone 703. In some embodiments, as the fluid accumulates within internal cone 703, pressure may rise and the fluid may be forced through entrance 729 into slanted tube 707. Once the fluid exits slanted tube 707 through exit 731, the fluid circulates within lumen 709 between the internal and external cones. Optionally, the circulation is helical. Optionally, as the lumen narrows, the velocity of the flow of fluid increases. In some embodiments, the helical circulation causes the fluid to exit nozzle 701 through exit aperture 715 of external cone 705 in the form of one or more angled fluid jets as describe above. In some embodiments, helical circulation continues once the fluid exits the nozzle, for example, the helical circulation continues in air (e.g. before impact with the root canal wall and/or fluid within the root canal). For example, in some embodiments, helical circulation continues in the root canal. In some embodiments, helical circulation continues due to surface tension of the flow (e.g. jet).

In some embodiments, a suction pulse is short enough in duration so that rotation in the root canal does not stop and/or does not reduce to below 10% of a maximum. In some embodiments, rotation of fluid in the root canal is stopped and/or reduced to zero e.g. by discharge of fluid at an opposing direction to rotation and/or by suction.

In some embodiments, rotating and/or helical movement of fluid within the nozzle continues when the fluid is discharged from the nozzle, and/or continues when the fluid enters a root canal which optionally contains or is full of fluid.

In some embodiments, due to the ratio between air and liquid, for example 90% air and 10% liquid, the fluid entering lumen 709 is an aerosol. A potential advantage of the aerosol includes reducing the friction created between the surface of the cones and the fluid, which may optionally allow for a higher velocity of the fluid (aerosol).

In some embodiments, any of the cones may be nonsymmetrical and/or otherwise distorted. In some embodiments, a needle-like tube can be assembled onto the nozzle, for example onto the exit aperture.

Figure 8A:
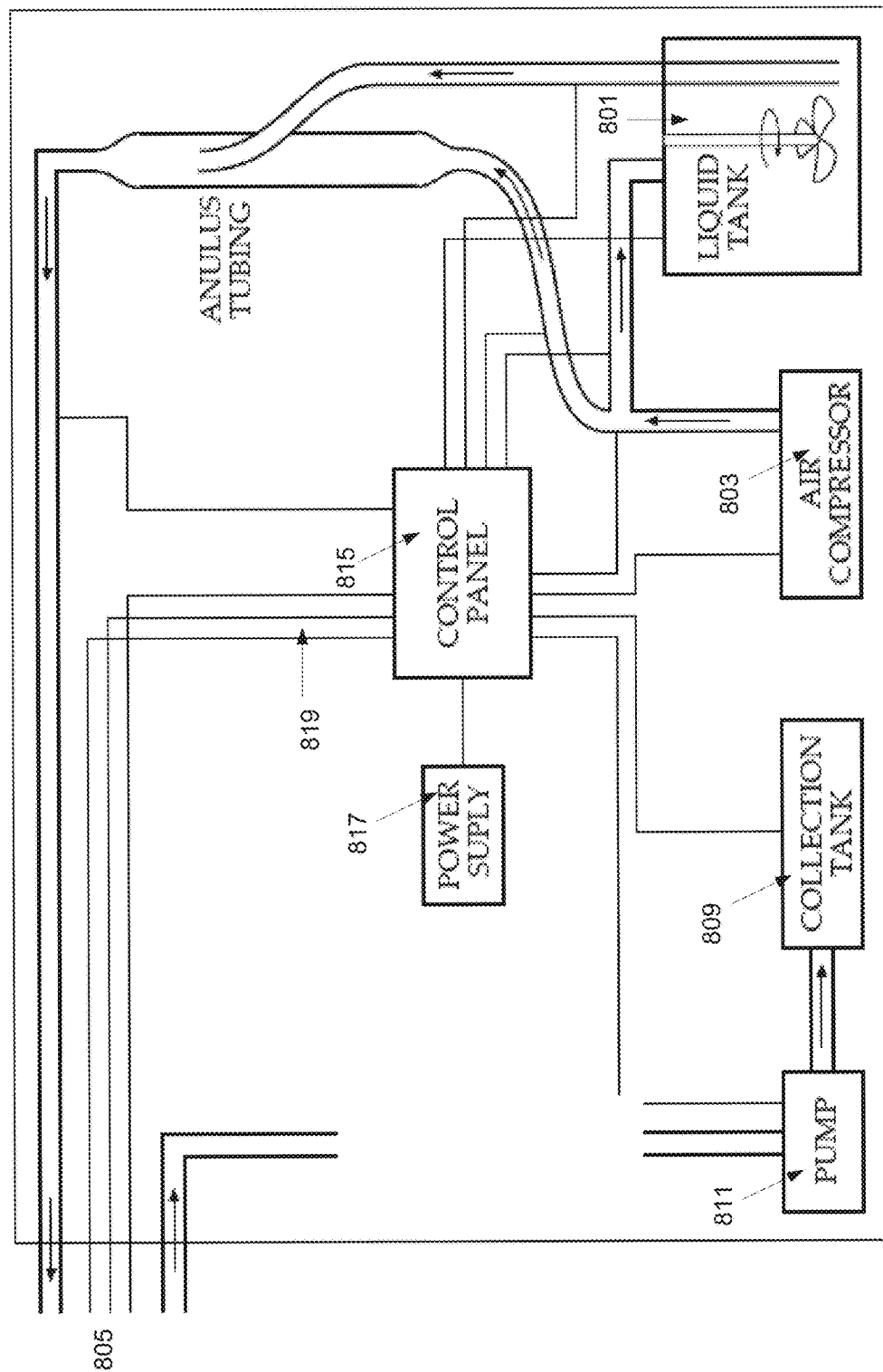
FIGS. 8A-8B are schematic diagrams of exemplary systems for treating a root canal, according to some embodiments of the invention.
Figure 8B:
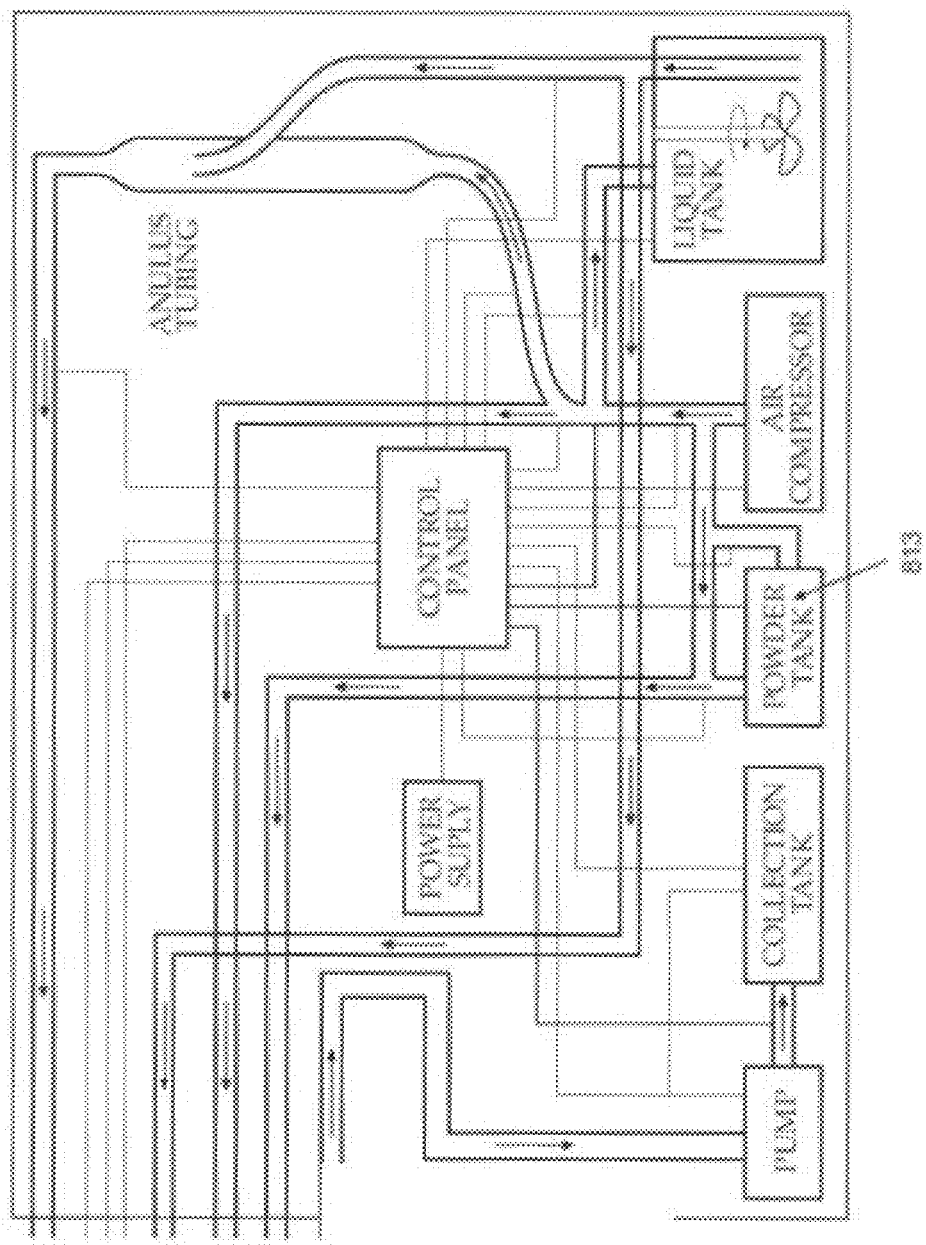

Exemplary Systems for Treating a Root Canal, According to Some Embodiments of the Invention FIGS. 8A and 8B are schematic diagrams of exemplary systems for treating a root canal, according to some embodiments of the invention.

In some embodiments, the system comprises a liquid tank 801, for example for storing liquid such as water, disinfectant, and/or medicine. Optionally, more than one liquid tank is used, for example for storing medicine separated from water, or disinfectant separated from medicine. In some embodiments, the capacity of the liquid tank ranges between 0.2-50 L. In some embodiments, the liquid tank may be made of aluminum, steel, plastic, or any material capable of containing the liquid and withstanding air pressure. In some embodiments, liquid tank 801 may comprise a mixing element, such as a mechanical, hydraulically, or electrical whirling element for continuous mixing of the liquid.

In some embodiments, liquid tank 801 is connected to an air compressor 803. In some embodiments, the air compressor pushes air into liquid tank 801. In some embodiments, the pressure created by the air compressor ranges between 5-500 PSI, 1-100 PSI, 100-200 PSI. Optionally, as the air compressor pushes air into the liquid tank, the pressure rises within the tank and liquid is forced through an exit aperture of the tank. In some embodiments, the exit aperture of the tank is connected a handle 805 of an apparatus as described above, for example connected by a pipe.

In some embodiments, the system comprises a collection tank 809. Optionally, collection tank 809 is used for the returning fluid exiting the root canal, which may comprise organic substance, nonorganic substance, and/or debris. In some embodiments, collection tank 809 is connected to a pump 811 and/or to a venturic connector. In some embodiments, the pump is used for suctioning the returning fluid, for example through a suctioning cone of a nozzle (not shown in this figure), through handle 805, and through one or more pipes leading to collection tank 809. Optionally, a suction cap may be placed on the tooth and/or inside the mouth for collecting returning fluid, saliva, and/or debris.

In some embodiments, as shown in FIG. 8B, a powder tank 813 is used for storing the abrasive powder. In some embodiments, powder tank 813 is connected to air compressor 803.

Air, liquid, abrasive powder and/or any combinations of them may pass through one or more pipes of the system.

In some embodiments, as shown in FIG. 8A, a pipe connected to air compressor 803 and a pipe connected to liquid tank 801 are joined at any point along a path leading to handle 805, so that the air and liquid are mixed together before entering handle 805. In some embodiments, as shown in FIG. 8B, a plurality of pipes may lead air, liquid, abrasive powder and air, liquid and air and/or any combination of them into handle 805. In some embodiments, liquid and air or any other combination may flow through co-centered pipes.

In some embodiments, a pipe includes micro pores, for example allowing air to flow inside but preventing liquid from exiting the pipe.

In some embodiments, any of the above described components and/or combinations of them are passed separately, and mixed together only at a lumen of the nozzle (not shown in this figure).

In some embodiments, a control panel 815 is used for example for controlling the passing of air, liquid, and/or abrasive powder. In some embodiments, pressure, velocity, volume, flow rate and/or any other parameters may be controlled. In some embodiments, the duration of treatment is controlled using control panel 815. In some embodiment, control panel 815 may be connected to a power supply 817.

In some embodiments, two or more components of the system such as the liquid tank, air compressor, pump, and/or any other components are connected by an electrical circuit 819. In some embodiments, control panel 815 is used for activating electrical circuit 819 to control the functioning of one or more components of the system. For example, an electrical signal may be sent using control panel 815 to activate air compressor 803, to release liquid from liquid tank 801, to pass fluid into the handle, open a valve along a pipe or junction, and/or any other functions of the system.

In some embodiments, the system is configured for connecting to a standardized pressurized air and/or gas source which may be available in a dental clinic, for example replacing and/or in addition to air compressor 803.

In this figure, the thin lines connecting between components may represent control and/or sensing connections, such as electrical connections, while the thick lines represent a pipeline in which liquid, gas, powder, or any combination thereof are delivered to and from the nozzle.

Various Structures of a Nozzle of the Apparatus, According to Some Embodiments of the Invention FIGS. 9A-9D illustrate an embodiment of a conical nozzle 901 comprising a pipe 903, extending between handle 905 and exit aperture 907 of nozzle 901. FIG. 39, as described above, illustrates an additional exemplary nozzle comprising a pipe.

Figure 9A:
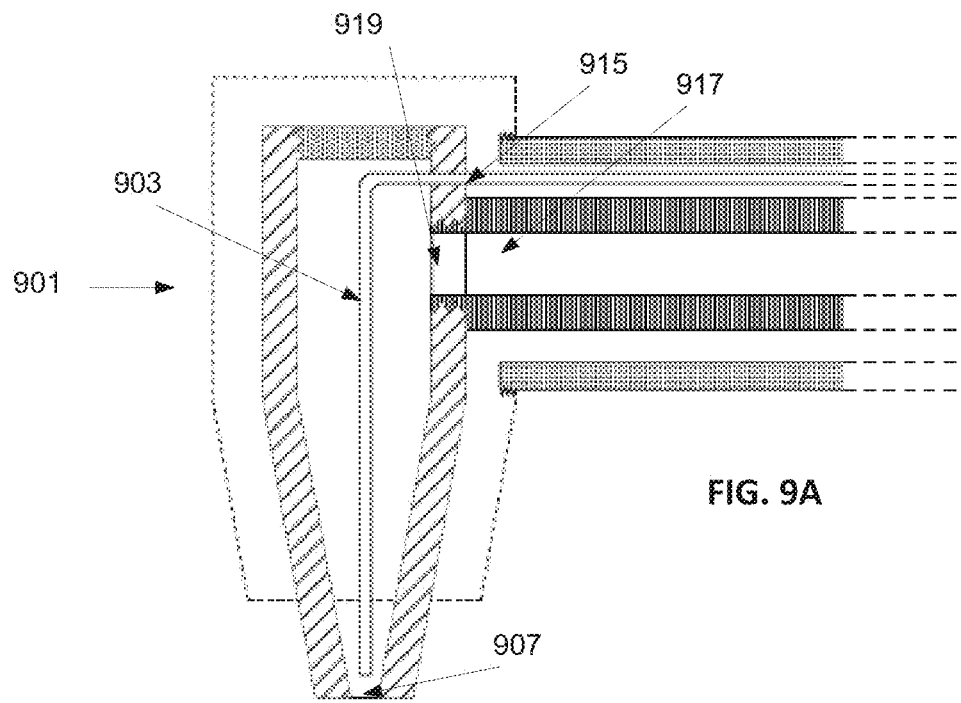
Figure 9B:
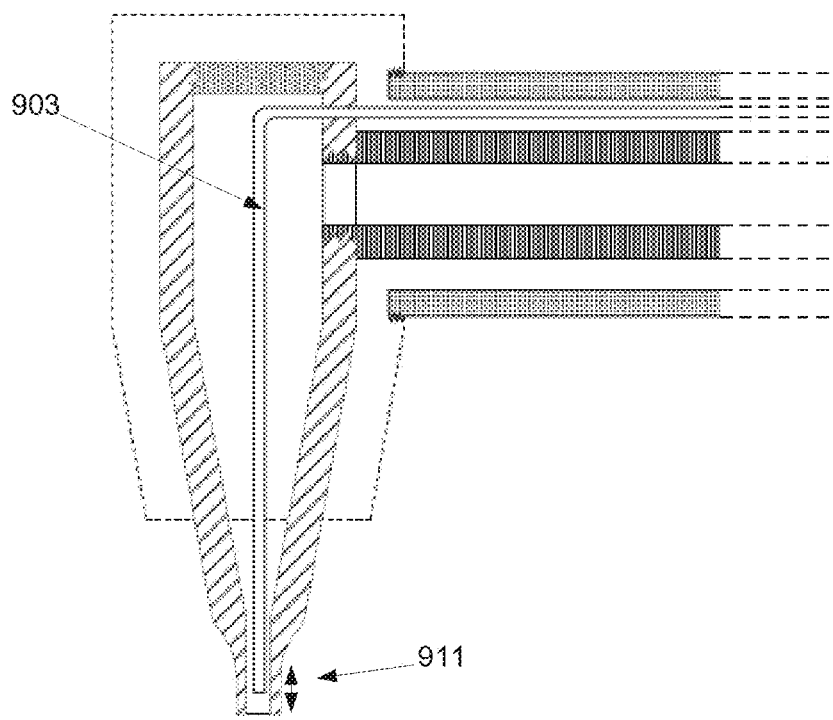

FIGS. 9A and 9B illustrate two embodiments including pipe 903. FIG. 9B shows conical nozzle 901 having a narrow tip portion 911 as previously described. FIG. 9A conical nozzle 901 having flat tip portion 913. FIG. 9C is a cross section of a nozzle similar to the one described in the above figures that further includes pipe 903. FIG. 9D is a side view of an internal cone of that nozzle.

In some embodiments, longitudinal pipe 903 is used for passing air, abrasive powder, liquid and/or combination of them flow through nozzle 901. In some embodiments, flowing is performed through pipe 903 in parallel to a fluid flowing through a main path of nozzle 901, as described above.

In some embodiments, a distal portion of pipe 903 protrudes from exit aperture 907. In some embodiments, for example as shown in FIG. 9B, if narrow tip portion 911 is inserted into at least a portion of the root canal, pipe 903 may be used for delivering any of the above materials into a location within the root canal.

In some embodiments, pipe 903 affects the direction of the discharged angled fluid jets by diverting them.

In some embodiments, a proximal end of pipe 903 is connected to any of the above described components of the system, such the fluid tank, the air compressor, the powder tank and/or any of the pipes.

In some embodiments, the internal and external cones comprising nozzle 901 include an aperture 915 for the passing of pipe 903, for example configured along a face of the upper cylindrical potion of both cones, such as above or below a recess 917 and entrance aperture 919 of the external and internal cones respectively.

In some embodiments, as shown on FIGS. 9C and 9D, pipe 903 passes on a parallel plain to slanted tube 909. In some embodiments, pipe 903 intersects tube 909, for example to enable mixing of the fluid with the substance passing through pipe 903.

In some embodiments, nozzle 901 does not include an internal cone.

Figure 10A:
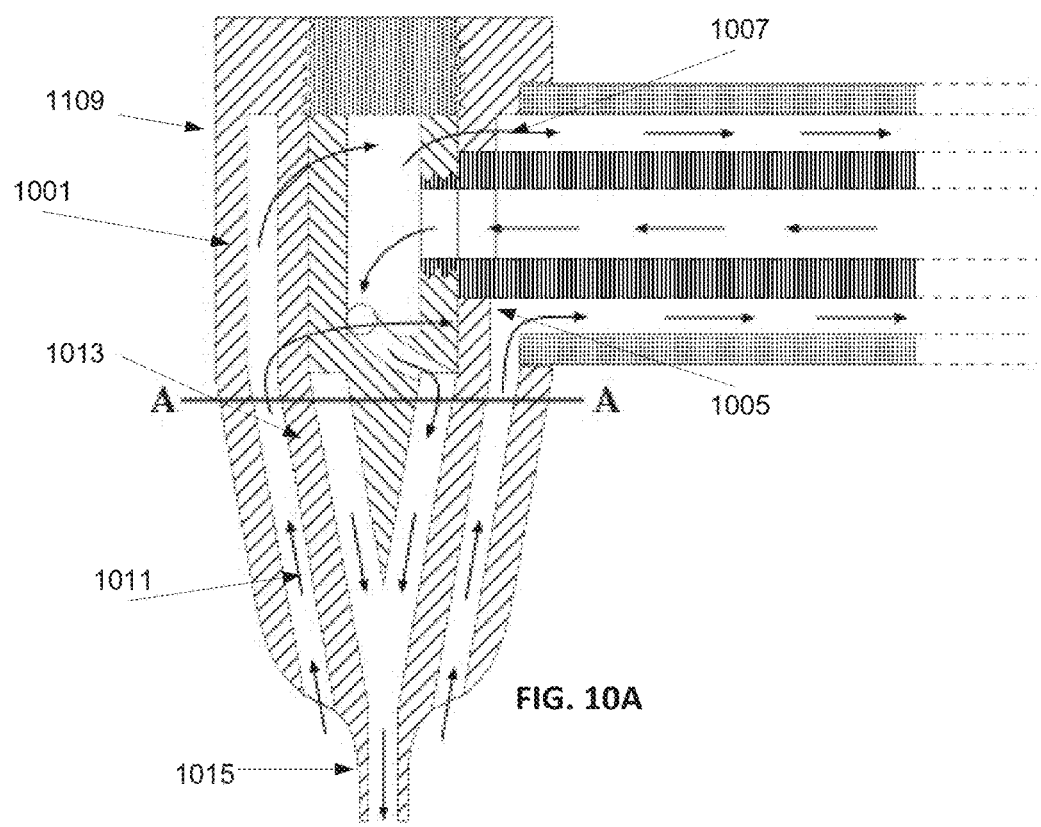
FIGS. 10A-10B are illustrations of a nozzle comprising a suction cone, and a horizontal cross section of the nozzle respectively.
Figure 10B:
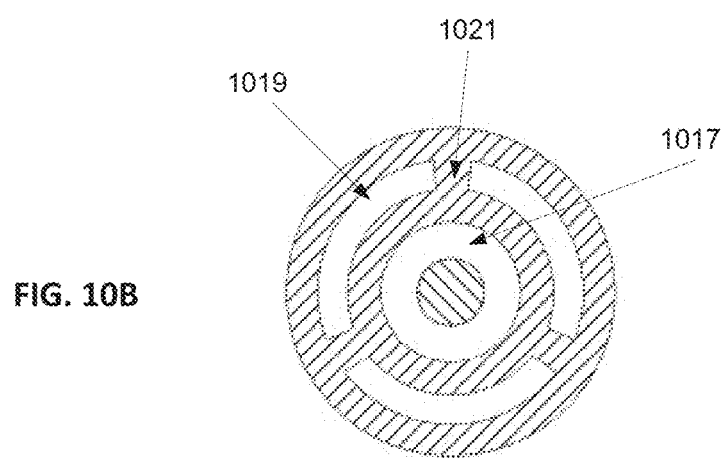

FIG. 10A illustrates a nozzle comprising a suction cone 1001, as previously mentioned, and FIG. 10B illustrates a horizontal cross section of the nozzle.

In some embodiments, suction cone 1001 is shaped and/or sized according to an external cone and/or an internal cone of the nozzle.

In some embodiments, suction cone 1001 is assembled externally to the nozzle. In some embodiments, suction cone is attached to the nozzle during a molding process. In some embodiments, other mechanical means such as pins or screws are used for attaching the suction cone.

Optionally, a lumen 1011 is formed between the narrowing portions of suction cone 1001 and an external cone 1013 of the nozzle. In some embodiments, this lumen comprises channels or tubes.

In some embodiments, the distal tip of the nozzle 1015 protrudes from suction cone 1001.

In some embodiments, suction cone 1001 has one or more exit apertures 1005 and/or 1007. Optionally, exit apertures 1005 and/or 1007 are configured along a cylindrical upper portion 1009 of suction cone 1001. In some embodiments, exit apertures 1005 and/or 1007 are connected to handle, optionally through pipes. In some embodiments, the pipes are connected to a pump such as a vacuum pump for sucking the returning fluid upwards through the nozzle and through the handle to dispose it, as previously described in FIG. 8.

In some embodiments, the sucked fluid may pass through suction cone 1001 in a lumen between an internal face of the suction cone and an external face of the external cone of the nozzle. In some embodiments, if the lumen comprises channels or tubes, the fluid may be sucked directly through the tubes.

In some embodiments, the fluid returning upwards through the root canal may contain the removed organic and/or inorganic substances such as pulp tissue, nerve tissue, blood vessels, abrasive powder, and/or other debris removed by the flow.

In some embodiments, suction cone 1001 is covered by a lid, which is optionally screwed on top of a lid of the external cone of the nozzle to prevent fluid from exiting through the top of suction cone 1001.

FIG. 10B shows a horizontal cross section of the nozzle along line AA. A central circular lumen 1017 is the lumen formed between the internal and external cones. The three arched lumens 1019 are the lumens formed between the external cone and suction cone 1001. In some embodiments, a space 1021 between arched lumens includes anchors for attaching suction cone 1001 to the narrowing portion of the nozzle.

Figure 11A:
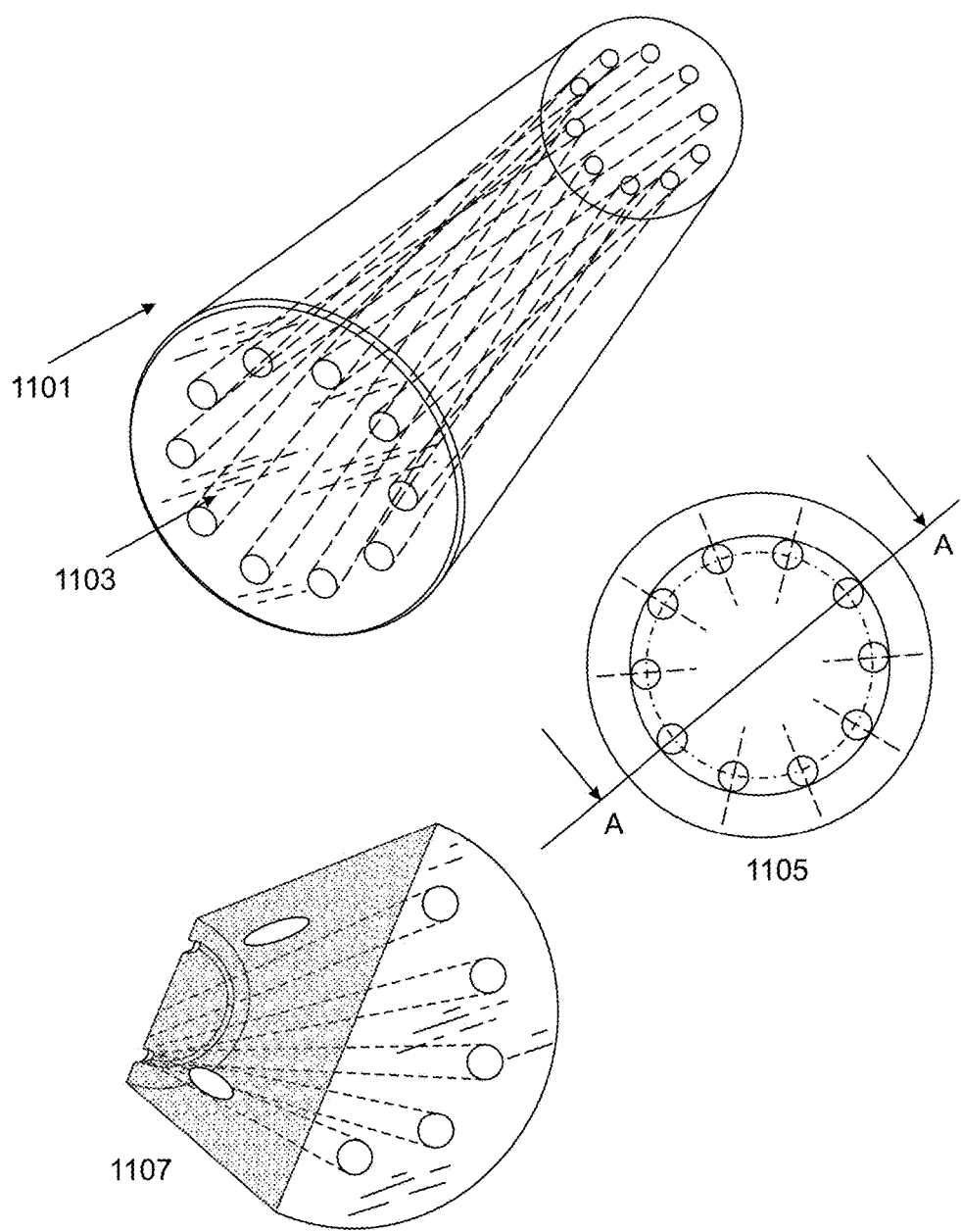
FIGS. 11A-11B are illustrations of a nozzle including one or more directing channels for creating the one or more angled fluid jets, according to some embodiments of the invention.
Figure 11B:
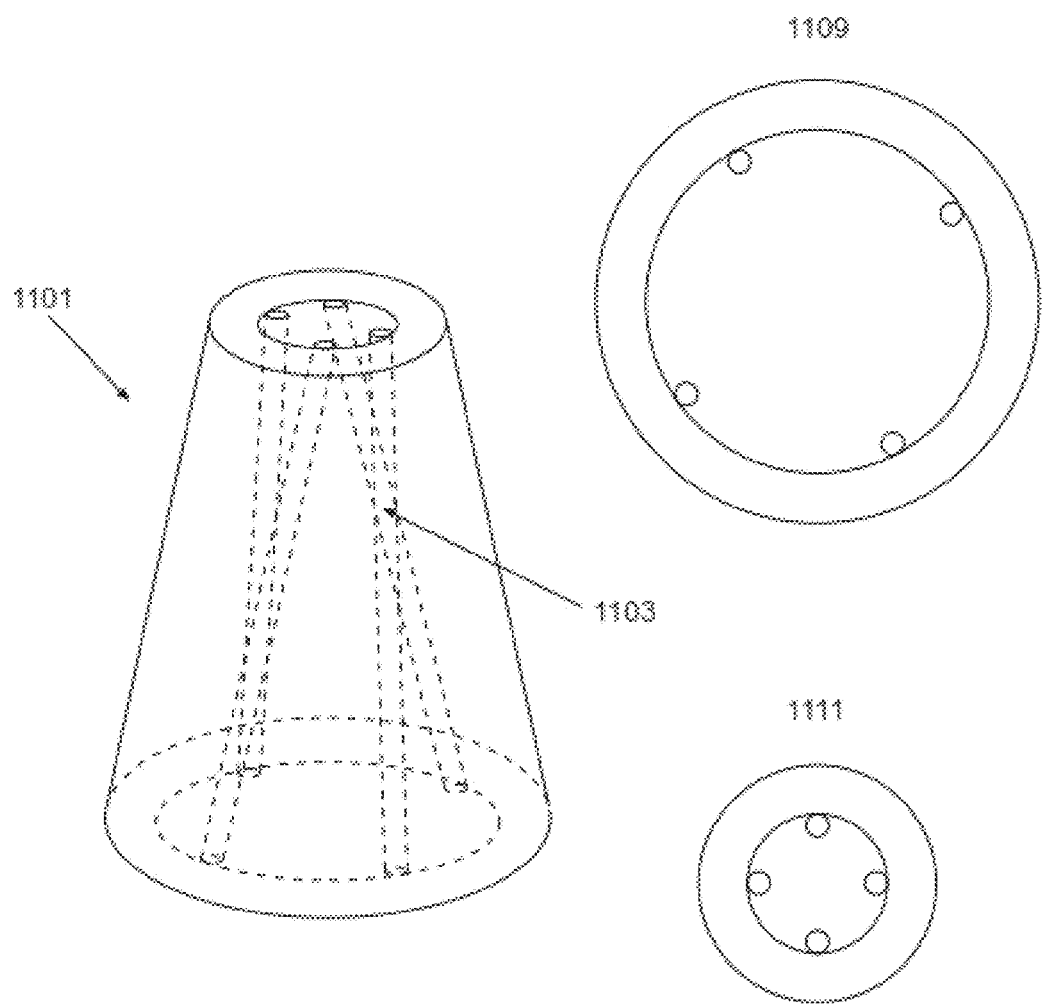

FIG. 11A-B show two embodiments of a nozzle including one or more directing channels for creating the one or more angled fluid jets, according to some embodiments of the invention. FIG. 11A includes a nozzle 1101, a horizontal cross section of the distal end of the nozzle 1105, and a longitudinal cross section of the nozzle 1107. FIG. 11B includes a conical nozzle 1101, a horizontal cross section 1109 of the distal tip of the nozzle (exit aperture), and a horizontal cross section 1111 of the proximal tip of the nozzle.

In some embodiments, a nozzle 1101 of an apparatus may comprise one or more channels for directing the angled fluid jets. In some embodiments, the channels are formed as tubes 1103. In some embodiments, nozzle 1101 is a cylinder. In some embodiments, tubes 1103 are configured along the internal wall of nozzle 1101.

In some embodiments, an angle of the tube is determined according to a resulting angle of the fluid jet formed by the tube. In some embodiments, the configuration (such as angle) of the tube is adjustable, for example by connecting a back plate of a tube using a screw to the wall of nozzle 1101.

In some embodiments, tubes 1103 have a similar diameter. In some embodiments, tubes 1103 have various diameters. In some embodiments, a single tube may change in diameter.

Figure 12A:
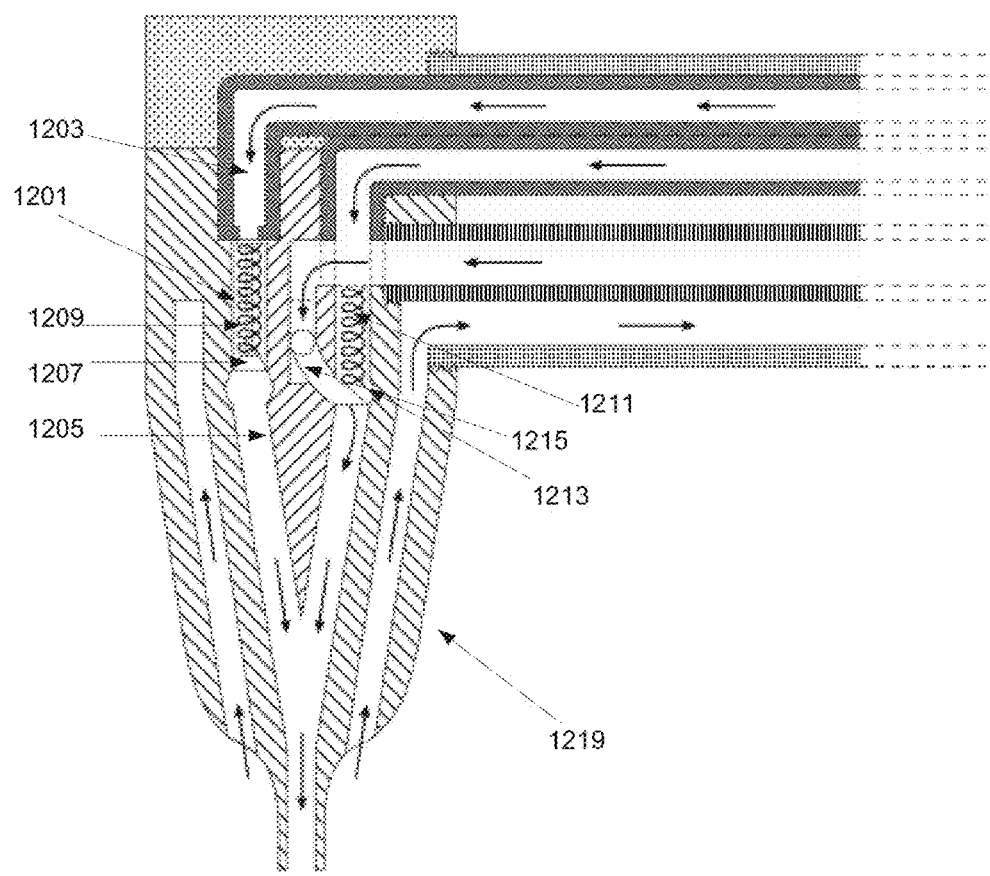
FIGS. 12A-12C are illustrations of a nozzle comprising a valve for controlling the flow through the nozzle, according to some embodiments of the invention.
Figure 12B:
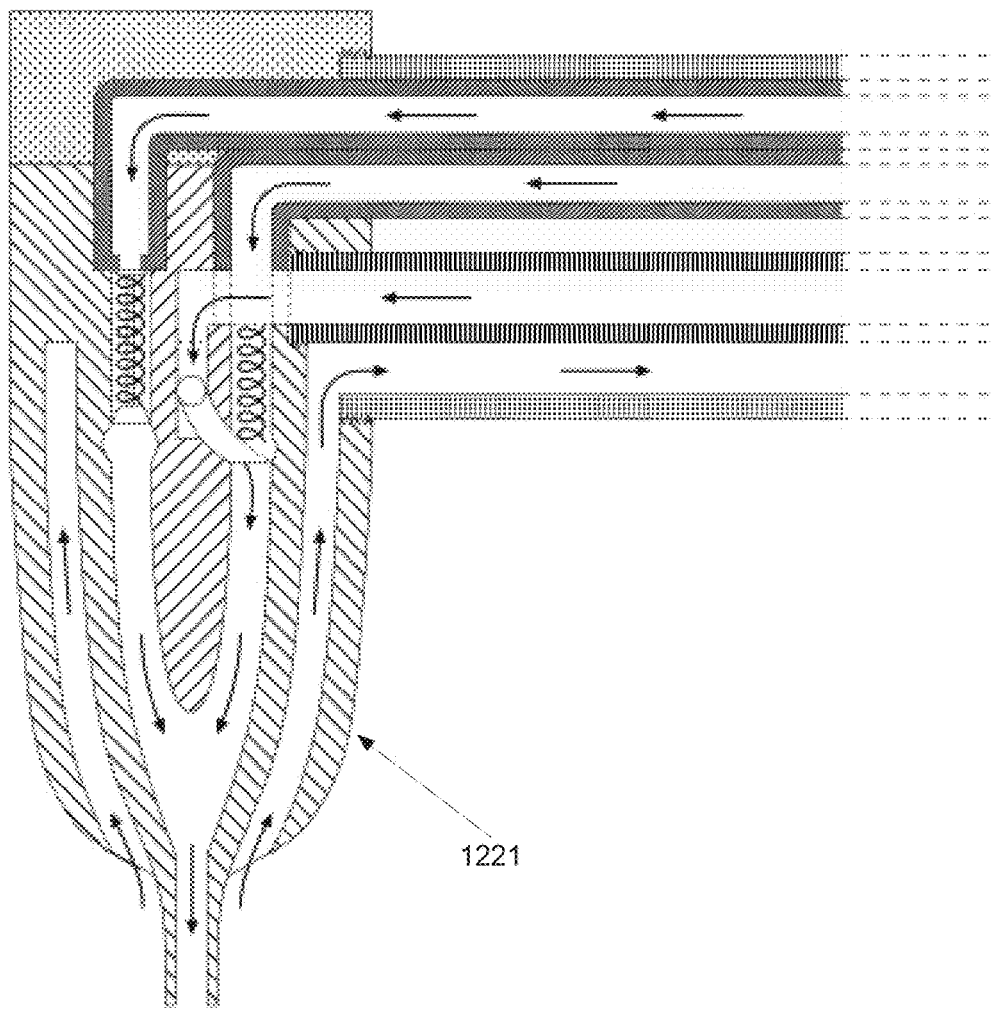
Figure 12C:
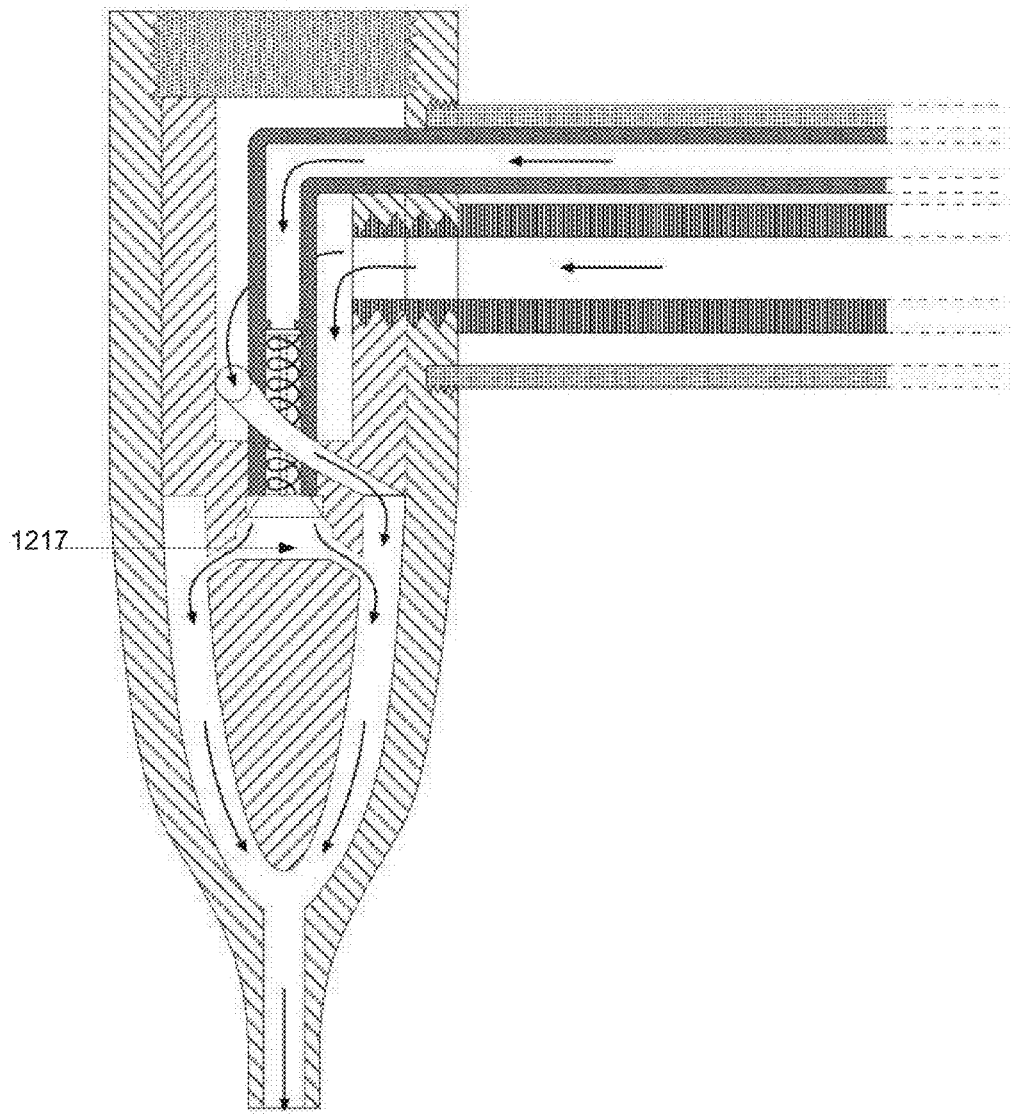

FIGS. 12A-12C are drawings of a nozzle comprising at least one valve for controlling the flow through the nozzle, according to some embodiments of the invention. In FIG. 12A, the nozzle has conically shaped outline 1219, and in FIG. 12B, the nozzle has an elliptically shaped outline 1221. In both FIGS. 12A and 12B, the nozzle is formed as one piece, for example formed using molding methods. In FIG. 12C, the nozzle may be formed of separate components, for example cones connected together, as will be further explained.

In some embodiments, a valve 1201 is used for controlling flow, for example the flow of air (or any other gas), liquid, abrasive powder and/or combinations of those into the nozzle. In some embodiments, as shown in FIGS. 12A and 12B, valve 1201 is positioned between the end of a pipe 1203 passing through the handle, and the lumen 1205 formed between an external and internal cones of the apparatus. In some embodiments, as shown in FIG. 12C, valve 1201 is positioned between the end of pipe 1203 and a connecting lumen 1217. Optionally, when the valve is in open position, a flow of any of the above substances and/or combinations of them enters connecting lumen 1217, from which it then passes to lumen 1205. Additionally and/or alternatively, at least one valve may be positioned between connecting lumen 1217 and lumen 1205. Additionally and/or alternatively, a valve is positioned at any junction, entrance aperture, exit aperture, along a pipe, a lumen of the nozzle, or any other portion of the nozzle.

In some embodiments, valve 1201 comprises a sealing element 1207. In some embodiments, the sealing element prevents fluid and/or any other substance from flowing upwards into pipe 1203.

In some embodiments, valve 1201 comprises a spring 1209. In some embodiments, the spring extends or compresses due to air and/or liquid pressure. In some embodiments, spring 1209 and/or sealing element 1207 is controlled using other means, such as mechanical means (for example by connecting valve 1201 to a lever controlled from the handle), hydraulic means (operated for example by the pressure of fluid passing through) and/or electrical means.

In some embodiments, when spring 1209 extends, it pulls sealing element 1207 into an open position. Optionally, in the open position, a material such as air, liquid, abrasive powder and/or combinations of them may flow into lumen 1205.

Additionally and/or alternatively, a valve 1211 is used for controlling the flow of fluid from a lumen of the internal cone into lumen 1205 between the external and internal cones. Optionally, sealing element 1213 of the valve is positioned at the end of slanted tube 1215. In some embodiments, this valve is used for controlling the treatment duration, for example by periodically pushing the valve to a closed position.

In some embodiments, other elements such as a cord may be used instead of a spring. In some embodiments, only sealing element 1207 may be used, for example formed as a flap which opens due to air pressure.

A potential advantage of using valve 1201 or similar includes the ability to add any substance to the fluid immediately before the fluid enters the root canal. In one example, abrasive powder that may dissolve in fluid, such as salt, may be passed (with or without air) through pipe 1203, and enter lumen 1205. Optionally, since the addition of salt to the fluid is performed at a relatively short time before entering the root canal, a portion of the salt does not dissolve and can be used as abrasive powder for the removal of soft tissue from the root canal.

Figure 13D:
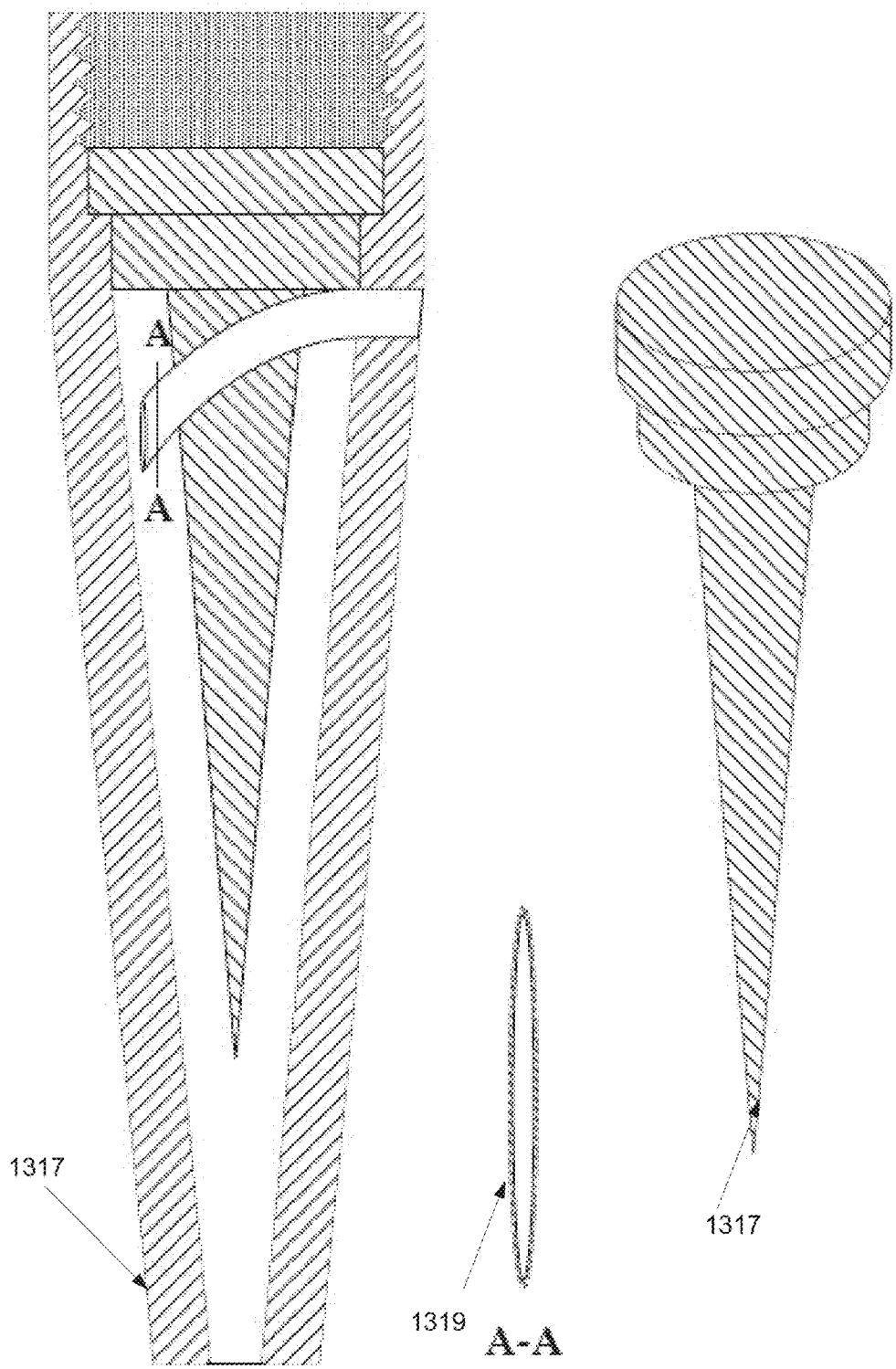

FIGS. 13A-13D illustrate a nozzle comprising a cone 1301 with a pin shaped element 1303 occupying at least a portion of the internal lumen of cone 1301, according to some embodiments of the invention. FIG. 13B is a horizontal cross section along line AA of the nozzle. FIG. 13C shows an enlarged view of pin shaped element 1303.

In some embodiments, a distal end of tube 1305 passes into a lumen 1307 of cone 1301 which is not occupied by pin shaped element 1303. In some embodiments, other elements, for example a cylinder, may be used for occupying a portion of the nozzle, to create a lumen which may be used for flowing fluid in a specific flow pattern and/or direction.

In some embodiments, pin shaped element 1303 has a diameter smaller than the diameter of cone 1301. In some embodiments, fluid passes within lumen 1307. In some embodiments, a distance between a face of the rod portion 1309 of pin shaped element 1303 and an internal face of cone 1303 ranges between 0.2-3 mm.

In some embodiments, as seen on FIG. 13A, rod portion 1309 is shaped as a cylinder comprising a rounded elliptical tip 1315. In some embodiments, as seen on FIG. 13D, rod portion 1309 is shaped as a narrowing cone, having a sharp pointed tip 1317.

In some embodiments, a head 1311 of pin shaped element 1303 fits within cone 1301 such that an upper portion of cone 1301 is fully occupied by head 1311. Optionally, this prevents fluid from passing through. In some embodiments, head 1311 is disposed on a long axis end of rod portion 1309. In some embodiments, pin-shaped element is inserted into a nozzle, providing an inner cone (inner cone is not necessarily cone shaped) within the nozzle. In some embodiments, head seals and/or closes a nozzle lumen.

In some embodiments, tube 1305 may be connected at its proximal end to a pipe in the handle (not shown in this figure). In some embodiments, fluid such as liquid, air, and/or abrasive powder or combinations of them may pass through tube 1305. In some embodiments, the fluid circulates within lumen 1307, for example in a helical flow.

Optionally, the helical flow is caused by rod portion 1309, since fluid is forced to pass around it. In some embodiments, the fluid exits the nozzle through exit aperture 1313 in the form of an angled jet due to the helical flow.

In some embodiments, tube 1305 has an elliptical cross section 1319. Alternatively, tube 1305 has a circular cross section, a rectangular cross section, or any other shape. In some embodiments, tube 1305 twists around rod 1309, for example adjacent to the rod.

In some embodiments, as seen on 13A, cone 1301 has a narrow elongated tip portion 1315. In some embodiments, as seen on 13D, cone 1301 has a flat-shaped tip portion 1317.

Figure 14:
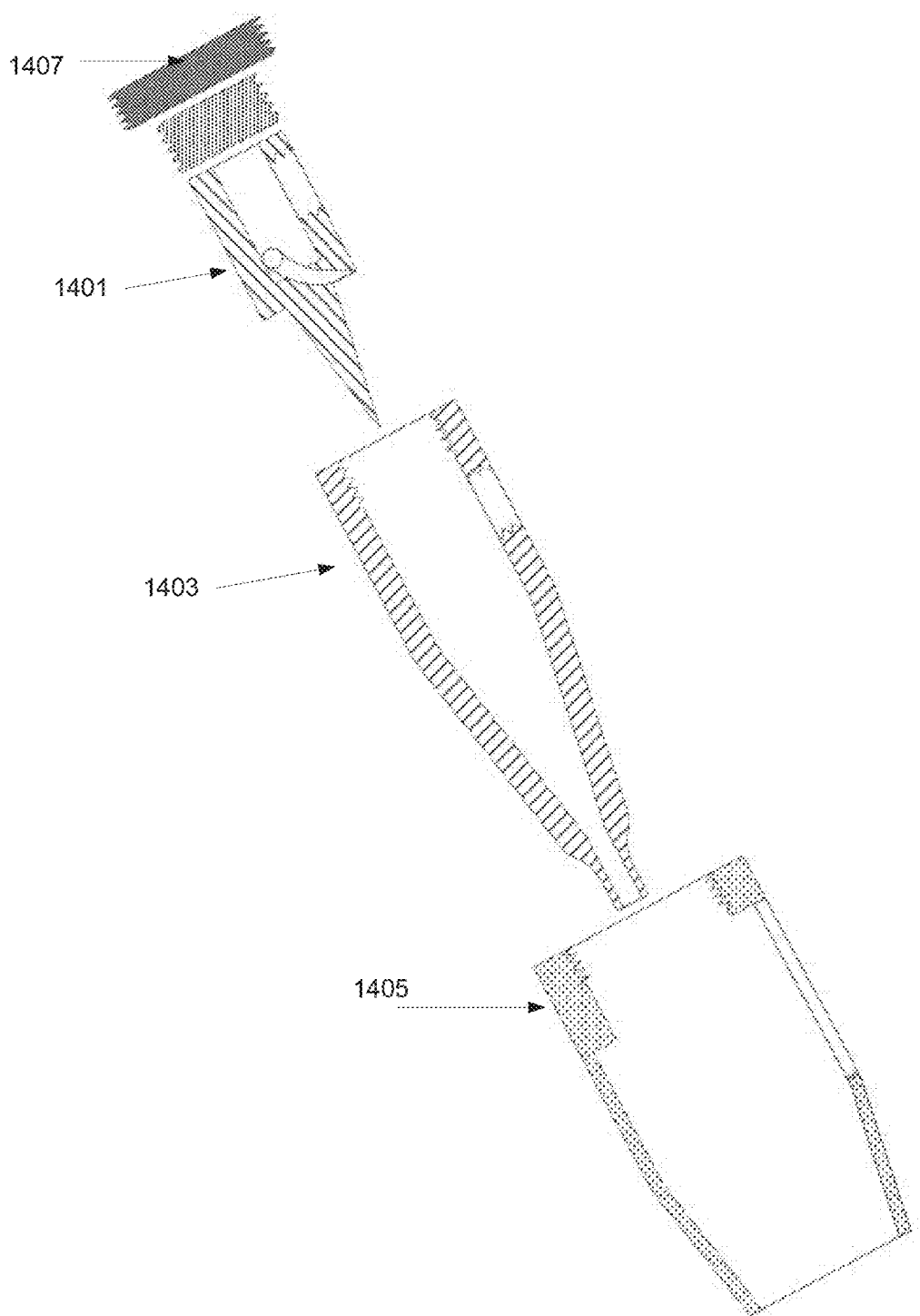
FIG. 14 shows an exemplary assembly of a nozzle, according to some embodiments of the invention.

FIG. 14 shows an exemplary assembly of a nozzle, according to some embodiments of the invention.

In some embodiments, the nozzle comprises an internal cone 1401, an external cone 1403, a suction cone 1405, and one or more lids 1407. In some embodiments, for example during manufacturing, internal cone 1401 is inserted into an external cone 1403. In some embodiments, internal cone 1401 is assembled within external cone 1403, and optionally both cones are assembled within suction cone 1405.

In some embodiments, at least two of the cones are connected by mechanical means, such as pins or screws. In some embodiments, the cones are connected by molding means, for example by casting at least two of the cones together using a designated mold. Optionally, any two and/or all cones are molded together, for example creating a nozzle made of one piece.

In some embodiments, any of the cones is detachable, for example to enable cleaning.

Figure 15:
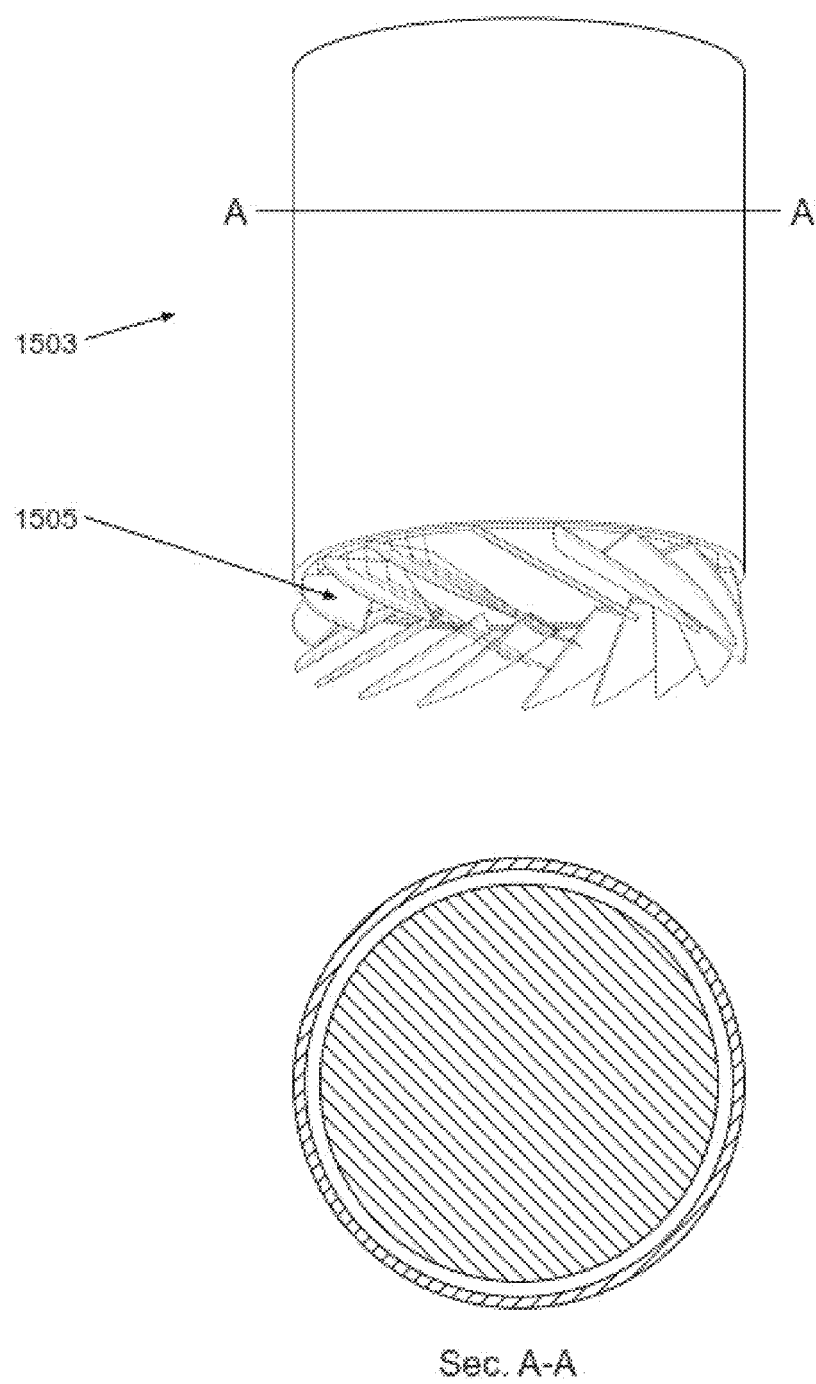
FIG. 15 is an illustration of a nozzle including exit flow shaping elements for creating the one or more angled fluid jets, according to some embodiments of the invention.

FIG. 15 is an illustration of a nozzle including exit flow shaping elements for creating the one or more angled fluid jets. In some embodiments, the exit flow shaping elements may be shaped as wings 1505.

In some embodiments, nozzle 1503 includes one or more wing elements 1505. In some embodiments, wing elements 1505 are used for diverting the fluid exiting nozzle 1503 to create one or more angled jets, for example, as previously described. In some embodiments, the fluid passes in a parallel flow through the cylindrical nozzle 1503, and wing elements 1505 shunt the parallel fluid to an angled direction. In some embodiments, nozzle 1503 comprises parallel tubes, and wing elements 1505 are positioned at a distal end of the tubes.

In some embodiments, wing elements 1505 are configured along an exit aperture of nozzle 1503.

Additional Features of the System and/or Apparatus, According to Some Embodiments of the Invention FIGS. 18A-18B illustrate a conical nozzle configured for modifying a positioning of an internal cone with respect to an external cone, according to some embodiments of the invention. In some embodiments, an internal cone orientation is modified. In some embodiments, an inner cone is non-symmetrical and/or can be rotated. In some embodiments, an inner cone includes at least a portion with textured surface e.g. grooves. In some embodiments, internal cone 1801 is movable with respect to external cone 1803. Optionally, movement of cone 1801 modifies a volume of lumen 1805 formed between the cones, for example reducing the volume. Optionally, modifying the volume includes changing an angle of positioning of internal cone 1801 with respect to external cone 1803. In some embodiments, movement of the internal cone reduces the spacing between the cones and increases the pressure and/or the rotation speed and/or the turbulence of the fluid in the lumen.

Optionally, modifying the volume affects the path of fluid. In some embodiments, cone 1801 is movable along the longitudinal axis of the nozzle, for example movable in the proximal and/or distal directions. FIG. 18A shows cone 1801 in a retracted position, closer to a proximal end of the nozzle. FIG. 18B shows cone 1801 in an advanced position, closer to a distal end of the nozzle, in which the shape of lumen 1805 is modified For example, cone 1801 is advanced towards exit aperture 1807 of the nozzle, reducing a size of a passage 1809 formed between the internal and external cones through which fluid advances to exit the nozzle. Optionally, cone 1801 is advanced in the distal direction by a distance ranging between 0.7-3 mm, or 0.1-0.9 mm, such as 0.3 mm, 0.5 mm, 0.7 mm or any intermediate, larger or smaller ranges and/or values. Optionally, tip 1819 of cone 1801 is advanced towards exit aperture 1807, and in some embodiments may level with the exit aperture. Optionally, by modifying a shape of lumen 1805, for example reducing a size of passage 1809, a velocity of fluid circulating between the cones (e.g. vertical and/or angular velocity components of the fluid) is increased. Optionally, by modifying a shape of lumen 1805, the fluid pressure of fluid approaching exit aperture 1807 may change. A potential advantage of increasing a velocity of the fluid circulating within the nozzle and/or within a guide tube assembled onto the nozzle may include increasing the velocity of the flow within the root canal. Optionally, the respective positioning of internal cone 1801 with respect to external cone 1803 is determined such as to change the velocity of the fluid circulating between the cones, for example increasing the velocity along some portions and/or decreasing the velocity along other portions of the nozzle. Optionally, the angle of a jet exiting the nozzle is modified as a result of modifying the lumen between the cones. Optionally, a diameter of a jet exiting the nozzle changes as a result of modifying the lumen, for example by modifying the lumen to change a velocity of the flow, which may increase or decrease the jet diameter. Optionally, the jet diameter is determined by the ratio between air and liquid in the flow. In some embodiments, the fluid jet may have a higher velocity, for example as a result of the lumen modification. A potential advantage of a jet having high velocity may include a higher eroding ability of the jet when entering and flowing within the root canal.

In some embodiments, when cone 1801 is advanced in the distal direction, for example as shown in FIG. 18B, a passage of the fluid is narrowed. If the flow pressure is maintained at a constant level, the velocity of the flow (e.g. the axial velocity component, the vertical velocity component, the angular velocity component and/or the total combined velocity changes. In some embodiments, a change in the angular velocity component and/or a change in the vertical velocity component of the flow may cause a change in the tangential velocity component of the flow exiting the nozzle.

In some embodiments, modifying the lumen changes the angle in which the jet hits the root canal wall and/or hits fluid within the root canal. Optionally, modifying the lumen includes changing a cross section shape and/or size of the lumen, thereby optionally affecting the flow rate.

Various mechanisms can be utilized for moving internal cone 1801. For example, a stepper motor 1811 is utilized for advancing and retracting cone 1801 along the longitudinal axis of the nozzle. Optionally, internal cone 1801 is connected to motor 1811, which in turn rotates in predetermined intervals for advancing and/or retracting cone 1801. Optionally, stepper motor 1811 is activated through a control panel of the system. In some embodiments, stepper motor 1811 is coupled to cone 1801 by a threaded element 1817. Optionally, stepper motor 1811 is configured to rotate a predefined step (i.e. rotate a certain angle) to lower and/or retract cone 1801.

In some embodiments, movement of nozzle parts, for example, the internal cone is manual e.g. where a user manually moves one or more part (e.g. by pressing a button mechanism optionally including a spring to move the internal cone).

In some embodiments, as shown at the transverse cross section profile along line BB, a track 1813 (only a cross section is shown here) extends along a portion of the internal wall of external cone 1803. A respective projection 1815 formed along the external wall of internal cone 1801 is received within the track, for example for preventing rotation of the cones with respect to each other during advancement and/or retraction of internal cone 1801. Optionally, the track prevents rotational movement of the internal cone when threaded element 1817 is rotated by motor 1811.

FIGS. 19A-B illustrate an additional configuration of an internal cone 1901 movable with respect to external cone 1903, according to some embodiments of the invention. FIG. 19A shows cone 1901 in a retracted position, closer to a proximal end of the nozzle. FIG. 19B shows cone 1901 in an advanced position, closer to a distal end of the nozzle, in which the shape of lumen 1905 is modified.

In some embodiments, a radial distance between internal cone 1901 and external cone 1903 remains constant. Alternatively, the radial distance changes, for example increases and/or decreases, for example decreasing in the proximal direction as shown by the following figure.

In this configuration, advancement of cone 1901 changes a position of lumen 1907 in which fluid accumulates before passing through tube 1909, with respect to the entrance 1911 to lumen 1907.

In some embodiments, advancing cone 1901 causes a modification of lumen 1905, for example of a distal portion 1903. In some embodiments, a passage within portion 1913 is reduced in size, for example narrowed. The narrowing may cause a change in flow parameters such as: the flow velocity, the flow pressure, the flow rate, the angle of the one or more jets exiting the nozzle, the shape of a beam of jets exiting the nozzle, the flow pattern within the nozzle, speed of circulation/rotation of fluid within the lumen, acceleration of flow within the lumen, or other flow related parameters.

Cross section A-A shows fluid entrance 1911 leading into lumen 1907.

FIGS. 20A-B illustrate an additional configuration of an internal cone 2001 movable with respect to external cone 2003, according to some embodiments of the invention. This configuration also includes a suction cone 2005, for example as described above. Optionally, suction cone 2005 is movable with respect to external cone 2003, for example it can be lifted or lowered such as by being connected to stepper motor 2007. Optionally, lumen 2009 between the cones is shaped such that a radial distance between the cones changes, for example with the narrowing of the cone. Optionally, a varying distance between the cones is obtained by the internal cone 2001 having an angle θ different than angle ʊ of external cone 2003. Optionally, one or both angles range between 10-85 degrees, such as 20 degrees, 35 degrees, 60 degrees, 70 degrees or intermediate, larger or smaller angles. In some embodiments, internal cone 2001 is advanced in the distal direction such that tip 2011 enters narrow needle portion 2013 of external cone 2003. The modification of lumen 2009 may cause a change in the axial (vertical) fluid velocity, the angular velocity, the flow pressure, the circular acceleration of the flow, the velocity of the exiting jet (e.g. vertical, angular, and/or tangential velocity components), the angle of the exiting jets, the shape of the beam of jets exiting the nozzle, and/or other flow related parameters.

Cross section B-B shows a locking configuration of internal cone 2001 to external cone 2003, whereby notch 2015 is received within a respective channel 2017 for example for preventing rotation of cone 2001 when motor 2007 is operated (e.g. rotated a certain step) to advance the internal cone.

Figure 21C:
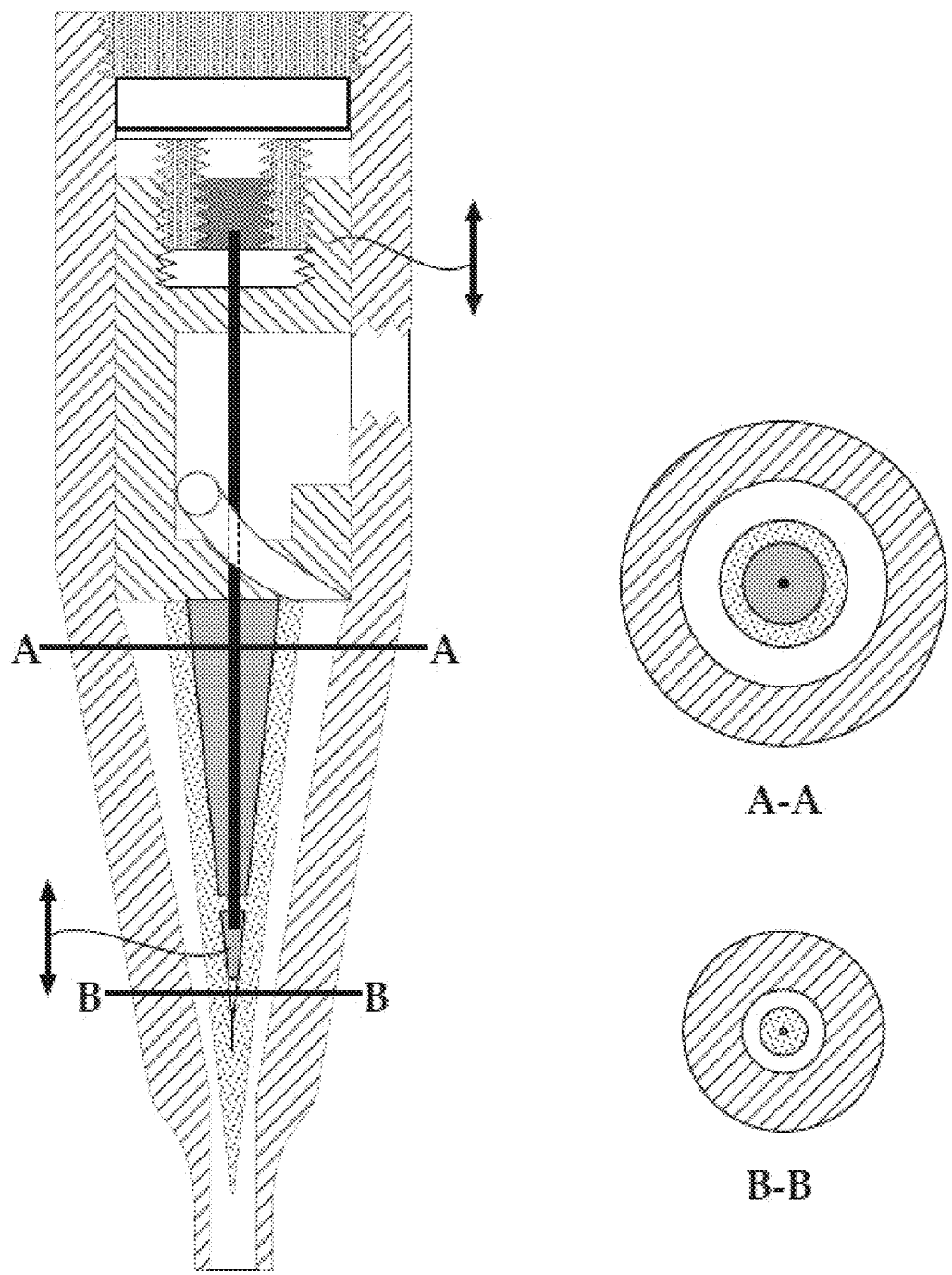

FIGS. 21A-C illustrate an internal cone comprising an expandable portion, according to some embodiments of the invention. FIG. 21A shows the non expanded configuration, FIG. 21B shows the expanded configuration, and FIG. 21C shows a non expanded configuration in which the internal cone is advanced in the distal direction. In some embodiments, internal cone 2101 comprises at least one portion 2103 adapted for expanding within lumen 2105 between the cones. Optionally, portion 2103 is formed of an elastic material, such as rubber. Optionally, expandable portion 2103 is configured for extending radially outwards, such as to occupy a larger volume with lumen 2105. Optionally, portion 2103 expands to occupy at least 10%, 30%, 40%, 60% or another larger, smaller, or intermediate percentage of lumen 2105. Optionally, expandable portion 2103 affects the flow of fluid along at least a portion of lumen 2105, for example a portion in proximity to the exit aperture of the nozzle. Optionally, by expanding portion 2103, the angle of the fluid jet discharged by the nozzle changes, for example a tangential angle of the jet with respect to the exit aperture may be modified. Optionally, by expanding portion 2103, the flow rate of fluid passing through may change. Optionally, expansion of portion 2103 affects the velocity of the flow.

In some embodiments, portion 2103 is caused to expand by a rigid structure, for example comprising a rod 2107, a conical portion 2109 and a conical tip 2111. Optionally, rod 2107 is coupled only to tip 2111. Tip 2111 may be positioned at various locations within lumen 2105.

Optionally, the structure is advanced and/or retracted by a stepper motor 2113. Optionally, advancement of the structure in the distal direction causes conical tip 2111 to press against the elastic walls of expandable portion 2103, thereby occupying a larger volume within lumen 2105. Optionally, expansion of portion 2103 is combined with modifying a positioning of internal cone 2101 with respect to external cone 2103, to define a shape of lumen 2105.

In some embodiments, cone 2115 is movable with respect to the external cone, by being coupled to motor 2213 for example by a threaded element. In some embodiments, by activation of motor 2213, radial expansion and/or movement of the internal cone can be obtained, simultaneously or separately.

In some embodiments, a distal portion 2115 of lumen 2105 is modified, for example the local expansion of portion 2103 narrows down the passage in which fluid flows. Optionally, this increases the velocity of the fluid, for example if the fluid pressure is maintained at a constant level. Optionally, this changes the angle in which the one or more jets exit the nozzle. Optionally, parameters such as the flow pressure, fluid velocity, and/or the angular velocity of the fluid within lumen 2105, and/or the shape of the beam of angled jets discharged by the nozzle are affected by the modification of lumen 2105.

In some embodiments, internal cone 2101 comprises one or more narrowing portions (not shown in this figure), which may modify a shape of lumen 2105.

FIG. 22 shows an additional configuration of an internal cone 2213 comprising an expandable portion 2203. FIG. 22A shows the internal cone in a non-expanded configuration, and FIG. 22B shows the internal cone expanded radially in the lumen between the cones, in the direction of the external cone. Optionally, expandable portion comprises a smaller cone 2201 constructing internal cone 2213. In this example, the expandable portion 2203 extends longitudinally within lumen 2205 so that when expanded radially, it may occupy most of the volume of lumen 2205, such as 51%, 70%, 80% or 90% of lumen 2205. Optionally, the expandable portion is an elastic layer surrounding cone 2201 of internal cone 2213. In some embodiments, as shown in this figure, the expansion is operated by a rod 2207 having a proximal end connected to a threaded element 2209, which in turn is coupled to a stepper motor 2211, and a distal end of the rod is connected to cone 2201. Optionally, motor 2211 is also connected to internal cone 2213, for example through a second threaded element 2215, for being movable for example in the distal and/or proximal directions within the external cone. Optionally, the distal tip 2217 of cone 2213 is advanced is in the distal direction towards exit aperture 2219 of the nozzle, any may optionally level with the aperture.

In some embodiments, by activation of motor 2211, the radial expansion and/or the movement of internal cone 2213 can be obtained, simultaneously or separately.

In some embodiments, lumen 2205 is modified by the radial expansion of portion 2203. Additionally or alternatively, lumen 2205 is modified by the movement of cone 2213. Optionally, a distal portion of lumen 2205, for example in proximity to exit aperture 2219, is reduced in volume. The modification of lumen 2205 may cause a change in the axial (vertical) velocity of the fluid within the nozzle. Additionally or alternatively, the modification of lumen 2205 may cause a change in the angular velocity of the fluid within the nozzle. Additionally or alternatively, the modification of lumen 2205 may cause a change in the angle of the jet exiting the nozzle.

In some embodiments, the modification of lumen 2205 is changed to cause a change in the flow regime, for example it is controlled by a dentist. Optionally, lumen 2205 is modified to suit a certain type of treatment, for example, a modification that causes a beam of jets having a relatively narrow profile or a wide profile may be more efficient when treating a root canal, for example a wide beam may be more suitable for treating a wide root canal, and a narrow beam may be more suitable for treating a narrow or complex canal, such as isthmus or webs canal. A wider beam may be more efficient when treating a complex shaped root canal, for example a root canal having many tubules, a root canal connected to a second root canal (webs canal or isthmus canal), or other canal forms.

Figure 23A:
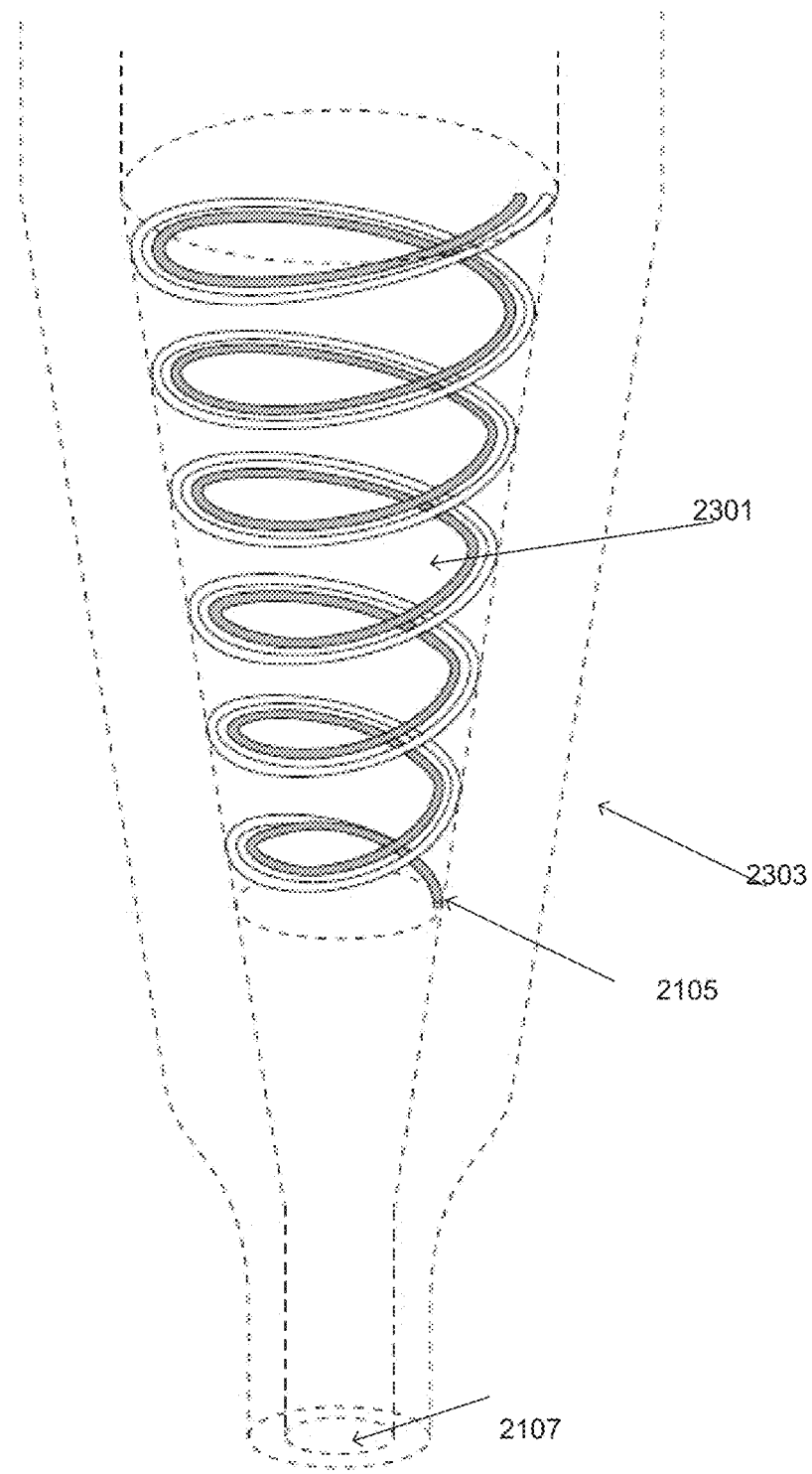
FIG. 23A illustrates a conical nozzle comprising one or more internal channels, according to some embodiments of the invention.

FIG. 23A illustrates a conical nozzle 2303 comprising one or more internal channels 2301, according to some embodiments of the invention. In some embodiments, channels 2301 are formed in a spiral configuration. Alternatively, channel 2301 is formed in other configurations such as parallel to the walls of nozzle 2303, parallel to a longitudinal axis of nozzle 2303, or transversely extending within nozzle 2303. In some embodiments, nozzle 2301 comprises more than one internal channel, such as 2, 4, 6, 8 or a larger or intermediate number. Optionally, a channel conducts a component such as liquid, gas (e.g. air), and/or abrasive powder and/or disinfection material and/or irrigation solutions. In some embodiments, exit aperture 2305 of channel 2301 is positioned close to an internal wall of cone 2303, so that flow exiting channel 2301 will flow along the walls of cone 2303 and optionally circulate at a high velocity along the walls, advancing towards exit aperture 2307. In some embodiments, the exit aperture 2305 of channel 2301 is positioned in proximity to exit aperture 2307 of nozzle 2303, for example to conduct abrasive powder. Such a channel may be especially useful if a powder that is dissolvable in liquid over time is used, such as salt, in order to mix it into the fluid right before the fluid enters the root canal. Optionally, channel 2301 is movable with respect to the internal lumen of nozzle 2303, for example by being connected at its proximal end to a stepper motor.

In some embodiments, as illustrated in FIG. 23A, channels 2301 includes more than one channel. In some embodiments, as illustrated in FIG. 23A channels merge into a single channel and the separate flows merge in a combined channel. In some embodiments, separate flows merge after emerging from separate channel exit apertures e.g. in some embodiments separate exit apertures are in close proximity (e.g. within 1 mm of each other) and the flows mix substantially immediately after emerging from the channels. Merging can occur at any point within the channel and/or nozzle.

Optionally, channel/s 2301 are movable with respect to the internal lumen of nozzle 2302, e.g. distally-proximally and/or by rotation. In some embodiments, movement of channel/s 2301 is by connection of the channel/s to a stepper motor. In some embodiments, movement of channel/s 2301 is manual.

Figure 23B:
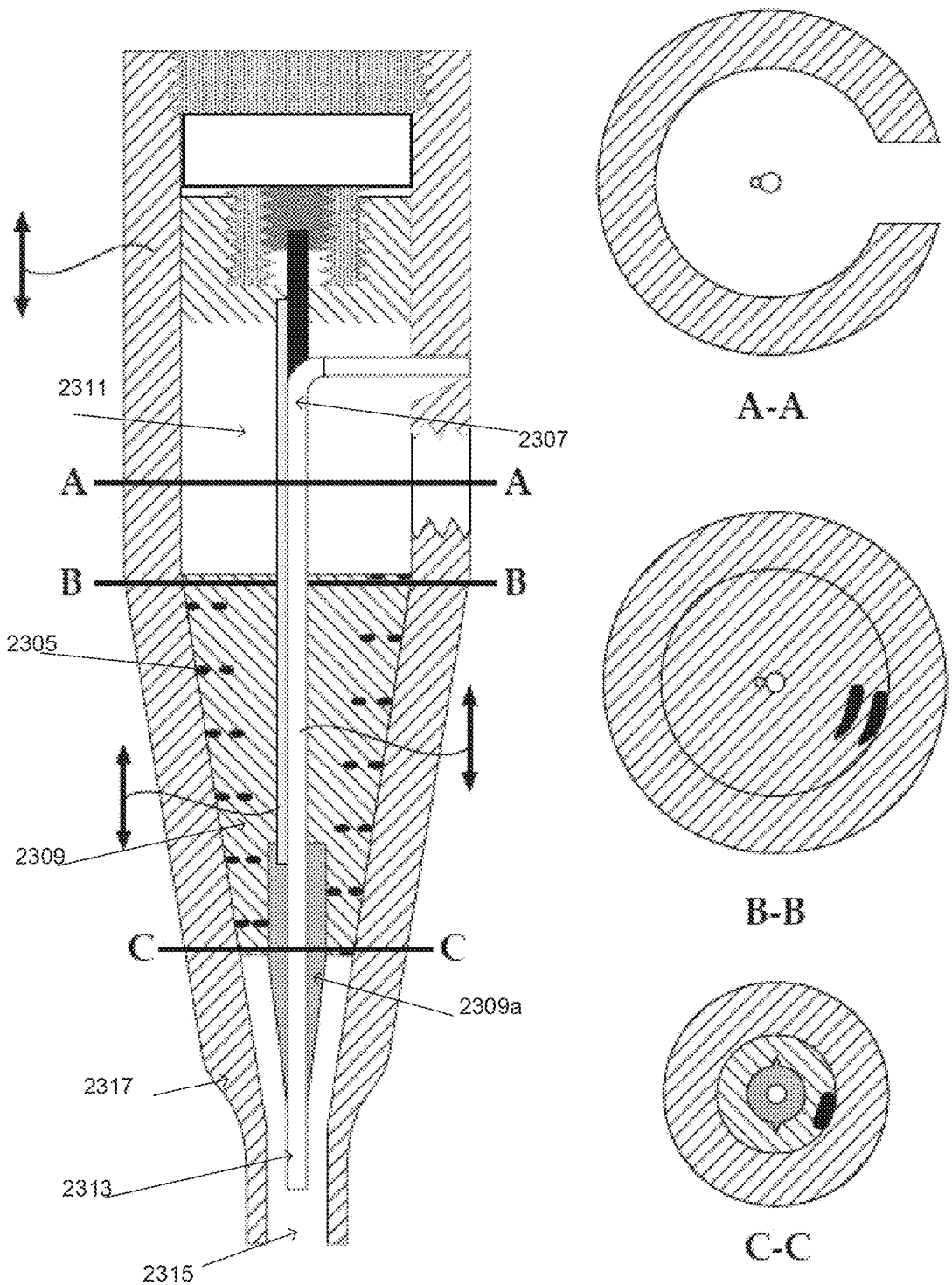
FIG. 23B illustrates a conical nozzle comprising a movable pipe, an internal channel, and a movable internal cone, according to some embodiments of the invention.

FIG. 23B illustrates a conical nozzle combining one or more internal channels 2305, a pipe 2307 movable along a longitudinal axis of the nozzle, and a movable internal cone 2309, for example as described herein.

In some embodiments, channel 2305, for example having a spiral configuration, conducts liquid, gas and/or abrasive powder and/or disinfection solution and/or irrigation solution. Optionally, channel 2305 is connected to a pipe configured within the handle, and/or connected to a fluid-receiving lumen 2311 within the nozzle. In some embodiments, a cross section profile of the channel is circular, for example having a diameter ranging between 0.2-4 mm. Alternatively, the cross section of the channel is elliptical or otherwise shaped.

In some embodiments, channels 2305 are formed by hollows in a solid component, for example, inner cone 2309.

In some embodiments, channels 2305 are formed by hollows in an non-solid component, for example channels 2305 being pipes supported by a mesh.

In some embodiments, movable pipe 2307 delivers at least one of liquid, gas, abrasive powder. Optionally, pipe 2307 delivers a disinfection solution (e.g. solution including antibacterial agent/s) and/or other medication and/or a flushing solution. In some embodiments, pipe 2307 is connected to a pipe configured within the handle. Optionally, pipe 2307 is movable along the longitudinal axis of the nozzle, for example it can be lifted up in the proximal direction (e.g. using the stepper motor) or lowered in the distal direction. Optionally, a distal end 2313 of pipe 2307 is positioned in proximity to exit aperture 2315. Optionally, the location of distal end 2313 with respect to external cone 2317 and/or with respect to exit aperture 2315 affects the flow of fluid within the nozzle and/or the angle or beam shape of fluid exiting the nozzle. Optionally, movement of pipe 2307, the flow within channel 2305, and/or movement of internal cone 2309 with respect to the external cone are combined to form a desired flow regime. Optionally, activation of the one or more components of the nozzle is performed using a controller.

In some embodiments, e.g. as illustrated in FIG. 23B, channel 2305 includes more than one channel (in the figure two channels are illustrated). In some embodiments channels 2305 merge into a single channel (in FIG. 23B channels 2305 merge at cross section C-C) and the separate flows merge in a combined channel.

In some embodiments, separate flows merge after emerging from separate channel exit apertures in inner cone 2309. In some embodiments separate exit apertures are in close proximity (e.g. within 1 mm of each other) and the flows mix substantially immediately after emerging from the channels.

In some embodiments, inner cone 2309 includes a portion 2309a adapted to move independently from inner cone: For example, to rotate at a different speed and/or in a direction and/or to move distally and proximally independently from inner cone 2309.

Figure 24A:
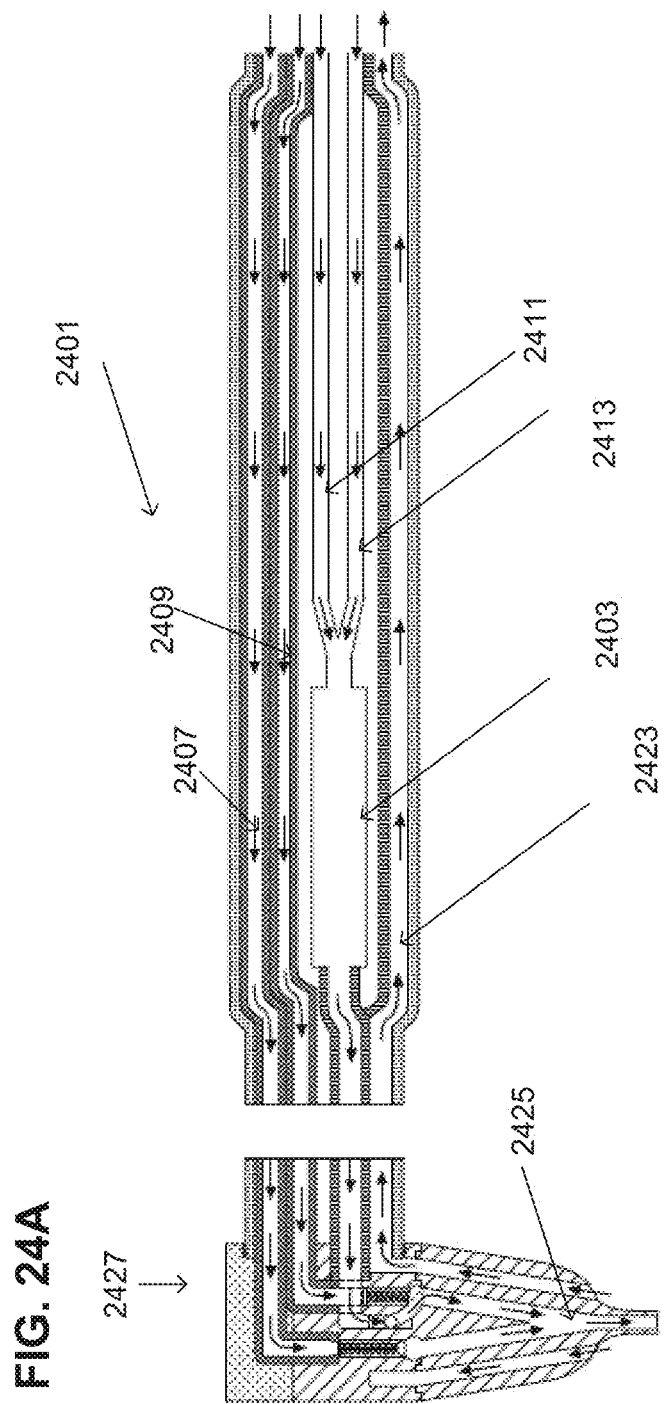
FIGS. 24A-24B are exemplary configurations of a handle comprising a fusion tube and a powder cartridge, according to some embodiment of the invention.
Figure 24B:
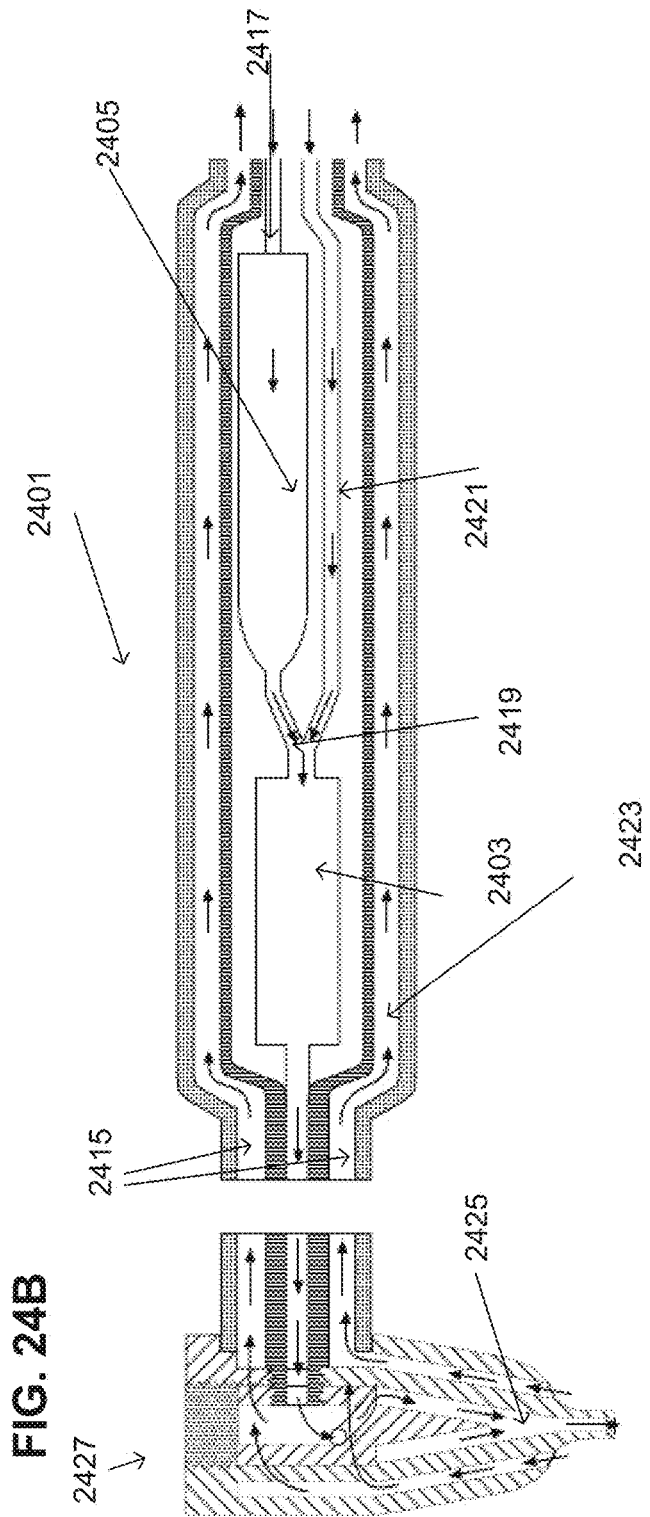

FIGS. 24A-B are two configurations of a handle 2401 comprising a fluid mixer 2403 for mixing between components of the fluid, such as gas, liquid and/or abrasive powder, in accordance with some embodiments of the invention.

In some embodiments, handle 2401 comprises a cartridge 2405, for example filled with abrasive powder. Alternatively, cartridge 2405 is filled with liquid such as medication, or any other component and/or particles intended to be delivered into the nozzle. Optionally, cartridge 2405 is replaceable and/or disposable, for example it can be replaced between patients and/or between treatments. Optionally, cartridge 2405 is refillable. Optionally, by mixing between components of the fluid within the handle, the need for external containers in which mixing is performed can be reduced, thereby optionally reducing the number of system components In some embodiments, the volume of the cartridge ranges between 0.5 CC-20 CC.

FIG. 24A shows a pipe 2407 configured for delivering air and/or powder into the nozzle, in accordance with some embodiments of the invention. Optionally, a valve is placed for example at the entrance to the nozzle to control the flow. Pipe 2409, also leading into the nozzle, may deliver air and/or powder, or liquid, into the nozzle. Pipe 2411 connects to fluid mixer 2403, and delivers, for example liquid. Pipe 2413 connects to fluid mixer 2403, delivering, for example, air and powder. In some embodiments, flows from pipes 2411, 2413 mix within fluid mixer 2403 (e.g. the flows mix uniformly to produce a uniform composition flow exiting the mixer).

Pipe 2423 is a suction pipe which delivers fluid and/or debris in an opposite direction from the nozzle. In some embodiments, each of pipes 2407, 2409, 2413, 2411 deliver one or more of gas (e.g. air) and/or fluid and/or powder and/or disinfection solution and/or irrigation liquid. In some embodiments, flows from pipes 2407, 2409, 2413, 2411 join and mix in a lumen 2425 (e.g. a region of lumen 2425 proximal to a nozzle exit aperture) of a nozzle 2427 before passing out of nozzle 2427 through a nozzle exit aperture.

In FIG. 24B, suction pipes 2415 lead fluid and/or debris away from the nozzle, pipe 2417 leads air and/or powder into cartridge 2405. The air and powder may be mixed within cartridge 2405 at dry conditions, where no moisture or humidity exist. Optionally, a valve is installed at junction 2419 for example for preventing fluid from fluid mixer 2403 entering cartridge 2405. Pipe 2421 leads fluid into fluid mixer 2403 where, in some embodiments, flow from pipe 2421 and flow from cartridge 2405 merge and flow into mixer 2403 for mixing. The mixed flow including liquid, air and abrasive powder then flows from mixer 2403 into the nozzle lumen 2427. In some embodiments, each of pipes 2417, 2421 deliver one or more of gas (e.g. air) and/or fluid and/or powder and/or disinfection solution and/or irrigation liquid.

The above exemplary pipeline configurations can be coupled to any type of nozzle, such as, for example, described herein.

Figure 25A:
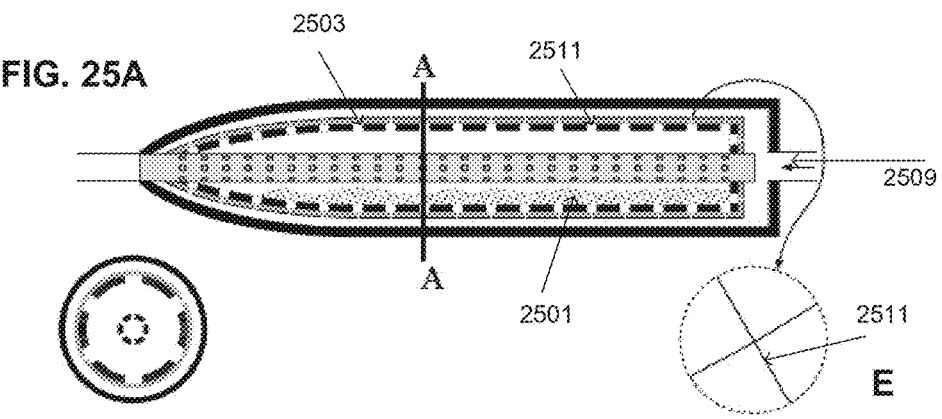
FIGS. 25A-25C illustrate various configurations of a powder cartridge supply system, according to some embodiments of the invention.
Figure 25B:
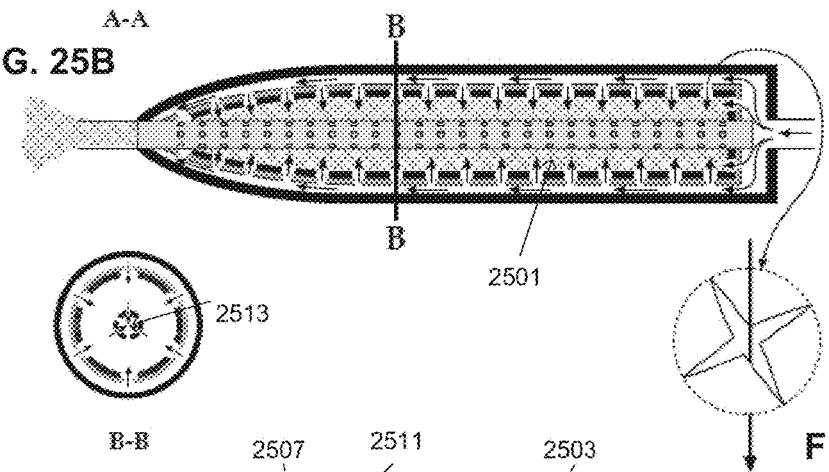
Figure 25C:
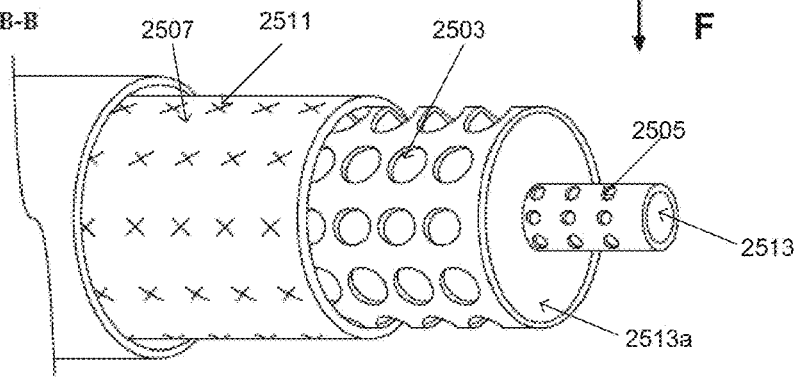

FIGS. 25A-C illustrate various configurations of a powder cartridge supply system, according to some embodiments of the invention. Optionally, the cartridge is disposable. Optionally, the cartridge is replaceable, and can be assembled or detached from the handle for example through a designated opening. In some embodiments, the powder cartridge supply system is configured for supply and mixing abrasive particles with gas immediately before the fluid enters fusing tank (e.g. fluid mixer 2403) before entering the nozzle. Optionally, the cartridge comprises a predefined amount of abrasive powder, for example suitable for performing 1, 3, 5, 10 or another number of treatments. FIG. 25A shows abrasive powder 2501 contained within the cartridge, prior to mixing with gas. The cartridge comprises a cylinder formed with a plurality of internal cylinders, as will be explained in FIG. 25C. Optionally, the one or more internal and/or external cylinders comprise holes. Optionally, the one or more cylinders are coated with a flexible cover.

FIG. 25B shows powder 2501 once gas and/or liquid have entered the cartridge, and the cross section B-B shows the direction in which air flows into the inner lumen 2513 for mixing with the powder. In some embodiments, a volume of the cartridge ranges between 0.2-10 cc, 5-15 cc, 10-25 cc, 25-60 cc, or intermediate, larger or smaller volumes. In some embodiments, the cartridge is formed of a metal, PPM, plastic, or any material that can withstand the pressure.

In some embodiments, gas such as air is compressibly forced into the cartridge, for example through opening 2509. In some embodiments, air is forced into the cartridge at a pressure ranging between 2-300 PSI. In some embodiments, the compressed air generates a circulation, turbulence or other swirling motion of the powder within the cartridge.

In some embodiments, as shown for example in FIG. 25C, the cartridge comprises one or more cylinders positioned one within the other. Optionally, the cylinders comprise one or more openings 2503, 2511, 2505 for enabling the passing of certain components through and blocking the passage of other components through. Optionally, a diameter of an opening may range between 40 μm-300μ, or 100 μm-2 mm or 20 μm-5 mm. For example, an internal cylinder 2505 may be formed with holes that allow powder 2501 to exit through in the radial direction, for example when air flows into the cartridge. Optionally, external cylinder 2507 comprises openings shaped as X shaped slots 2511 that enable only the passing of air entering the cartridge (e.g. blocking powder cartridges from returning). In some embodiments, x-shaped slots act as a one way valve. In some embodiments, external cylinder 2507 is formed of an elastic material. FIGS. 25E and F show an X shaped slot 2511 in its closed configuration (E) and expanded star shaped configuration (F) in which air is allowed into the cartridge, blocking powder cartridges from returning (e.g. one way valve). In some embodiments, the air passes through one or more openings 2503, 2511 in the cylinders and mixes with the powder, for example within lumen 2513a. In some embodiments, prior to entry of gas such as air into the lumen of the cartridge, the powder particles remain at a bottom of lumen 2513. In some embodiments, even when the pressurized air supply to the cartridge is reduced or stopped, the powder does not sink back to the bottom of the cartridge for example as shown in FIG. 25A.

In some embodiments, entrance 2509 to the cylinder is sealed by an external cylinder 2500 and/or by cover 2507 so that gas such as air which enters through entrance 2509 is forced to pass through slots 2511 to enter the internal cylinder 2502, for example through holes 2503. In some embodiments, fluid ejected through holes 2505 flows through lumen 2513 to a fusion tank within a handle connected to a nozzle.

Optionally, the fluid comprising the powder is then delivered to a fusion tank within the handle.

Figure 25D:
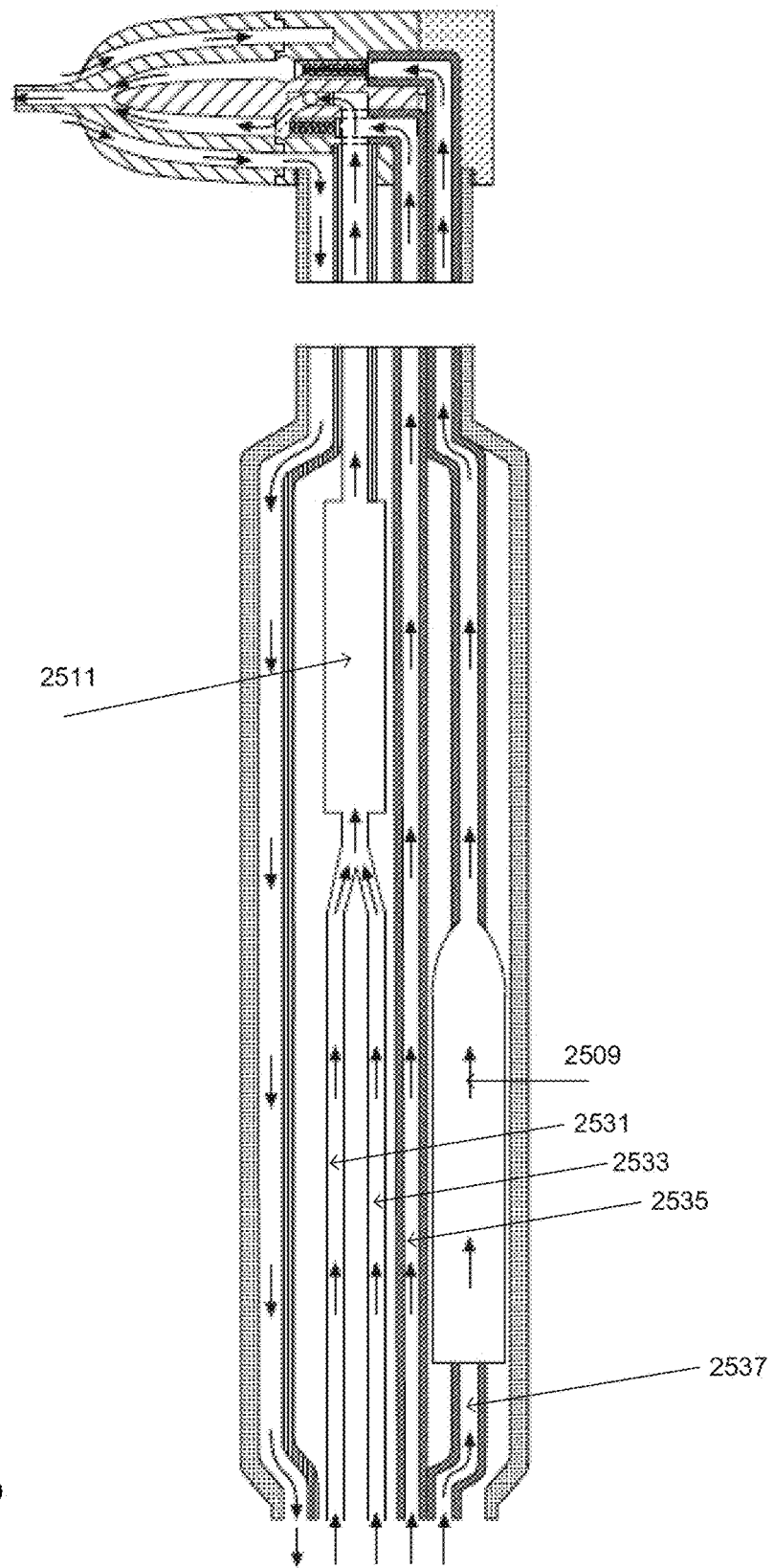
FIG. 25D is an exemplary configuration of a handle in which powder and gas are delivered separately from fluid, according to some embodiments of the invention.

FIG. 25D shows an exemplary configuration of a handle in which the air and powder supply, for example being mixed together in powder cartridge system 2509, are delivered into the nozzle separately from liquid (for example delivered through mixer/tank 2511). Optionally, by separating the liquid from the air and powder mixture, each component can be delivered separately into the nozzle, for example, mixing within the nozzle and/or root canal. For example, the nozzle may deliver only air and powder into the canal, and/or deliver only liquid into the canal.

In some embodiments, tube 2510 may be used for delivery of air, liquid, and/or powder and/or irrigation fluid and/or disinfection solution.

In some embodiments, suction tube 2512 is used to extract fluid and/or debris (e.g. from the root canal).

Alternatively, in some embodiments, suction tube 2512 in the handle may be used for discharge (e.g. of gas, liquid, and/or powder) instead of suction.

In some embodiments, the handle may be used with different types of nozzles, such as, for example, described herein.

In some embodiments, each of pipes 2531, 2533, 2535, 2537 deliver one or more of gas (e.g. air) and/or fluid and/or powder and/or disinfection solution and/or irrigation liquid.

Figure 26:
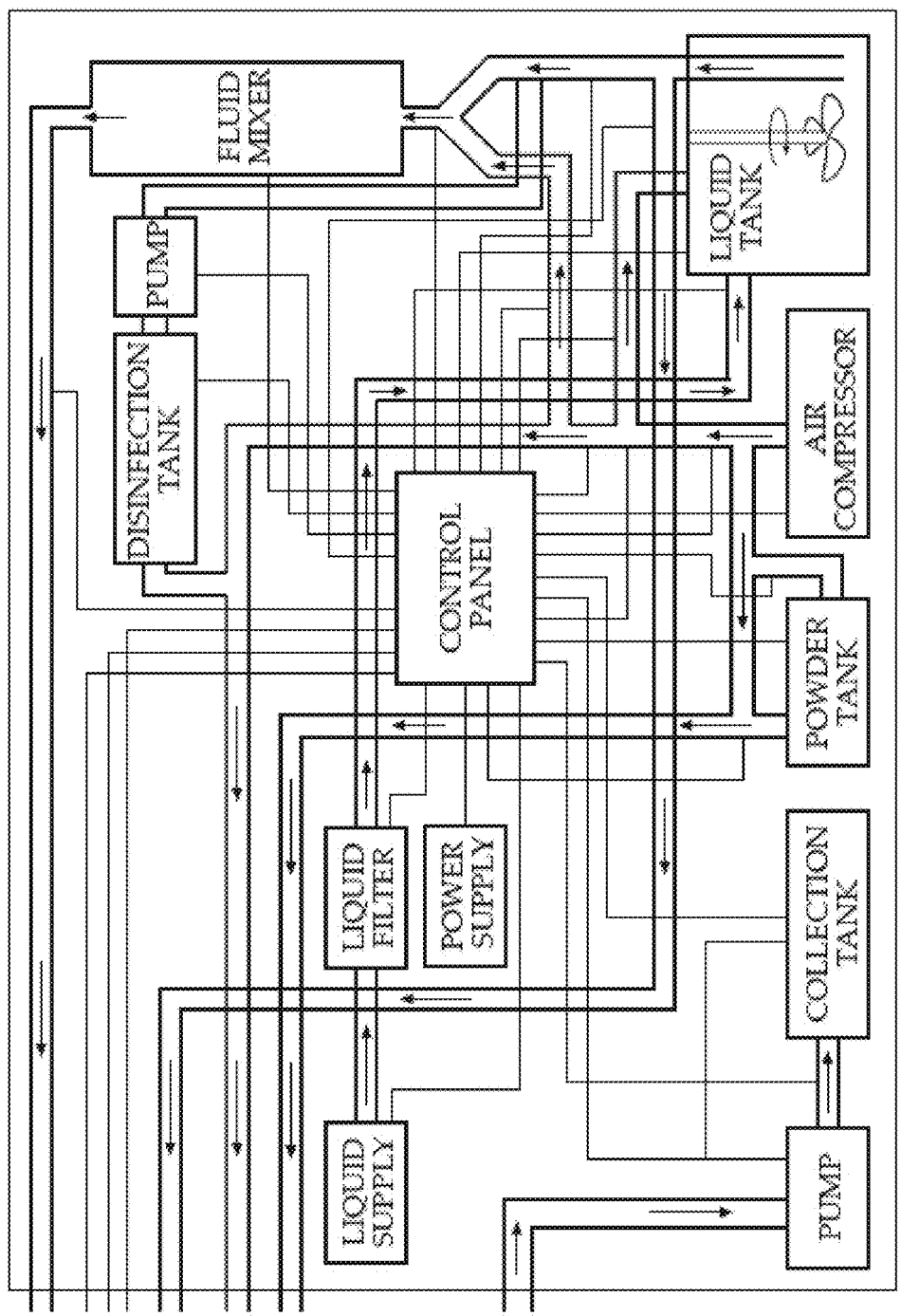
FIG. 26 is a schematic diagram of exemplary system for treating a root canal, according to some embodiments of the invention.
Figure 27:
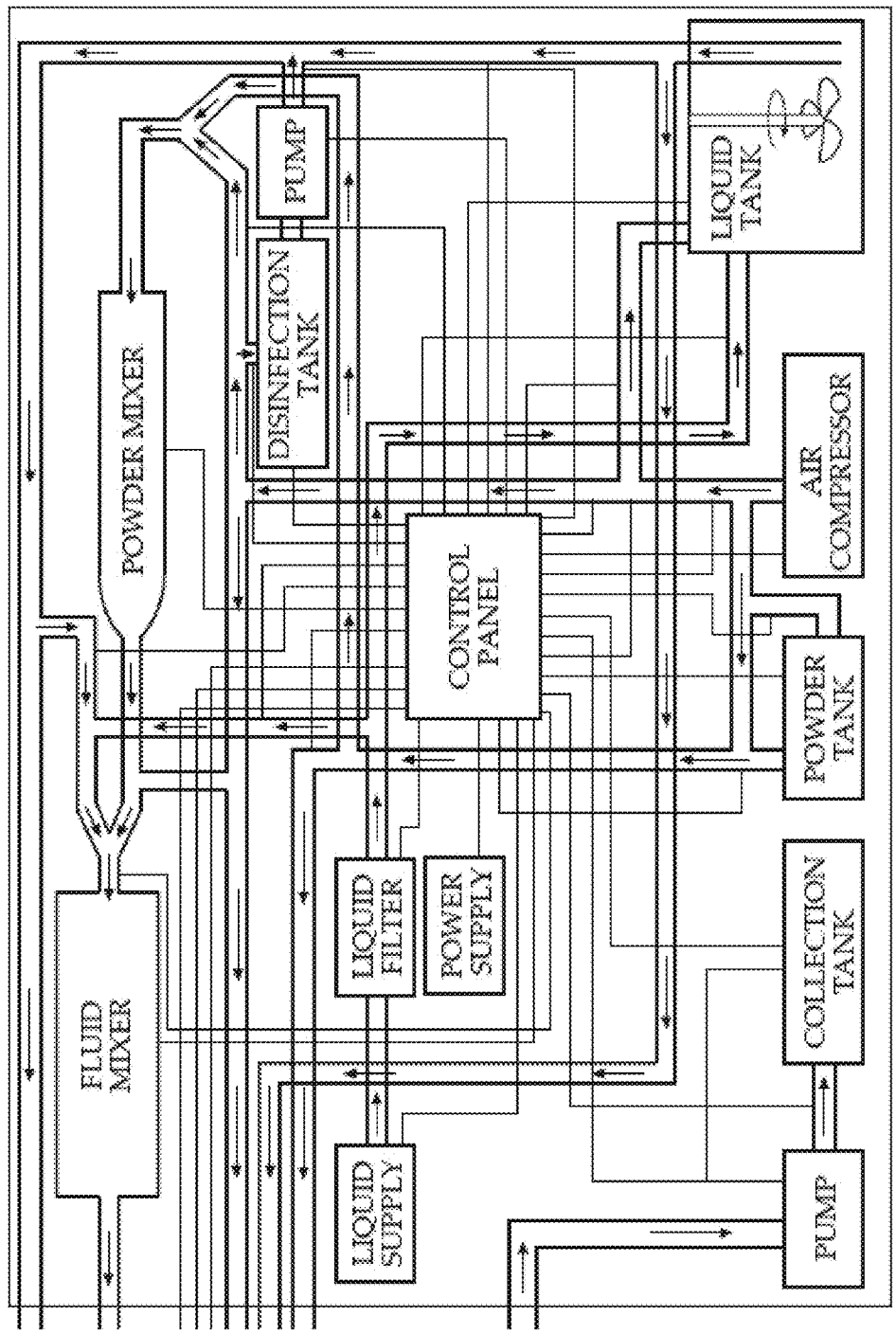
FIG. 27 is a schematic diagram of exemplary system for treating a root canal, according to some embodiments of the invention.

FIGS. 26 and 27 are schematic diagrams of exemplary system for treating a root canal, according to some embodiments of the invention. FIG. 26, for example, includes the system described in FIG. 8 above, further including a fluid mixer, a disinfecting fluid tank connected to a pump, and a liquid filter. Optionally, liquid flows directly into the handle and nozzle. Alternatively, fluid is first passed through the fluid mixer.

In some embodiments, one or more liquid tubes connects between the liquid tank and the fluid mixer, and/or connects the liquid tank directly to the handle. In some embodiments, one or more air tubes connect between the air compressor to the powder mixer, and/or from the air compressor directly to the handle.

FIG. 27 further includes a powder mixer, which mixes air and powder together for example before entering the handle. Optionally, one or more components of the system are activated through a control panel connected to a controller. In some embodiments, the components of the system are separately controllable and can be operated with or without other components (for example, the air pump may be operated independently of the fluid mixer).

Figure 28:
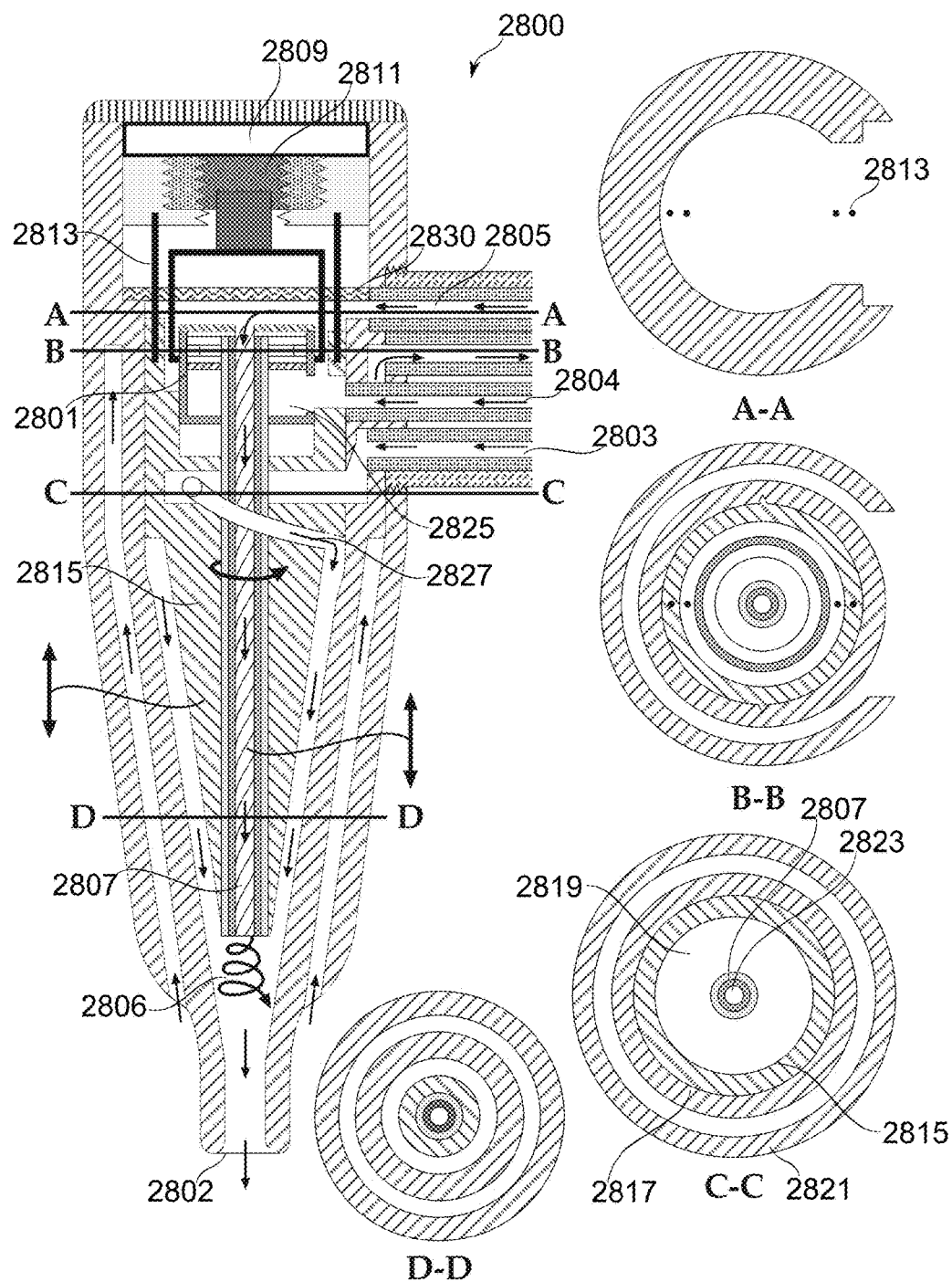
FIG. 28 illustrates a nozzle comprising a turbine for imparting spin to a working fluid, according to some exemplary embodiments of the invention.

FIG. 28, now made reference to, illustrates a nozzle 2800 comprising a turbine 2801 for imparting spin to a working fluid, according to some exemplary embodiments of the invention.

In some embodiments of the invention, there is provided a turbine 2801, operable to impart momentum to flow exiting the nozzle aperture 2802. The turbine design potentially allows transfer of energy from, for example, a pressurized gas supply, into a working fluid for cleaning and/or eroding of a root canal. In some embodiments, combining of turbine-driven and direct pressure-driven working fluid sources that meet in flow coming from 2827 into the lumen between the internal cone and external cone. Fusion of these flows potentially allows control to achieve a broadened range of exit jet and angles properties at the meeting between two flows 2806.

In some embodiments, the turbine 2801 is activated by a flow of air, for example from inlet 2804. Optionally, the flow of air enters through pipe 2804 configured within the handle. In some embodiments, the turbine is operable at one or more frequencies in a range of, for example: 2000-10,000 RPM, 5,000-25,000 RPM, 10,000-100,000 RPM, 10,000-400,000 RPM, 2000-400,000 RPM, or another range of rotational frequencies. In some embodiments, the pressure of air for driving the turbine is, for example: 10-20 PSI, 15-25 PSI, 10-30 PSI, 30-40 PSI, 30-60 PSI, or another range of driving pressures.

In some embodiments, turbine 2801 is operable to rotate pipe 2807, which extends from a fluid inlet in the region of the turbine toward a distal end of the nozzle 2800. In some embodiments, the turbine is operable to spin fluid that enters pipe 2807, provided, for example, through pipe 2805. Additionally or alternatively, fluid (provided, for example, from pipe 2803) flows into lumen 2825, and optionally passes through the slanted tube 2827. In some embodiments, turbine 2801 causes an axial rotation of pipe 2807, thereby spinning the fluid contained within. Optionally, the fluid exiting pipe 2807 has a helical flow profile. In some embodiments, spinning of the fluid within pipe 2807 affects a velocity and/or pressure of the fluid.

In some embodiments of the invention, pipe 2807 is provided with a helically formed lumen. A helically formed lumen provides a potential advantage for imparting directionality to fluid therein, by urging the fluid along the length and/or around the axis of pipe 2807.

In some embodiments, turbine 2801 is coupled to motor 2809, for being movable, for example, in the proximal and/or distal directions. In some embodiments, motor 2809 comprises a stepper motor. Optionally, coupling is through threaded element 2811 and/or rods 2813. In some embodiments, motor 2809 comprises, additionally or alternatively, a driving means for moving internal cone 2815 in distal and proximal directions, optionally coupled through threaded element 2811 and/or for moving pipe 2807 in distal and proximal directions. Optionally, movement of internal cone 2815 and pipe 2807 in distal and proximal directions is independent for example, at different speeds and/or directions and/or frequencies e.g. as internal cone 2815 moves distally, pipe 2807 moves proximally. Alternatively, movement of internal cone 2815 and pipe 2807 is synchronized.

In some embodiments, movement of the internal cone and/or pipe is manual, e.g. where a user manually moves one or more part (e.g. by pressing a button mechanism optionally including a spring) to move the internal cone and/or pipe.

The cross section along line A-A shows rods 2813. The cross section along lines C-C, for example, shows the internal cone 2815, external cone 2817, a lumen 2819 within the internal cone 2815, pipe 2807, a lumen 2823 of pipe 2807 through which fluid passes, and a suction cone 2821 positioned externally to both cones.

In some embodiments, the turbine is sealed by a sealing element 2830, for example preventing fluid and/or air to pass in the proximal direction.

In an example of nozzle operation, fluid injected into pipe 2803 finds its way to region 2806 from tube 2807, having acquired during its transit a pattern of flow which may be, for example, helical. Some control of flow pattern properties is optionally exercised by relative motion of inner cone 2815 relative to external cone 2817, driven, for example, by stepper motor 2809. In some embodiments, fluid injected into pipe 2805 finds it way, optionally simultaneously, through pipe 2807, also reaching region 2806. In some embodiments, the two fluid flows are combinable at region 2806. In some embodiments, advancing or retracting pipe 2807 potentially allows control of parameters of fluid flow patterns exiting from aperture 2802. Parameters adjustable potentially include, for example, the cone exit angle and/or the vertical and/or horizontal velocity components of exiting fluid. In some embodiments, fluid of different compositions is supplied to pipes 2805 and 2803 (or one of pipes 2805, 2803), and control of mixing is provided, for example, by positioning of pipe 2807 and inner cone 2815.

It should be noted that the turbine and its related features such as the frame connecting to the motor can be assembled in nozzles of various configurations, such as nozzles having a geometry other than conical (for example, cylindrical).

Figure 29:
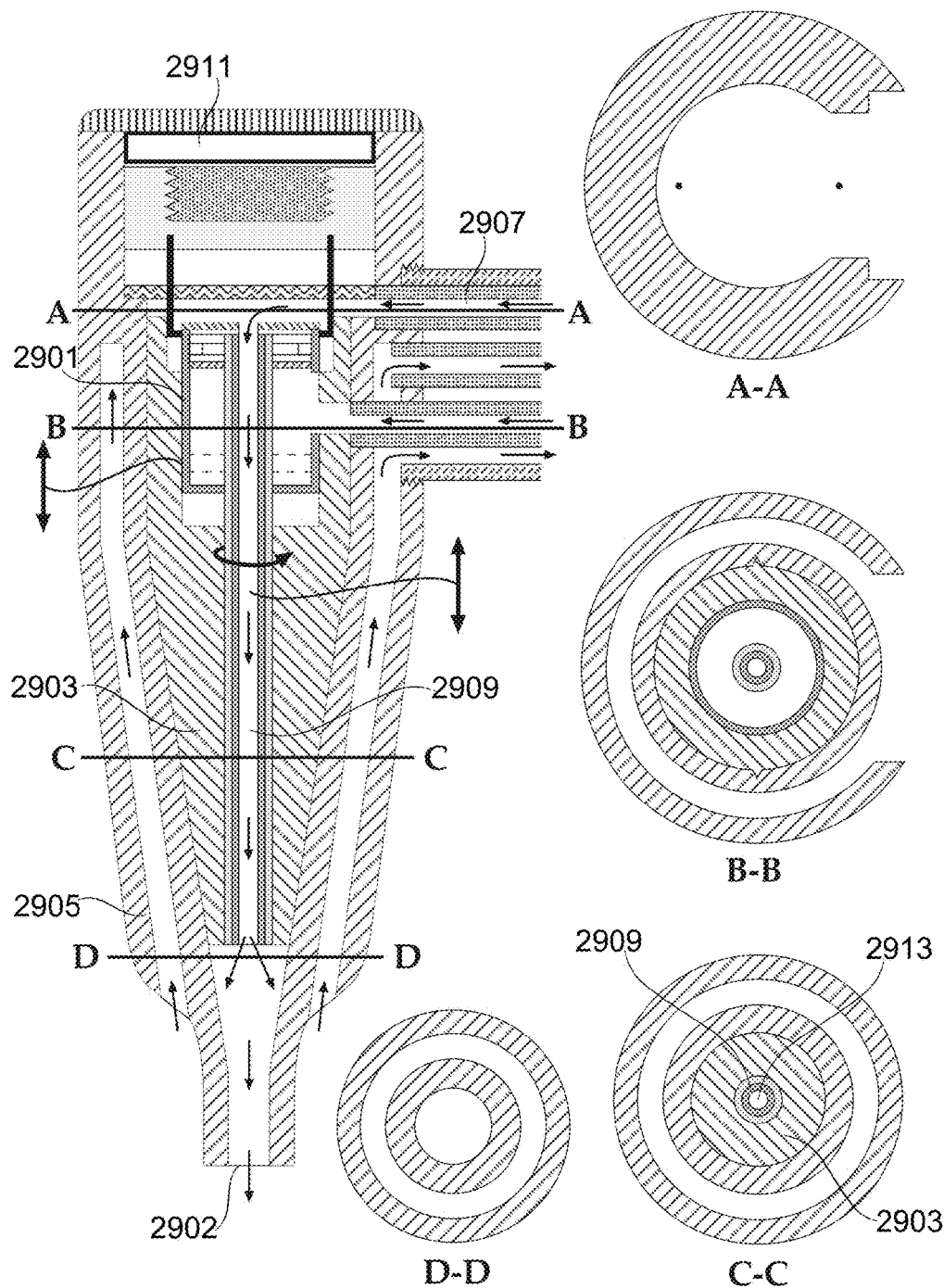
FIG. 29 illustrates a nozzle comprising an air turbine coupled to a pipe of the nozzle for spinning the fluid, according to some exemplary embodiments of the invention.

FIG. 29, now made reference to, illustrates a nozzle comprising a turbine 2901, according to some exemplary embodiments of the invention.

In some embodiments of the invention, turbine 2901 is driven by pressurized air, for example as described in connection with FIG. 28, hereinabove.

In some embodiments the nozzle does not comprise an internal and external cone, but rather one solid cone 2903 which is optionally positioned within a suction cone 2905. In this figure, fluid entering the nozzle—for example, through pipe 2907 in the handle flows into pipe 2909 which is coupled to turbine 2901, for example as described hereinabove.

In some embodiments corresponding to FIG. 29, fluid passes to the nozzle tip only through pipe 2909. In some embodiments, pipe 2909 is axially rotated by turbine 2901, causing fluid passing through it to spin. Potentially, the spun fluid within pipe 2909 exits nozzle tip 2902 at an angle imparted by its momentum. In some embodiments, stepper motor 2911 is coupled to turbine 2901 and/or to pipe 2909 for moving one or both of them in the proximal and/or distal directions. The cross section along line C-C shows cone 2903, pipe 2909, a lumen 2913 formed within pipe 2909 through which fluid passes, and the external suction cone 2905.

In some embodiments, the turbine is operable at one or more frequencies in a range of, for example: 2,000-10,000 RPM, 5,000-25,000 RPM, 10,000-100,000 RPM, 10,000-400,000 RPM, 2,000-400,000 RPM, or another larger or smaller range of rotational frequencies. In some embodiments, the pressure of air for driving the turbine is, for example: 10-20 PSI, 15-25 PSI, 10-30 PSI, 30-40 PSI, 30-60 PSI, or another larger or smaller range of driving pressures.

In some embodiments, pipe 2909 is smooth-bored. Potentially, spinning motion is imparted to fluid passing therethrough by viscous forces acting between the fluid and the lumenal wall of pipe 2909. Advancing and retraction of pipe 2909 relative to nozzle aperture 2902 potentially regulates the characteristics and/or parameters of flow exiting aperture 2902, for example, by changing its pathway through the nozzle chamber between a distal end of pipe 2909 and aperture 2902.

In some embodiments, the adjustment up and down of motor 2911 (e.g. moving pipe 2909) increases or decreases the vertical velocity and pressure in the space under the exit of the distal end of tube 2907 in the conical lumen.

Figure 30:
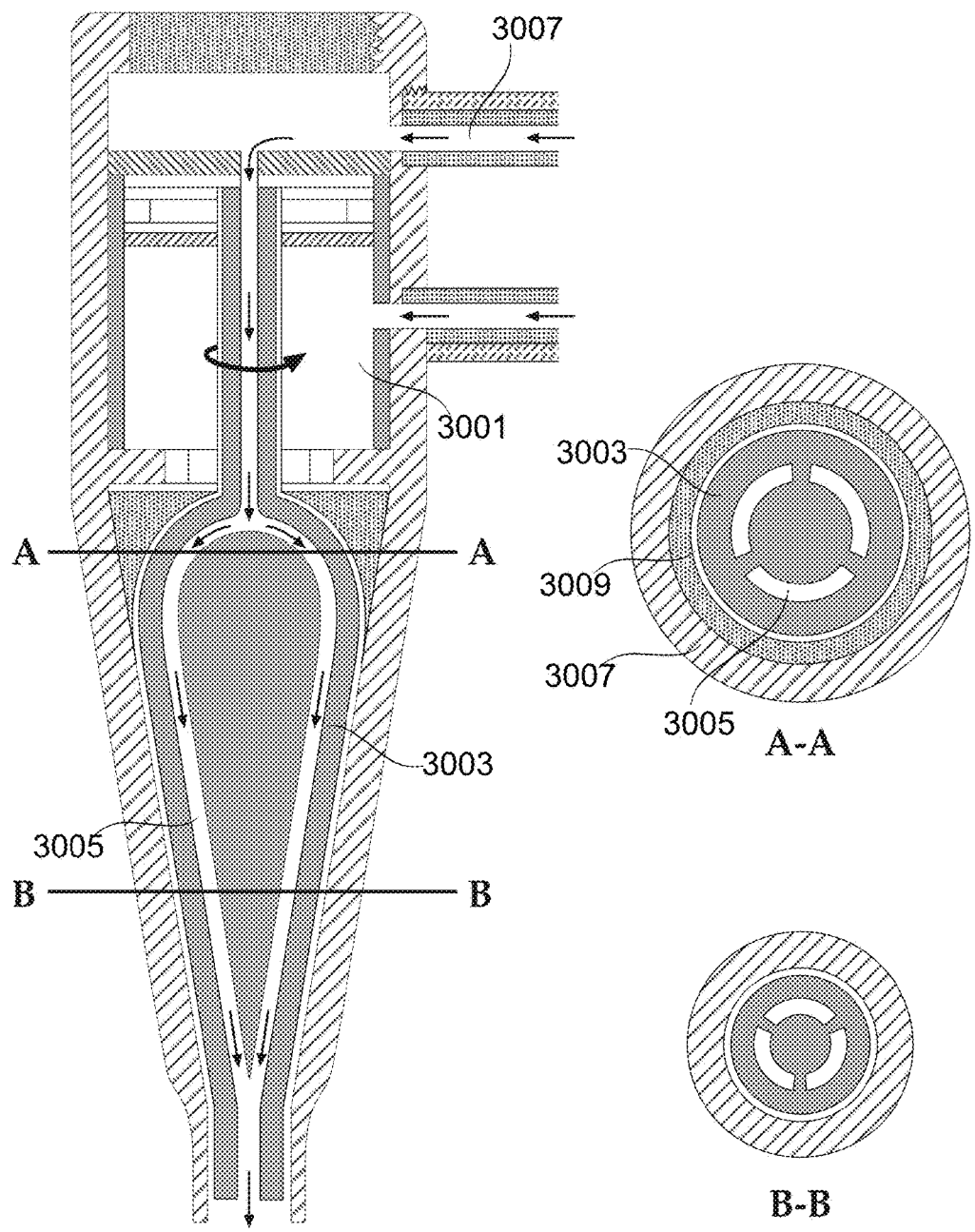
FIG. 30 illustrates a conical nozzle comprising an air turbine configured for rotating an internal cone, according to some exemplary embodiments of the invention.

FIG. 30, now made reference to, illustrates a nozzle comprising a turbine 3001 coupled to an internal cone 3003 for rotating the cone around its axis, according to some exemplary embodiments of the invention. FIG. 30 is an example of using a flow to rotate a flow modifying element.

In some embodiments, the internal cone 3003 is formed from a single solid piece comprising inner channels 3005 through which the fluid flows. In some embodiments, fluid enters the nozzle through pipe 3007 within the handle. In some embodiments, turbine 3001 rotates cone 3003 fast enough so that a centripetal force causes the fluid to flow along the walls of channels 3005 and/or causes fluid within the channels to spin and/or rotate. In some embodiments of the invention, momentum, potentially including angular momentum, is transferred from the motion of the turbine to the working fluid passing through cone 3003 before it is ejected from the nozzle. In some embodiments, fluid ejected from the nozzle is spinning/rotating/has helical flow.

Potentially, fluid exiting the nozzle does so at an angle which is broadened by the tangential component of its momentum at the exit aperture of the nozzle.

Cross section A-A shows rotating cone 3003, channels 3005, and an external cone 3007. The cross section also shows a lumen 3009 between the rotating cone 3003 and external cone 3007.

It should be noted that fluid exiting the distal aperture of cone 3003 is potentially in direct association with fluid external to the nozzle, the distal aperture being isolated from the surrounding tissue only by a relatively short sheathing length of the nozzle's outer wall. In some embodiments, this potentially improves the efficiency of energy transfer from the nozzle interior to the exteriorly acting working fluid.

Figure 31A:
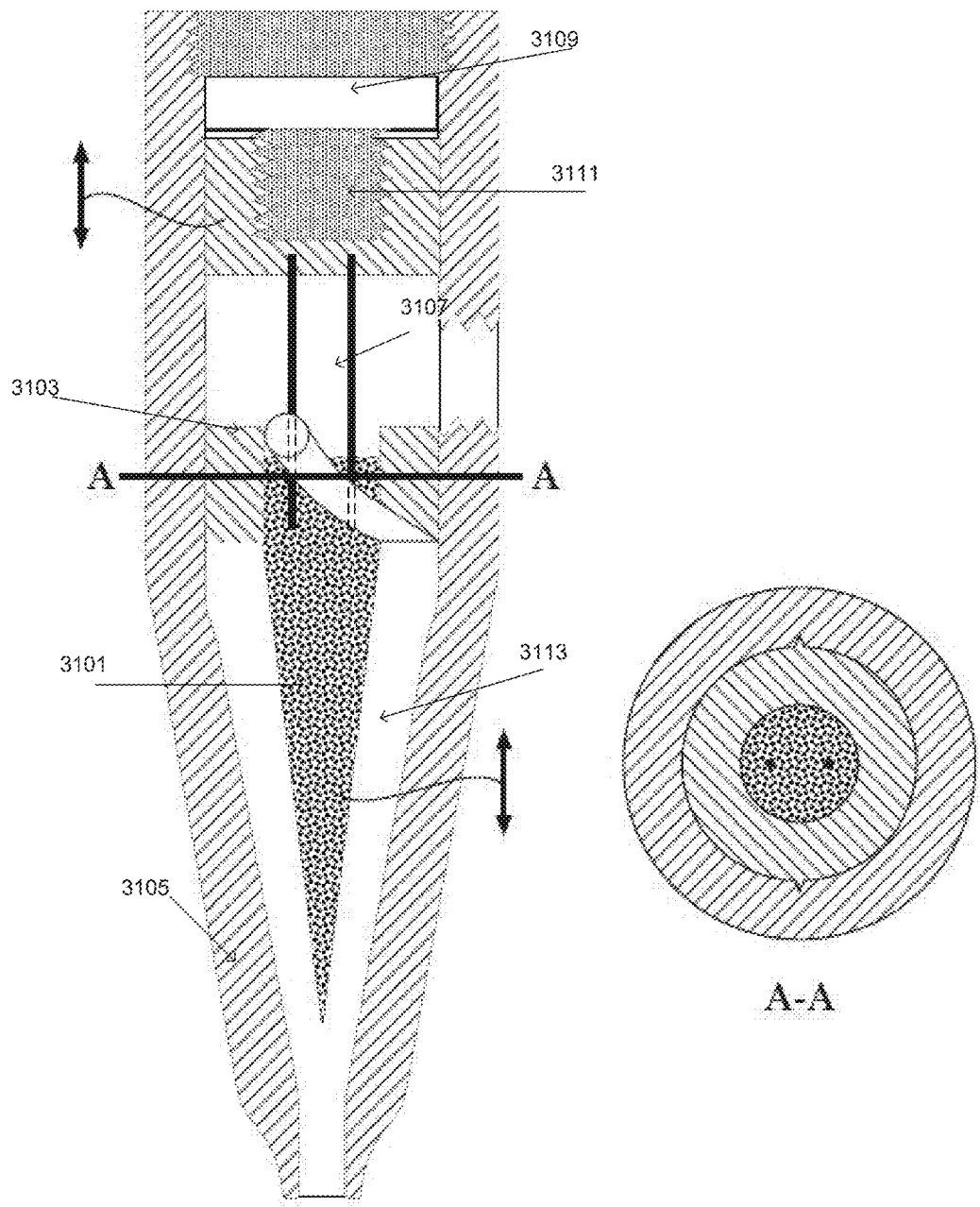
FIGS. 31A-31B show a conical nozzle in which only a narrowing portion of the internal cone is movable with respect to the external cone, according to some exemplary embodiments of the invention.
Figure 31B:
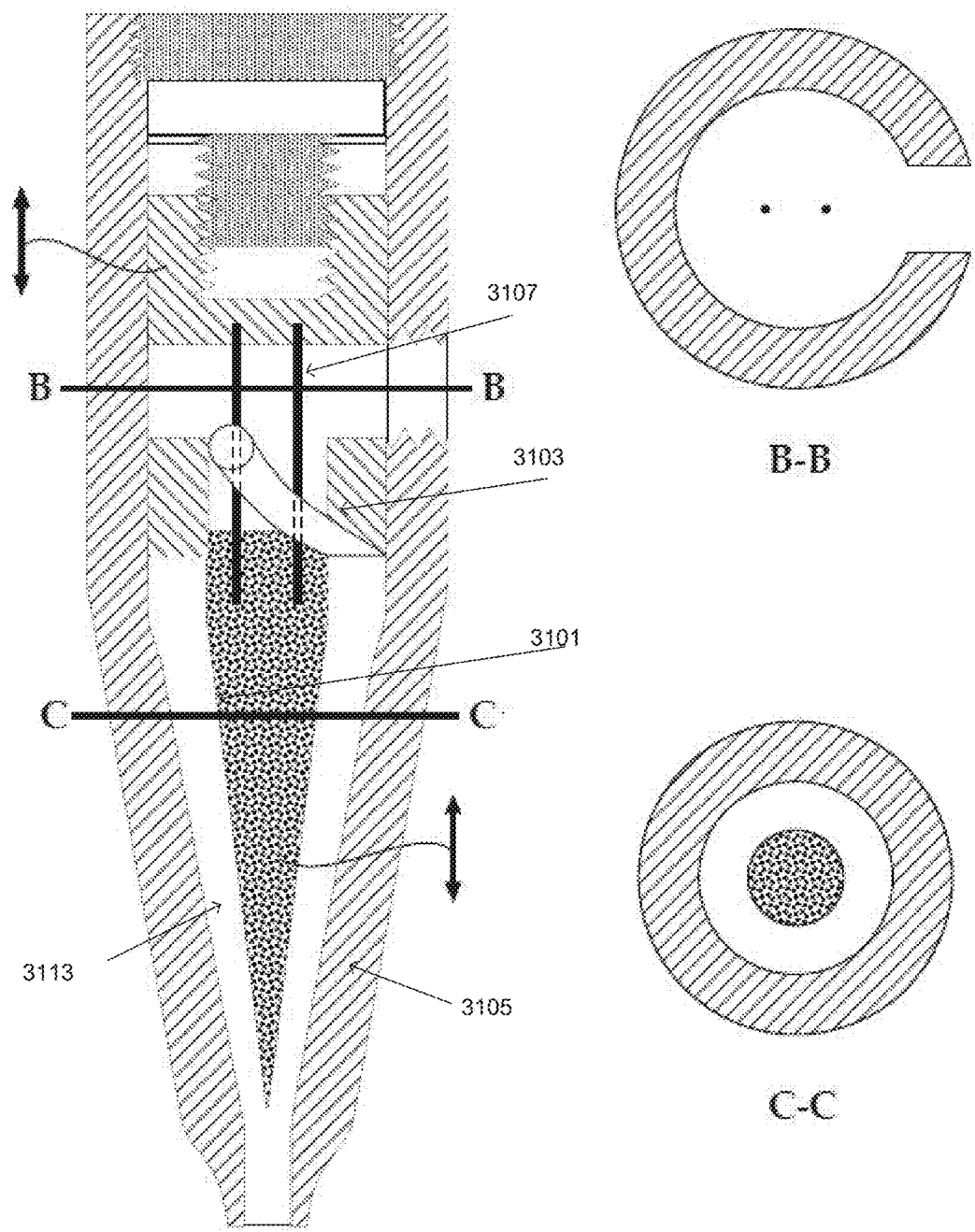

FIGS. 31A-31B, now made reference to, show a conical nozzle in which only the narrowing portion 3101 of internal cone 3103 is movable with respect to external cone 3105, according to some exemplary embodiments of the invention.

In some embodiments, inner walls of a (optionally needle-like) nozzle tip have a helical shape and/or grooves.

In some embodiments, different geometry of a nozzle tip, for example shape and/or diameter affect beam and/or angle jet axial velocity.

In some embodiments, geometry of the cross section of the nozzle tip has different geometries which affect fluid flow parameters.

In some embodiments of the invention, portion 3101 is connected to one or more rods 3107 which are distally/proximally positionable by stepper motor 3109. Optionally, rods 3107 are coupled to a threaded element 3111. In FIG. 31A, narrowing portion 3101 is shown lifted in the proximal direction, while in FIG. 31B, narrowing portion 3101 is shown advanced in the distal direction. Optionally, movement of the narrowing portion 3101 modifies a lumen between the cones, as described hereinabove.

In some embodiments, movement of the internal cone and/or pipe is manual, e.g. where a user manually moves one or more part (e.g. by pressing a button mechanism optionally including a spring) to move the internal cone and/or pipe.

In some embodiments, there is, for example, a ratchet or rotation of a rotating element via thread sets in different locations.

FIGS. 32-37 show various modes of operation of a system in accordance with some embodiments of the invention. Such modes are optionally achieved by varying parameters of the system such as one or more of pulse time, duty cycle, pulse rate, air/liquid ratio, and/or added powder.

Figure 32:
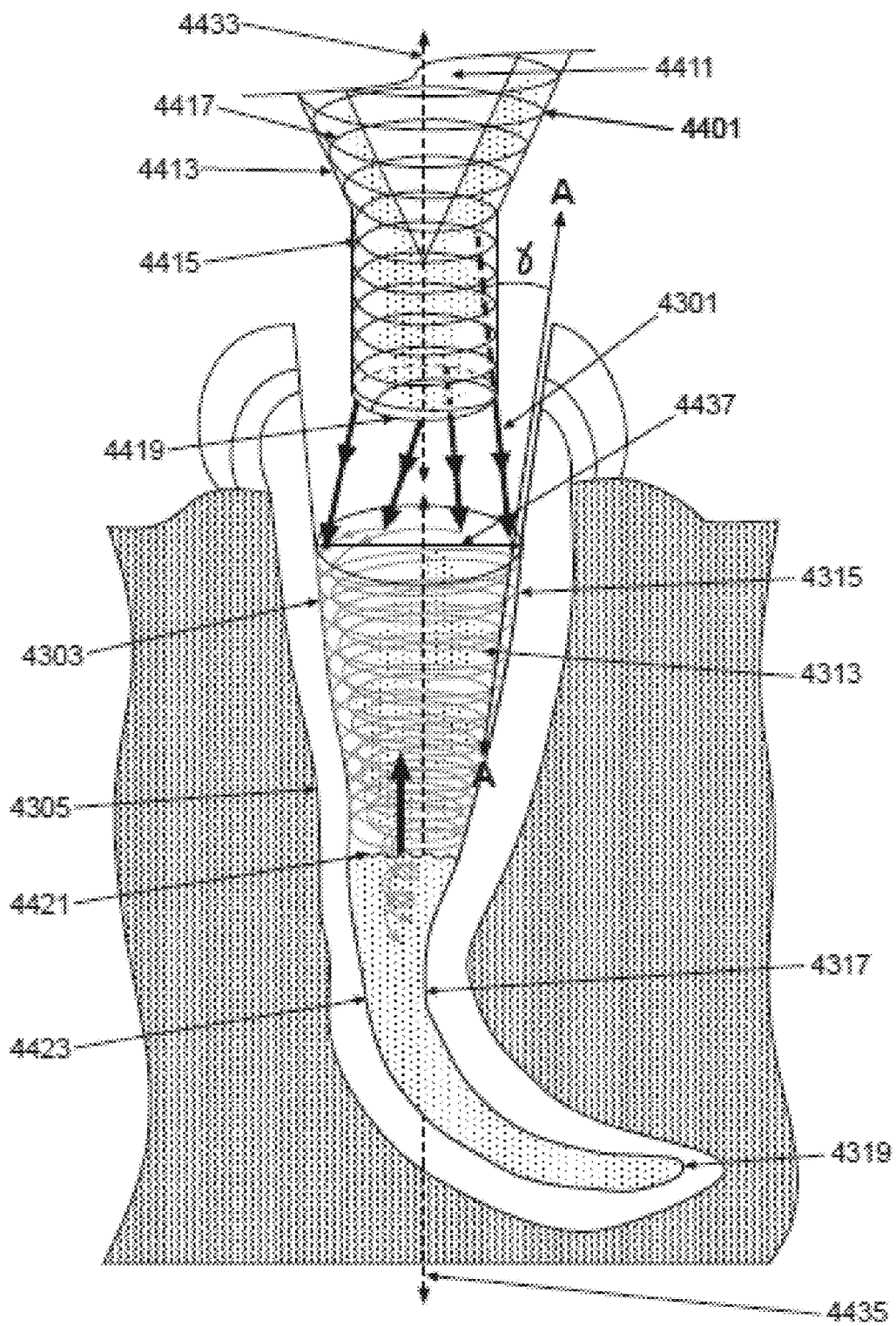
FIGS. 32, 33 and 34 show the operation of a system in which a plurality of jets are discharged by the nozzle, according to some embodiments of the invention.
Figure 33:
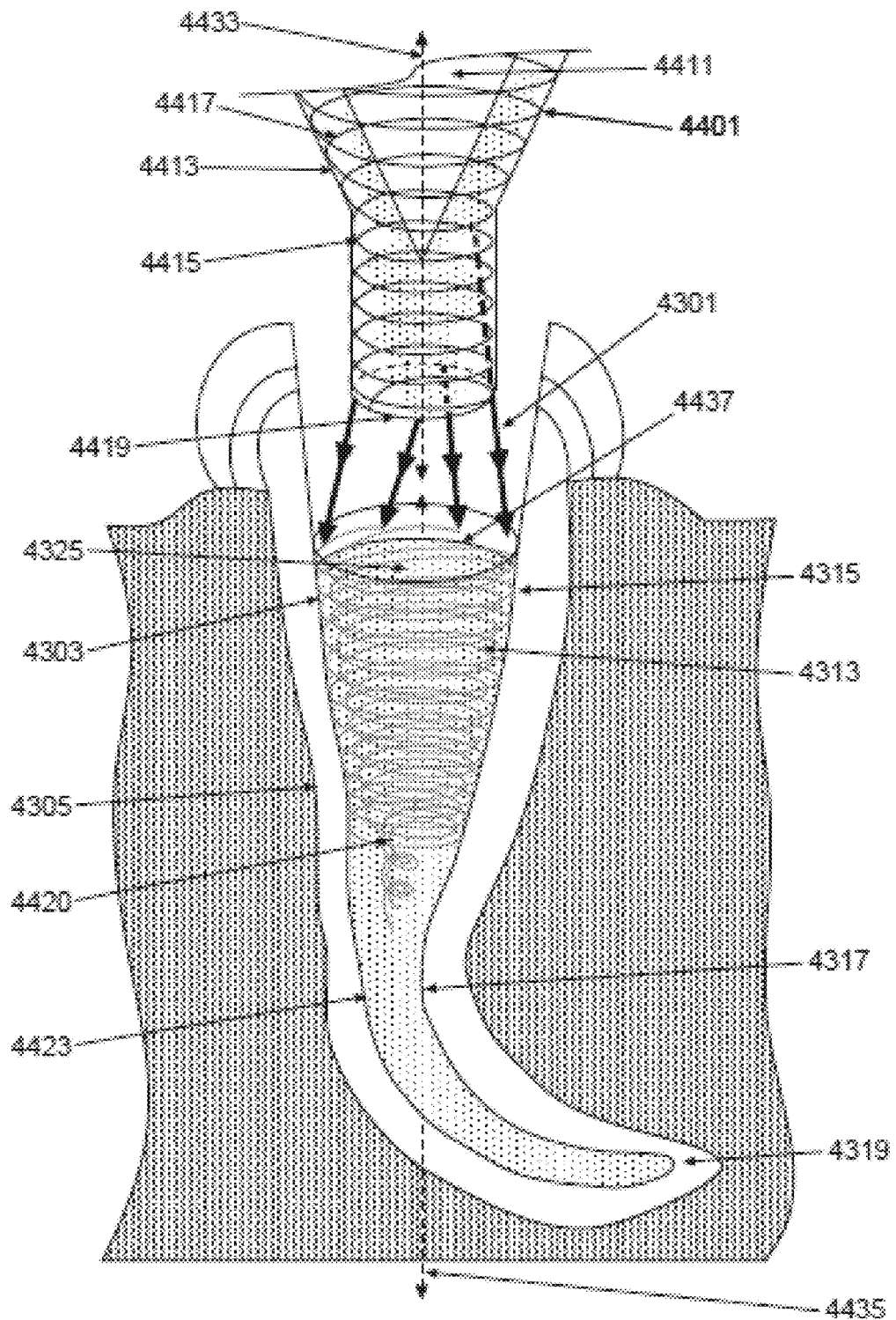
Figure 34:
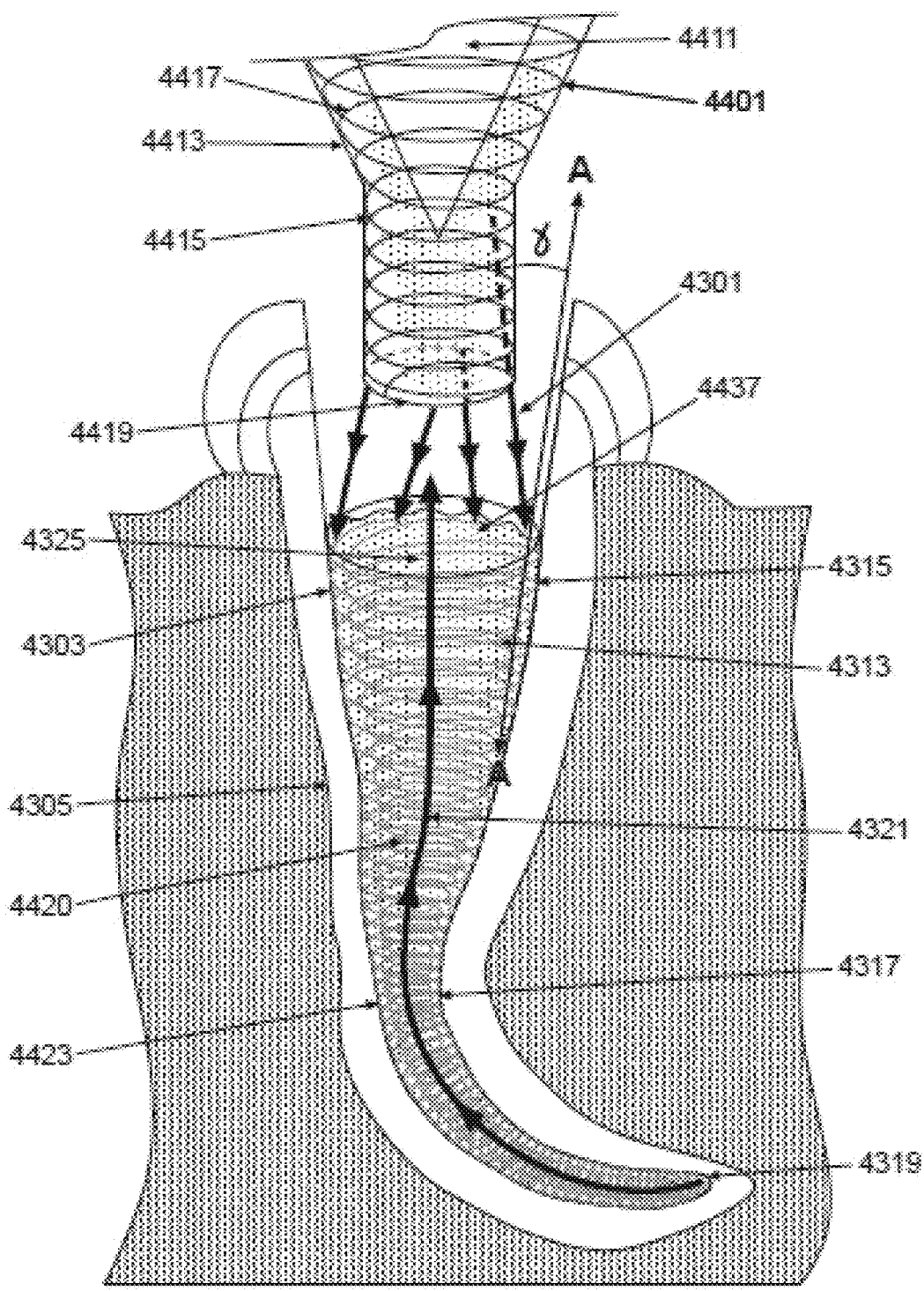

FIGS. 32-34 show the operation of a system, in accordance with some embodiments of the invention, where a plurality of jets 4301 (optionally a part of, or in the form of, a continuous cone of fluid or other beam shape) are discharged by the nozzle. As shown in a first condition in FIG. 32, a root canal 4315 has fluid up to a level 4421, in parameter conditions where a fluid level is formed. Jets 4301 hit a wall 4303 of root canal 4315 and form a cyclone 4313. In some embodiments, the cyclone comprises an aerosol combination of fluid droplet and gas.

In a second condition shown in FIG. 33, after a brief time (which may be, for example, 10-20 msec, 10-50 msec, 25-100 msec, 50-200 msec, or another larger or smaller interval of time), an evolution of conditions has occurred. Potentially, a density of fluid has increased above fluid level 4421, as fluid is injected into the root canal. In some embodiments, gas which initially exited the nozzle has been displaced by heavier fluid exiting the nozzle during the interval of evolution. In some embodiments, fluid which initially exited the nozzle has lost a portion of its velocity to interactions with the environment of the root canal. Potentially, less energetic fluid is displaced toward the center of the developing cyclone as new fluid is injected. A counterflow upwards potentially also begins as additional fluid is introduced from above with sufficient axial velocity to force its way downward. In some embodiments, the energetic fluid also begins to set up turbulent zones, which potentially change their position, velocity, and/or size over time.

In a third condition, shown in FIG. 34, a fully developed cyclone has arisen. In some embodiments and conditions, the fully developed cyclone arises after brief interval from the situation shown in FIG. 33. The interval is, for example, 10-20 msec, 10-50 msec, 25-100 msec, 50-200 msec, or another larger or smaller interval of time. In some embodiments of the invention, the cyclone develops to reach an apex 4319 of the root canal.

In some embodiments, the cyclone comprises fluid that was previously below the fluid level 4421 which has received energy transferred to from the injected fluid. Additionally or alternatively, the fluid injected form the nozzle carries sufficient energy to force its way down to the tip. In some embodiments of the invention and conditions, a counterflow develops such that fluid which reaches the apex 4319 is forced upward again in a counterflow by new fluid following behind it. Optionally, this flow occurs in addition to or instead of rotation caused by fluid traveling along the wall. In some cases, fluid below the fluid level 4421 are turbulent and include significant flow vectors other than parallel to and along the wall of the root canal 4315. Optionally, the turbulence helps remove debris, dentine, and/or soft tissues from the wall, tubules, and/or out of the canal. In some embodiments, a fluid level can be achieved, theoretically, even when the tooth is turned upside down.

It should be understood that the interactions of air and water (gas and fluid) in the root canal potentially create a condition in which inertial forces strongly dominate viscous forces (a high Reynolds number). As new air/water mixture is injected into the root canal, energetic and potentially turbulent flow is carried with relatively great freedom throughout the region being irrigated, as losses due to viscosity become relatively negligible. It should be understood that the boundaries of various relative fractions of gas and fluid at various depths of the root canal are potentially continuous and/or indistinct during active irrigation, as turbulence and other activity cause fluctuations in flow. In some embodiments, the boundary deeper than which (reaching into the root canal) the total volume of fluid and air in the channel is at least 50% fluid is, for example, about 3-4 mm, about 4-5 mm, about 4-8 mm, about 6-9 mm, or another larger or smaller depth. The conditions of initial gas/fluid mixing associated with these depths are, for example, selected from among those described in connection with Table 1, hereinabove.

Figure 35:
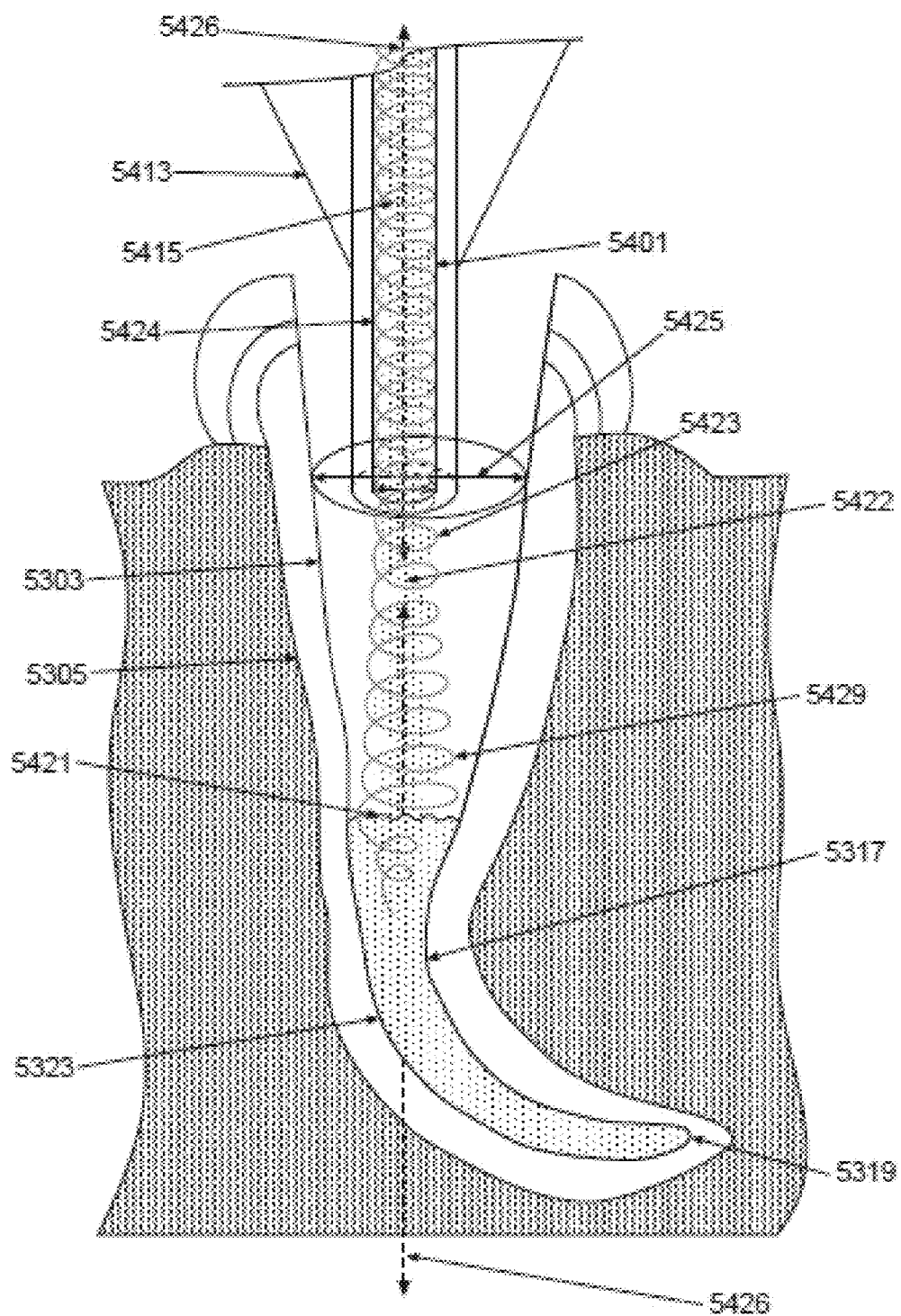
FIGS. 35, 36 and 37 show the operation of a system in which fluid is delivered through a needle-like cylinder, according to some embodiments of the invention.
Figure 36:
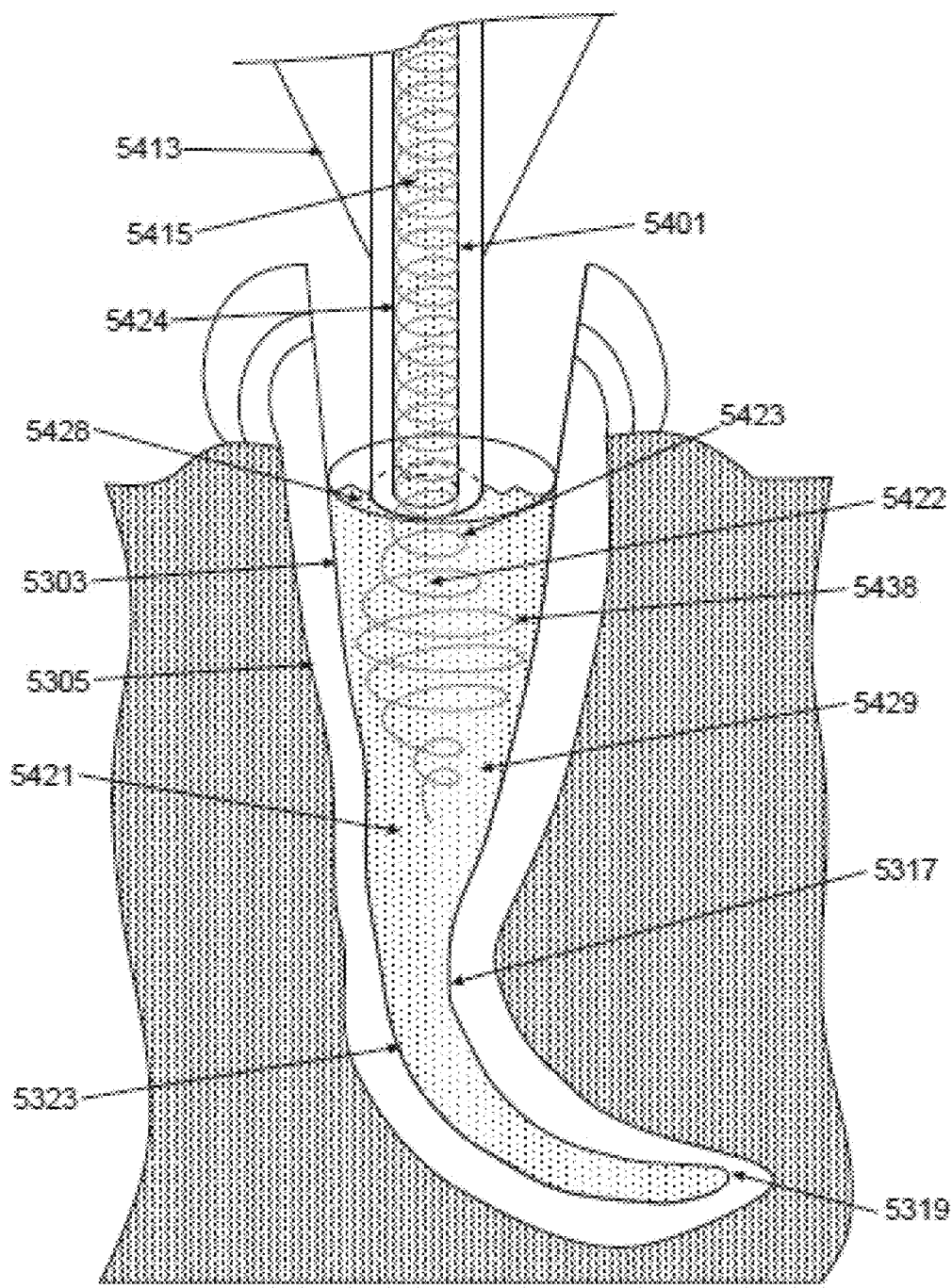
Figure 37:
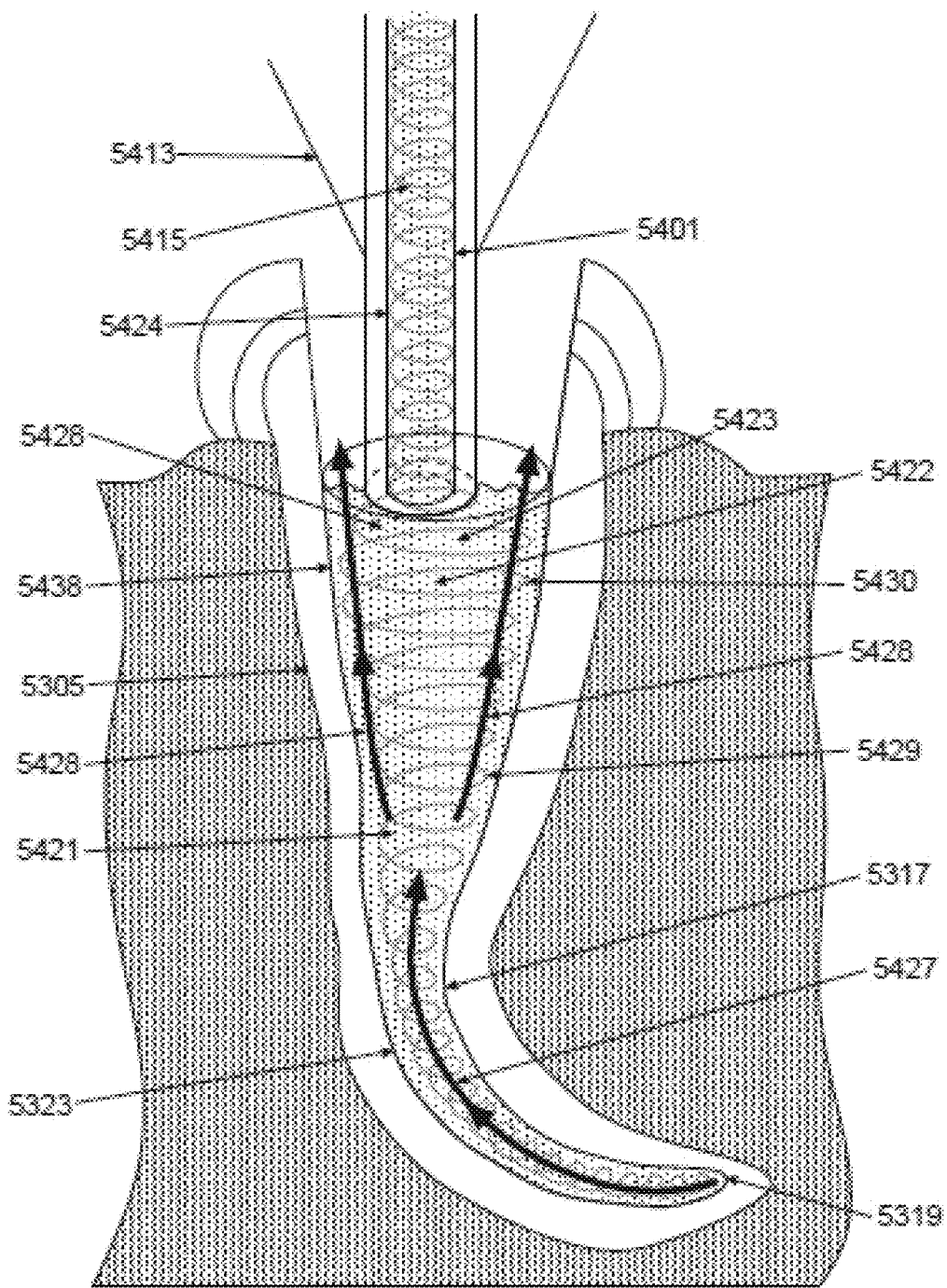

FIGS. 35-37 show the operation of a system, in accordance with some embodiments of the invention, where fluid is delivered through a needle-like cylinder 5401. Optionally, cylinder 5401 is axially rotated within the nozzle, for example by a turbine as described above. Optionally, a distal end of the cylinder is positioned above root canal entrance 5425. Alternatively, a distal end of cylinder 5401 is entered, at least partially, into the root canal, as in FIGS. 35-37. Optionally, an exit aperture of cylinder 5401 is leveled with a level of fluid 5421 within the canal. Alternatively, the exit aperture of cylinder 5401 is advanced into the fluid within the canal, for example 0.1 mm, 0.5 mm, 1 mm, 2 mm, 4 mm. or intermediate, larger or smaller distances.

In some embodiments, the rotating cylinder 5401 directly couples to fluid within the canal to rotate it (for example, as in FIG. 36). In some embodiments, the helical flow exiting cylinder 5401 induces a helical, rotational and/or turbulent flow within the canal, for example when the hitting fluid that accumulated within the canal (FIG. 35), and additionally or alternatively by replacement of the accumulated fluid with fluid and/or air that has been energetically injected into the root canal. In some embodiments, the rotating cylinder forms a cone shaped beam of fluid exiting the cylinder. In some embodiments, the flow of the cone shaped beam has an angular component (i.e. not only a vertical component) so that the conical beam is effectively formed of a plurality of angled jets.

In some embodiments, flows, counterflows, turbulence, and other features of the motion of fluid described hereinabove in relation, for example, to FIGS. 32-34, are induced. In particular, helical and/or turbulent flow potentially propagates all the way to the apex 5319 of the root canal. Potentially, full penetration of the root canal is assisted by high energy and relatively low viscosity of an air/water mix ejected from the tip of the nozzle.

FIG. 38 shows various configurations of needle-like tubes which can be assembled onto a nozzle, for example assembled on a distal exit aperture of the nozzle. The various configurations are suitable for use with root canals having different anatomical structures. The various configurations may comprise different lengths, different profiles of exit apertures, different diameters. In some embodiments, a proximal end of the needle like tube is coupled to a distal end of a nozzle. Optionally, the needle like tube is attachable by a threaded connection. In some embodiments, a nozzle is structured such as to connect, such as by fastening means (a screw, clasp or other) by adhesive means, and/or by a structural geometrical connection to one or more types of needle-like tubes. In some embodiments, the needle like tubes form different types of beams and flow patterns. Optionally, a needle like tube is selected to affect the velocity of the flow, for example between the angular velocity of the fluid circulating within the nozzle and the tangential velocity of the flow exiting the nozzle. In some embodiments, the distal aperture of the needle like tube comprises a circular profile, an elliptical profile, an oval profile, a beveled form, a trapezoid profile, a triangular profile or any other profile and/or geometry.

Figures 39A, 39B:
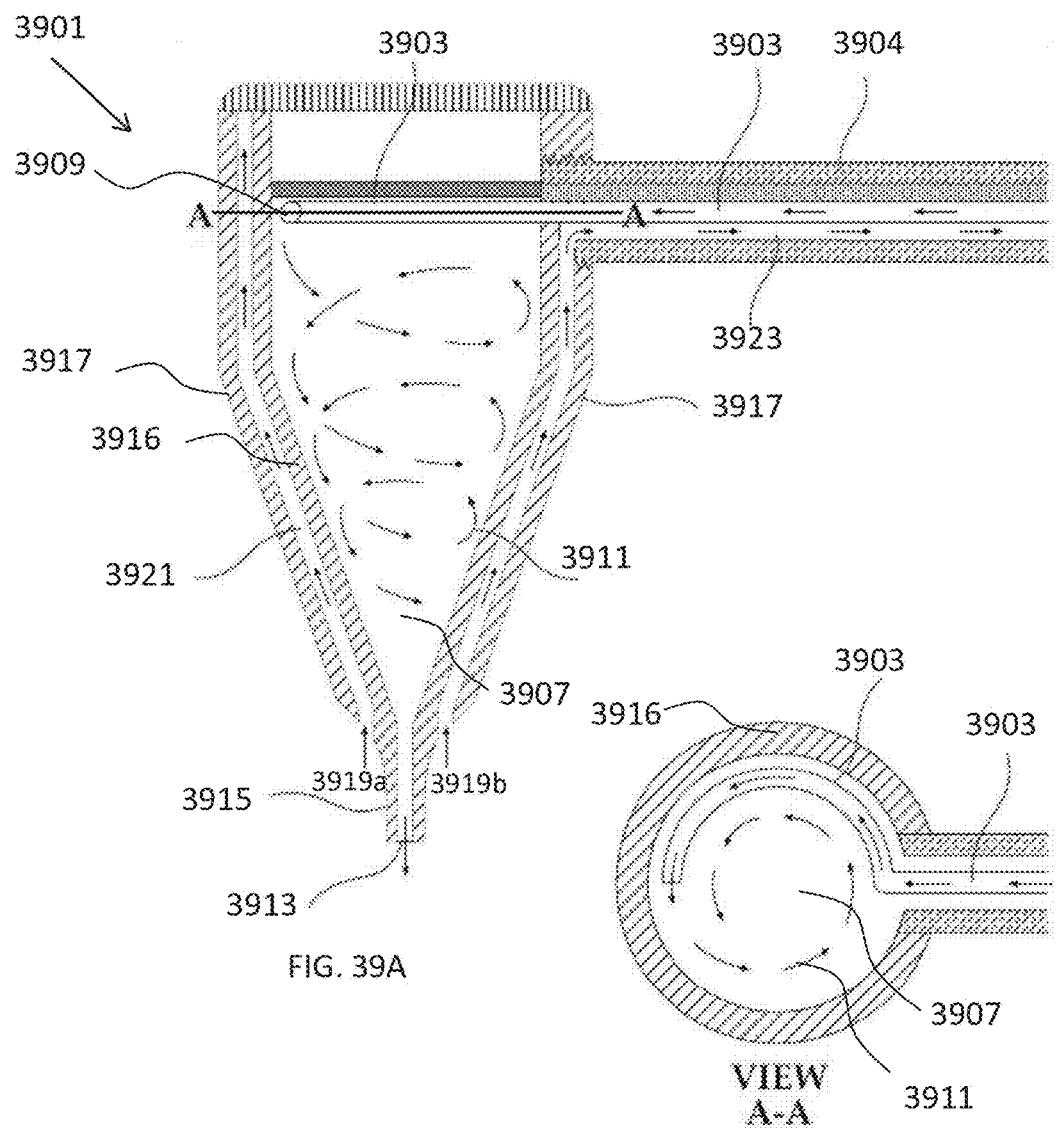
FIG. 39A is a simplified schematic cross sectional view of a nozzle lacking an internal cone, according to some embodiments of the invention.
FIG. 39B is a simplified schematic cross sectional view of a nozzle lacking an internal cone, according to some embodiments of the invention.

FIG. 39A is a simplified schematic cross sectional view of a nozzle 3901 lacking an internal cone, according to some embodiments of the invention. In some embodiments, one or more angled jet (e.g. a jet at an angle which does not intersect a vertical axis of the nozzle) is discharged from a cone lacking an internal cone. In some embodiments, fluid discharged from a jet without an internal cone intensifies or causes rotation of fluid within an at least partially filled root canal.

In some embodiments, fluid flows through a nozzle lumen lacking an inner cone with a helical and/or rotating path and/or the fluid flows in contact with lumen walls.

In some embodiments, a pipe 3903 (optionally, in some embodiments, more than one pipe) carrying material (e.g. fluid including one or more of liquid, air, abrasive powder, disinfection component/s) extends into nozzle lumen 3907 and pipe 3903 includes a pipe outlet 3909 which is proximal to a portion nozzle lumen walls 3916. In some embodiments, the pipe and/or pipe outlet is angled and/or positioned and/or shaped such that a flow 3911 (e.g. jet) of fluid from pipe 3903 impacting a portion of nozzle lumen walls 3916 flows in a radial and/or centrifugal and/or helical and/or spiral manner, e.g. spiraling downwards through nozzle lumen 3907. In some embodiments, an angle of the flow (e.g.) exiting pipe 3907 is at an angle which does not intersect a vertical axis of the nozzle.

In some embodiments, flow speed and/or pressure and/or composition contribute to helical flow of fluid within the nozzle and/or characteristics and/or parameters of jet/s discharged from the nozzle.

In some embodiments, pipe 3903 is runs through a handle 3904 attached to nozzle 3901.

In some embodiments, flow 3911 substantially remains in contact with the nozzle lumen wall (e.g. flowing within 5 mm of, or within 2 mm of, or within 1 mm of, or within 0.5 mm of, or within 0.1 mm of or within 0.01 mm, of the walls or smaller, or larger, or intermediate measurements. In some embodiments, flow 3911 exits nozzle 3901 through a nozzle outlet (also termed nozzle exit aperture) 3913.

Optionally, nozzle 3901 includes a narrow, needle like tip 3915, e.g. with a diameter of, for example, less than 5 mm, or less than 2 mm, or less than 1 mm, or less than 0.5 mm, or less than 0.2 mm, or less than 0.1 mm, or less than 0.05 mm, or less than 0.01 mm. Alternatively, in some embodiments, nozzle tip 3915 is larger e.g. with a diameter of more than 0.5 mm, or more than 1 mm, or more than 2 mm, or more than 5 mm, or more than 10 mm.

Optionally, at least a portion of an inner surface of nozzle lumen walls 3916 is textured (e.g. grooved), potentially assisting and/or enabling helical flow of the fluid. In some embodiments, grooves are helical and/or spiral downward towards nozzle outlet 3913. In some embodiments, grooves are other than helical, for example in some embodiments, grooves form a double helix, in some embodiments grooves form two opposing helixes. Optionally, in some embodiments, nozzle outlet 3913 is textured (e.g. grooved) potentially assisting and/or enabling helical flow of the fluid as it exits through outlet 3913.

In some embodiments, helical and/or spinning and/or rotating of the flow within the nozzle results in emission from the nozzle outlet of angled fluid jet/s.

Optionally, nozzle 3901 includes one or more inlet through which material is removed from the tooth, e.g. by suction. In an exemplary embodiment, nozzle 3901 includes a suction cone 3917 which, in some embodiments, is a structure (optionally cone-shaped) at least partially surrounding the nozzle lumen walls where there is a lumen 3921 (optionally cone shaped) between the nozzle lumen walls 3916 and suction cone 3917. In some embodiments, lumen 3921 connects to an extraction pipe 3923 within handle 3904 and suction of material through inlets 3919a, 3919b is applied by pressure reduction at extraction pipe 3923 (e.g. using a pump connected to extraction pipe 3923).

FIG. 39B is a simplified schematic cross sectional view of a nozzle 3901 lacking an internal cone, according to some embodiments of the invention. FIG. 39B shows a cross section perpendicular to the cross section illustrated in FIG. 39A taken along the line A-A illustrated on FIG. 39A. In some embodiments, as illustrated in FIG. 39B, the portion of pipe 3903 which extends into nozzle lumen 3911 is curved and/or bent, for example, bending so that the pipe is in close proximity to nozzle lumen walls 3916.

In some embodiments, one or more inlet into a nozzle lumen moves, for example, rotates. FIG. 40A is a simplified schematic cross sectional view of a nozzle 4001 including a rotating inlet element 4005, according to some embodiments of the invention.

In some embodiments, fluid is inserted into a nozzle through a rotating inlet element 4005. In some embodiments, rotating inlet element 4005 includes one or more exit aperture (e.g. two exit apertures 4023) through which fluid is inserted into a nozzle lumen 4007. In some embodiments, each exit aperture 4023 is located on a rotating inlet element arm 4025. In some embodiments, fluid (e.g. including one or more of liquid, gas (e.g. air), abrasive powder, disinfection component/s, and flushing fluid) is supplied to rotating inlet element 4005 through a pipe 4003 connected to rotating inlet element 4005. In some embodiments, pipe 4003 runs through a handle 4037 connected to the nozzle 4001.

In some embodiments rotating inlet element 4005 is disposed within a nozzle lumen 4007 where the lumen is a space between an inner cone 4019 and an outer cone including nozzle lumen walls 4021. In some embodiments, nozzle 4001 includes a nozzle tip 4041 through which fluid is discharged. Alternatively, the nozzle does not include an inner lumen and the rotating element is disposed inside a nozzle lumen defined by nozzle lumen walls 4021.

In some embodiments, rotation and/or movement of rotating element 4005 and/or the shape of the conical lumen causes the fluid to flow in a rotating and/or helical downwards motion.

In some embodiments, rotating element 4005 and fluid flow within the nozzle is not exposed to the atmosphere, a potential benefit being that fluid flowing through the nozzle is not exposed to the atmosphere, for example, preventing degradation of the fluid and/or component/s of the fluid e.g. by exposure to atmospheric contaminants such as dirt, bacteria, e.g. by exposure of reactive component/s to atmospheric oxygen.

In some embodiments of the invention, momentum, potentially including angular momentum, is transferred from the motion of the rotating element 4005 to the working fluid passing through lumen 4007 before it is ejected from nozzle. In some embodiments, fluid ejected from the nozzle is spinning/rotating/has helical flow.

Potentially, fluid exiting the nozzle does so at an angle which is broadened by the tangential component of its momentum at the exit aperture of the nozzle.

Optionally, in some embodiments, nozzle 4001 includes one or more additional pipe, e.g. a second pipe 4003a through which air flows into an air turbine 4043. In some embodiments, rotating inlet element 4005 is rotated by air turbine 4043. Alternatively, rotating inlet element 4005 is rotated by mechanical and/or electrical means e.g. by a stepper motor connected to the rotating inlet element.

Optionally, in some embodiments, a second material is inserted into lumen 4007. In some embodiments, the second material is air and/or pressurized gas (e.g. pressurized air)

which optionally pushes fluid towards a nozzle outlet 4015. Optionally, movement and/or rotation of rotating inlet element 4005 mixes the second material with the fluid inserted through pipe 4003.

Optionally, in some embodiments, an additional pipe, a third pipe 4003*b* inserts material and/or fluid into a second conical lumen 4029. In some embodiments, third pipe discharges disinfecting fluid and/or flushing fluid.

Optionally, nozzle 4001 includes one or more inlet through which material is removed from the tooth, e.g. by suction. In an exemplary embodiment, nozzle 4001 includes a suction cone 4017 which, in some embodiments, is a structure (optionally cone-shaped) at least partially surrounding the nozzle lumen walls 4021 where there is a lumen 4031 between nozzle lumen walls 4021 and suction cone 4017 through which material is extracted. In some embodiments, lumen 4031 connects to an extraction pipe 4033 within handle 4037 and suction of material is by pressure reduction at extraction pipe 4033 (e.g. using a pump connected to extraction pipe 4033).

In some embodiments, suction of material from the root canal reduces pressure in a root canal apex and/or an apical area (portion of the root canal proximal to the apex).

In some embodiments, movement of nozzle parts, for example, movement of the internal cone, is manual e.g. where a user manually moves one or more part (e.g. by pressing a button).

In some embodiments, suction can be used to control an extent of rotation and/or fluid within a root canal. For example, in some embodiments, increased suction reduces a length and/or strength (e.g. velocity of flow) of a water column within the root canal.

FIGS. 40B-40C are simplified schematic cross sectional views of a nozzle including a rotating inlet element 4005, according to some embodiments of the invention. FIGS. 40B and FIG. 40C show cross sections perpendicular to the cross section illustrated in FIG. 40A taken along the line A-A and line B-B illustrated on FIG. 40A respectively. In some embodiments, as illustrated in FIG. 40C, lumen 4007 is optionally divided by one or more divider 4035 for dividing the flow through lumen 4007. Optionally, in some embodiments, dividers are located along the length of lumen 4007.

Figure 41:
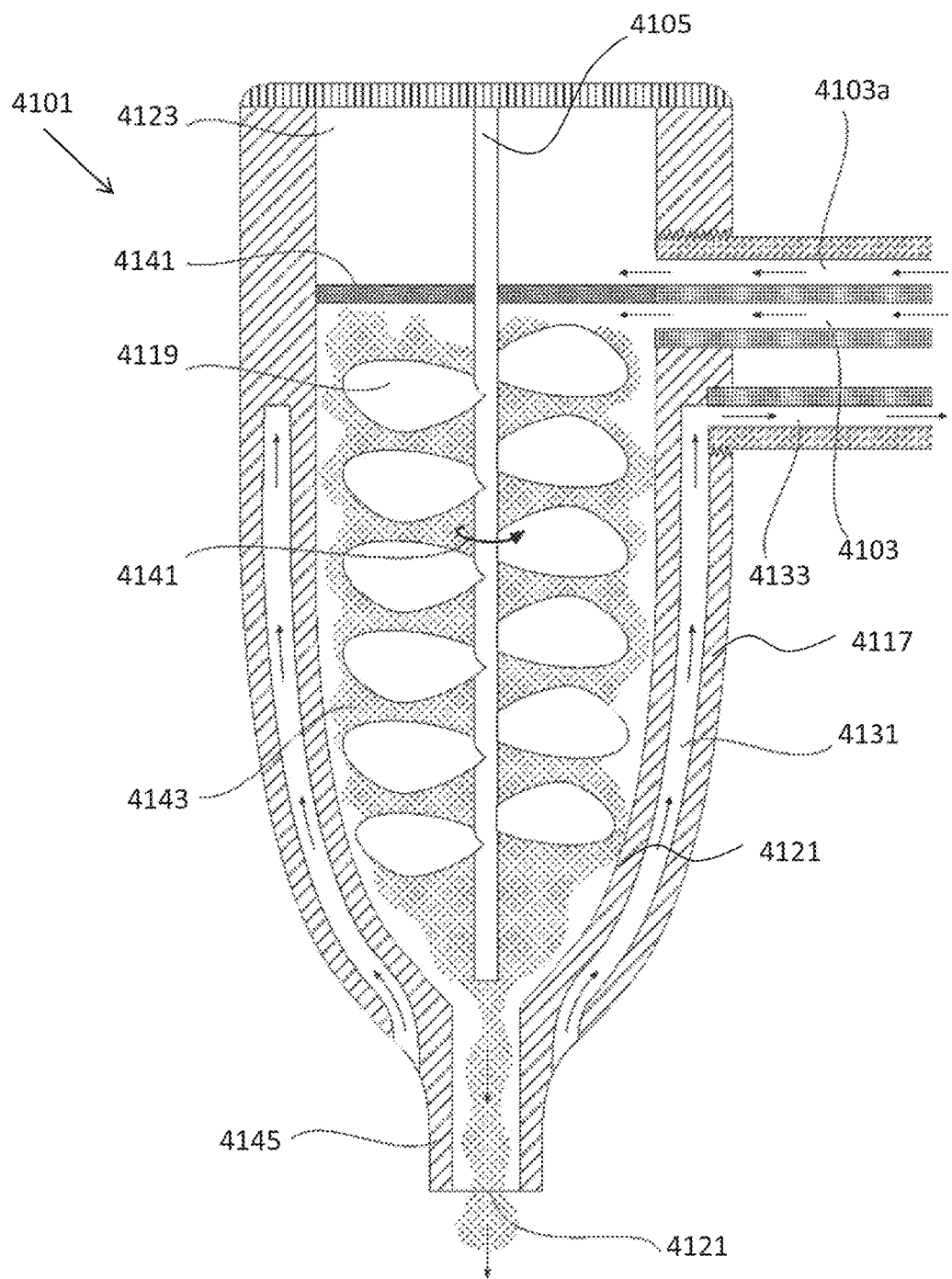
FIG. 41 is a simplified schematic cross section of a nozzle including a rotating element, according to some embodiments of the invention.

In some embodiments, a rotating element mixes and/or agitates fluid flowing through a nozzle lumen. FIG. 41 is a simplified schematic cross section of a nozzle 4101 including a rotating element 4105, according to some embodiments of the invention.

In some embodiments, rotating element 4105 rotates 4141 around a rotating element long axis. In some embodiments, rotating element 4105 includes one or more protruding element, e.g. blades 4119. In some embodiments, blades have a flattened shape, for example, where a thickness of the blade is less than half, or a quarter, or a tenth or smaller, larger or intermediate proportions, of a length and/or a depth of the blade. In some embodiments, the blades provide a large surface area of contact between the rotating element and fluid flowing through the nozzle, potentially increasing energy and/or momentum transfer between the rotating element and the fluid.

In some embodiments, the blade/s are shaped such that the blades push and/or pump the fluid through the nozzle toward a nozzle exit aperture 4121, for example, the rotating element acts as an impellor. For example, in some embodiments, one or more blade is at an angle to a vertical axis of the nozzle where a length-depth plane of the blade is at an angle to the vertical axis of the nozzle e.g. by at least 2 degrees, or 10 degrees, or 25 degrees, or 45 degrees, or 90 degrees, or smaller, or larger, or intermediate angles.

In some embodiments, fluid (e.g. including one or more of liquid, air, abrasive powder, disinfection component/s) is inserted into the lumen through a fluid pipe 4103.

In some embodiments, rotating element is rotated by an air turbine 4123 where air is supplied to the turbine through a second pipe 4103*a*.

In some embodiments, a second material, for example, air and/or another gas is inserted into the lumen through pipe 4103. In some embodiments, pressurized material inserted through pipe 4103 (e.g. pressurized air) pushes fluid inside lumen 4143 towards outlet 4121 and/or rotating element blades 4119.

In some embodiments, movement of rotating element 4105 mixes material inserted into nozzle lumen 4143. For example, mixing fluid inserted through pipe 4103.

For example, in some embodiments, materials are inserted separately, e.g. through pipe 4103 where different materials are inserted in alternative pulses, e.g. through pipe 4103 and optionally through additional pipe/s.

In some embodiments, helical and/or spinning and/or rotating of the flow within the nozzle results in emission from the nozzle outlet of angled fluid jet/s.

A potential benefit of mixing materials within a nozzle lumen is that the materials are not exposed to the atmosphere, for example, preventing degradation of the materials e.g. by exposure to atmospheric contaminants such as dirt, bacteria, e.g. by exposure of reactive materials to atmospheric oxygen.

Optionally, nozzle 4101 includes one or more inlet through which material is removed from the tooth, e.g. by suction. In an exemplary embodiment, nozzle 4101 includes a suction cone 4117 which, in some embodiments, is a structure (optionally cone-shaped) at least partially surrounding the nozzle lumen walls 4121 where there is a lumen 4131 between nozzle lumen walls 4121 and suction cone 4117 through which material is extracted. In some embodiments, lumen 4131 connects to an extraction pipe 4133 within handle 4125 and suction of material is by pressure reduction at extraction pipe 4133 (e.g. using a pump connected to extraction pipe 4133).

Optionally, rotating element 4105 includes a hollow portion through which material is inserted into lumen 4143.

Optionally, nozzle 4101 does not include an internal cone.

Additionally and/or alternatively, rotating element 4105 moves within lumen 4143, e.g. proximally-distally.

In some embodiments, nozzle 4101 includes a nozzle tip 4145 through which fluid is discharged.

In some embodiments the pressure in apical area and apex is controlled (e.g. kept low), for example, by spreading or dividing the flow of fluid. In some embodiments, fluid is discharged into a root canal such that the fluid does not directly impact the apex and/or apical area. For example, in some embodiments, fluid is discharged such that fluid hits a wall of the root canal above (coronal) an apical area of the root canal. For example, in some embodiments, fluid is discharged at an angle at least 10 degrees, or at least 30 degrees, or at least 90 degrees from an angle of a straight line connecting a discharge point of the fluid from the nozzle and the apex.

A potential benefit of helical flow of fluid within a root canal is that fluid is less likely to directly impact the apex and/or apical region, for example, in a time period at a beginning of a treatment and/or at a beginning of discharging of fluid (e.g. the first 0.1 s, 0.5 s, or 1 s, or 5 s or higher, lower or intermediate times) into a root canal before the root canal fills with fluid. In some embodiments, a root canal is filled with fluid e.g. manually and/or through the nozzle (e.g. at a low speed and/or pressure and/or flow rate) potentially protecting the apex.

In some embodiments, a needle tip 4241 including a needle tip lumen which increases in cross sectional area distally towards a nozzle aperture 4243. The liquid exiting from the nozzle through tip 4241 exits with a wide angle of, for example, 20-70 degrees, or lower, or higher, or intermediate angles, flowing and filling the root canal e.g. from the apex of the canal upward (coronal), with wide angle of flow, meaning that the pressure of the flow is divided along the wall surface e.g. as a non-direct flow.

In some embodiments, pulsed suction and/or discharging reduces pressure of fluid flow at the apex and/or apical area e.g. fluid is extracted before it reaches the apex and/or apical area. In some embodiments, for example, due to the narrow space in the apical area pressure reduction from suction is more rapid than in the remainder of the root canal (e.g. at 1.5× the rate, or at double the rate, or at triple the rate).

FIG. 42A is a simplified schematic cross sectional view of a nozzle 4201 treating a root canal 4203, controlling apical parameters, according to some embodiments of the invention. FIG. 42B is an enlarged view of a portion of FIG. 42A.

In some embodiments, flow of fluid within a root canal is controlled and/or balanced by control of insertion of fluid into the root canal and suction of material from the root canal. In some embodiments, depth of penetration (e.g. to the apex, e.g. not past the apex in the apical direction) of flow into the root canal is controlled. In some embodiments, pressure of flow and/or amount of abrasion at an apex of a root canal is controlled.

In some embodiments, pressure inside a root canal is controlled and/or balanced, for example, by controlling insertion of fluid into the root canal (increasing pressure in the canal) and suction of material from a root canal (decreasing pressure in the canal). In some embodiments, rhythms and/or durations of pulses of insertion (jetting) and/or suction control pressure in the canal e.g. with suction and jetting independently and/or simultaneously, e.g. with suction and/or jetting periodically.

A potential benefit of controlling pressure within the canal is the ability to control pressure at the root canal apex e.g. reducing pressure at the apex, e.g. potentially preventing rupture of the tooth e.g. at the root canal apex.

In some embodiments, suction and/or insertion of fluid is controlled to reduce pressure inside the root canal e.g. at and/or including pressure at the apex of the root canal. A potential benefit of reduced pressure within the root canal is a reduction in risk of breaking and/or rupturing the root canal and/or tooth.

In some embodiments, the root canal is sealed such that material can only enter or exit the root canal through a nozzle (e.g. the root canal is sealed at a coronal opening of the root canal). In some embodiments, control of pressure within the canal is enhanced by sealing of the root canal. In some embodiments, sealing of the root canal enables the nozzle to apply higher and/or lower pressures to the root canal.

In some embodiments, a nozzle 4201 and a sealing element 4207 are placed at an entrance to a root canal 4203, sealing the root canal, for example, only allowing movement of material in and out of the root canal through nozzle 4201 (e.g. only allowing movement of material out of the root canal through a suction cone 4217).

In some embodiments, sealing element 4207 surrounds the nozzle, for example, is ring-shaped. In an exemplary embodiment, the sealing element includes rubber e.g. silicone rubber. In some embodiments, sealing element 4207 is a separate component. In some embodiments, sealing element is coupled to and/or forms part of the nozzle.

In some embodiments, nozzle 4201 introduces fluid (e.g. fluid jet/s optionally including air and/or abrasive material) into the root canal 4203, for example, to clean the root canal. In some embodiments, nozzle 4201 includes a suction cone 4217 which extracts material through channel 4235, where suction cone inlets 4239 are apical of sealing element 4207. In some embodiments, a cross sectional area of a nozzle tip 4241 enlarges distally.

In some embodiments, the jet does not flow straight downwards towards the apex of the root canal e.g. the jet flows along the canal walls cleaning the walls. In some embodiments, one or more jet meets the root canal wall at an angle of 20-45 degrees, or 30-45 degrees to the root canal wall. Jet flow along the wall potentially reduces pressure at the apex, for example, as pressure of the jet is spread over a surface of the root canal wall.

FIG. 42C is a simplified schematic cross sectional view of a nozzle surrounded by a sealing element 4207, according to some embodiments of the invention. FIG. 42C shows a cross section perpendicular to the cross section illustrated in FIG. 42A taken along the line A-A illustrated on FIG. 42A. Visible in FIG. 42C is sealing element 4207 surrounding the nozzle. Also visible is a nozzle inner cone 4245.

Optionally, nozzle 4201 includes an internal cone with a lumen e.g. as illustrated in FIG. 31A.

In some embodiments, nozzle 4201 includes a pipe 4231 for supplying fluid to a nozzle lumen 4237.

In some embodiments, a wide or fan-like beam of fluid is discharged. For example, a wide or fan-like beam is discharged from a nozzle tip where a tip lumen cross sectional areal (perpendicular to nozzle tip long axis) increases distally. For example, a wide or fan-like beam where the beam broadens as a distance between the beam and nozzle exit aperture increases e.g. at least doubles in cross sectional area (cross section perpendicular to nozzle vertical axis) at 0.01 mm, or 0.1 mm, or 0.5 mm. or 1 mm. or 1 mm. or 5 mm from the nozzle exit aperture.

In some embodiments, a wide and/or fan-like beam has lower pressure. Potentially reducing pressure at a root canal apex or apical area.

In some embodiments, the lumen walls and/or the internal cone include a hollow portion, for example, increasing a length of a path of fluid within the nozzle.

Figures 43A, 43B:
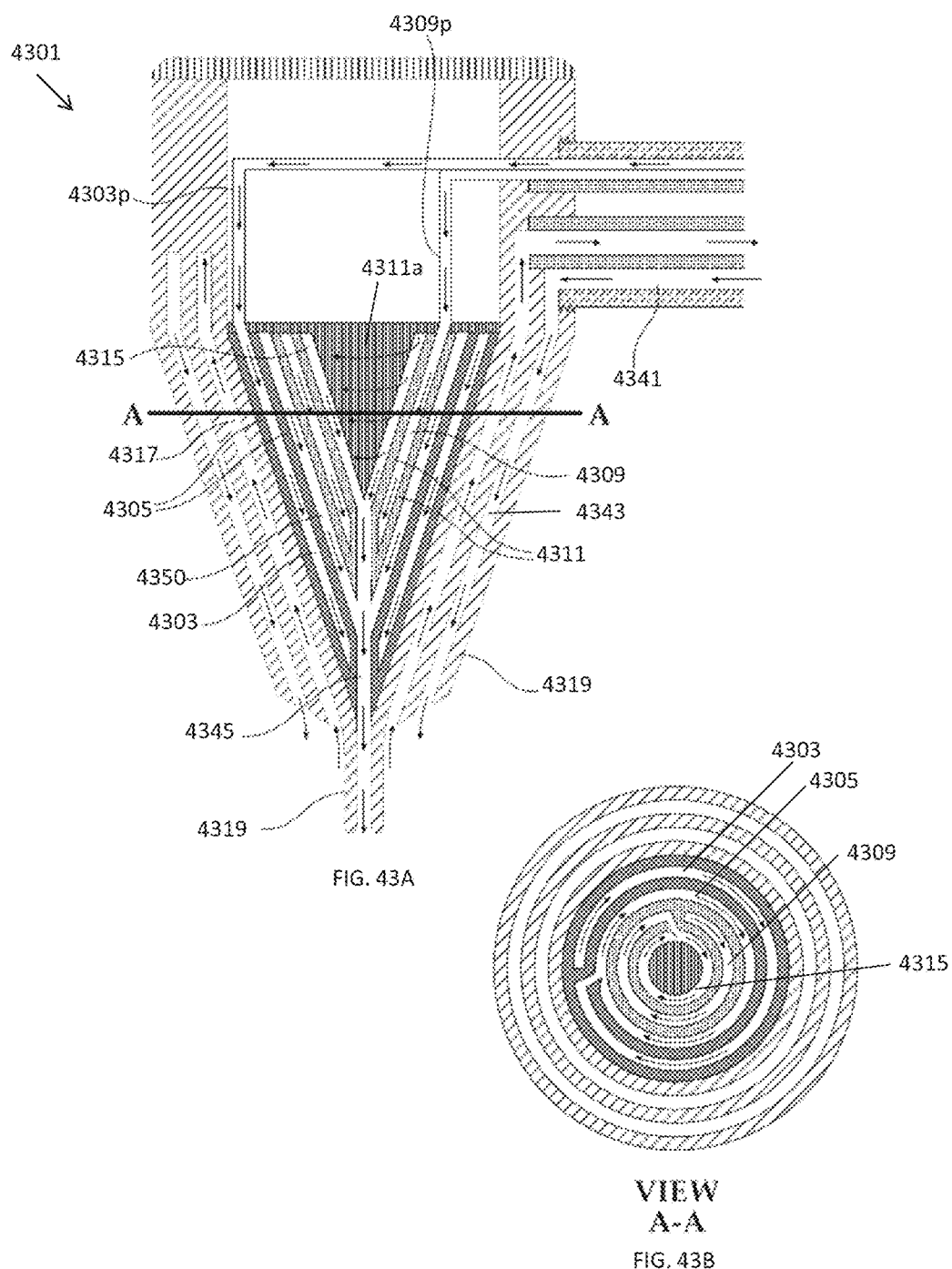
FIG. 43A is a simplified schematic side view of a nozzle including an external cone with a hollow portion and an internal cone with a hollow portion, according to some embodiments of the invention.
FIG. 43B is a simplified schematic cross sectional view of a nozzle including external cone with a hollow portion and an internal cone with a hollow portion, according to some embodiments of the invention.

FIG. 43A is a simplified schematic side view of a nozzle 4301 including an external cone 4305 with a hollow portion 4303 and an internal cone 4311 with a hollow portion 4309, according to some embodiments of the invention. FIG. 43B is a simplified schematic cross sectional view of a nozzle 4301 including external cone 4305 with a hollow portion and an internal cone 4311 with a hollow portion, according to some embodiments of the invention. FIG. 43B shows a cross section perpendicular to the cross section illustrated in FIG. 43B taken along the line A-A illustrated on FIG. 43A.

In some embodiments, external cone 4305 includes hollow walls and internal cone 4311 includes hollow walls: A first lumen 4303 is within external cone 4305 and a second lumen 4309 is within internal cone walls 4311.

In some embodiments, internal cone 4311 is smaller than and located within a lumen within external cone, forming a third lumen 4350 in the space between the external cone and the internal cone. In some embodiments, internal cone 4311 includes a fourth lumen 4315. In some embodiments, an additional internal cone 4311a is located inside internal cone 4311.

Referring now to FIG. 43B, In some embodiments, external cone and/or internal cone 4311 rotate, for example, to increase energy and/or momentum of discharged fluid from the nozzle (e.g. to enhance rotation of fluid within the root canal and/or enhance cleaning of the root canal). Optionally, external cone 4305 and internal cone 4311 rotate at different times and/or with different speeds and/or with different direction of rotation, for example, to increase mixing of the fluid from the internal and external cone when the flows meet.

In some embodiments, fluid is inserted into lumens 4303, 4309 is supplied by pipes 4303p, 4309p respectively.

Referring now to FIG. 43B, fluid inserted into the hollow portion of the inner cone (lumen 4309) flows radially and/or helically through the hollow portion of inner cone to the lumen between the inner cone and the additional inner cone (lumen 4315). Fluid inserted into the hollow portion of the external cone (lumen 4303) flows radially and/or helically through the hollow portion of external cone to the lumen between the external cone and the inner cone (lumen 4305).

In some embodiments, flows emerging from lumens 4350 and 4315 merge and/or mix in a central lumen 4345 before being discharged.

In some embodiments, fluid is inserted into lumens 4303, 4309 concurrently and/or in a pulse pattern e.g. where material is inserted into one or more lumen intermittently. In some embodiments, fluid inserted into lumens 4303, 4309 combines and/or mixes adjacent to a nozzle tip 4319.

Optionally, nozzle 4301 includes one or more lumen 4317 through which fluid is extracted.

Optionally, nozzle 4301 includes an additional cone 4319 external to external cone 4305, and fluid from pipe 4341 (e.g. flushing and/or disinfecting fluid) is inserted into the tooth through a lumen 4343 between additional cone 4319 and external cone 4305.

In some embodiments, fluid flows through one or more lumen with helical movement. In some embodiments, rotation of the cone/s and/or a shape of the lumen/s causes emission from the nozzle outlet of angled fluid jet/s and/or a flow with helical flow.

In some embodiments, a system for cleaning and/or abrading a root canal operates without an external compressor. In some embodiments, the system includes one or more pressurized container.

Figure 44:
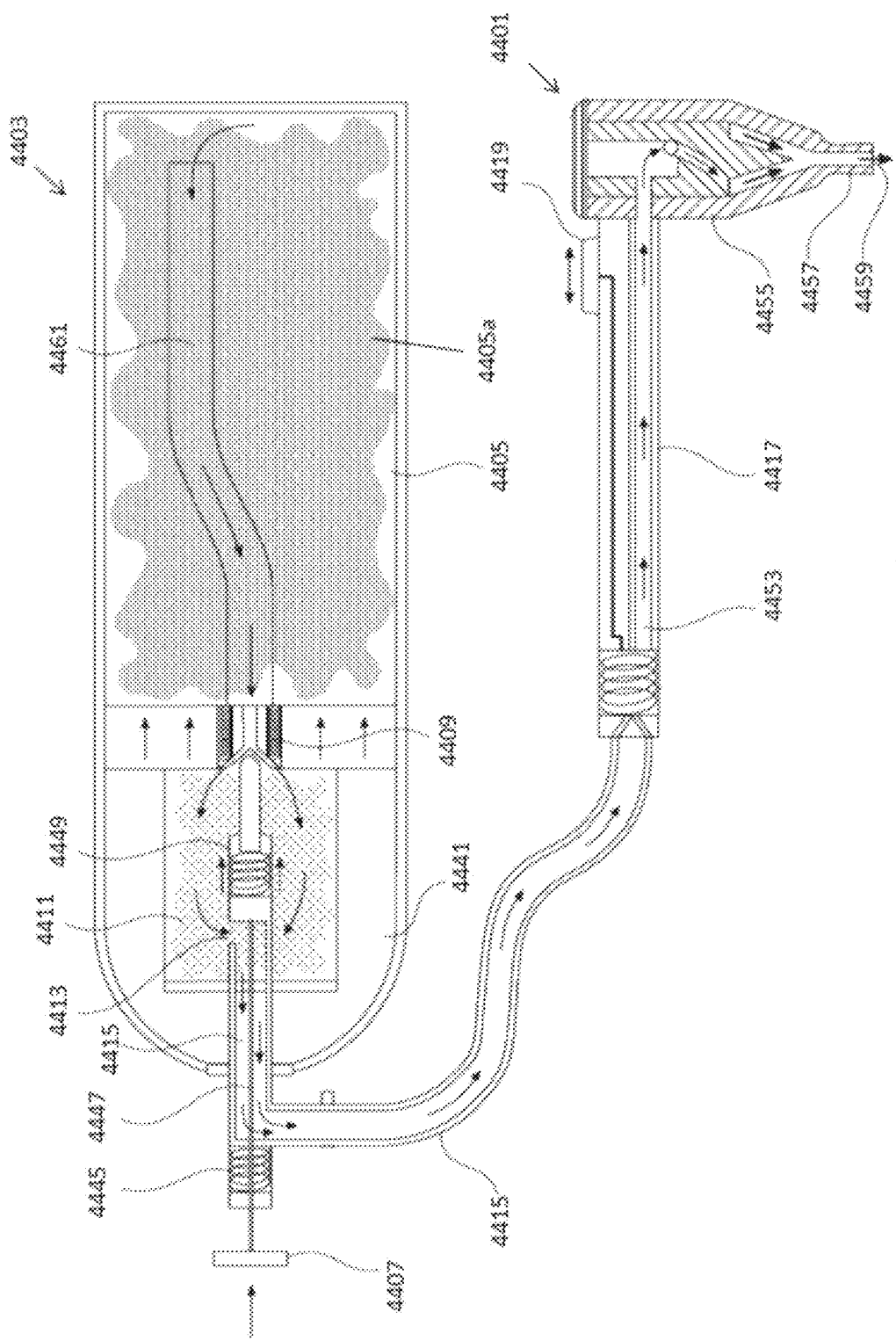
FIG. 44 is a simplified schematic cross sectional view of a system including a supply apparatus connected to a nozzle, according some embodiments of the invention.

FIG. 44 is a simplified schematic cross sectional view of a system including a supply apparatus 4403 connected to a nozzle 4401, according some embodiments of the invention.

In some embodiments, a supply apparatus is disposable and/or includes one or more disposable part. In some embodiments, a supply apparatus including one or more chamber containing pressurized gas, is located within a handle connected to a nozzle, forming a hand held endodontic cleaning device. A potential benefit being high portability and/or maneuverability of the device and/or a cleaning device which operates without any other infrastructure (e.g. compressor and/or external power supply).

Alternatively, in some embodiments, a supply apparatus is not located in the handle, e.g. supply apparatus includes a standing box.

In an exemplary embodiment, supply apparatus 4403 includes a first chamber 4405 which holds pressurized gas and fluid 4405a. Optionally, the chamber comprises a predefined amount of gas and fluid, for example suitable for performing 1, 3, 5, 10, 20, 50, 100 or another number of treatments. Upon opening first chamber 4405, the pressurized gas forces dispensing of fluid from the chamber (operation e.g. similar to an aerosol canister). In some embodiments, the gas includes air and/or $CO_2$.

In some embodiments, the chamber is opened by pressing a button 4407 which opens a valve 4409 between first chamber 4405 and a second chamber 4411 and opens a second valve 4413. In some embodiment, button 4407 is connected to a rod 4447 which pushes element 4449 towards valve 4409, opening valve 4409. In some embodiments, second chamber is enclosed inside a housing 4441. In some embodiments, pushing button 4407 compresses a spring 4445. In some embodiments, spring 4445 returns button 4407 to an original position after the button is released.

In some embodiments, second chamber 4411 holds abrasive powder and optionally pressurized gas. Optionally, the chamber comprises a predefined amount of abrasive powder and/or fluid, for example suitable for performing 1, 3, 5, 10, 20, 50, 100 or another number of treatments. Gas and fluid flow from first chamber 4405 through second chamber 4411, collecting and/or mixing (optionally, mixing uniformly) with abrasive material from second chamber 4411. The fluid mixture of gas, fluid and abrasive material then travels through pipe 4415 to a handle 4417 connected to nozzle 4401. Optionally, in some embodiments (e.g. so that the user can switch the flow on and off at a location near to the nozzle) flow through handle 4417 (e.g. passing through a pipe 4453 in handle 4417) is upon activation of the handle, e.g. by sliding a switch 4419 on the handle to an on position. The fluid mixture then flows through the nozzle, passing through a nozzle tip 4457, and is discharged through a nozzle exit aperture 4459. In some embodiments, nozzle 4401 includes outer walls 4455.

In some embodiments, pressure inside one or both chambers 4405, 4411 is 100-120 PSI, or 50-200 PSI or higher, or lower or intermediate pressure ranges or values. In some embodiments, a starting pressure of the first chamber is sufficient to dispense all of the fluid within the first chamber. In some embodiments, as a chamber empties a chamber size is reduced (e.g. second chamber moves towards first chamber) so that a chamber internal pressure is maintained.

In some embodiments, a ratio of gas to fluid within first chamber 4405 is 75% air 25% fluid, or 50% fluid 20% air, or 90% air 60%, or lower, higher or intermediate ratios. In some embodiments, the fluid mixture dispensed from supply apparatus through pipe 4415 includes 3-5% abrasive material (e.g. abrasive powder).

In some embodiments, the supply apparatus is and/or includes a part (e.g. a chamber) which is designed for single use, for example the apparatus or part is disposed after a single treatment. Alternatively, the supply apparatus and/or a part of the supply apparatus contains sufficient materials for 1, or 2, or 3, or 4, or 5, or, 10, or 50, or 100 treatments, or lower, or higher, or intermediate numbers of treatments.

In some embodiments, the supply apparatus weighs 20 g-3 kg, or 50 g-1 kg, or 50 g-500 g, or 50 g-200 g, or lower, higher or intermediate weights. In some embodiments, the supply apparatus is light enough so that it can be maneuvered by a user e.g. with one hand.

Optionally, in some embodiments, one or more chamber is refilled when empty. In some embodiments, one or more chamber and/or the supply apparatus is changed when empty and/or between treatments and/or between patients. A potential advantage of a supply apparatus operating using pressurized gas is that the nozzle need not be connected to a compressor and/or electricity supply.

Optionally, in some embodiments, a supply apparatus includes less than or more than two chambers, each chamber including one or more of gas, fluid, abrasive powder, and disinfecting material.

In some embodiments, two or more flows of material mix within a lumen of a nozzle, e.g. before discharge of the mixed flow into a root canal. In some embodiments, flows which mix inside the lumen of the nozzle are supplied by a supply apparatus including more than one pressurized chamber.

Figure 45:
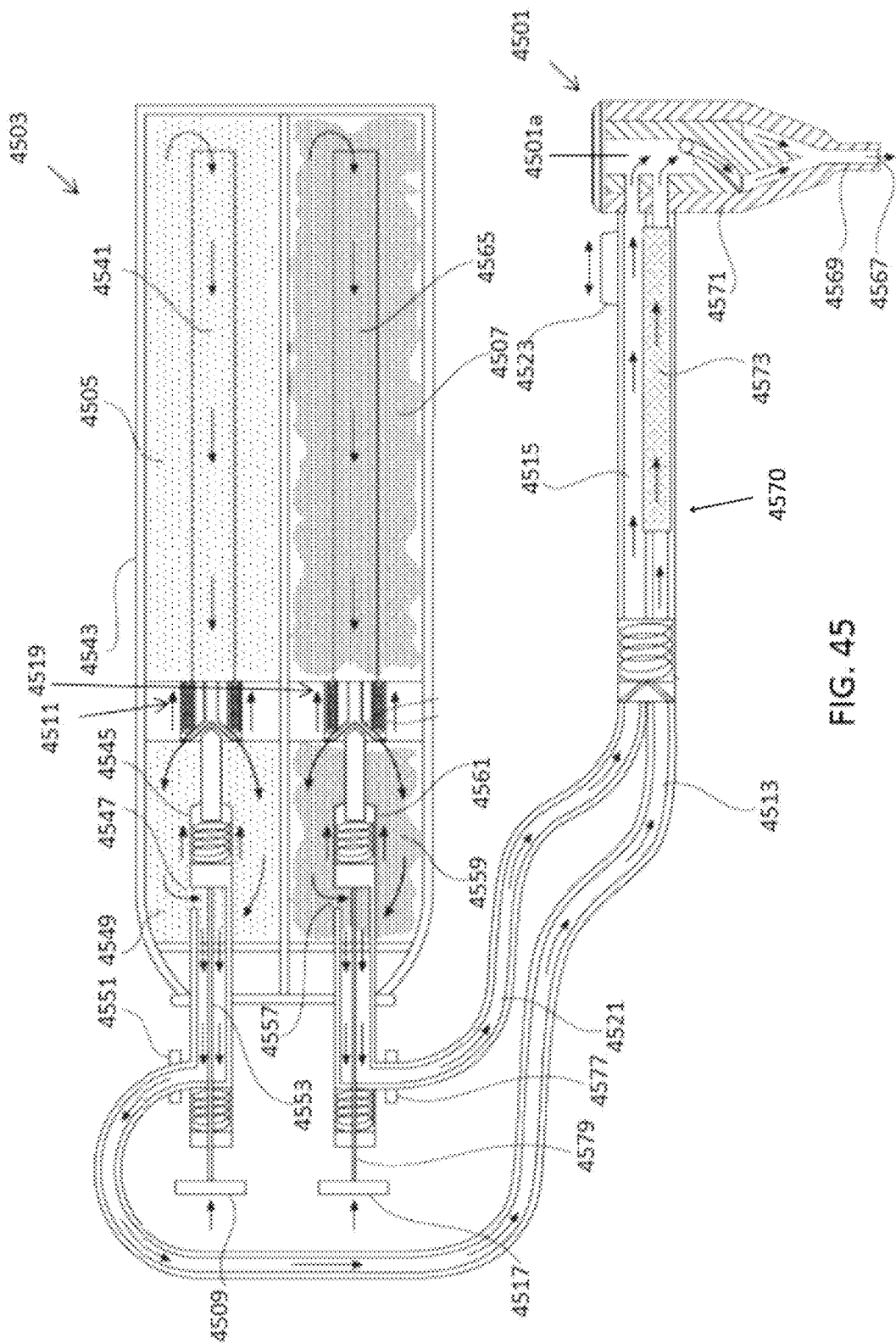
FIG. 45 is a simplified schematic cross sectional view of a supply apparatus supplying two separate flows to a nozzle, according to some embodiments of the invention.

FIG. 45 is a simplified schematic cross sectional view of a supply apparatus 4503 supplying two separate flows to a nozzle 4501, according to some embodiments of the invention.

In an exemplary embodiment, supply apparatus 4503 includes two chambers supplying two flows of material to the nozzle, for example, through two separate channels (e.g. pipes) which connect the chambers to the nozzle. In some embodiments, pressure within one or more chamber is 100-120 PSI, or 50-200 PSI or higher, or lower or intermediate pressure ranges or values.

In some embodiments, a first chamber 4505 contains pressurized gas (e.g. air) and a second chamber 4507 contains pressurized gas and fluid. In some embodiments, activating first chamber 4505, for example by pressing on first button 4509 opens the chamber (e.g. by opening a first chamber valve 4511) allowing flow of air from first chamber 4505 (optionally through a pipe 4541) through valve 4511 into chamber 4549, and then to exit chamber 4549 through an opening 4547 connected to first pipe 4513.

In some embodiments, first button 4509 is attached to a rod 4553 and pushing the first button pushes element 4545 towards valve 4511, opening the valve.

Flow then flows through a powder cartridge 4573 optionally located in a nozzle handle 4570 and passes to the nozzle 4501. The powder and air mix with fluid in a lumen 4501a of nozzle 4501. Fluid in lumen 4501a flows through nozzle, and through a nozzle tip 4569 before being discharged through nozzle exit aperture 4567.

In some embodiments, pressing on a second button 4517 opens a second chamber valve 4519, allowing flow of air and fluid from second chamber 4507 (optionally through a pipe 4565) to flow into chamber 4559 and then to pass through opening 4557 connected to a second pipe 4521, and then through a pipe 4515 in handle 4570 to the nozzle lumen mixing with the abrasive powder and air in the nozzle lumen. Optionally, one or more flow is controlled by an activation element (e.g. slide switch 4523) on the handle. Optionally, one or more of the flows passes through a powder cartridge 4573 (optionally located in the handle), collecting and/or mixing with abrasive material which the flow then carries to the nozzle lumen.

In some embodiments, second button 4517 is attached to a rod 4579 and pushing second button 4517 pushes an element 4561 towards valve 4519, opening the valve. In some embodiments, pipes 4513 and 4521 can be closed by valves 4551 and 4577 respectively. In some embodiments, the chambers include a housing 4543.

In some embodiments, more than two flows emanating from more than one chamber mix within the nozzle where each chamber contains one or more of gas, fluid, abrasive powder, and disinfecting material.

Experimental Examples

Reference is now made to the following examples, which together with the above descriptions illustrate some embodiments of the invention in a non limiting fashion.

An Experiment for Testing the Feasibility of an Apparatus and Method for Endodontic Treatment Using Angled Fluid Jets The inventors conducted an experiment for testing the feasibility of a system which comprises an apparatus for cleaning, abrading, and/or disinfecting a root canal as described above.

Experimental Design 41 human teeth specimens were extracted from patients. The specimens included a group of molars having 2-4 root canals, and a group of incisors having a single root canal. In total, 182 root canals were tested in the experiment. Each tooth specimen had one or various types of root canals, as indicated below.

5 types of root canals were tested: a standard root canal (53 specimens), a curved root canal (40 specimens), a sharp curved root canal (32 specimens), a root canal with an enlarged opening at the apex, ranging between 2-3 mm, which was created naturally as a result of calcification (33 specimens), and specimens with an extremely narrow root canal (24).

11 teeth specimens having 2-3 root canals each were extremely narrow, having an entrance aperture with a diameter smaller than 0.5 mm.

Immediately after the extraction, the specimens were placed in a 10% bleach solution, containing 10% chlorine and 90% water, (other solutions may also be used), to prevent dehydration of the root canals.

The following procedure was performed for each specimen. At first, an access cavity was drilled through the crown of the tooth to enable access through the pulp chamber to the root canal. An entrance to the root canal was exposed, and the specimen was placed back in the bleach solution. The specimen was then removed from the solution, and placed in a rubber mold. At this stage, the specimen was imaged using a 320 slices CT imaging device. Optionally, other imaging devices may be used.

An apparatus and system for example as described in FIG. 8 above were used for cleaning, abrading, and disinfecting each of the specimens. A nozzle of the apparatus was inserted through the pulp chamber and positioned such that an exit aperture of the nozzle was configured vertically above the entrance to a root canal, at an approximate distance of 1-3 mm.

The fluid used for the treatment of the root canals contained water, air, and glass powder (used as an abrasive powder). The pressures used were a water pressure of 80 PSI, and an air pressure of 80 PSI. The fluid passed through the pipeline of the system, for example through pipes in the handle of the apparatus, reaching the nozzle and exiting through the exit aperture in the form of angled fluid jets, as previously described.

Cleaning, abrading and disinfecting of the root canal of each specimen was achieved by the flow of fluid advancing along the root canal wall, removing organic substance such as nerve tissue, pulp tissue, and/or debris, as previously described.

The treatment duration for each of the specimens was determined according to parameters such as the existence of a narrowing portion, the existence of curvature, the length of the root canal, and/or other parameters or combinations of them. The treatment duration used in this experiment was 15 seconds (applied to 13 specimens), 30 seconds (applied to 15 specimens), and 45 seconds (applied to 13 specimens). Optionally, other durations may be used.

Imaging of each specimen using a 320 slices CT imaging device was performed again at the end of the process.

Each specimen was tested for apex penetration (referred to in this example as further widening of a natural, normal opening of the apex), grade of apex penetration (if occurred), penetration along the canal wall, and the thickness of the eroded layer.

To prove that the root canals of the specimen are clean, an electro-scan microscope image was acquired from each specimen, as will be further explained.

Data Analysis and Results

FIG. 16A-B is a table of the experiment results. The table shows that in all tested root canals, the apex was not penetrated (i.e. an initial natural opening was not widened). The table also shows that in all tested root canals, the root canal wall was not penetrated as well. The thickness of the removed dentin layer ranged between 100-200 µm for all tested root canals.

Figure 17:
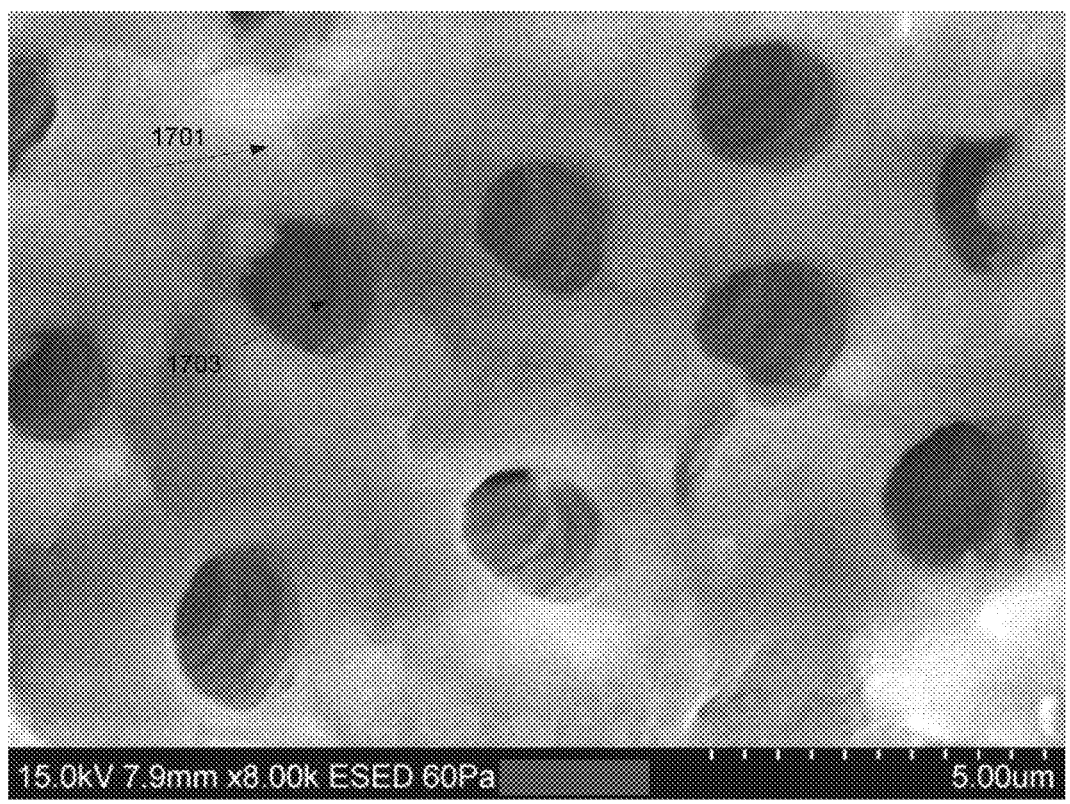
FIG. 17 is an image of a dentin layer and dentinal tubules taken by an electro scan microscope after treating a root canal using the apparatus.

FIG. 17 shows an image of the dentin layer and dentinal tubules of one of the specimens, taken at the end of the experiment described above. This image was taken by an electro scan microscope, using a magnification of ×5000.

Before acquiring the image, the specimen was stored in the bleach solution. Once the specimen was removed from the solution, it was sliced along a longitudinal cross section, to expose the internal lumen of the root canal. This exemplary image shows that the dentin layer 1701 and the tubules 1703 shave been cleaned and cleared by the flow of fluid, and do not have a smear layer.

General

It is expected that during the life of a patent maturing from this application many relevant endodontic apparatuses will be developed and the scope of the term endodontic apparatuses is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for endodontic treatment comprising:
   a nozzle comprising:
      a tip sized and shaped to be inserted into a pulp chamber of a tooth and comprising an exit aperture;
      a lumen fluidly connected to said exit aperture;
      a first channel extending away from the lumen terminating at a first outlet inside said lumen;
      a second channel extending away from the lumen terminating at a second outlet terminating inside said lumen;
   wherein said lumen is configured and said first and said second outlets are positioned such that material exiting said first outlet and material exiting said second outlet mix within said lumen, exiting said nozzle through said exit aperture as a beam which:

includes at least one fluid jet at an angle to a vertical axis of said nozzle;
or which broadens as a distance between the beam and said exit aperture increases.

2. The apparatus of claim 1, wherein said first channel and said second channel carry material selected from gas, liquid, abrasive material and combinations thereof.

3. The apparatus of claim 2, wherein said first channel carries gas and said second channel carries liquid.

4. The apparatus of claim 3, wherein said first channel carries abrasive material.

5. The apparatus of claim 2, wherein said liquid comprises one or more of disinfection solution, irrigation solution, medication.

6. The apparatus of claim 1, wherein each said channel is connected to one or more source of material.

7. The apparatus of claim 1, wherein at least one of said channels includes at least a portion of the channel which is disposed within said lumen.

8. The apparatus of claim 1, wherein both of said channels include at least a portion of the channel which is disposed within said lumen.

9. The apparatus of claim 8, wherein said channels have a helical shape.

10. The apparatus of claim 1, wherein said outlets are within 1 mm of each other.

11. The apparatus of claim 1, wherein one or more of said channels has circular cross section with diameter between 0.2-4 mm.

12. The apparatus of claim 1, wherein one or more of said channels has elliptical cross section.

13. The apparatus of claim 1, wherein said channels are moveable with respect to said lumen.

14. The apparatus of claim 13, wherein said channels are connected to an actuator configured to move said channels with respect to said lumen.

15. The apparatus of claim 14, wherein said actuator is a stepper motor.

16. The apparatus of claim 1, wherein said beam at least doubles in cross sectional area at a distance of 5 mm from said nozzle exit aperture.

17. The apparatus of claim 1, wherein said beam comprises at least one fluid jet at an angle to a vertical axis of said nozzle.

18. The apparatus of claim 17, wherein said fluid jet does not intersect said vertical axis of said nozzle.

19. The apparatus of claim 1, wherein said lumen has a tapering shape.

20. The apparatus of claim 1, wherein said nozzle includes an external tapering portion, said lumen defined within said external tapering portion.

21. The apparatus of claim 20, wherein said channels are positioned along an inner surface of an outer wall of said external tapering portion.

22. The apparatus of claim 20, wherein said nozzle includes an inner tapering portion, wherein said lumen is defined between said inner tapering portion and said external tapering portion.

23. The apparatus of claim 20, wherein said channels are formed by hollows in said inner tapering portion.

24. The apparatus of claim 23, wherein said inner tapering portion is a solid component.

25. The apparatus of claim 23, wherein said inner tapering portion is a non-solid component.

26. The apparatus of claim 20, wherein said inner tapering portion and said external tapering portion both have a cone shape.

27. The apparatus of claim 20, wherein said inner tapering portion is moveable with respect to said external tapering portion.

28. The apparatus of claim 1, wherein said nozzle includes more than two channels.

29. The apparatus of claim 1, comprising a handle coupled to said nozzle, where said channels receive material through said handle.

30. The apparatus according to claim 1, wherein said apparatus comprises a suction cone for collecting returning fluid and debris, wherein said suction cone has a tip sized to fit within a pulp chamber of a tooth.

31. The apparatus according to claim 30,
wherein said nozzle is configured to discharge said beam in discharge pulses;
wherein said suction cone is configured to collect said fluid and debris in collection pulses;
wherein said discharge pulses and said collection pulses are controlled by a control panel electrically connected to said apparatus.

32. The apparatus according to claim 1, wherein said fluid circulates in a helical flow through said lumen for exiting the nozzle in an angle.

33. The apparatus according to claim 1, wherein said apparatus is connected to an air compressor with a pressure ranging between 5-300 PSI.

34. The apparatus according to claim 1, wherein said apparatus is connected to a fluid tank which provides fluid at a volumetric flow rate ranging between 0.1-50 ml/second.

35. The apparatus according to claim 1, wherein said at least one fluid jet comprises between 5-98% gas and between 2-90% liquid.

36. A method of endodontic treatment comprising:
positioning a tip of a nozzle above an entrance to a root canal;
discharging a first flow of material into a lumen of said nozzle through a first channel extending away from the lumen and a second flow of material into said lumen of said nozzle through a second channel extending away from the lumen allowing said flows to mix within said lumen to form a beam of material exiting said lumen through an exit aperture, where said beam has a shape which:
includes at least one fluid jet at an angle to a vertical axis of said nozzle;
or broadens as a distance between the beam and said exit aperture increases.

37. The method according to claim 36, wherein said at least one fluid jet at an angle has tangential and vertical velocity components in respect to a wall of said root canal.

38. The method of endodontic treatment of claim 36, comprising:
moving at least one of said channels within said lumen.

39. The method of claim 38, wherein said moving comprises one or more of distal-proximal movement and rotation.

40. The method of endodontic treatment of claim 36, wherein said channels are formed by hollows within an inner tapering portion disposed within said lumen,
wherein said method comprises moving said inner tapering portion to adjust an inner geometry of said nozzle changing flow parameters of said beam.

41. The method of claim 40, wherein said moving of said inner tapering portion is longitudinal movement or radial expansion simultaneously or separately.

42. The method of claim 40, wherein said flow parameters include:

fluid flow velocity, fluid flow pressure, fluid flow rate, an angle of one or more fluid jets exiting the nozzle, a shape of a beam of jets exiting the nozzle, a flow pattern within the nozzle, a speed of circulation of fluid.

43. The method according to claim 42, wherein said flow parameters prevent tissue removal in an apical direction of a root canal apex.

44. The method according to claim 42, wherein said flow parameters are sufficient to remove tissue from said root canal including an apex of said root canal.

45. The method of claim 36, wherein said first flow and said second flow comprise one or more of gas, liquid, abrasive material and mixtures thereof.

46. The method of claim 36, wherein said first flow comprises liquid and said second flow comprises gas and said flows mix within said nozzle to form an aerosol.

47. The method of claim 36, wherein said shape of said beam causes said beam to hit a wall of said root canal and to flow along said wall of said root canal so that said flow removes material from said wall of said root canal.

48. The method of claim 47, wherein said flow comprises a helical flow along said wall of a root canal.

49. The method of claim 47, comprising separating soft tissue from said wall of a root canal.

50. The method of claim 47, comprising eroding a layer of dentin tissue from at least a portion of said wall of said root canal.

51. The method according to claim 50, wherein said beam includes abrasive material;
wherein said eroding includes abrasive particles of said root canal fluid applying radially outward force onto said root canal wall.

52. The method of claim 36, wherein said beam comprises a mixture of two or more of gas, liquid and abrasive material.

53. The method of claim 52, wherein said liquid comprises one or more of disinfection solution, irrigation solution, medication.

54. The method of claim 36, wherein said fluid jet is at an angle which does not intersect said vertical axis of said nozzle, which angle causes said at least one fluid jet to hit a wall of said root canal; and to flow along said wall of said root canal so that said flow removes material from said wall of said root canal.

55. The method according to claim 36, wherein said positioning comprises aligning a vertical axis of said nozzle with a vertical axis of a pulp chamber connected to said root canal.

56. The method according to claim 55, wherein said beam is configured to rotate root canal fluid within said canal does such that said fluid does not directly hit an apex of said root canal.

57. The method according to claim 36, wherein said beam is cone shaped.

58. The method according to claim 36, wherein said beam is configured to flow helically along a wall of said root canal.

59. The method according to claim 36, wherein said root canal comprises at least one narrowing portion, and said beam is configured to flow through said narrowing portion along a wall of the root canal.

60. The method according to claim 36, wherein said root canal comprises at least one of a curvature and branching, and said beam is configured to flow through said at least one curvature and branching.

61. The method according to claim 36, wherein fluid returns upwards along at least a portion of a central lumen of said root canal.

62. The method according to claim 36, wherein said beam is configured to erode a layer with thickness of 40-400 μm from said root canal.

63. The method according to claim 36, wherein said beam is configured to remove a layer of tissue 100-200 μm thick from a wall of said root canal in 15-45 seconds.

64. The method according to claim 36, wherein a pressure of said at least one fluid jet exiting the nozzle is between 10 and 200 PSI.

65. The method according to claim 36, wherein a pressure of said at least one fluid jet when it hits a wall of the root canal is between 5 and 150 PSI.

66. The method according to claim 36, wherein said angled jet is created by circulating said fluid in a helical flow within said nozzle.

67. The method according to claim 36, wherein said beam is configured to remove soft tissue comprises at least one of nerve tissue, pulp tissue, and or blood vessels.

68. The method according to claim 36, wherein said method does not leave a smear layer on a wall of said root canal.

69. The method according to claim 36, wherein said discharging comprises directing said at least one fluid jet in pulses.

70. The method according to claim 36, wherein said discharging comprises clearing a root canal to prepare for sealing.

71. The method according to claim 36, wherein said beam includes abrasive material and a flow of abrasive material is adjustable so that said at least one fluid jet comprises between 0.01 to 3% of the fluid exiting the nozzle.

72. The method according to claim 71, wherein the abrasive material is in the form of powder grains having a diameter ranging between 2 and 500 μm.

73. The method according to claim 71, wherein said abrasive material comprises one or more of crystallite, silicon powder, garnet powder, aluminum powder, magnesium powder, ceramic powder, plastic powder, synthetic, emery powders, sea shell powder, cement powder, salt, ground seeds, diamond powder, carbide powder, glass powder, iron/iron oxide powder, steel powder, aluminum oxide powder, baking soda, acrylic powder, granite powder, fruit powder, tree shell powder, plant seed powder, sea sand powder, synthetic diamond powder, stone powder, marble powder, copper powder, silica.

74. The method according to claim 36, a volumetric fluid flow rate of fluid exiting said nozzle is between 0.1-50 ml/sec.

75. The method according to claim 36, wherein a velocity of said beam along the root canal wall is between 0.5 and 50 m/sec.

76. The method according to claim 36, wherein said beam comprises gas bubbles which abrade a wall of said root canal.

77. The method according to claim 36, comprising collecting returning fluid and debris by suction.

78. The method according to claim 77, wherein said collecting comprises collecting fluid and debris in pulses.

79. The method according to claim 77, wherein said collecting comprises controlling a pressure at an apical area of said root canal.

80. The method according to claim 79, wherein said controlling comprises reducing said pressure to prevent break through at the apex of said root canal.

81. The method according to claim 36, wherein said beam is configured to rotate root canal fluid within said root canal to remove material from tubules extending from said root canal.

82. An apparatus for endodontic treatment comprising:
a nozzle comprising:
- a tip sized and shaped to be inserted into a pulp chamber of a tooth and comprising an exit aperture;
- a lumen fluidly connected to said exit aperture;
- a first channel extending away from the lumen;
- a second channel extending away from the lumen which merges with said first channel to form a third channel, material from said first channel merging with material from said second channel;
- an outlet in said third channel inside said lumen;
wherein said lumen and channels are configured and said outlet is positioned such that material exiting said nozzle through a nozzle exit aperture as a beam which:
includes at least one fluid jet at an angle to a vertical axis of said nozzle;
or which broadens as a distance between the beam and said exit aperture increases.

\* \* \* \* \*